(12) United States Patent
Pollak et al.

(10) Patent No.: US 8,686,114 B2
(45) Date of Patent: Apr. 1, 2014

(54) VARIANT SUCROSE TRANSPORTER POLYPEPTIDES

(75) Inventors: Dana Michelle Walters Pollak, Media, PA (US); Tina K Van Dyk, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 129 days.

(21) Appl. No.: 13/412,124

(22) Filed: Mar. 5, 2012

(65) Prior Publication Data

US 2013/0230892 A1 Sep. 5, 2013

(51) Int. Cl.
*C07K 14/245* (2006.01)
(52) U.S. Cl.
USPC .......................................... 530/350; 536/23.7
(58) Field of Classification Search
None
See application file for complete search history.

(56) References Cited

U.S. PATENT DOCUMENTS

| | | | |
|---|---|---|---|
| 4,683,202 | A | 7/1987 | Mullis et al. |
| 6,013,494 | A | 1/2000 | Nakamura et al. |
| 6,136,576 | A | 10/2000 | Diaz et al. |
| 6,514,733 | B1 | 2/2003 | Emptage et al. |
| 6,610,836 | B1 | 8/2003 | Breton et al. |
| 6,960,455 | B2 | 11/2005 | Livshits et al. |
| 7,005,291 | B1 | 2/2006 | Nair et al. |
| 7,041,814 | B1 | 5/2006 | Weinstock et al. |
| 7,132,527 | B2 | 11/2006 | Payne et al. |
| 7,317,558 | B2 | 1/2008 | Chiba |
| 7,371,558 | B2 | 5/2008 | Cervin et al. |
| 7,524,660 | B2 | 4/2009 | Caimi et al. |
| 8,129,170 | B1 | 3/2012 | Van Dyk |
| 8,222,000 | B2 | 7/2012 | Van Dyk |
| 2011/0136190 | A1 | 6/2011 | Eliot et al. |
| 2011/0144377 | A1 | 6/2011 | Eliot et al. |
| 2013/0045518 | A1* | 2/2013 | Chen et al. ............ 435/146 |

FOREIGN PATENT DOCUMENTS

| | | |
|---|---|---|
| EP | 1227152 A1 | 7/2002 |
| WO | 2009078687 A2 | 6/2009 |
| WO | 2010051849 A1 | 5/2010 |
| WO | 2010093182 A2 | 8/2010 |
| WO | 2010101359 A2 | 9/2010 |
| WO | 2010101360 A2 | 9/2010 |

OTHER PUBLICATIONS

Olson et al., Appl. Microbiol. Biotechnol. 74:1031-1040, 2007.
Jahreis et al., J. Bacteriol. 184(19):5307-5316, 2002.
Moniruzzaman et al., J. Bacteriol. 179(6):1880-1886, 1997.
Lee et al., Appl. Microbiol. Biotechnol. 88(4):905-913, 2010.
Menick et al., Biochemistry 26(2), 6638-6644, 1987.
Vadyvaloo et al., J. Mol. Biol. 358, 1051-1059, 2006.
Chen et al., U.S. Appl. No. 13/210,488, filed Aug. 16, 2011.
Ruebling-Jass et al., U.S. Appl. No. 13/412,193, filed Mar. 5, 2012.

* cited by examiner

*Primary Examiner* — Rebecca Prouty

(57) ABSTRACT

Variant sucrose transporter polypeptides that enable bacterial growth over a wide range of gene expression levels and sucrose concentrations are described. Additionally, recombinant bacteria comprising these variant sucrose transporter polypeptides, and methods of utilizing the bacteria to produce products such as glycerol and glycerol-derived products are provided.

3 Claims, No Drawings

SEQUENCE LISTING

<160> NUMBER OF SEQ ID NOS: 136

<210> SEQ ID NO 1
<211> LENGTH: 1176
<212> TYPE: DNA
<213> ORGANISM: Saccharomyces cerevisiae

<400> SEQUENCE: 1

```
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt tcgctccaat agtacaaatg tgggtgttcg aagaagagat caatggtgaa     240
aaattgactg aaatcataaa tactagacat caaaacgtga atacttgcc tggcatcact      300
ctacccgaca atttggttgc taatccagac ttgattgatt cagtcaagga tgtcgacatc     360
atcgttttca acattccaca tcaattttg ccccgtatct gtagccaatt gaaaggtcat      420
gttgattcac acgtcagagc tatctcctgt ctaaagggtt ttgaagttgg tgctaaaggt     480
gtccaattgc tatcctctta catcactgag gaactaggta ttcaatgtgg tgctctatct     540
ggtgctaaca ttgccaccga agtcgctcaa gaacactggt ctgaaacaac agttgcttac     600
cacattccaa aggatttcag aggcgagggc aaggacgtcg accataaggt tctaaaggcc     660
ttgttccaca gacctactt ccacgttagt gtcatcgaag atgttgctgg tatctccatc      720
tgtggtgctt tgaagaacgt tgttgcctta ggttgtggtt tcgtcgaagg tctaggctgg     780
ggtaacaacg cttctgctgc catccaagga gtcggtttgg gtgagatcat cagattcggt     840
caaatgtttt tcccagaatc tagagaagaa acatactacc aagagtctgc tggtgttgct     900
gatttgatca ccacctgcgc tggtggtaga aacgtcaagg ttgctaggct aatggctact     960
tctggtaagg acgcctggga atgtgaaaag gagttgttga atggccaatc cgctcaaggt    1020
ttaattacct gcaaagaagt tcacgaatgg ttggaaacat gtggctctgt cgaagacttc    1080
ccattatttg aagccgtata ccaaatcgtt tacaacaact acccaatgaa gaacctgccg    1140
gacatgattg aagaattaga tctacatgaa gattag                              1176
```

<210> SEQ ID NO 2
<211> LENGTH: 391
<212> TYPE: PRT
<213> ORGANISM: Saccharomyces cerevisiae

<400> SEQUENCE: 2

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110
```

```
Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
                180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
        210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
                260                 265                 270

Leu Gly Glu Ile Ile Arg Phe Gly Gln Met Phe Phe Pro Glu Ser Arg
            275                 280                 285

Glu Glu Thr Tyr Tyr Gln Glu Ser Ala Gly Val Ala Asp Leu Ile Thr
        290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
        370                 375                 380

Glu Leu Asp Leu His Glu Asp
385                 390

<210> SEQ ID NO 3
<211> LENGTH: 1323
<212> TYPE: DNA
<213> ORGANISM: Saccharomyces cerevisiae

<400> SEQUENCE: 3
atgcttgctg tcagaagatt aacaagatac acattcctta agcgaacgca tccggtgtta      60
tatactcgtc gtgcatataa aatttttgcct tcaagatcta ctttcctaag aagatcatta    120
ttacaaacac aactgcactc aaagatgact gctcatacta atatcaaaca gcacaaacac    180
tgtcatgagg accatcctat cagaagatcg gactctgccg tgtcaattgt acatttgaaa    240
cgtgcgccct tcaaggttac agtgattggt tctggtaact gggggaccac catcgccaaa    300
gtcattgcgg aaaacacaga attgcattcc catatcttcg agccagaggt gagaatgtgg    360 gttttttgatg aaaagatcgg cgacgaaaat ctgacggata tcataaatac aagacaccag    420
aacgttaaat atctacccaa tattgacctg ccccataatc tagtggccga tcctgatctt    480
ttacactcca tcaagggtgc tgacatcctt gttttcaaca tccctcatca atttttacca    540
```

```
aacatagtca aacaattgca aggccacgtg gcccctcatg taagggccat ctcgtgtcta    600
aaagggttcg agttgggctc caagggtgtg caattgctat cctcctatgt tactgatgag    660
ttaggaatcc aatgtggcgc actatctggt gcaaacttgg caccggaagt ggccaaggag    720
cattggtccg aaaccaccgt ggcttaccaa ctaccaaagg attatcaagg tgatggcaag    780
gatgtagatc ataagatttt gaaattgctg ttccacagac cttacttcca cgtcaatgtc    840
atcgatgatg ttgctggtat atccattgcc ggtgccttga agaacgtcgt ggcacttgca    900
tgtggtttcg tagaaggtat gggatggggt aacaatgcct ccgcagccat tcaaaggctg    960
ggtttaggtg aaattatcaa gttcggtaga atgttttcc cagaatccaa agtcgagacc    1020
tactatcaag aatccgctgg tgttgcagat ctgatcacca cctgctcagg cggtagaaac    1080
gtcaaggttg ccacatacat ggccaagacc ggtaagtcag ccttggaagc agaaaaggaa    1140
ttgcttaacg tcaatccgc caagggata atcacatgca gagaagttca cgagtggcta    1200
caaacatgtg agttgaccca agaattccca ttattcgagg cagtctacca gatagtctac    1260
aacaacgtcc gcatggaaga cctaccggag atgattgaag agctagacat cgatgacgaa    1320
tag                                                                 1323

<210> SEQ ID NO 4
<211> LENGTH: 440
<212> TYPE: PRT
<213> ORGANISM: Saccharomyces cerevisiae

<400> SEQUENCE: 4

Met Leu Ala Val Arg Arg Leu Thr Arg Tyr Thr Phe Leu Lys Arg Thr
1               5                   10                  15

His Pro Val Leu Tyr Thr Arg Arg Ala Tyr Lys Ile Leu Pro Ser Arg
            20                  25                  30

Ser Thr Phe Leu Arg Arg Ser Leu Leu Gln Thr Gln Leu His Ser Lys
        35                  40                  45

Met Thr Ala His Thr Asn Ile Lys Gln His Lys His Cys His Glu Asp
    50                  55                  60

His Pro Ile Arg Arg Ser Asp Ser Ala Val Ser Ile Val His Leu Lys
65                  70                  75                  80

Arg Ala Pro Phe Lys Val Thr Val Ile Gly Ser Gly Asn Trp Gly Thr
                85                  90                  95

Thr Ile Ala Lys Val Ile Ala Glu Asn Thr Glu Leu His Ser His Ile
            100                 105                 110

Phe Glu Pro Glu Val Arg Met Trp Val Phe Asp Glu Lys Ile Gly Asp
        115                 120                 125

Glu Asn Leu Thr Asp Ile Ile Asn Thr Arg His Gln Asn Val Lys Tyr
    130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
            180                 185                 190

His Val Arg Ala Ile Ser Cys Leu Lys Gly Phe Glu Leu Gly Ser Lys
        195                 200                 205

Gly Val Gln Leu Leu Ser Ser Tyr Val Thr Asp Glu Leu Gly Ile Gln
    210                 215                 220

Cys Gly Ala Leu Ser Gly Ala Asn Leu Ala Pro Glu Val Ala Lys Glu
```

```
                225                 230                 235                 240
His Trp Ser Glu Thr Thr Val Ala Tyr Gln Leu Pro Lys Asp Tyr Gln
                    245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
        275                 280                 285

Ile Ala Gly Ala Leu Lys Asn Val Val Ala Leu Ala Cys Gly Phe Val
    290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
            340                 345                 350

Thr Thr Cys Ser Gly Gly Arg Asn Val Lys Val Ala Thr Tyr Met Ala
        355                 360                 365

Lys Thr Gly Lys Ser Ala Leu Glu Ala Glu Lys Glu Leu Leu Asn Gly
    370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
                405                 410                 415

Gln Ile Val Tyr Asn Asn Val Arg Met Glu Asp Leu Pro Glu Met Ile
            420                 425                 430

Glu Glu Leu Asp Ile Asp Asp Glu
        435                 440

<210> SEQ ID NO 5
<211> LENGTH: 816
<212> TYPE: DNA
<213> ORGANISM: Saccharomyces cerevisiae

<400> SEQUENCE: 5
atgaaacgtt tcaatgtttt aaaatatatc agaacaacaa aagcaaatat acaaaccatc      60
gcaatgcctt tgaccacaaa acctttatct ttgaaaatca cgccgctct attcgatgtt     120 gacggtacca tcatcatctc tcaaccagcc attgctgctt tctggagaga tttcggtaaa     180
gacaagcctt acttcgatgc cgaacacgtt attcacatct ctcacggttg agagaacttac     240 gatgccattg ccaagttcgc tccagacttt gctgatgaag aatacgttaa caagctagaa     300
ggtgaaatcc agaaaagta cggtgaacac tccatcgaag ttccaggtgc tgtcaagttg     360
tgtaatgctt tgaacgcctt gccaaaggaa aaatgggctg tcgccacctc tggtacccgt     420
gacatggcca gaaatggtt cgacatttg aagatcaaga gaccagaata cttcatcacc     480
gccaatgatg tcaagcaagg taagcctcac ccagaaccat acttaaaggg tagaaacggt     540
ttgggtttcc caattaatga acaagaccca tccaaatcta aggttgttgt ctttgaagac     600
gcaccagctg gtattgctgc tggtaaggct gctggctgta aaatcgttgg tattgctacc     660
actttcgatt ggacttctt gaaggaaaag ggttgtgaca tcattgtcaa gaaccacgaa     720
tctatcagag tcggtgaata caacgctgaa accgatgaag tcgaattgat ctttgatgac     780
tacttatacg ctaaggatga cttgttgaaa tggtaa                              816

<210> SEQ ID NO 6
<211> LENGTH: 271
```

-continued

<212> TYPE: PRT
<213> ORGANISM: Saccharomyces cerevisiae

<400> SEQUENCE: 6

```
Met Lys Arg Phe Asn Val Leu Lys Tyr Ile Arg Thr Thr Lys Ala Asn
1               5                   10                  15

Ile Gln Thr Ile Ala Met Pro Leu Thr Thr Lys Pro Leu Ser Leu Lys
            20                  25                  30

Ile Asn Ala Ala Leu Phe Asp Val Asp Gly Thr Ile Ile Ser Gln
        35                  40                  45

Pro Ala Ile Ala Ala Phe Trp Arg Asp Phe Gly Lys Asp Lys Pro Tyr
    50                  55                  60

Phe Asp Ala Glu His Val Ile His Ile Ser His Gly Trp Arg Thr Tyr
65              70                  75                  80

Asp Ala Ile Ala Lys Phe Ala Pro Asp Phe Ala Glu Glu Tyr Val
                85                  90                  95

Asn Lys Leu Glu Gly Glu Ile Pro Glu Lys Tyr Gly Glu His Ser Ile
            100                 105                 110

Glu Val Pro Gly Ala Val Lys Leu Cys Asn Ala Leu Asn Ala Leu Pro
        115                 120                 125

Lys Glu Lys Trp Ala Val Ala Thr Ser Gly Thr Arg Asp Met Ala Lys
    130                 135                 140

Lys Trp Phe Asp Ile Leu Lys Ile Lys Arg Pro Glu Tyr Phe Ile Thr
145                 150                 155                 160

Ala Asn Asp Val Lys Gln Gly Lys Pro His Pro Glu Pro Tyr Leu Lys
                165                 170                 175

Gly Arg Asn Gly Leu Gly Phe Pro Ile Asn Glu Gln Asp Pro Ser Lys
            180                 185                 190

Ser Lys Val Val Val Phe Glu Asp Ala Pro Ala Gly Ile Ala Ala Gly
        195                 200                 205

Lys Ala Ala Gly Cys Lys Ile Val Gly Ile Ala Thr Thr Phe Asp Leu
    210                 215                 220

Asp Phe Leu Lys Glu Lys Gly Cys Asp Ile Ile Val Lys Asn His Glu
225                 230                 235                 240

Ser Ile Arg Val Gly Glu Tyr Asn Ala Glu Thr Asp Glu Val Glu Leu
                245                 250                 255

Ile Phe Asp Asp Tyr Leu Tyr Ala Lys Asp Asp Leu Leu Lys Trp
            260                 265                 270
```

<210> SEQ ID NO 7
<211> LENGTH: 753
<212> TYPE: DNA
<213> ORGANISM: Saccharomyces cerevisiae

<400> SEQUENCE: 7

```
atgggattga ctactaaacc tctatctttg aaagttaacg ccgctttgtt cgacgtcgac      60
ggtaccatta tcatctctca accagccatt gctgcattct ggagggattt cggtaaggac     120
aaaccttatt tcgatgctga acacgttatc caagtctcgc atggttggag aacgtttgat     180
gccattgcta agttcgctcc agactttgcc aatgaagagt atgttaacaa attagaagct     240
gaaattccgg tcaagtacgg tgaaaaatcc attgaagtcc aggtgcagt taagctgtgc      300 aacgctttga cgctctacc aaaagagaaa tgggctgtgg caacttccgg tacccgtgat     360
atggcacaaa atggttcga gcatctggga atcaggagac caaagtactt cattaccgct     420
aatgatgtca aacagggtaa gcctcatcca gaaccatatc tgaagggcag gaatggctta    480
```

| | |
|---|---|
| ggatatccga tcaatgagca agacccttcc aaatctaagg tagtagtatt tgaagacgct | 540 |
| ccagcaggta ttgccgccgg aaaagccgcc ggttgtaaga tcattggtat tgccactact | 600 |
| ttcgacttgg acttcctaaa ggaaaaaggc tgtgacatca ttgtcaaaaa ccacgaatcc | 660 |
| atcagagttg gcggctacaa tgccgaaaca gacgaagttg aattcatttt tgacgactac | 720 |
| ttatatgcta aggacgatct gttgaaatgg taa | 753 |

<210> SEQ ID NO 8
<211> LENGTH: 250
<212> TYPE: PRT
<213> ORGANISM: Saccharomyces cerevisiae

<400> SEQUENCE: 8

Met Gly Leu Thr Thr Lys Pro Leu Ser Leu Lys Val Asn Ala Ala Leu
1               5                   10                  15

Phe Asp Val Asp Gly Thr Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile Gln Val Ser His Gly Trp Arg Thr Phe Asp Ala Ile Ala Lys
    50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His
        115                 120                 125

Leu Gly Ile Arg Arg Pro Lys Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val
                165                 170                 175

Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250

<210> SEQ ID NO 9
<211> LENGTH: 1668
<212> TYPE: DNA
<213> ORGANISM: Klebsiella pneumoniae
<220> FEATURE:
<221> NAME/KEY: CDS
<222> LOCATION: (1)..(1668)

<400> SEQUENCE: 9

| | | |
|---|---|---|
| atg aaa aga tca aaa cga ttt gca gta ctg gcc cag cgc ccc gtc aat | 48 |
| Met Lys Arg Ser Lys Arg Phe Ala Val Leu Ala Gln Arg Pro Val Asn | | |
| 1               5                   10                  15 | | |

```
cag gac ggg ctg att ggc gag tgg cct gaa gag ggg ctg atc gcc atg      96
Gln Asp Gly Leu Ile Gly Glu Trp Pro Glu Glu Gly Leu Ile Ala Met
         20                  25                  30 gac agc ccc ttt gac ccg gtc tct tca gta aaa gtg gac aac ggt ctg     144
Asp Ser Pro Phe Asp Pro Val Ser Ser Val Lys Val Asp Asn Gly Leu
             35                  40                  45 atc gtc gaa ctg gac ggc aaa cgc cgg gac cag ttt gac atg atc gac     192
Ile Val Glu Leu Asp Gly Lys Arg Arg Asp Gln Phe Asp Met Ile Asp
 50                  55                  60 cga ttt atc gcc gat tac gcg atc aac gtt gag cgc aca gag cag gca     240
Arg Phe Ile Ala Asp Tyr Ala Ile Asn Val Glu Arg Thr Glu Gln Ala
 65                  70                  75                  80 atg cgc ctg gag gcg gtg gaa ata gcc cgt atg ctg gtg gat att cac     288
Met Arg Leu Glu Ala Val Glu Ile Ala Arg Met Leu Val Asp Ile His
                 85                  90                  95 gtc agc cgg gag gag atc att gcc atc act acc gcc atc acg ccg gcc     336
Val Ser Arg Glu Glu Ile Ile Ala Ile Thr Thr Ala Ile Thr Pro Ala
            100                 105                 110 aaa gcg gtc gag gtg atg gcg cag atg aac gtg gtg gag atg atg atg     384
Lys Ala Val Glu Val Met Ala Gln Met Asn Val Val Glu Met Met Met
        115                 120                 125 gcg ctg cag aag atg cgt gcc cgc cgg acc ccc tcc aac cag tgc cac     432
Ala Leu Gln Lys Met Arg Ala Arg Arg Thr Pro Ser Asn Gln Cys His
130                 135                 140 gtc acc aat ctc aaa gat aat ccg gtg cag att gcc gct gac gcc gcc     480
Val Thr Asn Leu Lys Asp Asn Pro Val Gln Ile Ala Ala Asp Ala Ala
145                 150                 155                 160 gag gcc ggg atc cgc ggc ttc tca gaa cag gag acc acg gtc ggt atc     528
Glu Ala Gly Ile Arg Gly Phe Ser Glu Gln Glu Thr Thr Val Gly Ile
                165                 170                 175 gcg cgc tac gcg ccg ttt aac gcc ctg gcg ctg ttg gtc ggt tcg cag     576
Ala Arg Tyr Ala Pro Phe Asn Ala Leu Ala Leu Leu Val Gly Ser Gln
            180                 185                 190 tgc ggc cgc ccc ggc gtg ttg acg cag tgc tcg gtg gaa gag gcc acc     624
Cys Gly Arg Pro Gly Val Leu Thr Gln Cys Ser Val Glu Glu Ala Thr
        195                 200                 205 gag ctg gag ctg ggc atg cgt ggc tta acc agc tac gcc gag acg gtg     672
Glu Leu Glu Leu Gly Met Arg Gly Leu Thr Ser Tyr Ala Glu Thr Val
210                 215                 220 tcg gtc tac ggc acc gaa gcg gta ttt acc gac ggc gat gat acg ccg     720
Ser Val Tyr Gly Thr Glu Ala Val Phe Thr Asp Gly Asp Asp Thr Pro
225                 230                 235                 240 tgg tca aag gcg ttc ctc gcc tcg gcc tac gcc tcc cgc ggg ttg aaa     768
Trp Ser Lys Ala Phe Leu Ala Ser Ala Tyr Ala Ser Arg Gly Leu Lys
                245                 250                 255 atg cgc tac acc tcc ggc acc gga tcc gaa gcg ctg atg ggc tat tcg     816
Met Arg Tyr Thr Ser Gly Thr Gly Ser Glu Ala Leu Met Gly Tyr Ser
            260                 265                 270 gag agc aag tcg atg ctc tac ctc gaa tcg cgc tgc atc ttc att act     864
Glu Ser Lys Ser Met Leu Tyr Leu Glu Ser Arg Cys Ile Phe Ile Thr
        275                 280                 285 aaa ggc gcc ggg gtt cag gga ctg caa aac ggc gcg gtg agc tgt atc     912
Lys Gly Ala Gly Val Gln Gly Leu Gln Asn Gly Ala Val Ser Cys Ile
290                 295                 300 ggc atg acc ggc gct gtg ccg tcg ggc att cgg gcg gtg ctg gcg gaa     960
Gly Met Thr Gly Ala Val Pro Ser Gly Ile Arg Ala Val Leu Ala Glu
305                 310                 315                 320 aac ctg atc gcc tct atg ctc gac ctc gaa gtg gcg tcc gcc aac gac    1008
Asn Leu Ile Ala Ser Met Leu Asp Leu Glu Val Ala Ser Ala Asn Asp
                325                 330                 335
```

```
cag act ttc tcc cac tcg gat att cgc cgc acc gcg cgc acc ctg atg    1056
Gln Thr Phe Ser His Ser Asp Ile Arg Arg Thr Ala Arg Thr Leu Met
            340                 345                 350 cag atg ctg ccg ggc acc gac ttt att ttc tcc ggc tac agc gcg gtg    1104
Gln Met Leu Pro Gly Thr Asp Phe Ile Phe Ser Gly Tyr Ser Ala Val
        355                 360                 365 ccg aac tac gac aac atg ttc gcc ggc tcg aac ttc gat gcg gaa gat    1152
Pro Asn Tyr Asp Asn Met Phe Ala Gly Ser Asn Phe Asp Ala Glu Asp
    370                 375                 380 ttt gat gat tac aac atc ctg cag cgt gac ctg atg gtt gac ggc ggc    1200
Phe Asp Asp Tyr Asn Ile Leu Gln Arg Asp Leu Met Val Asp Gly Gly
385                 390                 395                 400 ctg cgt ccg gtg acc gag gcg gaa acc att gcc att cgc cag aaa gcg    1248
Leu Arg Pro Val Thr Glu Ala Glu Thr Ile Ala Ile Arg Gln Lys Ala
                405                 410                 415 gcg cgg gcg atc cag gcg gtt ttc cgc gag ctg ggg ctg ccg cca atc    1296
Ala Arg Ala Ile Gln Ala Val Phe Arg Glu Leu Gly Leu Pro Pro Ile
            420                 425                 430 gcc gac gag gag gtg gag gcc gcc acc tac gcg cac ggc agc aac gag    1344
Ala Asp Glu Glu Val Glu Ala Ala Thr Tyr Ala His Gly Ser Asn Glu
        435                 440                 445 atg ccg ccg cgt aac gtg gtg gag gat ctg agt gcg gtg gaa gag atg    1392
Met Pro Pro Arg Asn Val Val Glu Asp Leu Ser Ala Val Glu Glu Met
    450                 455                 460 atg aag cgc aac atc acc ggc ctc gat att gtc ggc gcg ctg agc cgc    1440
Met Lys Arg Asn Ile Thr Gly Leu Asp Ile Val Gly Ala Leu Ser Arg
465                 470                 475                 480 agc ggc ttt gag gat atc gcc agc aat att ctc aat atg ctg cgc cag    1488
Ser Gly Phe Glu Asp Ile Ala Ser Asn Ile Leu Asn Met Leu Arg Gln
                485                 490                 495 cgg gtc acc ggc gat tac ctg cag acc tcg gcc att ctc gat cgg cag    1536
Arg Val Thr Gly Asp Tyr Leu Gln Thr Ser Ala Ile Leu Asp Arg Gln
            500                 505                 510 ttc gag gtg gtg agt gcg gtc aac gac atc aat gac tat cag ggg ccg    1584
Phe Glu Val Val Ser Ala Val Asn Asp Ile Asn Asp Tyr Gln Gly Pro
        515                 520                 525 ggc acc ggc tat cgc atc tct gcc gaa cgc tgg gcg gag atc aaa aat    1632
Gly Thr Gly Tyr Arg Ile Ser Ala Glu Arg Trp Ala Glu Ile Lys Asn
    530                 535                 540 att ccg ggc gtg gtt cag ccc gac acc att gaa taa                    1668
Ile Pro Gly Val Val Gln Pro Asp Thr Ile Glu
545                 550                 555
```

<210> SEQ ID NO 10
<211> LENGTH: 555
<212> TYPE: PRT
<213> ORGANISM: Klebsiella pneumoniae

<400> SEQUENCE: 10

```
Met Lys Arg Ser Lys Arg Phe Ala Val Leu Ala Gln Arg Pro Val Asn
1               5                   10                  15

Gln Asp Gly Leu Ile Gly Glu Trp Pro Glu Glu Gly Leu Ile Ala Met
            20                  25                  30

Asp Ser Pro Phe Asp Pro Val Ser Ser Val Lys Val Asp Asn Gly Leu
        35                  40                  45

Ile Val Glu Leu Asp Gly Lys Arg Arg Asp Gln Phe Asp Met Ile Asp
    50                  55                  60

Arg Phe Ile Ala Asp Tyr Ala Ile Asn Val Glu Arg Thr Glu Gln Ala
65                  70                  75                  80
```

-continued

Met Arg Leu Glu Ala Val Glu Ile Ala Arg Met Leu Val Asp Ile His
                85                  90                  95

Val Ser Arg Glu Glu Ile Ile Ala Ile Thr Thr Ala Ile Thr Pro Ala
            100                 105                 110

Lys Ala Val Glu Val Met Ala Gln Met Asn Val Glu Met Met Met
            115                 120                 125

Ala Leu Gln Lys Met Arg Ala Arg Arg Thr Pro Ser Asn Gln Cys His
        130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Thr Thr Val Gly Ile
                165                 170                 175

Ala Arg Tyr Ala Pro Phe Asn Ala Leu Ala Leu Leu Val Gly Ser Gln
            180                 185                 190

Cys Gly Arg Pro Gly Val Leu Thr Gln Cys Ser Val Glu Glu Ala Thr
        195                 200                 205

Glu Leu Glu Leu Gly Met Arg Gly Leu Thr Ser Tyr Ala Glu Thr Val
        210                 215                 220

Ser Val Tyr Gly Thr Glu Ala Val Phe Thr Asp Gly Asp Thr Pro
225                 230                 235                 240

Trp Ser Lys Ala Phe Leu Ala Ser Ala Tyr Ala Ser Arg Gly Leu Lys
            245                 250                 255

Met Arg Tyr Thr Ser Gly Thr Gly Ser Glu Ala Leu Met Gly Tyr Ser
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
        290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
            325                 330                 335

Gln Thr Phe Ser His Ser Asp Ile Arg Arg Thr Ala Arg Thr Leu Met
        340                 345                 350

Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
    370                 375                 380

Phe Asp Asp Tyr Asn Ile Leu Gln Arg Asp Leu Met Val Asp Gly Gly
385                 390                 395                 400

Leu Arg Pro Val Thr Glu Ala Glu Thr Ile Ala Ile Arg Gln Lys Ala
                405                 410                 415

Ala Arg Ala Ile Gln Ala Val Phe Arg Glu Leu Gly Leu Pro Pro Ile
            420                 425                 430

Ala Asp Glu Glu Val Glu Ala Ala Thr Tyr Ala His Gly Ser Asn Glu
        435                 440                 445

Met Pro Pro Arg Asn Val Val Glu Asp Leu Ser Ala Val Glu Glu Met
        450                 455                 460

Met Lys Arg Asn Ile Thr Gly Leu Asp Ile Val Gly Ala Leu Ser Arg
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
            500                 505                 510

```
Phe Glu Val Val Ser Ala Val Asn Asp Ile Asn Asp Tyr Gln Gly Pro
        515                 520                 525

Gly Thr Gly Tyr Arg Ile Ser Ala Glu Arg Trp Ala Glu Ile Lys Asn
        530                 535                 540

Ile Pro Gly Val Val Gln Pro Asp Thr Ile Glu
545                 550                 555

<210> SEQ ID NO 11
<211> LENGTH: 585
<212> TYPE: DNA
<213> ORGANISM: Klebsiella pneumoniae
<220> FEATURE:
<221> NAME/KEY: CDS
<222> LOCATION: (1)..(585)

<400> SEQUENCE: 11 gtg caa cag aca acc caa att cag ccc tct ttt acc ctg aaa acc cgc      48
Val Gln Gln Thr Thr Gln Ile Gln Pro Ser Phe Thr Leu Lys Thr Arg
1               5                   10                  15 gag ggc ggg gta gct tct gcc gat gaa cgc gcc gat gaa gtg gtg atc      96
Glu Gly Gly Val Ala Ser Ala Asp Glu Arg Ala Asp Glu Val Val Ile
            20                  25                  30 ggc gtc ggc cct gcc ttc gat aaa cac cag cat cac act ctg atc gat     144
Gly Val Gly Pro Ala Phe Asp Lys His Gln His His Thr Leu Ile Asp
        35                  40                  45 atg ccc cat ggc gcg atc ctc aaa gag ctg att gcc ggg gtg gaa gaa     192
Met Pro His Gly Ala Ile Leu Lys Glu Leu Ile Ala Gly Val Glu Glu
    50                  55                  60 gag ggg ctt cac gcc cgg gtg gtg cgc att ctg cgc acg tcc gac gtc     240
Glu Gly Leu His Ala Arg Val Val Arg Ile Leu Arg Thr Ser Asp Val
65                  70                  75                  80 tcc ttt atg gcc tgg gat gcg gcc aac ctg agc ggc tcg ggg atc ggc     288
Ser Phe Met Ala Trp Asp Ala Ala Asn Leu Ser Gly Ser Gly Ile Gly
                85                  90                  95 atc ggt atc cag tcg aag ggg acc acg gtc atc cat cag cgc gat ctg     336
Ile Gly Ile Gln Ser Lys Gly Thr Thr Val Ile His Gln Arg Asp Leu
            100                 105                 110 ctg ccg ctc agc aac ctg gag ctg ttc tcc cag gcg ccg ctg ctg acg     384
Leu Pro Leu Ser Asn Leu Glu Leu Phe Ser Gln Ala Pro Leu Leu Thr
        115                 120                 125 ctg gag acc tac cgg cag att ggc aaa aac gct gcg cgc tat gcg cgc     432
Leu Glu Thr Tyr Arg Gln Ile Gly Lys Asn Ala Ala Arg Tyr Ala Arg
    130                 135                 140 aaa gag tca cct tcg ccg gtg ccg gtg gtg aac gat cag atg gtg cgg     480
Lys Glu Ser Pro Ser Pro Val Pro Val Val Asn Asp Gln Met Val Arg
145                 150                 155                 160 ccg aaa ttt atg gcc aaa gcc gcg cta ttt cat atc aaa gag acc aaa     528
Pro Lys Phe Met Ala Lys Ala Ala Leu Phe His Ile Lys Glu Thr Lys
                165                 170                 175 cat gtg gtg cag gac gcc gag ccc gtc acc ctg cac atc gac tta gta     576
His Val Val Gln Asp Ala Glu Pro Val Thr Leu His Ile Asp Leu Val
            180                 185                 190 agg gag tga                                                          585
Arg Glu <210> SEQ ID NO 12
<211> LENGTH: 194
<212> TYPE: PRT
<213> ORGANISM: Klebsiella pneumoniae

<400> SEQUENCE: 12
```

```
Val Gln Gln Thr Thr Gln Ile Gln Pro Ser Phe Thr Leu Lys Thr Arg
1               5                   10                  15

Glu Gly Gly Val Ala Ser Ala Asp Glu Arg Ala Asp Glu Val Val Ile
            20                  25                  30

Gly Val Gly Pro Ala Phe Asp Lys His Gln His His Thr Leu Ile Asp
        35                  40                  45

Met Pro His Gly Ala Ile Leu Lys Glu Leu Ile Ala Gly Val Glu Glu
50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Ala Glu Pro Val Thr Leu His Ile Asp Leu Val
            180                 185                 190

Arg Glu

<210> SEQ ID NO 13
<211> LENGTH: 426
<212> TYPE: DNA
<213> ORGANISM: Klebsiella pneumoniae
<220> FEATURE:
<221> NAME/KEY: CDS
<222> LOCATION: (1)..(426)

<400> SEQUENCE: 13 atg agc gag aaa acc atg cgc gtg cag gat tat ccg tta gcc acc cgc      48
Met Ser Glu Lys Thr Met Arg Val Gln Asp Tyr Pro Leu Ala Thr Arg
1               5                   10                  15 tgc ccg gag cat atc ctg acg cct acc ggc aaa cca ttg acc gat att      96
Cys Pro Glu His Ile Leu Thr Pro Thr Gly Lys Pro Leu Thr Asp Ile
            20                  25                  30 acc ctc gag aag gtg ctc tct ggc gag gtg ggc ccg cag gat gtg cgg     144
Thr Leu Glu Lys Val Leu Ser Gly Glu Val Gly Pro Gln Asp Val Arg
        35                  40                  45 atc tcc cgc cag acc ctt gag tac cag gcg cag att gcc gag cag atg     192
Ile Ser Arg Gln Thr Leu Glu Tyr Gln Ala Gln Ile Ala Glu Gln Met
50                  55                  60 cag cgc cat gcg gtg gcg cgc aat ttc cgc cgc gcg gcg gag ctt atc     240
Gln Arg His Ala Val Ala Arg Asn Phe Arg Arg Ala Ala Glu Leu Ile
65                  70                  75                  80 gcc att cct gac gag cgc att ctg gct atc tat aac gcg ctg cgc ccg     288
Ala Ile Pro Asp Glu Arg Ile Leu Ala Ile Tyr Asn Ala Leu Arg Pro
                85                  90                  95 ttc cgc tcc tcg cag gcg gag ctg ctg gcg atc gcc gac gag ctg gag     336
Phe Arg Ser Ser Gln Ala Glu Leu Leu Ala Ile Ala Asp Glu Leu Glu
            100                 105                 110 cac acc tgg cat gcg aca gtg aat gcc gcc ttt gtc cgg gag tcg gcg     384
His Thr Trp His Ala Thr Val Asn Ala Ala Phe Val Arg Glu Ser Ala
        115                 120                 125
```

| | | |
|---|---|---|
| gaa gtg tat cag cag cgg cat aag ctg cgt aaa gga agc taa<br>Glu Val Tyr Gln Gln Arg His Lys Leu Arg Lys Gly Ser<br>    130                         135                     140 | | 426 |

<210> SEQ ID NO 14
<211> LENGTH: 141
<212> TYPE: PRT
<213> ORGANISM: Klebsiella pneumoniae

<400> SEQUENCE: 14

Met Ser Glu Lys Thr Met Arg Val Gln Asp Tyr Pro Leu Ala Thr Arg
1               5                   10                  15

Cys Pro Glu His Ile Leu Thr Pro Thr Gly Lys Pro Leu Thr Asp Ile
                20                  25                  30

Thr Leu Glu Lys Val Leu Ser Gly Glu Val Gly Pro Gln Asp Val Arg
            35                  40                  45

Ile Ser Arg Gln Thr Leu Glu Tyr Gln Ala Gln Ile Ala Glu Gln Met
        50                  55                  60

Gln Arg His Ala Val Ala Arg Asn Phe Arg Arg Ala Ala Glu Leu Ile
65                  70                  75                  80

Ala Ile Pro Asp Glu Arg Ile Leu Ala Ile Tyr Asn Ala Leu Arg Pro
                85                  90                  95

Phe Arg Ser Ser Gln Ala Glu Leu Leu Ala Ile Ala Asp Glu Leu Glu
                100                 105                 110

His Thr Trp His Ala Thr Val Asn Ala Ala Phe Val Arg Glu Ser Ala
            115                 120                 125

Glu Val Tyr Gln Gln Arg His Lys Leu Arg Lys Gly Ser
        130                 135                 140

<210> SEQ ID NO 15
<211> LENGTH: 1539
<212> TYPE: DNA
<213> ORGANISM: Escherichia coli
<220> FEATURE:
<221> NAME/KEY: CDS
<222> LOCATION: (1)..(1539)

<400> SEQUENCE: 15

| | | |
|---|---|---|
| atg acc aat aat ccc cct tca gca cag att aag ccc ggc gag tat ggt<br>Met Thr Asn Asn Pro Pro Ser Ala Gln Ile Lys Pro Gly Glu Tyr Gly<br>1               5                   10                  15 | | 48 |
| ttc ccc ctc aag tta aaa gcc cgc tat gac aac ttt att ggc ggc gaa<br>Phe Pro Leu Lys Leu Lys Ala Arg Tyr Asp Asn Phe Ile Gly Gly Glu<br>                20                  25                  30 | | 96 |
| tgg gta gcc cct gcc gac ggc gag tat tac cag aat ctg acg ccg gtg<br>Trp Val Ala Pro Ala Asp Gly Glu Tyr Tyr Gln Asn Leu Thr Pro Val<br>            35                  40                  45 | | 144 |
| acc ggg cag ctg ctg tgc gaa gtg gcg tct tcg ggc aaa cga gac atc<br>Thr Gly Gln Leu Leu Cys Glu Val Ala Ser Ser Gly Lys Arg Asp Ile<br>        50                  55                  60 | | 192 |
| gat ctg gcg ctg gat gct gcg cac aaa gtg aaa gat aaa tgg gcg cac<br>Asp Leu Ala Leu Asp Ala Ala His Lys Val Lys Asp Lys Trp Ala His<br>65                  70                  75                  80 | | 240 |
| acc tcg gtg cag gat cgt gcg gcg att ctg ttt aag att gcc gat cga<br>Thr Ser Val Gln Asp Arg Ala Ala Ile Leu Phe Lys Ile Ala Asp Arg<br>                85                  90                  95 | | 288 |
| atg gaa caa aac ctc gag ctg tta gcg aca gct gaa acc tgg gat aac<br>Met Glu Gln Asn Leu Glu Leu Leu Ala Thr Ala Glu Thr Trp Asp Asn<br>                100                 105                 110 | | 336 |
| ggc aaa ccc att cgc gaa acc agt gct gcg gat gta ccg ctg gcg att<br> | | 384 |

```
                Gly Lys Pro Ile Arg Glu Thr Ser Ala Ala Asp Val Pro Leu Ala Ile
                    115                 120                 125 gac cat ttc cgc tat ttc gcc tcg tgt att cgg gcg cag gaa ggt ggg          432
Asp His Phe Arg Tyr Phe Ala Ser Cys Ile Arg Ala Gln Glu Gly Gly
    130                 135                 140 atc agt gaa gtt gat agc gaa acc gtg gcc tat cat ttc cat gaa ccg          480
Ile Ser Glu Val Asp Ser Glu Thr Val Ala Tyr His Phe His Glu Pro
145                 150                 155                 160 tta ggc gtg gtg ggg cag att atc ccg tgg aac ttc ccg ctg ctg atg          528
Leu Gly Val Val Gly Gln Ile Ile Pro Trp Asn Phe Pro Leu Leu Met
                165                 170                 175 gcg agc tgg aaa atg gct ccc gcg ctg gcg gcg ggc aac tgt gtg gtg          576
Ala Ser Trp Lys Met Ala Pro Ala Leu Ala Ala Gly Asn Cys Val Val
            180                 185                 190 ctg aaa ccc gca cgt ctt acc ccg ctt tct gta ctg ctg ctc atg gaa          624
Leu Lys Pro Ala Arg Leu Thr Pro Leu Ser Val Leu Leu Leu Met Glu
        195                 200                 205 att gtc ggt gat tta ctg ccg ccg ggc gtg gtg aac gtg gtc aat ggc          672
Ile Val Gly Asp Leu Leu Pro Pro Gly Val Val Asn Val Val Asn Gly
    210                 215                 220 gca ggt ggg gta att ggc gaa tat ctg gcg acc tcg aaa cgc atc gcc          720
Ala Gly Gly Val Ile Gly Glu Tyr Leu Ala Thr Ser Lys Arg Ile Ala
225                 230                 235                 240 aaa gtg gcg ttt acc ggc tca acg gaa gtg ggc caa caa att atg caa          768
Lys Val Ala Phe Thr Gly Ser Thr Glu Val Gly Gln Gln Ile Met Gln
                245                 250                 255 tac gca acg caa aac att att ccg gtg acg ctg gag ttg ggc ggt aag          816
Tyr Ala Thr Gln Asn Ile Ile Pro Val Thr Leu Glu Leu Gly Gly Lys
            260                 265                 270 tcg cca aat atc ttc ttt gct gat gtg atg gat gaa gaa gat gcc ttt          864
Ser Pro Asn Ile Phe Phe Ala Asp Val Met Asp Glu Glu Asp Ala Phe
        275                 280                 285 ttc gat aaa gcg ctg gaa ggc ttt gca ctg ttt gcc ttt aac cag ggc          912
Phe Asp Lys Ala Leu Glu Gly Phe Ala Leu Phe Ala Phe Asn Gln Gly
    290                 295                 300 gaa gtt tgc acc tgt ccg agt cgt gct tta gtg cag gaa tct atc tac          960
Glu Val Cys Thr Cys Pro Ser Arg Ala Leu Val Gln Glu Ser Ile Tyr
305                 310                 315                 320 gaa cgc ttt atg gaa cgc gcc atc cgc cgt gtc gaa agc att cgt agc         1008
Glu Arg Phe Met Glu Arg Ala Ile Arg Arg Val Glu Ser Ile Arg Ser
                325                 330                 335 ggt aac ccg ctc gac agc gtg acg caa atg ggc gcg cag gtt tct cac         1056
Gly Asn Pro Leu Asp Ser Val Thr Gln Met Gly Ala Gln Val Ser His
            340                 345                 350 ggg caa ctg gaa acc atc ctc aac tac att gat atc ggt aaa aaa gag         1104
Gly Gln Leu Glu Thr Ile Leu Asn Tyr Ile Asp Ile Gly Lys Lys Glu
        355                 360                 365 ggc gct gac gtg ctc aca ggc ggg cgg cgc aag ctg ctg gaa ggt gaa         1152
Gly Ala Asp Val Leu Thr Gly Gly Arg Arg Lys Leu Leu Glu Gly Glu
    370                 375                 380 ctg aaa gac ggc tac tac ctc gaa ccg acg att ctg ttt ggt cag aac         1200
Leu Lys Asp Gly Tyr Tyr Leu Glu Pro Thr Ile Leu Phe Gly Gln Asn
385                 390                 395                 400 aat atg cgg gtg ttc cag gag gag att ttt ggc ccg gtg ctg gcg gtg         1248
Asn Met Arg Val Phe Gln Glu Glu Ile Phe Gly Pro Val Leu Ala Val
                405                 410                 415 acc acc ttc aaa acg atg gaa gaa gcg ctg gag ctg gcg aac gat acg         1296
Thr Thr Phe Lys Thr Met Glu Glu Ala Leu Glu Leu Ala Asn Asp Thr
            420                 425                 430 caa tat ggc ctg ggc gcg ggc gtc tgg agc cgc aac ggt aat ctg gcc         1344
Gln Tyr Gly Leu Gly Ala Gly Val Trp Ser Arg Asn Gly Asn Leu Ala
```

-continued

```
Gln Tyr Gly Leu Gly Ala Gly Val Trp Ser Arg Asn Gly Asn Leu Ala
        435                 440                 445 tat aag atg ggg cgc ggc ata cag gct ggg cgc gtg tgg acc aac tgt      1392
Tyr Lys Met Gly Arg Gly Ile Gln Ala Gly Arg Val Trp Thr Asn Cys
    450                 455                 460 tat cac gct tac ccg gca cat gcg gcg ttt ggt ggc tac aaa caa tca      1440
Tyr His Ala Tyr Pro Ala His Ala Ala Phe Gly Gly Tyr Lys Gln Ser
465                 470                 475                 480 ggt atc ggt cgc gaa acc cac aag atg atg ctg gag cat tac cag caa      1488
Gly Ile Gly Arg Glu Thr His Lys Met Met Leu Glu His Tyr Gln Gln
                485                 490                 495 acc aag tgc ctg ctg gtg agc tac tcg gat aaa ccg ttg ggg ctg ttc      1536
Thr Lys Cys Leu Leu Val Ser Tyr Ser Asp Lys Pro Leu Gly Leu Phe
            500                 505                 510 tga                                                                  1539

<210> SEQ ID NO 16
<211> LENGTH: 512
<212> TYPE: PRT
<213> ORGANISM: Escherichia coli

<400> SEQUENCE: 16

Met Thr Asn Asn Pro Ser Ala Gln Ile Lys Pro Gly Glu Tyr Gly
1               5                   10                  15

Phe Pro Leu Lys Leu Lys Ala Arg Tyr Asp Asn Phe Ile Gly Gly Glu
                20                  25                  30

Trp Val Ala Pro Ala Asp Gly Glu Tyr Tyr Gln Asn Leu Thr Pro Val
            35                  40                  45

Thr Gly Gln Leu Leu Cys Glu Val Ala Ser Ser Gly Lys Arg Asp Ile
        50                  55                  60

Asp Leu Ala Leu Asp Ala Ala His Lys Val Lys Asp Lys Trp Ala His
65                  70                  75                  80

Thr Ser Val Gln Asp Arg Ala Ala Ile Leu Phe Lys Ile Ala Asp Arg
                85                  90                  95

Met Glu Gln Asn Leu Glu Leu Leu Ala Thr Ala Glu Thr Trp Asp Asn
            100                 105                 110

Gly Lys Pro Ile Arg Glu Thr Ser Ala Ala Asp Val Pro Leu Ala Ile
        115                 120                 125

Asp His Phe Arg Tyr Phe Ala Ser Cys Ile Arg Ala Gln Glu Gly Gly
    130                 135                 140

Ile Ser Glu Val Asp Ser Glu Thr Val Ala Tyr His Phe His Glu Pro
145                 150                 155                 160

Leu Gly Val Val Gly Gln Ile Ile Pro Trp Asn Phe Pro Leu Leu Met
                165                 170                 175

Ala Ser Trp Lys Met Ala Pro Ala Leu Ala Ala Gly Asn Cys Val Val
            180                 185                 190

Leu Lys Pro Ala Arg Leu Thr Pro Leu Ser Val Leu Leu Leu Met Glu
        195                 200                 205

Ile Val Gly Asp Leu Leu Pro Pro Gly Val Val Asn Val Val Asn Gly
    210                 215                 220

Ala Gly Gly Val Ile Gly Glu Tyr Leu Ala Thr Ser Lys Arg Ile Ala
225                 230                 235                 240

Lys Val Ala Phe Thr Gly Ser Thr Glu Val Gly Gln Gln Ile Met Gln
                245                 250                 255

Tyr Ala Thr Gln Asn Ile Ile Pro Val Thr Leu Glu Leu Gly Gly Lys
            260                 265                 270
```

```
Ser Pro Asn Ile Phe Phe Ala Asp Val Met Asp Glu Glu Asp Ala Phe
    275                 280                 285

Phe Asp Lys Ala Leu Glu Gly Phe Ala Leu Phe Ala Phe Asn Gln Gly
    290                 295                 300

Glu Val Cys Thr Cys Pro Ser Arg Ala Leu Val Gln Glu Ser Ile Tyr
305                 310                 315                 320

Glu Arg Phe Met Glu Arg Ala Ile Arg Val Glu Ser Ile Arg Ser
                325                 330                 335

Gly Asn Pro Leu Asp Ser Val Thr Gln Met Gly Ala Gln Val Ser His
            340                 345                 350

Gly Gln Leu Glu Thr Ile Leu Asn Tyr Ile Asp Ile Gly Lys Lys Glu
        355                 360                 365

Gly Ala Asp Val Leu Thr Gly Arg Arg Lys Leu Leu Glu Gly Glu
    370                 375                 380

Leu Lys Asp Gly Tyr Tyr Leu Glu Pro Thr Ile Leu Phe Gly Gln Asn
385                 390                 395                 400

Asn Met Arg Val Phe Gln Glu Ile Phe Gly Pro Val Leu Ala Val
                405                 410                 415

Thr Thr Phe Lys Thr Met Glu Glu Ala Leu Glu Leu Ala Asn Asp Thr
                420                 425                 430

Gln Tyr Gly Leu Gly Ala Gly Val Trp Ser Arg Asn Gly Asn Leu Ala
        435                 440                 445

Tyr Lys Met Gly Arg Gly Ile Gln Ala Gly Arg Val Trp Thr Asn Cys
    450                 455                 460

Tyr His Ala Tyr Pro Ala His Ala Ala Phe Gly Gly Tyr Lys Gln Ser
465                 470                 475                 480

Gly Ile Gly Arg Glu Thr His Lys Met Met Leu Glu His Tyr Gln Gln
                485                 490                 495

Thr Lys Cys Leu Leu Val Ser Tyr Ser Asp Lys Pro Leu Gly Leu Phe
            500                 505                 510

<210> SEQ ID NO 17
<211> LENGTH: 1440
<212> TYPE: DNA
<213> ORGANISM: Escherichia coli
<220> FEATURE:
<221> NAME/KEY: CDS
<222> LOCATION: (1)..(1440)

<400> SEQUENCE: 17 atg tca gta ccc gtt caa cat cct atg tat atc gat gga cag ttt gtt      48
Met Ser Val Pro Val Gln His Pro Met Tyr Ile Asp Gly Gln Phe Val
1               5                   10                  15 acc tgg cgt gga gac gca tgg att gat gtg gta aac cct gct aca gag      96
Thr Trp Arg Gly Asp Ala Trp Ile Asp Val Val Asn Pro Ala Thr Glu
                20                  25                  30 gct gtc att tcc cgc ata ccc gat ggt cag gcc gag gat gcc gtg aag     144
Ala Val Ile Ser Arg Ile Pro Asp Gly Gln Ala Glu Asp Ala Arg Lys
            35                  40                  45 gca atc gat gca gca gaa cgt gca caa cca gaa tgg gaa gcg ttg cct     192
Ala Ile Asp Ala Ala Glu Arg Ala Gln Pro Glu Trp Glu Ala Leu Pro
        50                  55                  60 gct att gaa cgc gcc agt tgg ttg cgc aaa atc tcc gcc ggg atc cgc     240
Ala Ile Glu Arg Ala Ser Trp Leu Arg Lys Ile Ser Ala Gly Ile Arg
65                  70                  75                  80 gaa cgc gcc agt gaa atc agt gcg ctg att gtt gaa gaa ggg ggc aag     288
Glu Arg Ala Ser Glu Ile Ser Ala Leu Ile Val Glu Glu Gly Gly Lys
                85                  90                  95
```

| | | |
|---|---|---|
| atc cag cag ctg gct gaa gtc gaa gtg gct ttt act gcc gac tat atc<br>Ile Gln Gln Leu Ala Glu Val Glu Val Ala Phe Thr Ala Asp Tyr Ile<br>100                         105                   110 | 336 | |
| gat tac atg gcg gag tgg gca cgg cgt tac gag ggc gag att att caa<br>Asp Tyr Met Ala Glu Trp Ala Arg Arg Tyr Glu Gly Glu Ile Ile Gln<br>          115                    120                    125 | 384 | |
| agc gat cgt cca gga gaa aat att ctt ttg ttt aaa cgt gcg ctt ggt<br>Ser Asp Arg Pro Gly Glu Asn Ile Leu Leu Phe Lys Arg Ala Leu Gly<br>130                         135                   140 | 432 | |
| gtg act acc ggc att ctg ccg tgg aac ttc ccg ttc ttc ctc att gcc<br>Val Thr Thr Gly Ile Leu Pro Trp Asn Phe Pro Phe Phe Leu Ile Ala<br>145                       150                    155                160 | 480 | |
| cgc aaa atg gct ccc gct ctt ttg acc ggt aat acc atc gtc att aaa<br>Arg Lys Met Ala Pro Ala Leu Leu Thr Gly Asn Thr Ile Val Ile Lys<br>                  165                  170                 175 | 528 | |
| cct agt gaa ttt acg cca aac aat gcg att gca ttc gcc aaa atc gtc<br>Pro Ser Glu Phe Thr Pro Asn Asn Ala Ile Ala Phe Ala Lys Ile Val<br>                  180                  185                190 | 576 | |
| gat gaa ata ggc ctt ccg cgc ggc gtg ttt aac ctt gta ctg ggg cgt<br>Asp Glu Ile Gly Leu Pro Arg Gly Val Phe Asn Leu Val Leu Gly Arg<br>              195                    200                  205 | 624 | |
| ggt gaa acc gtt ggg caa gaa ctg gcg ggt aac cca aag gtc gca atg<br>Gly Glu Thr Val Gly Gln Glu Leu Ala Gly Asn Pro Lys Val Ala Met<br>210                       215                    220 | 672 | |
| gtc agt atg aca ggc agc gtc tct gca ggt gag aag atc atg gcg act<br>Val Ser Met Thr Gly Ser Val Ser Ala Gly Glu Lys Ile Met Ala Thr<br>225                       230                   235                240 | 720 | |
| gcg gcg aaa aac atc acc aaa gtg tgt ctg gaa ttg ggg ggt aaa gca<br>Ala Ala Lys Asn Ile Thr Lys Val Cys Leu Glu Leu Gly Gly Lys Ala<br>                        245                  250                255 | 768 | |
| cca gct atc gta atg gac gat gcc gat ctt gaa ctg gca gtc aaa gcc<br>Pro Ala Ile Val Met Asp Asp Ala Asp Leu Glu Leu Ala Val Lys Ala<br>                    260                  265                270 | 816 | |
| atc gtt gat tca cgc gtc att aat agt ggg caa gtg tgt aac tgt gca<br>Ile Val Asp Ser Arg Val Ile Asn Ser Gly Gln Val Cys Asn Cys Ala<br>              275                    280                  285 | 864 | |
| gaa cgt gtt tat gta cag aaa ggc att tat gat cag ttc gtc aat cgg<br>Glu Arg Val Tyr Val Gln Lys Gly Ile Tyr Asp Gln Phe Val Asn Arg<br>290                       295                    300 | 912 | |
| ctg ggt gaa gcg atg cag gcg gtt caa ttt ggt aac ccc gct gaa cgc<br>Leu Gly Glu Ala Met Gln Ala Val Gln Phe Gly Asn Pro Ala Glu Arg<br>305                       310                   315                320 | 960 | |
| aac gac att gcg atg ggg ccg ttg att aac gcc gcg gcg ctg gaa agg<br>Asn Asp Ile Ala Met Gly Pro Leu Ile Asn Ala Ala Ala Leu Glu Arg<br>                        325                  330                335 | 1008 | |
| gtc gag caa aaa gtg gcg cgc gca gta gaa gaa ggg gcg aga gtg gcg<br>Val Glu Gln Lys Val Ala Arg Ala Val Glu Glu Gly Ala Arg Val Ala<br>                    340                  345                350 | 1056 | |
| ttc ggt ggc aaa gcg gta gag ggg aaa gga tat tat tat ccg ccg aca<br>Phe Gly Gly Lys Ala Val Glu Gly Lys Gly Tyr Tyr Tyr Pro Pro Thr<br>              355                    360                  365 | 1104 | |
| ttg ctg ctg gat gtt cgc cag gaa atg tcg att atg cat gag gaa acc<br>Leu Leu Leu Asp Val Arg Gln Glu Met Ser Ile Met His Glu Glu Thr<br>370                       375                   380 | 1152 | |
| ttt ggc ccg gtg ctg cca gtt gtc gca ttt gac acg ctg gaa gat gct<br>Phe Gly Pro Val Leu Pro Val Val Ala Phe Asp Thr Leu Glu Asp Ala<br>385                       390                   395                400 | 1200 | |
| atc tca atg gct aat gac agt gat tac ggc ctg acc tca tca atc tat<br>Ile Ser Met Ala Asn Asp Ser Asp Tyr Gly Leu Thr Ser Ser Ile Tyr<br>                    405                  410                415 | 1248 | |

```
acc caa aat ctg aac gtc gcg atg aaa gcc att aaa ggg ctg aag ttt      1296
Thr Gln Asn Leu Asn Val Ala Met Lys Ala Ile Lys Gly Leu Lys Phe
            420                 425                 430 ggt gaa act tac atc aac cgt gaa aac ttc gaa gct atg caa ggc ttc      1344
Gly Glu Thr Tyr Ile Asn Arg Glu Asn Phe Glu Ala Met Gln Gly Phe
        435                 440                 445 cac gcc gga tgg cgt aaa tcc ggt att ggc ggc gca gat ggt aaa cat      1392
His Ala Gly Trp Arg Lys Ser Gly Ile Gly Gly Ala Asp Gly Lys His
    450                 455                 460 ggc ttg cat gaa tat ctg cag acc cag gtg gtt tat tta cag tct taa      1440
Gly Leu His Glu Tyr Leu Gln Thr Gln Val Val Tyr Leu Gln Ser
465                 470                 475
```

<210> SEQ ID NO 18
<211> LENGTH: 479
<212> TYPE: PRT
<213> ORGANISM: Escherichia coli

<400> SEQUENCE: 18

```
Met Ser Val Pro Val Gln His Pro Met Tyr Ile Asp Gly Gln Phe Val
1               5                   10                  15

Thr Trp Arg Gly Asp Ala Trp Ile Asp Val Val Asn Pro Ala Thr Glu
            20                  25                  30

Ala Val Ile Ser Arg Ile Pro Asp Gly Gln Ala Glu Asp Ala Arg Lys
        35                  40                  45

Ala Ile Asp Ala Ala Glu Arg Ala Gln Pro Glu Trp Glu Ala Leu Pro
    50                  55                  60

Ala Ile Glu Arg Ala Ser Trp Leu Arg Lys Ile Ser Ala Gly Ile Arg
65                  70                  75                  80

Glu Arg Ala Ser Glu Ile Ser Ala Leu Ile Val Glu Glu Gly Gly Lys
                85                  90                  95

Ile Gln Gln Leu Ala Glu Val Glu Val Ala Phe Thr Ala Asp Tyr Ile
            100                 105                 110

Asp Tyr Met Ala Glu Trp Ala Arg Arg Tyr Glu Gly Glu Ile Ile Gln
        115                 120                 125

Ser Asp Arg Pro Gly Glu Asn Ile Leu Leu Phe Lys Arg Ala Leu Gly
    130                 135                 140

Val Thr Thr Gly Ile Leu Pro Trp Asn Phe Pro Phe Phe Leu Ile Ala
145                 150                 155                 160

Arg Lys Met Ala Pro Ala Leu Leu Thr Gly Asn Thr Ile Val Ile Lys
                165                 170                 175

Pro Ser Glu Phe Thr Pro Asn Asn Ala Ile Ala Phe Ala Lys Ile Val
            180                 185                 190

Asp Glu Ile Gly Leu Pro Arg Gly Val Phe Asn Leu Val Leu Gly Arg
        195                 200                 205

Gly Glu Thr Val Gly Gln Glu Leu Ala Gly Asn Pro Lys Val Ala Met
    210                 215                 220

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
            260                 265                 270

Ile Val Asp Ser Arg Val Ile Asn Ser Gly Gln Val Cys Asn Cys Ala
        275                 280                 285

Glu Arg Val Tyr Val Gln Lys Gly Ile Tyr Asp Gln Phe Val Asn Arg
    290                 295                 300
```

```
Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Leu Glu Arg
            325                 330                 335

Val Glu Gln Lys Val Ala Arg Ala Val Glu Gly Ala Arg Val Ala
        340                 345                 350

Phe Gly Lys Ala Val Glu Gly Lys Gly Tyr Tyr Pro Pro Thr
    355                 360                 365

Leu Leu Leu Asp Val Arg Gln Glu Met Ser Ile Met His Glu Thr
370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
                405                 410                 415

Thr Gln Asn Leu Asn Val Ala Met Lys Ala Ile Lys Gly Leu Lys Phe
            420                 425                 430

Gly Glu Thr Tyr Ile Asn Arg Glu Asn Phe Glu Ala Met Gln Gly Phe
        435                 440                 445

His Ala Gly Trp Arg Lys Ser Gly Ile Gly Gly Ala Asp Gly Lys His
    450                 455                 460

Gly Leu His Glu Tyr Leu Gln Thr Gln Val Val Tyr Leu Gln Ser
465                 470                 475

<210> SEQ ID NO 19
<211> LENGTH: 1488
<212> TYPE: DNA
<213> ORGANISM: Escherichia coli
<220> FEATURE:
<221> NAME/KEY: CDS
<222> LOCATION: (1)..(1488)

<400> SEQUENCE: 19 atg aat ttt cat cat ctg gct tac tgg cag gat aaa gcg tta agt ctc    48
Met Asn Phe His His Leu Ala Tyr Trp Gln Asp Lys Ala Leu Ser Leu
1               5                   10                  15 gcc att gaa aac cgc tta ttt att aac ggt gaa tat act gct gcg gcg    96
Ala Ile Glu Asn Arg Leu Phe Ile Asn Gly Glu Tyr Thr Ala Ala Ala
            20                  25                  30 gaa aat gaa acc ttt gaa acc gtt gat ccg gtc acc cag gca ccg ctg   144
Glu Asn Glu Thr Phe Glu Thr Val Asp Pro Val Thr Gln Ala Pro Leu
        35                  40                  45 gcg aaa att gcc cgc ggc aag agc gtc gat atc gac cgt gcg atg agc   192
Ala Lys Ile Ala Arg Gly Lys Ser Val Asp Ile Asp Arg Ala Met Ser
    50                  55                  60 gca gca cgc ggc gta ttt gaa cgc ggc gac tgg tca ctc tct tct ccg   240
Ala Ala Arg Gly Val Phe Glu Arg Gly Asp Trp Ser Leu Ser Ser Pro
65                  70                  75                  80 gct aaa cgt aaa gcg gta ctg aat aaa ctc gcc gat tta atg gaa gcc   288
Ala Lys Arg Lys Ala Val Leu Asn Lys Leu Ala Asp Leu Met Glu Ala
                85                  90                  95 cac gcc gaa gag ctg gca ctg ctg gaa act ctc gac acc ggc aaa ccg   336
His Ala Glu Glu Leu Ala Leu Leu Glu Thr Leu Asp Thr Gly Lys Pro
            100                 105                 110 att cgt cac agt ctg cgt gat gat att ccc ggc gcg gcg cgc gcc att   384
Ile Arg His Ser Leu Arg Asp Asp Ile Pro Gly Ala Ala Arg Ala Ile
        115                 120                 125 cgc tgg tac gcc gaa gcg atc gac aaa gtg tat ggc gaa gtg gcg acc   432
Arg Trp Tyr Ala Glu Ala Ile Asp Lys Val Tyr Gly Glu Val Ala Thr
    130                 135                 140
```

```
acc agt agc cat gag ctg gcg atg atc gtg cgt gaa ccg gtc ggc gtg    480
Thr Ser Ser His Glu Leu Ala Met Ile Val Arg Glu Pro Val Gly Val
145                 150                 155                 160 att gcc gcc atc gtg ccg tgg aac ttc ccg ctg ttg ctg act tgc tgg    528
Ile Ala Ala Ile Val Pro Trp Asn Phe Pro Leu Leu Leu Thr Cys Trp
                165                 170                 175 aaa ctc ggc ccg gcg ctg gcg gcg gga aac agc gtg att cta aaa ccg    576
Lys Leu Gly Pro Ala Leu Ala Ala Gly Asn Ser Val Ile Leu Lys Pro
            180                 185                 190 tct gaa aaa tca ccg ctc agt gcg att cgt ctc gcg ggg ctg gcg aaa    624
Ser Glu Lys Ser Pro Leu Ser Ala Ile Arg Leu Ala Gly Leu Ala Lys
        195                 200                 205 gaa gca ggc ttg ccg gat ggt gtg ttg aac gtg gtg acg ggt ttt ggt    672
Glu Ala Gly Leu Pro Asp Gly Val Leu Asn Val Val Thr Gly Phe Gly
210                 215                 220 cat gaa gcc ggg cag gcg ctg tcg cgt cat aac gat atc gac gcc att    720
His Glu Ala Gly Gln Ala Leu Ser Arg His Asn Asp Ile Asp Ala Ile
225                 230                 235                 240 gcc ttt acc ggt tca acc cgt acc ggg aaa cag ctg ctg aaa gat gcg    768
Ala Phe Thr Gly Ser Thr Arg Thr Gly Lys Gln Leu Leu Lys Asp Ala
                245                 250                 255 ggc gac agc aac atg aaa cgc gtc tgg ctg gaa gcg ggc ggc aaa agc    816
Gly Asp Ser Asn Met Lys Arg Val Trp Leu Glu Ala Gly Gly Lys Ser
            260                 265                 270 gcc aac atc gtt ttc gct gac tgc ccg gat ttg caa cag gcg gca agc    864
Ala Asn Ile Val Phe Ala Asp Cys Pro Asp Leu Gln Gln Ala Ala Ser
        275                 280                 285 gcc acc gca gca ggc att ttc tac aac cag gga cag gtg tgc atc gcc    912
Ala Thr Ala Ala Gly Ile Phe Tyr Asn Gln Gly Gln Val Cys Ile Ala
290                 295                 300 gga acg cgc ctg ttg ctg gaa gag agc atc gcc gat gaa ttc tta gcc    960
Gly Thr Arg Leu Leu Leu Glu Glu Ser Ile Ala Asp Glu Phe Leu Ala
305                 310                 315                 320 ctg tta aaa cag cag gcg caa aac tgg cag ccg ggc cat cca ctt gat   1008
Leu Leu Lys Gln Gln Ala Gln Asn Trp Gln Pro Gly His Pro Leu Asp
                325                 330                 335 ccc gca acc acc atg ggc acc tta atc gac tgc gcc cac gcc gac tcg   1056
Pro Ala Thr Thr Met Gly Thr Leu Ile Asp Cys Ala His Ala Asp Ser
            340                 345                 350 gtc cat agc ttt att cgg gaa ggc gaa agc aaa ggg caa ctg ttg ttg   1104
Val His Ser Phe Ile Arg Glu Gly Glu Ser Lys Gly Gln Leu Leu Leu
        355                 360                 365 gat ggc cgt aac gcc ggg ctg gct gcc gcc atc ggc ccg acc atc ttt   1152
Asp Gly Arg Asn Ala Gly Leu Ala Ala Ala Ile Gly Pro Thr Ile Phe
370                 375                 380 gtg gat gtg gac ccg aat gcg tcc tta agt cgc gaa gag att ttc ggt   1200
Val Asp Val Asp Pro Asn Ala Ser Leu Ser Arg Glu Glu Ile Phe Gly
385                 390                 395                 400 ccg gtg ctg gtg gtc acg cgt ttc aca tca gaa gaa cag gcg cta cag   1248
Pro Val Leu Val Val Thr Arg Phe Thr Ser Glu Glu Gln Ala Leu Gln
                405                 410                 415 ctt gcc aac gac agc cag tac ggc ctt ggc gcg gcg gta tgg acg cgc   1296
Leu Ala Asn Asp Ser Gln Tyr Gly Leu Gly Ala Ala Val Trp Thr Arg
            420                 425                 430 gac ctc tcc cgc gcg cac cgc atg agc cga cgc ctg aaa gcc ggt tcc   1344
Asp Leu Ser Arg Ala His Arg Met Ser Arg Arg Leu Lys Ala Gly Ser
        435                 440                 445 gtc ttc gtc aat aac tac aac gac ggc gat atg acc gtg ccg ttt ggc   1392
Val Phe Val Asn Asn Tyr Asn Asp Gly Asp Met Thr Val Pro Phe Gly
450                 455                 460
```

```
ggc tat aag cag agc ggc aac ggt cgc gac aaa tcc ctg cat gcc ctt      1440
Gly Tyr Lys Gln Ser Gly Asn Gly Arg Asp Lys Ser Leu His Ala Leu
465                 470                 475                 480 gaa aaa ttc act gaa ctg aaa acc atc tgg ata agc ctg gag gcc tga      1488
Glu Lys Phe Thr Glu Leu Lys Thr Ile Trp Ile Ser Leu Glu Ala
            485                 490                 495

<210> SEQ ID NO 20
<211> LENGTH: 495
<212> TYPE: PRT
<213> ORGANISM: Escherichia coli

<400> SEQUENCE: 20

Met Asn Phe His His Leu Ala Tyr Trp Gln Asp Lys Ala Leu Ser Leu
1               5                   10                  15

Ala Ile Glu Asn Arg Leu Phe Ile Asn Gly Glu Tyr Thr Ala Ala Ala
            20                  25                  30

Glu Asn Glu Thr Phe Glu Thr Val Asp Pro Val Thr Gln Ala Pro Leu
        35                  40                  45

Ala Lys Ile Ala Arg Gly Lys Ser Val Asp Ile Asp Arg Ala Met Ser
 50                  55                  60

Ala Ala Arg Gly Val Phe Glu Arg Gly Asp Trp Ser Leu Ser Ser Pro
65                  70                  75                  80

Ala Lys Arg Lys Ala Val Leu Asn Lys Leu Ala Asp Leu Met Glu Ala
                85                  90                  95

His Ala Glu Glu Leu Ala Leu Leu Glu Thr Leu Asp Thr Gly Lys Pro
            100                 105                 110

Ile Arg His Ser Leu Arg Asp Asp Ile Pro Gly Ala Ala Arg Ala Ile
        115                 120                 125

Arg Trp Tyr Ala Glu Ala Ile Asp Lys Val Tyr Gly Glu Val Ala Thr
130                 135                 140

Thr Ser Ser His Glu Leu Ala Met Ile Val Arg Glu Pro Val Gly Val
145                 150                 155                 160

Ile Ala Ala Ile Val Pro Trp Asn Phe Pro Leu Leu Leu Thr Cys Trp
                165                 170                 175

Lys Leu Gly Pro Ala Leu Ala Ala Gly Asn Ser Val Ile Leu Lys Pro
            180                 185                 190

Ser Glu Lys Ser Pro Leu Ser Ala Ile Arg Leu Ala Gly Leu Ala Lys
        195                 200                 205

Glu Ala Gly Leu Pro Asp Gly Val Leu Asn Val Val Thr Gly Phe Gly
210                 215                 220

His Glu Ala Gly Gln Ala Leu Ser Arg His Asn Asp Ile Asp Ala Ile
225                 230                 235                 240

Ala Phe Thr Gly Ser Thr Arg Thr Gly Lys Gln Leu Leu Lys Asp Ala
                245                 250                 255

Gly Asp Ser Asn Met Lys Arg Val Trp Leu Glu Ala Gly Gly Lys Ser
            260                 265                 270

Ala Asn Ile Val Phe Ala Asp Cys Pro Asp Leu Gln Gln Ala Ala Ser
        275                 280                 285

Ala Thr Ala Ala Gly Ile Phe Tyr Asn Gln Gly Gln Val Cys Ile Ala
    290                 295                 300

Gly Thr Arg Leu Leu Leu Glu Glu Ser Ile Ala Asp Glu Phe Leu Ala
305                 310                 315                 320

Leu Leu Lys Gln Gln Ala Gln Asn Trp Gln Pro Gly His Pro Leu Asp
                325                 330                 335
```

```
Pro Ala Thr Thr Met Gly Thr Leu Ile Asp Cys Ala His Ala Asp Ser
            340                 345                 350

Val His Ser Phe Ile Arg Glu Gly Glu Ser Lys Gly Gln Leu Leu Leu
        355                 360                 365

Asp Gly Arg Asn Ala Gly Leu Ala Ala Ala Ile Gly Pro Thr Ile Phe
    370                 375                 380

Val Asp Val Asp Pro Asn Ala Ser Leu Ser Arg Glu Glu Ile Phe Gly
385                 390                 395                 400

Pro Val Leu Val Val Thr Arg Phe Thr Ser Glu Gln Ala Leu Gln
                405                 410                 415

Leu Ala Asn Asp Ser Gln Tyr Gly Leu Gly Ala Ala Val Trp Thr Arg
            420                 425                 430

Asp Leu Ser Arg Ala His Arg Met Ser Arg Arg Leu Lys Ala Gly Ser
    435                 440                 445

Val Phe Val Asn Asn Tyr Asn Asp Gly Asp Met Thr Val Pro Phe Gly
450                 455                 460

Gly Tyr Lys Gln Ser Gly Asn Gly Arg Asp Lys Ser Leu His Ala Leu
465                 470                 475                 480

Glu Lys Phe Thr Glu Leu Lys Thr Ile Trp Ile Ser Leu Glu Ala
            485                 490                 495

<210> SEQ ID NO 21
<211> LENGTH: 1395
<212> TYPE: DNA
<213> ORGANISM: Escherichia coli

<400> SEQUENCE: 21
atgcctgacg ctaaaaaaca ggggcggtca acaaggcaa tgacgttttt cgtctgcttc      60
cttgccgctc tggcgggatt actctttggc ctggatatcg gtgtaattgc tggcgcactg     120
ccgtttattg cagatgaatt ccagattact tcgcacacgc aagaatgggt cgtaagctcc     180
atgatgttcg gtgcggcagt cggtgcggtg ggcagcggct ggctctcctt taaactcggg     240
cgcaaaaaga gcctgatgat cggcgcaatt ttgtttgttg ccggttcgct gttctctgcg     300
gctgcgccaa cgttgaagt actgattctt tcccgcgttc tactggggct ggcggtgggt     360
gtggcctctt ataccgcacc gctgtacctc tctgaaattg cgccggaaaa aattcgtggc     420
agtatgatct cgatgtatca gttgatgatc actatcggga tcctcggtgc ttatctttct     480
gataccgcct tcagctacac cggtgcatgg cgctggatgc tgggtgtgat tatcatcccg     540 gcaatttttgc tgctgattgg tgtcttcttc ctgccagaca gcccacgttg gtttgccgcc     600
aaacgccgtt tgttgatgc cgaacgcgtg ctgctacgcc tgcgtgacac cagcgcggaa     660
gcgaaacgcg aactggatga aatccgtgaa agtttgcagg ttaaacagag tggctgggcg     720
ctgtttaaag agaacagcaa cttccgccgc gcggtgttcc ttggcgtact gttgcaggta     780
atgcagcaat tcaccgggat gaacgtcatc atgtattacg cgccgaaaat cttcgaactg     840
gcgggttata ccaacactac cgagcaaatg tgggggaccg tgattgtcgg cctgaccaac     900
gtacttgcca cctttatcgc aatcggcctt gttgaccgct gggacgtaa accaacgcta     960 acgctgggct tcctggtgat ggctgctggc atgggcgtac tcggtacaat gatgcatatc    1020
ggtattcact ctccgtcggc gcagtatttc gccatcgcca tgctgctgat gtttattgtc    1080
ggttttgcca tgagtgccgg tccgctgatt tgggtactgt gctccgaaat tcagccgctg    1140
aaaggccgcg attttggcat cacctgctcc actgccacca actggattgc caacatgatc    1200
gttggcgcaa cgttcctgac catgctcaac acgctgggta acgccaacac cttctggggtg    1260
```

-continued

```
tatgcggctc tgaacgtact gtttatcctg ctgacattgt ggctggtacc ggaaaccaaa    1320
cacgtttcgc tggaacatat tgaacgtaat ctgatgaaag gtcgtaaact gcgcgaaata    1380
ggcgctcacg attaa                                                     1395
```

<210> SEQ ID NO 22
<211> LENGTH: 464
<212> TYPE: PRT
<213> ORGANISM: Escherichia coli

<400> SEQUENCE: 22

```
Met Pro Asp Ala Lys Lys Gln Gly Arg Ser Asn Lys Ala Met Thr Phe
1               5                   10                  15

Phe Val Cys Phe Leu Ala Ala Leu Ala Gly Leu Leu Phe Gly Leu Asp
                20                  25                  30

Ile Gly Val Ile Ala Gly Ala Leu Pro Phe Ile Ala Asp Glu Phe Gln
            35                  40                  45

Ile Thr Ser His Thr Gln Glu Trp Val Val Ser Ser Met Met Phe Gly
        50                  55                  60

Ala Ala Val Gly Ala Val Gly Ser Gly Trp Leu Ser Phe Lys Leu Gly
65                  70                  75                  80

Arg Lys Lys Ser Leu Met Ile Gly Ala Ile Leu Phe Val Ala Gly Ser
                85                  90                  95

Leu Phe Ser Ala Ala Pro Asn Val Glu Val Leu Ile Leu Ser Arg
                100                 105                 110

Val Leu Leu Gly Leu Ala Val Gly Val Ala Ser Tyr Thr Ala Pro Leu
            115                 120                 125

Tyr Leu Ser Glu Ile Ala Pro Glu Lys Ile Arg Gly Ser Met Ile Ser
        130                 135                 140

Met Tyr Gln Leu Met Ile Thr Ile Gly Ile Leu Gly Ala Tyr Leu Ser
145                 150                 155                 160

Asp Thr Ala Phe Ser Tyr Thr Gly Ala Trp Arg Trp Met Leu Gly Val
                165                 170                 175

Ile Ile Ile Pro Ala Ile Leu Leu Ile Gly Val Phe Phe Leu Pro
            180                 185                 190

Asp Ser Pro Arg Trp Phe Ala Ala Lys Arg Arg Phe Val Asp Ala Glu
        195                 200                 205

Arg Val Leu Leu Arg Leu Arg Asp Thr Ser Ala Glu Ala Lys Arg Glu
210                 215                 220

Leu Asp Glu Ile Arg Glu Ser Leu Gln Val Lys Gln Ser Gly Trp Ala
225                 230                 235                 240

Leu Phe Lys Glu Asn Ser Asn Phe Arg Arg Ala Val Phe Leu Gly Val
                245                 250                 255

Leu Leu Gln Val Met Gln Gln Phe Thr Gly Met Asn Val Ile Met Tyr
            260                 265                 270

Tyr Ala Pro Lys Ile Phe Glu Leu Ala Gly Tyr Thr Asn Thr Thr Glu
        275                 280                 285

Gln Met Trp Gly Thr Val Ile Val Gly Leu Thr Asn Val Leu Ala Thr
290                 295                 300

Phe Ile Ala Ile Gly Leu Val Asp Arg Trp Gly Arg Lys Pro Thr Leu
305                 310                 315                 320

Thr Leu Gly Phe Leu Val Met Ala Ala Gly Met Gly Val Leu Gly Thr
                325                 330                 335

Met Met His Ile Gly Ile His Ser Pro Ser Ala Gln Tyr Phe Ala Ile
            340                 345                 350
```

Ala Met Leu Leu Met Phe Ile Val Gly Phe Ala Met Ser Ala Gly Pro
            355                 360                 365

Leu Ile Trp Val Leu Cys Ser Glu Ile Gln Pro Leu Lys Gly Arg Asp
        370                 375                 380

Phe Gly Ile Thr Cys Ser Thr Ala Thr Asn Trp Ile Ala Asn Met Ile
385                 390                 395                 400

Val Gly Ala Thr Phe Leu Thr Met Leu Asn Thr Leu Gly Asn Ala Asn
                405                 410                 415

Thr Phe Trp Val Tyr Ala Ala Leu Asn Val Leu Phe Ile Leu Leu Thr
            420                 425                 430

Leu Trp Leu Val Pro Glu Thr Lys His Val Ser Leu Glu His Ile Glu
        435                 440                 445

Arg Asn Leu Met Lys Gly Arg Lys Leu Arg Glu Ile Gly Ala His Asp
450                 455                 460

<210> SEQ ID NO 23
<211> LENGTH: 1248
<212> TYPE: DNA
<213> ORGANISM: Escherichia coli

<400> SEQUENCE: 23

```
atggcactga atattccatt cagaaatgcg tactatcgtt ttgcatccag ttactcattt      60
ctcttttta tttcctggtc gctgtggtgg tcgttatacg ctatttggct gaaaggacat     120
ctaggattaa cagggacgga attaggtaca ctttattcgg tcaaccagtt taccagcatt     180
ctatttatga tgttctacgg catcgttcag gataaactcg gtctgaagaa accgctcatc     240
tggtgtatga gtttcattct ggtcttgacc ggaccgttta tgatttacgt ttatgaaccg     300
ttactgcaaa gcaattttc tgtaggtcta attctggggg cgctcttttt tggcctgggg     360
tatctggcgg atgcggttt gcttgacagc ttcaccgaaa aaatggcgcg aaattttcat     420
ttcgaatatg aacagcgcg cgcctgggga tcttttggct atgctattgg cgcgttcttt     480
gccggtatat tttttagtat cagtccccat atcaacttct ggttggtctc gctatttggc     540
gctgtattta tgatgatcaa catgcgtttt aaagataagg atcaccagtg catagcggcg     600
gatgcgggag gggtaaaaaa agaggatttt atcgcagttt caaggatcg aaacttctgg     660
gttttcgtca tatttattgt ggggacgtgg tctttctata acatttttga tcaacaactc     720
tttcctgtct tttatgcagg tttattcgaa tcacacgatg taggaacgcg cctgtatggt     780
tatctcaact cattccaggt ggtactcgaa gcgctgtgca tggcgattat tcctttcttt     840
gtgaatcggg tagggccaaa aaatgcatta cttatcggtg ttgtgattat ggcgttgcgt     900
atcctttcct gcgcgttgtt cgttaacccc tggattattt cattagtgaa gctgttacat     960
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg gcattttctt cctgagtaaa    1200
aaacgcgagc aaatagttat ggaaacgcct gtaccttcag caatatag                 1248
```

<210> SEQ ID NO 24
<211> LENGTH: 415
<212> TYPE: PRT
<213> ORGANISM: Escherichia coli

<400> SEQUENCE: 24

Met Ala Leu Asn Ile Pro Phe Arg Asn Ala Tyr Tyr Arg Phe Ala Ser

```
              1               5              10              15
Ser Tyr Ser Phe Leu Phe Phe Ile Ser Trp Ser Leu Trp Ser Leu
                         20              25              30

Tyr Ala Ile Trp Leu Lys Gly His Leu Gly Leu Thr Gly Thr Glu Leu
                 35              40              45

Gly Thr Leu Tyr Ser Val Asn Gln Phe Thr Ser Ile Leu Phe Met Met
         50              55              60

Phe Tyr Gly Ile Val Gln Asp Lys Leu Gly Lys Lys Pro Leu Ile
 65              70              75              80

Trp Cys Met Ser Phe Ile Leu Val Leu Thr Gly Pro Phe Met Ile Tyr
                 85              90              95

Val Tyr Glu Pro Leu Leu Gln Ser Asn Phe Ser Val Gly Leu Ile Leu
                 100             105             110

Gly Ala Leu Phe Phe Gly Leu Gly Tyr Leu Ala Gly Cys Gly Leu Leu
                 115             120             125

Asp Ser Phe Thr Glu Lys Met Ala Arg Asn Phe His Phe Glu Tyr Gly
                 130             135             140

Thr Ala Arg Ala Trp Gly Ser Phe Gly Tyr Ala Ile Gly Ala Phe Phe
145                 150             155             160

Ala Gly Ile Phe Phe Ser Ile Ser Pro His Ile Asn Phe Trp Leu Val
                 165             170             175

Ser Leu Phe Gly Ala Val Phe Met Met Ile Asn Met Arg Phe Lys Asp
                 180             185             190

Lys Asp His Gln Cys Ile Ala Ala Asp Ala Gly Gly Val Lys Lys Glu
                 195             200             205

Asp Phe Ile Ala Val Phe Lys Asp Arg Asn Phe Trp Val Phe Val Ile
                 210             215             220

Phe Ile Val Gly Thr Trp Ser Phe Tyr Asn Ile Phe Asp Gln Gln Leu
225                 230             235             240

Phe Pro Val Phe Tyr Ala Gly Leu Phe Glu Ser His Asp Val Gly Thr
                 245             250             255

Arg Leu Tyr Gly Tyr Leu Asn Ser Phe Gln Val Val Leu Glu Ala Leu
                 260             265             270

Cys Met Ala Ile Ile Pro Phe Phe Val Asn Arg Val Gly Pro Lys Asn
                 275             280             285

Ala Leu Leu Ile Gly Val Val Ile Met Ala Leu Arg Ile Leu Ser Cys
                 290             295             300

Ala Leu Phe Val Asn Pro Trp Ile Ile Ser Leu Val Lys Leu Leu His
305                 310             315             320

Ala Ile Glu Val Pro Leu Cys Val Ile Ser Val Phe Lys Tyr Ser Val
                 325             330             335

Ala Asn Phe Asp Lys Arg Leu Ser Ser Thr Ile Phe Leu Ile Gly Phe
                 340             345             350

Gln Ile Ala Ser Ser Leu Gly Ile Val Leu Leu Ser Thr Pro Thr Gly
                 355             360             365

Ile Leu Phe Asp His Ala Gly Tyr Gln Thr Val Phe Phe Ala Ile Ser
                 370             375             380

Gly Ile Val Cys Leu Met Leu Leu Phe Gly Ile Phe Phe Leu Ser Lys
385                 390             395             400

Lys Arg Glu Gln Ile Val Met Glu Thr Pro Val Pro Ser Ala Ile
                 405             410             415

<210> SEQ ID NO 25
<211> LENGTH: 1248
```

```
<212> TYPE: DNA
<213> ORGANISM: Escherichia coli

<400> SEQUENCE: 25
atggcactga atattccatt cagaaatgcg tactatcgtt ttgcatccag ttactcattt      60
ctctttttta tttcctggtc gctgtggtgg tcgttatacg ctatttggct gaaaggacat    120
ctagggttga cagggacgga attaggtaca ctttattcgg tcaaccagtt taccagcatt    180
ctatttatga tgttctacgg catcgttcag gataaactcg gtctgaagaa accgctcatc    240
tggtgtatga gtttcatcct ggtcttgacc ggaccgttta tgatttacgt ttatgaaccg    300
ttactgcaaa gcaattttc tgtaggtcta attctggggg cgctattttt tggcttgggg    360
tatctggcgg gatgcggttt gcttgatagc ttcaccgaaa aaatggcgcg aaattttcat    420
ttcgaatatg gaacagcgcg cgcctgggga tcttttggct atgctattgg cgcgttcttt    480
gccggcatat tttttagtat cagtccccat atcaacttct ggttggtctc gctatttggc    540
gctgtattta tgatgatcaa catgcgtttt aaagataagg atcaccagtg cgtagcggca    600
gatgcgggag ggtaaaaaaa agaggatttt atcgcagttt tcaaggatcg aaacttctgg    660
gttttcgtca tatttattgt ggggacgtgg tctttctata acattttttga tcaacaactt    720
tttcctgtct tttattcagg tttattcgaa tcacacgatg taggaacgcg cctgtatggt    780
tatctcaact cattccaggt ggtactcgaa gcgctgtgca tggcgattat tcctttcttt    840
gtgaatcggg tagggccaaa aaatgcatta cttatcggag ttgtgattat ggcgttgcgt    900
atcctttcct gcgcgctgtt cgttaaccc tggattattt cattagtgaa gttgttacat    960
gccattgagg ttccactttg tgtcatatcc gtcttcaaat acagcgtggc aaactttgat   1020
aagcgcctgt cgtcgacgat ctttctgatt ggttttcaaa ttgccagttc gcttgggatt   1080
gtgctgcttt caacgccgac tgggatactc tttgaccacg caggctacca gacagttttc   1140
ttcgcaattt cgggtattgt ctgcctgatg ttgctatttg gcattttctt cttgagtaaa   1200
aaacgcgagc aaatagttat ggaaacgcct gtaccttcag caatatag                1248

<210> SEQ ID NO 26
<211> LENGTH: 415
<212> TYPE: PRT
<213> ORGANISM: Escherichia coli

<400> SEQUENCE: 26

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
                20                  25                  30

Tyr Ala Ile Trp Leu Lys Gly His Leu Gly Leu Thr Gly Thr Glu Leu
            35                  40                  45

Gly Thr Leu Tyr Ser Val Asn Gln Phe Thr Ser Ile Leu Phe Met Met
        50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
                100                 105                 110

Gly Ala Leu Phe Phe Gly Leu Gly Tyr Leu Ala Gly Cys Gly Leu Leu
            115                 120                 125

Asp Ser Phe Thr Glu Lys Met Ala Arg Asn Phe His Phe Glu Tyr Gly
```

```
                130                 135                 140
Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
                180                 185                 190

Lys Asp His Gln Cys Val Ala Ala Asp Ala Gly Gly Val Lys Lys Glu
                195                 200                 205

Asp Phe Ile Ala Val Phe Lys Asp Arg Asn Phe Trp Val Phe Val Ile
210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
                260                 265                 270

Cys Met Ala Ile Ile Pro Phe Phe Val Asn Arg Val Gly Pro Lys Asn
                275                 280                 285

Ala Leu Leu Ile Gly Val Val Ile Met Ala Leu Arg Ile Leu Ser Cys
290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
                340                 345                 350

Gln Ile Ala Ser Ser Leu Gly Ile Val Leu Leu Ser Thr Pro Thr Gly
                355                 360                 365

Ile Leu Phe Asp His Ala Gly Tyr Gln Thr Val Phe Phe Ala Ile Ser
                370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 27
<211> LENGTH: 1434
<212> TYPE: DNA
<213> ORGANISM: Escherichia coli

<400> SEQUENCE: 27
atgacgcaat ctcgattgca tgcggcgcaa aacgcactag caaaacttca cgagcgccga    60
ggtaacactt tctatcccca tttttcacctc gcgcctcctg ccgggtggat gaacgatcca   120
aacggcctga tctggtttaa cgatcgttat cacgcgtttt atcaacatca cccgatgagc   180
gaacactggg ggccaatgca ctggggacat gccaccagcg acgatatgat ccactggcag   240
catgagccta ttgcgctagc gccaggagac gagaatgaca agacggggtg ttttttcaggt   300 agtgctgtcg atgacaatgg tgtcctctca cttatctaca ccggacacgt ctggctcgat   360
ggtgcaggta atgacgatgc aattcgcgaa gtacaatgtc tggctaccag tcgggatggt   420
attcatttcg agaaacaggg tgtgatcctc actccaccag aaggcatcat gcacttccgc   480
gatcctaaag tgtggcgtga agccgacaca tggtggatgg tagtcggggc gaaagaccca   540
ggcaacacgg ggcagatcct gctttatcgc ggcagttcat tgcgtgaatg gactttcgat   600
```

```
cgcgtactgg cccacgctga tgcgggtgaa agctatatgt gggaatgtcc ggactttttc    660
agccttggcg atcagcatta tctgatgttt tccccgcagg gaatgaatgc cgagggatac    720
agttatcgaa atcgctttca aagtggcgta atacccggaa tgtggtcgcc aggacgactt    780
tttgcacaat ccgggcattt tactgaactt gataacgggc atgactttta tgcaccacaa    840
agctttgtag cgaaggatgg tcggcgtatt gttatcggct ggatggatat gtgggaatcg    900
ccaatgccct caaaacgtga aggctgggca ggctgcatga cgctggcgcg cgagctatca    960
gagagcaatg gcaaactcct acaacgcccg gtacacgaag ctgagtcgtt acgccagcag   1020
catcaatcta tctctccccg cacaatcagc aataaatatg ttttgcagga aaacgcgcaa   1080
gcagttgaga ttcagttgca gtgggcgctg aagaacagtg atgccgaaca ttacggatta   1140
cagctcggcg ctggaatgcg gctgtatatt gataaccaat ctgagcgact tgttttgtgg   1200
cggtattacc cacacgagaa tttagatggc taccgtagta ttcccctccc gcagggtgac   1260
atgctcgccc taaggatatt tatcgataca tcatccgtgg aagtatttat taacgacggg   1320
gaggcggtga tgagtagccg aatatatccg cagccagaag aacgggaact gtcgctctat   1380
gcctcccacg gagtggctgt gctgcaacat ggagcactct ggcaactggg ttaa          1434
```

<210> SEQ ID NO 28
<211> LENGTH: 477
<212> TYPE: PRT
<213> ORGANISM: Escherichia coli

<400> SEQUENCE: 28

```
Met Thr Gln Ser Arg Leu His Ala Ala Gln Asn Ala Leu Ala Lys Leu
1               5                   10                  15

His Glu Arg Arg Gly Asn Thr Phe Tyr Pro His Phe His Leu Ala Pro
            20                  25                  30

Pro Ala Gly Trp Met Asn Asp Pro Asn Gly Leu Ile Trp Phe Asn Asp
        35                  40                  45

Arg Tyr His Ala Phe Tyr Gln His His Pro Met Ser Glu His Trp Gly
    50                  55                  60

Pro Met His Trp Gly His Ala Thr Ser Asp Asp Met Ile His Trp Gln
65                  70                  75                  80

His Glu Pro Ile Ala Leu Ala Pro Gly Asp Glu Asn Asp Lys Asp Gly
                85                  90                  95

Cys Phe Ser Gly Ser Ala Val Asp Asp Asn Gly Val Leu Ser Leu Ile
            100                 105                 110

Tyr Thr Gly His Val Trp Leu Asp Gly Ala Gly Asn Asp Asp Ala Ile
        115                 120                 125

Arg Glu Val Gln Cys Leu Ala Thr Ser Arg Asp Gly Ile His Phe Glu
    130                 135                 140

Lys Gln Gly Val Ile Leu Thr Pro Pro Glu Gly Ile Met His Phe Arg
145                 150                 155                 160

Asp Pro Lys Val Trp Arg Glu Ala Asp Thr Trp Trp Met Val Val Gly
                165                 170                 175

Ala Lys Asp Pro Gly Asn Thr Gly Gln Ile Leu Leu Tyr Arg Gly Ser
            180                 185                 190

Ser Leu Arg Glu Trp Thr Phe Asp Arg Val Leu Ala His Ala Asp Ala
        195                 200                 205

Gly Glu Ser Tyr Met Trp Glu Cys Pro Asp Phe Phe Ser Leu Gly Asp
    210                 215                 220

Gln His Tyr Leu Met Phe Ser Pro Gln Gly Met Asn Ala Glu Gly Tyr
```

```
                    225                 230                 235                 240
Ser Tyr Arg Asn Arg Phe Gln Ser Gly Val Ile Pro Gly Met Trp Ser
                245                 250                 255

Pro Gly Arg Leu Phe Ala Gln Ser Gly His Phe Thr Glu Leu Asp Asn
            260                 265                 270

Gly His Asp Phe Tyr Ala Pro Gln Ser Phe Val Ala Lys Asp Gly Arg
        275                 280                 285

Arg Ile Val Ile Gly Trp Met Asp Met Trp Glu Ser Pro Met Pro Ser
    290                 295                 300

Lys Arg Glu Gly Trp Ala Gly Cys Met Thr Leu Ala Arg Glu Leu Ser
305                 310                 315                 320

Glu Ser Asn Gly Lys Leu Leu Gln Arg Pro Val His Glu Ala Glu Ser
                325                 330                 335

Leu Arg Gln Gln His Gln Ser Ile Ser Pro Arg Thr Ile Ser Asn Lys
            340                 345                 350

Tyr Val Leu Gln Glu Asn Ala Gln Ala Val Gly Ile Gln Leu Gln Trp
        355                 360                 365

Ala Leu Lys Asn Ser Asp Ala Glu His Tyr Gly Leu Gln Leu Gly Ala
    370                 375                 380

Gly Met Arg Leu Tyr Ile Asp Asn Gln Ser Gly Arg Leu Val Leu Trp
385                 390                 395                 400

Arg Tyr Tyr Pro His Glu Asn Leu Asp Gly Tyr Arg Ser Ile Pro Leu
                405                 410                 415

Pro Gln Gly Asp Met Leu Ala Leu Arg Ile Phe Ile Asp Thr Ser Ser
            420                 425                 430

Val Glu Val Phe Ile Asn Asp Gly Glu Ala Val Met Ser Ser Arg Ile
        435                 440                 445

Tyr Pro Gln Pro Glu Glu Arg Glu Leu Ser Leu Tyr Ala Ser His Gly
    450                 455                 460

Val Ala Val Leu Gln His Gly Ala Leu Trp Gln Leu Gly
465                 470                 475

<210> SEQ ID NO 29
<211> LENGTH: 1434
<212> TYPE: DNA
<213> ORGANISM: Escherichia coli

<400> SEQUENCE: 29
atgacgcaat ctcgattgca tgcggcgcaa aacgccctag caaaacttca tgagcaccgg      60
ggtaacactt tctatcccca ttttcacctc gcgcctcctg ccgggtggat gaacgatcca     120
aacggcctga tctggtttaa cgatcgttat cacgcgtttt atcaacatca tccgatgagc     180
gaacactggg ggccaatgca ctggggacat gccaccagcg acgatatgat ccactggcag     240
catgagccta ttgcgctagc gccaggagac gataatgaca agacgggtgt tttttcaggt     300
agtgctgtcg atgacaatgg tgtcctctca cttatctaca ccggacacgt ctggctcgat     360
ggtgcaggta atgacgatgc aattcgcgaa gtacaatgtc tggctaccag tcggatggt      420 attcatttcg agaaacaggg tgtgatcctc actccaccag aaggaatcat gcacttccgc     480
gatcctaaag tgtggcgtga agccgacaca tggtggatgg tagtcggggc gaaagatcca     540
ggcaacacgg ggcagatcct gctttatcgc ggcagttcgt tgcgtgaatg gaccttcgat     600
cgcgtactgg cccacgctga tgcgggtgaa agctatatgt gggaatgtcc ggacttttc     660 agccttggcg atcagcatta tctgatgttt tcccgcagg gaatgaatgc cgagggatac     720
agttaccgaa atcgctttca agtggcgta ataccccggaa tgtggtcgcc aggacgactt     780
```

```
tttgcacaat ccgggcattt tactgaactt gataacgggc atgacttta tgcaccacaa    840 agcttttag cgaaggatgg tcggcgtatt gttatcggct ggatggatat gtgggaatcg    900
ccaatgccct caaaacgtga aggatgggca ggctgcatga cgctggcgcg cgagctatca    960
gagagcaatg gcaaacttct acaacgcccg gtacacgaag ctgagtcgtt acgccagcag   1020
catcaatctg tctctccccg cacaatcagc aataaatatg ttttgcagga aaacgcgcaa   1080
gcagttgaga ttcagttgca gtgggcgctg aagaacagtg atgccgaaca ttacggatta   1140
cagctcggca ctggaatgcg gctgtatatt gataaccaat ctgagcgact tgttttgtgg   1200
cggtattacc cacacgagaa tttagacggc taccgtagta ttcccctccc gcagcgtgac   1260
acgctcgccc taaggatatt tatcgataca tcatccgtgg aagtatttat taacgacggg   1320
gaagcggtga tgagtagtcg aatctatccg cagccagaag aacgggaact gtcgctttat   1380
gcctcccacg gagtggctgt gctgcaacat ggagcactct ggctactggg ttaa         1434
```

<210> SEQ ID NO 30
<211> LENGTH: 477
<212> TYPE: PRT
<213> ORGANISM: Escherichia coli

<400> SEQUENCE: 30

```
Met Thr Gln Ser Arg Leu His Ala Ala Gln Asn Ala Leu Ala Lys Leu
1               5                   10                  15

His Glu His Arg Gly Asn Thr Phe Tyr Pro His Phe His Leu Ala Pro
            20                  25                  30

Pro Ala Gly Trp Met Asn Asp Pro Asn Gly Leu Ile Trp Phe Asn Asp
        35                  40                  45

Arg Tyr His Ala Phe Tyr Gln His His Pro Met Ser Glu His Trp Gly
    50                  55                  60

Pro Met His Trp Gly His Ala Thr Ser Asp Asp Met Ile His Trp Gln
65                  70                  75                  80

His Glu Pro Ile Ala Leu Ala Pro Gly Asp Asp Asn Asp Lys Asp Gly
                85                  90                  95

Cys Phe Ser Gly Ser Ala Val Asp Asp Asn Gly Val Leu Ser Leu Ile
            100                 105                 110

Tyr Thr Gly His Val Trp Leu Asp Gly Ala Gly Asn Asp Asp Ala Ile
        115                 120                 125

Arg Glu Val Gln Cys Leu Ala Thr Ser Arg Asp Gly Ile His Phe Glu
    130                 135                 140

Lys Gln Gly Val Ile Leu Thr Pro Pro Glu Gly Ile Met His Phe Arg
145                 150                 155                 160

Asp Pro Lys Val Trp Arg Glu Ala Asp Thr Trp Met Val Val Gly
                165                 170                 175

Ala Lys Asp Pro Gly Asn Thr Gly Gln Ile Leu Leu Tyr Arg Gly Ser
            180                 185                 190

Ser Leu Arg Glu Trp Thr Phe Asp Arg Val Leu Ala His Ala Asp Ala
        195                 200                 205

Gly Glu Ser Tyr Met Trp Glu Cys Pro Asp Phe Phe Ser Leu Gly Asp
    210                 215                 220

Gln His Tyr Leu Met Phe Ser Pro Gln Gly Met Asn Ala Glu Gly Tyr
225                 230                 235                 240

Ser Tyr Arg Asn Arg Phe Gln Ser Gly Val Ile Pro Gly Met Trp Ser
                245                 250                 255

Pro Gly Arg Leu Phe Ala Gln Ser Gly His Phe Thr Glu Leu Asp Asn
```

```
                260             265             270
Gly His Asp Phe Tyr Ala Pro Gln Ser Phe Leu Ala Lys Asp Gly Arg
        275                 280                 285

Arg Ile Val Ile Gly Trp Met Asp Met Trp Glu Ser Pro Met Pro Ser
290                 295                 300

Lys Arg Glu Gly Trp Ala Gly Cys Met Thr Leu Ala Arg Glu Leu Ser
305                 310                 315                 320

Glu Ser Asn Gly Lys Leu Leu Gln Arg Pro Val His Glu Ala Glu Ser
                325                 330                 335

Leu Arg Gln Gln His Gln Ser Val Ser Pro Arg Thr Ile Ser Asn Lys
        340                 345                 350

Tyr Val Leu Gln Glu Asn Ala Gln Ala Val Glu Ile Gln Leu Gln Trp
            355                 360                 365

Ala Leu Lys Asn Ser Asp Ala Glu His Tyr Gly Leu Gln Leu Gly Thr
370                 375                 380

Gly Met Arg Leu Tyr Ile Asp Asn Gln Ser Glu Arg Leu Val Leu Trp
385                 390                 395                 400

Arg Tyr Tyr Pro His Glu Asn Leu Asp Gly Tyr Arg Ser Ile Pro Leu
                405                 410                 415

Pro Gln Arg Asp Thr Leu Ala Leu Arg Ile Phe Ile Asp Thr Ser Ser
            420                 425                 430

Val Glu Val Phe Ile Asn Asp Gly Glu Ala Val Met Ser Ser Arg Ile
                435                 440                 445

Tyr Pro Gln Pro Glu Gly Arg Glu Leu Ser Leu Tyr Ala Ser His Gly
        450                 455                 460

Val Ala Val Leu Gln His Gly Ala Leu Trp Leu Leu Gly
465                 470                 475

<210> SEQ ID NO 31
<211> LENGTH: 1599
<212> TYPE: DNA
<213> ORGANISM: Bifidobacterium lactis

<400> SEQUENCE: 31
atggcaaccc ttcccaccaa tattcccgcc aacggcattc tgaccccga cccggcgctc      60 gaccctgtgc tcacgccgat ctcggaccat gccgagcagc tgtcactcgc gaagcaggc     120 gtgtcggcac tggaaaccac ccgcaacgac cgctggtacc cgaagttcca cattgcctcc    180
aatggcgggt ggatcaacga cccgaacggc ctgtgccgct acaacggacg ctggcacgtg    240
ttctaccagc tgcatcccca cggcacacag tggggcccga tgcattgggg ccacgtctcc    300
tccgacaaca tggtcgactg gcaccgcgaa cccatcgcct tcgcgccaag cctcgaacag    360
gaacgccacg gtgtgttctc cggttccgcc gtgattggcg acgacggcaa gccgtggatt    420
ttctacaccg ccaccgctg gccaacggc aaggacaaca ccggaggcga ctggcaggtg     480
cagatgctcg ccaagccgaa cgacgacgaa ctgaagacct tcacgaagga gggcatgatc    540
atcgactgcc ccaccgacga ggtggaccac cacttccgcg acccgaaggt gtggaagacc    600
ggtgacacct ggtatatgac cttcggtgtc tcgtcgaagg agcatcgtgg ccagatgtgg    660
ctgtacacgt cgagcgacat ggtgcactgg agcttcgatc gggtgctgtt cgagcatccg    720
gatccgaacg tgttcatgct tgaatgcccc gatttcttcc cgatccgcga tgcgcggggc    780
aacgagaaat gggtcatcgg cttctccgcg atgggtgcca agccaaatgg cttcatgaac    840
cgcaacgtga acaatgccgg ctacatggtg ggcacatgga agccaggcga gagcttcaag    900
ccggagaccg agttccgcct gtgggacgaa ggccataact tctatgcacc acagtcgttc    960
```

-continued

```
aacaccgaag ggcgccagat catgtacggc tggatgagcc cgttcgtcgc ccccatcccg    1020
atggaggagg acggctggtg cggcaacctc accctccccc gcgagatcac gctgggcgat    1080
gacggtgacc tggtcaccgc ccccaccatc gaaatggagg ggctgcgcga gaataccata    1140
ggcttcgact cgctcgacct tggtacgaac cagacctcca cgatcctcga cgatgacggc    1200
ggcgccctgg aaatcgagat gagactcgat ctgaacaaaa ccaccgccga acgcgccgga    1260
ctgcatgtgc atgccacaag cgacggccac tacacggcaa tcgtattcga cgcgcagatc    1320
ggcggcgtcg tcatcgaccg gcagaacgtg cgaacggag acaaaggcta ccgggtggcc    1380
aagctcagcg acaccgagct cgcagccgat acgcttgact tgcgcgtgtt catcgaccgc    1440
ggatgcgtcg aggtctacgt cgacggcggc aagcatgcga tgagctcgta ctcgttccct    1500
ggcgatggcg cacgcgccgt cgaactcgtg agcgaatccg gcaccacgca catcgacacc    1560
ctcaccatgc actcgctcaa gtccatcgga ctcgagtga                          1599
```

<210> SEQ ID NO 32
<211> LENGTH: 532
<212> TYPE: PRT
<213> ORGANISM: Bifidobacterium lactis

<400> SEQUENCE: 32

```
Met Ala Thr Leu Pro Thr Asn Ile Pro Ala Asn Gly Ile Leu Thr Pro
1               5                   10                  15

Asp Pro Ala Leu Asp Pro Val Leu Thr Pro Ile Ser Asp His Ala Glu
            20                  25                  30

Gln Leu Ser Leu Ala Glu Ala Gly Val Ser Ala Leu Glu Thr Thr Arg
        35                  40                  45

Asn Asp Arg Trp Tyr Pro Lys Phe His Ile Ala Ser Asn Gly Gly Trp
    50                  55                  60

Ile Asn Asp Pro Asn Gly Leu Cys Arg Tyr Asn Gly Arg Trp His Val
65                  70                  75                  80

Phe Tyr Gln Leu His Pro His Gly Thr Gln Trp Gly Pro Met His Trp
                85                  90                  95

Gly His Val Ser Ser Asp Asn Met Val Asp Trp His Arg Glu Pro Ile
            100                 105                 110

Ala Phe Ala Pro Ser Leu Glu Gln Glu Arg His Gly Val Phe Ser Gly
        115                 120                 125

Ser Ala Val Ile Gly Asp Asp Gly Lys Pro Trp Ile Phe Tyr Thr Gly
    130                 135                 140

His Arg Trp Ala Asn Gly Lys Asp Asn Thr Gly Gly Asp Trp Gln Val
145                 150                 155                 160

Gln Met Leu Ala Lys Pro Asn Asp Asp Glu Leu Lys Thr Phe Thr Lys
                165                 170                 175

Glu Gly Met Ile Ile Asp Cys Pro Thr Asp Glu Val Asp His His Phe
            180                 185                 190

Arg Asp Pro Lys Val Trp Lys Thr Gly Asp Thr Trp Tyr Met Thr Phe
        195                 200                 205

Gly Val Ser Ser Lys Glu His Arg Gly Gln Met Trp Leu Tyr Thr Ser
    210                 215                 220

Ser Asp Met Val His Trp Ser Phe Asp Arg Val Leu Phe Glu His Pro
225                 230                 235                 240

Asp Pro Asn Val Phe Met Leu Glu Cys Pro Asp Phe Phe Pro Ile Arg
                245                 250                 255

Asp Ala Arg Gly Asn Glu Lys Trp Val Ile Gly Phe Ser Ala Met Gly
```

```
                260                 265                 270
Ala Lys Pro Asn Gly Phe Met Asn Arg Asn Val Asn Asn Ala Gly Tyr
        275                 280                 285

Met Val Gly Thr Trp Lys Pro Gly Glu Ser Phe Lys Pro Glu Thr Glu
    290                 295                 300

Phe Arg Leu Trp Asp Glu Gly His Asn Phe Tyr Ala Pro Gln Ser Phe
305                 310                 315                 320

Asn Thr Glu Gly Arg Gln Ile Met Tyr Gly Trp Met Ser Pro Phe Val
                325                 330                 335

Ala Pro Ile Pro Met Glu Glu Asp Gly Trp Cys Gly Asn Leu Thr Leu
            340                 345                 350

Pro Arg Glu Ile Thr Leu Gly Asp Asp Gly Asp Leu Val Thr Ala Pro
        355                 360                 365

Thr Ile Glu Met Glu Gly Leu Arg Glu Asn Thr Ile Gly Phe Asp Ser
    370                 375                 380

Leu Asp Leu Gly Thr Asn Gln Thr Ser Thr Ile Leu Asp Asp Asp Gly
385                 390                 395                 400

Gly Ala Leu Glu Ile Glu Met Arg Leu Asp Leu Asn Lys Thr Thr Ala
                405                 410                 415

Glu Arg Ala Gly Leu His Val His Ala Thr Ser Asp Gly His Tyr Thr
            420                 425                 430

Ala Ile Val Phe Asp Ala Gln Ile Gly Gly Val Val Ile Asp Arg Gln
        435                 440                 445

Asn Val Ala Asn Gly Asp Lys Gly Tyr Arg Val Ala Lys Leu Ser Asp
    450                 455                 460

Thr Glu Leu Ala Ala Asp Thr Leu Asp Leu Arg Val Phe Ile Asp Arg
465                 470                 475                 480

Gly Cys Val Glu Val Tyr Val Asp Gly Gly Lys His Ala Met Ser Ser
                485                 490                 495

Tyr Ser Phe Pro Gly Asp Gly Ala Arg Ala Val Glu Leu Val Ser Glu
            500                 505                 510

Ser Gly Thr Thr His Ile Asp Thr Leu Thr Met His Ser Leu Lys Ser
        515                 520                 525

Ile Gly Leu Glu
    530

<210> SEQ ID NO 33
<211> LENGTH: 1599
<212> TYPE: DNA
<213> ORGANISM: Saccharomyces cerevisiae

<400> SEQUENCE: 33
atgcttttgc aagctttcct tttccttttg gctggttttg cagccaaaat atctgcatca       60
atgacaaacg aaactagcga tagacctttg gtccacttca cacccaacaa gggctggatg      120
aatgacccaa atgggttgtg gtacgatgaa aaagatgcca atggcatct gtactttcaa       180 tacaacccaa atgacaccgt atggggtacg ccattgtttt ggggccatgc tacttccgat      240
gatttgacta attgggaaga tcaacccatt gctatcgctc ccaagcgtaa cgattcaggt      300
gctttctctg ctccatggt ggttgattac aacaacacga gtgggttttt caatgatact       360
attgatccaa gacaaagatg cgttgcgatt tggacttata cactcctga agtgaagag         420 caatacatta gctattctct tgatggtggt tacactttta ctgaatacca aagaaccct       480 gttttagctg ccaactccac tcaattcaga gatccaaagg tgttctggta tgaaccttct      540
caaaaatgga ttatgacggc tgccaaatca aagactaca aaattgaaat ttactcctct       600
```

```
gatgacttga agtcctggaa gctagaatct gcatttgcca atgaaggttt cttaggctac    660
caatacgaat gtccaggttt gattgaagtc ccaactgagc aagatccttc caaatcttat    720
tgggtcatgt ttatttctat caacccaggt gcacctgctg gcggttcctt caaccaatat    780
tttgttggat ccttcaatgg tactcatttt gaagcgtttg acaatcaatc tagagtggta    840
gattttggta aggactacta tgccttgcaa actttcttca acactgaccc aacctacggt    900
tcagcattag gtattgcctg gcttcaaac tgggagtaca gtgcctttgt cccaactaac     960
ccatggagat catccatgtc tttggtccgc aagttttctt tgaacactga atatcaagct   1020
aatccagaga ctgaattgat caatttgaaa gccgaaccaa tattgaacat tagtaatgct   1080
ggtccctggt ctcgttttgc tactaacaca actctaacta aggccaattc ttacaatgtc   1140
gatttgagca actcgactgg taccctagag tttgagttgg tttacgctgt taacaccaca   1200
caaaccatat ccaaatccgt ctttgccgac ttatcacttt ggttcaaggg tttagaagat   1260
cctgaagaat atttgagaat gggttttgaa gtcagtgctt cttccttctt tttggaccgt   1320
ggtaactcta aggtcaagtt tgtcaaggag aacccatatt tcacaaacag aatgtctgtc   1380
aacaaccaac cattcaagtc tgagaacgac ctaagttact ataaagtgta cggcctactg   1440
gatcaaaaca tcttggaatt gtacttcaac gatggagatg tggtttctac aaatacctac   1500
ttcatgacca ccgtaacgc tctaggatct gtgaacatga ccactggtgt cgataatttg    1560
ttctacattg acaagttcca agtaagggaa gtaaaatag                          1599

<210> SEQ ID NO 34
<211> LENGTH: 532
<212> TYPE: PRT
<213> ORGANISM: Saccharomyces cerevisiae

<400> SEQUENCE: 34

Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
                20                  25                  30

Phe Thr Pro Asn Lys Gly Trp Met Asn Asp Pro Asn Gly Leu Trp Tyr
            35                  40                  45

Asp Glu Lys Asp Ala Lys Trp His Leu Tyr Phe Gln Tyr Asn Pro Asn
        50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
```

```
        195                 200                 205
Glu Ser Ala Phe Ala Asn Glu Gly Phe Leu Gly Tyr Gln Tyr Glu Cys
210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                    245                 250                 255

Phe Asn Gln Tyr Phe Val Gly Ser Phe Asn Gly Thr His Phe Glu Ala
                260                 265                 270

Phe Asp Asn Gln Ser Arg Val Val Asp Phe Gly Lys Asp Tyr Tyr Ala
            275                 280                 285

Leu Gln Thr Phe Phe Asn Thr Asp Pro Thr Tyr Gly Ser Ala Leu Gly
        290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
                340                 345                 350

Pro Ile Leu Asn Ile Ser Asn Ala Gly Pro Trp Ser Arg Phe Ala Thr
            355                 360                 365

Asn Thr Thr Leu Thr Lys Ala Asn Ser Tyr Asn Val Asp Leu Ser Asn
        370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
                420                 425                 430

Ala Ser Ser Phe Phe Leu Asp Arg Gly Asn Ser Lys Val Lys Phe Val
            435                 440                 445

Lys Glu Asn Pro Tyr Phe Thr Asn Arg Met Ser Val Asn Asn Gln Pro
        450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
                500                 505                 510

Met Thr Thr Gly Val Asp Asn Leu Phe Tyr Ile Asp Lys Phe Gln Val
            515                 520                 525

Arg Glu Val Lys
        530

<210> SEQ ID NO 35
<211> LENGTH: 1302
<212> TYPE: DNA
<213> ORGANISM: Corynebacterium glutamicum

<400> SEQUENCE: 35
gtgtgtgggg ctatgcacac agaactttcc agtttgcgcc ctgcgtacca tgtgactcct      60
ccgcagggca ggctcaatga tcccaacgga atgtacgtcg atggcgatac cctccacgtc     120
tactaccagc acgatccagg tttccccttc gcaccaaagc gcaccggctg ggctcacacc     180
accacgccgt tgaccggacc gcagcgattg cagtggacgc acctgcccga cgctctttac     240
```

```
ccggatgcat cctatgacct ggatggatgc tattccggtg agccgtatt tactgacggc    300 acacttaaac ttttctacac cggcaaccta aaaattgacg gcaagcgccg cgccacccaa    360
aacctcgtcg aagtcgagga cccaactggg ctgatgggcg gcattcatcg ccgttcgcct    420
aaaaatccgc ttatcgacgg acccgccagc ggtttcacac cccattaccg cgatcccatg    480
atcagccctg atggtgatgg ttggaaaatg gttcttgggg cccaacgcga aaacctcacc    540
ggtgcagcgg ttctataccg ctcgacagat cttgaaaact gggaattctc cggtgaaatc    600
acctttgacc tcagtgatgc acaacctggt tctgctcctg atctcgttcc cggtggctac    660
atgtgggaat gccccaacct ttttacgctt cgcgatgaag aaactggcga agatctcgac    720
gtgctgattt tctgtccaca aggattggac cgaatccacg atgaggttac tcactacgca    780
agctctgacc agtgcggata tgtcgtcggc aagcttgaag gaacgacctt ccgcgtcttg    840
cgaggattca gcgagctgga tttcggccat gaattctacg caccgcaggt tgcagtaaac    900
ggttctgatg cctggctcgt gggctggatg gggctgcccg cgcaggatga tcacccaaca    960
gttgcacggg aaggatgggt gcactgcctg actgtgcccc gcaagcttca tttgcgcaac   1020
cacgcgatct atcaagagct tcttctccca gaggggagt caggggtaat cagatctgta   1080
ttaggttctg aacctgtccg agtagacatc cgaggcaata tttccctcga gtgggatggt   1140
gtccgtttgt ctgtggatcg tggtggtgat cgtcgcgtag ctgaggtaaa acctggcgaa   1200
ttagtgatcg cggacgataa tacagccatt gagataactg caggtgatgg acaggtttca   1260
ttcgctttcc gggctttcaa aggtgacact attgagagat aa                     1302
```

<210> SEQ ID NO 36
<211> LENGTH: 433
<212> TYPE: PRT
<213> ORGANISM: Corynebacterium glutamicum

<400> SEQUENCE: 36

```
Met Cys Gly Ala Met His Thr Glu Leu Ser Ser Leu Arg Pro Ala Tyr
1               5                   10                  15

His Val Thr Pro Pro Gln Gly Arg Leu Asn Asp Pro Asn Gly Met Tyr
            20                  25                  30

Val Asp Gly Asp Thr Leu His Val Tyr Tyr Gln His Asp Pro Gly Phe
        35                  40                  45

Pro Phe Ala Pro Lys Arg Thr Gly Trp Ala His Thr Thr Pro Leu
    50                  55                  60

Thr Gly Pro Gln Arg Leu Gln Trp Thr His Leu Pro Asp Ala Leu Tyr
65                  70                  75                  80

Pro Asp Ala Ser Tyr Asp Leu Asp Gly Cys Tyr Ser Gly Gly Ala Val
                85                  90                  95

Phe Thr Asp Gly Thr Leu Lys Leu Phe Tyr Thr Gly Asn Leu Lys Ile
            100                 105                 110

Asp Gly Lys Arg Arg Ala Thr Gln Asn Leu Val Glu Val Glu Asp Pro
        115                 120                 125

Thr Gly Leu Met Gly Gly Ile His Arg Arg Ser Pro Lys Asn Pro Leu
    130                 135                 140

Ile Asp Gly Pro Ala Ser Gly Phe Thr Pro His Tyr Arg Asp Pro Met
145                 150                 155                 160

Ile Ser Pro Asp Gly Asp Gly Trp Lys Met Val Leu Gly Ala Gln Arg
                165                 170                 175

Glu Asn Leu Thr Gly Ala Ala Val Leu Tyr Arg Ser Thr Asp Leu Glu
            180                 185                 190
```

Asn Trp Glu Phe Ser Gly Glu Ile Thr Phe Asp Leu Ser Asp Ala Gln
            195                 200                 205

Pro Gly Ser Ala Pro Asp Leu Val Pro Gly Gly Tyr Met Trp Glu Cys
            210                 215                 220

Pro Asn Leu Phe Thr Leu Arg Asp Glu Glu Thr Gly Glu Asp Leu Asp
225                 230                 235                 240

Val Leu Ile Phe Cys Pro Gln Gly Leu Asp Arg Ile His Asp Glu Val
            245                 250                 255

Thr His Tyr Ala Ser Ser Asp Gln Cys Gly Tyr Val Val Gly Lys Leu
            260                 265                 270

Glu Gly Thr Thr Phe Arg Val Leu Arg Gly Phe Ser Glu Leu Asp Phe
            275                 280                 285

Gly His Glu Phe Tyr Ala Pro Gln Val Ala Val Asn Gly Ser Asp Ala
            290                 295                 300

Trp Leu Val Gly Trp Met Gly Leu Pro Ala Gln Asp Asp His Pro Thr
305                 310                 315                 320

Val Ala Arg Glu Gly Trp Val His Cys Leu Thr Val Pro Arg Lys Leu
            325                 330                 335

His Leu Arg Asn His Ala Ile Tyr Gln Glu Leu Leu Pro Glu Gly
            340                 345                 350

Glu Ser Gly Val Ile Arg Ser Val Leu Gly Ser Glu Pro Val Arg Val
            355                 360                 365

Asp Ile Arg Gly Asn Ile Ser Leu Glu Trp Asp Gly Val Arg Leu Ser
370                 375                 380

Val Asp Arg Gly Gly Asp Arg Arg Val Ala Glu Val Lys Pro Gly Glu
385                 390                 395                 400

Leu Val Ile Ala Asp Asp Asn Thr Ala Ile Glu Ile Thr Ala Gly Asp
            405                 410                 415

Gly Gln Val Ser Phe Ala Phe Arg Ala Phe Lys Gly Asp Thr Ile Glu
            420                 425                 430

Arg

<210> SEQ ID NO 37
<211> LENGTH: 1473
<212> TYPE: DNA
<213> ORGANISM: Leuconostoc mesenteroides

<400> SEQUENCE: 37
atggaaattc aaaacaaagc aatgttgatc acttatgctg attcgttggg caaaaactta      60
aaagatgttc atcaagtctt gaaagaagat attggagatg cgattggtgg ggttcatttg     120 ttgccttttct tcccttcaac aggtgatcgc ggttttgcgc cagccgatta tactcgtgtt     180
gatgccgcat tggtgattg gcagatgtc gaagcattgg gtgaagaata ctatttgatg     240
tttgacttca tgattaacca tatttctcgt gaatcagtga tgtatcaaga ttttaagaag     300
aatcatgacg attcaaagta taagatttc tttattcgtt gggaaaagtt ctgggcaaag     360
gccggcgaaa accgtccaac acaagccgat gttgacttaa tttacaagcg taaagataag     420
gcaccaacgc aagaaatcac ttttgatgat ggcacaacag aaaacttgtg gaatactttt     480
ggtgaagaac aaattgacat tgatgttaat tcagccattg ccaaggaatt tattaagaca     540
acccttgaag acatggtaaa acatggtgct aacttgattc gtttggatgc ctttgcgtat     600
gcagttaaaa aagttgacac aaatgacttc ttcgttgagc cagaaatctg ggacactttg     660
aatgaagtac gtgaaatttt gacaccatta aaggctgaaa ttttaccaga aattcatgaa     720

```
cattactcaa tccctaaaaa gatcaatgat catggttact tcacctatga ctttgcatta    780
ccaatgacaa cgctttacac attgtattca ggtaagacaa atcaattggc aaagtggttg    840
aagatgtcac caatgaagca attcacaaca ttggacacgc atgatggtat tggtgtcgtt    900
gatgcccgtg atattctaac tgatgatgaa attgactacg cttctgaaca actttacaag    960
gttggcgcga atgtcaaaaa gacatattca tctgcttcat acaacaacct tgatatttac   1020
caaattaact caactattta ttcagcattg ggaaatgatg atgcagcata cttgttgagt   1080
cgtgtcttcc aagtctttgc gcctggaatt ccacaaattt attacgttgg tttgttggca   1140
ggtgaaaacg atatcgcgct tttggagtca actaaagaag gtcgtaatat taaccgtcat   1200
tactatacgc gtgaagaagt taagtcagaa gttaagcgac cagttgttgc taacttattg   1260
aagctattgt catggcgtaa tgaaagccct gcatttgatt tggctggctc aatcacagtt   1320
gacacgccaa ctgatacaac aattgtggtg acacgtcaag atgaaaatgg tcaaaacaaa   1380
gctgtattaa cagccgatgc ggccaacaaa acttttgaaa tcgttgagaa tggtcaaact   1440
gttatgagca gtgataattt gactcagaac taa                                1473
```

<210> SEQ ID NO 38
<211> LENGTH: 490
<212> TYPE: PRT
<213> ORGANISM: Leuconostoc mesenteroides

<400> SEQUENCE: 38

```
Met Glu Ile Gln Asn Lys Ala Met Leu Ile Thr Tyr Ala Asp Ser Leu
1               5                   10                  15

Gly Lys Asn Leu Lys Asp Val His Gln Val Leu Lys Glu Asp Ile Gly
            20                  25                  30

Asp Ala Ile Gly Gly Val His Leu Leu Pro Phe Phe Pro Ser Thr Gly
        35                  40                  45

Asp Arg Gly Phe Ala Pro Ala Asp Tyr Thr Arg Val Asp Ala Ala Phe
    50                  55                  60

Gly Asp Trp Ala Asp Val Glu Ala Leu Gly Glu Glu Tyr Tyr Leu Met
65                  70                  75                  80

Phe Asp Phe Met Ile Asn His Ile Ser Arg Glu Ser Val Met Tyr Gln
                85                  90                  95

Asp Phe Lys Lys Asn His Asp Asp Ser Lys Tyr Lys Asp Phe Phe Ile
            100                 105                 110

Arg Trp Glu Lys Phe Trp Ala Lys Ala Gly Glu Asn Arg Pro Thr Gln
        115                 120                 125

Ala Asp Val Asp Leu Ile Tyr Lys Arg Lys Asp Lys Ala Pro Thr Gln
    130                 135                 140

Glu Ile Thr Phe Asp Asp Gly Thr Thr Glu Asn Leu Trp Asn Thr Phe
145                 150                 155                 160

Gly Glu Glu Gln Ile Asp Ile Asp Val Asn Ser Ala Ile Ala Lys Glu
                165                 170                 175

Phe Ile Lys Thr Thr Leu Glu Asp Met Val Lys His Gly Ala Asn Leu
            180                 185                 190

Ile Arg Leu Asp Ala Phe Ala Tyr Ala Val Lys Lys Val Asp Thr Asn
        195                 200                 205

Asp Phe Phe Val Glu Pro Glu Ile Trp Asp Thr Leu Asn Glu Val Arg
    210                 215                 220

Glu Ile Leu Thr Pro Leu Lys Ala Glu Ile Leu Pro Glu Ile His Glu
225                 230                 235                 240

His Tyr Ser Ile Pro Lys Lys Ile Asn Asp His Gly Tyr Phe Thr Tyr
```

```
                    245                 250                 255
Asp Phe Ala Leu Pro Met Thr Thr Leu Tyr Thr Leu Tyr Ser Gly Lys
            260                 265                 270

Thr Asn Gln Leu Ala Lys Trp Leu Lys Met Ser Pro Met Lys Gln Phe
        275                 280                 285

Thr Thr Leu Asp Thr His Asp Gly Ile Gly Val Val Asp Ala Arg Asp
    290                 295                 300

Ile Leu Thr Asp Asp Glu Ile Asp Tyr Ala Ser Glu Gln Leu Tyr Lys
305                 310                 315                 320

Val Gly Ala Asn Val Lys Lys Thr Tyr Ser Ser Ala Ser Tyr Asn Asn
                325                 330                 335

Leu Asp Ile Tyr Gln Ile Asn Ser Thr Tyr Tyr Ser Ala Leu Gly Asn
            340                 345                 350

Asp Asp Ala Ala Tyr Leu Leu Ser Arg Val Phe Gln Val Phe Ala Pro
        355                 360                 365

Gly Ile Pro Gln Ile Tyr Tyr Val Gly Leu Leu Ala Gly Glu Asn Asp
    370                 375                 380

Ile Ala Leu Leu Glu Ser Thr Lys Glu Gly Arg Asn Ile Asn Arg His
385                 390                 395                 400

Tyr Tyr Thr Arg Glu Glu Val Lys Ser Glu Val Lys Arg Pro Val Val
                405                 410                 415

Ala Asn Leu Leu Lys Leu Leu Ser Trp Arg Asn Glu Ser Pro Ala Phe
            420                 425                 430

Asp Leu Ala Gly Ser Ile Thr Val Asp Thr Pro Thr Asp Thr Thr Ile
        435                 440                 445

Val Val Thr Arg Gln Asp Glu Asn Gly Gln Asn Lys Ala Val Leu Thr
    450                 455                 460

Ala Asp Ala Ala Asn Lys Thr Phe Glu Ile Val Glu Asn Gly Gln Thr
465                 470                 475                 480

Val Met Ser Ser Asp Asn Leu Thr Gln Asn
                485                 490

<210> SEQ ID NO 39
<211> LENGTH: 1515
<212> TYPE: DNA
<213> ORGANISM: Bifidobacterium adolescentis

<400> SEQUENCE: 39
atgaaaaaca aggtgcagct catcacttac gccgaccgcc ttggcgacgg caccatcaag      60
tcgatgaccg acattctgcg caccgcttc gacggcgtgt acgacggcgt tcacatcctg     120
ccgttcttca ccccgttcga cggcgccgac gcaggcttcg acccgatcga ccacaccaag     180
gtcgacgaac gtctcggcag ctgggacgac gtcgccgaac tctccaagac ccacaacatc     240
atggtcgacg ccatcgtcaa ccacatgagt tgggaatcca agcagttcca ggacgtgctg     300
gccaagggcg aggagtccga atactatccg atgttcctca ccatgagctc cgtgttcccg     360
aacggcgcca ccgaagagga cctggccggc atctaccgtc gcgtccgggg cctgccgttc     420
acccactaca gttcgccgg caagaccgc ctcgtgtggg tcagcttcac cccgcagcag     480
gtggacatcg acaccgattc gacaagggt tgggaatacc tcatgtcgat tttcgaccag     540
atggccgcct ctcacgtcag ctacatccgc ctcgacgccg tcggctatgg cgccaaggaa     600
gccggcacca gctgcttcat gaccccgaag accttcaagc tgatctcccg tctgcgtgag     660
gaaggcgtca agcgcggtct ggaaatcctc atcgaagtgc actcctacta caagaagcag     720
gtcgaaatcg catccaaggt ggaccgcgtc tacgacttcg ccctgcctcc gctgctgctg     780
```

-continued

```
cacgcgctga gcaccggcca cgtcgagccc gtcgcccact ggaccgacat acgcccgaac   840
aacgccgtca ccgtgctcga tacgcacgac ggcatcggcg tgatcgacat cggctccgac   900
cagctcgacc gctcgctcaa gggtctcgtg ccggatgagg acgtggacaa cctcgtcaac   960
accatccacg ccaacaccca cggcgaatcc caggcagcca ctggcgccgc cgcatccaat  1020
ctcgacctct accaggtcaa cagcacctac tattcggcgc tcgggtgcaa cgaccagcac  1080
tacatcgccg cccgcgcggt gcagttcttc ctgccgggcg tgccgcaagt ctactacgtc  1140
ggcgcgctcg ccggcaagaa cgacatggag ctgctgcgta agacgaataa cggccgcgac  1200
atcaatcgcc attactactc caccgcggaa atcgacgaga acctcaagcg tccggtcgtc  1260
aaggccctga cgcgctcgc caagttccgc aacgagctcg acgcgttcga cggcacgttc  1320
tcgtacacca ccgatgacga cacgtccatc agcttcacct ggcgcggcga aaccagccag  1380
gccacgctga cgttcgagcc gaagcgcggt ctcggtgtgg acaacactac gccggtcgcc  1440
atgttggaat gggaggattc cgcgggagac caccgttcgg atgatctgat cgccaatccg  1500
cctgtcgtcg cctga                                                   1515
```

<210> SEQ ID NO 40
<211> LENGTH: 504
<212> TYPE: PRT
<213> ORGANISM: Bifidobacterium adolescentis

<400> SEQUENCE: 40

```
Met Lys Asn Lys Val Gln Leu Ile Thr Tyr Ala Asp Arg Leu Gly Asp
1               5                   10                  15

Gly Thr Ile Lys Ser Met Thr Asp Ile Leu Arg Thr Arg Phe Asp Gly
            20                  25                  30

Val Tyr Asp Gly Val His Ile Leu Pro Phe Phe Thr Pro Phe Asp Gly
        35                  40                  45

Ala Asp Ala Gly Phe Asp Pro Ile Asp His Thr Lys Val Asp Glu Arg
    50                  55                  60

Leu Gly Ser Trp Asp Asp Val Ala Glu Leu Ser Lys Thr His Asn Ile
65                  70                  75                  80

Met Val Asp Ala Ile Val Asn His Met Ser Trp Glu Ser Lys Gln Phe
                85                  90                  95

Gln Asp Val Leu Ala Lys Gly Glu Glu Ser Glu Tyr Tyr Pro Met Phe
            100                 105                 110

Leu Thr Met Ser Ser Val Phe Pro Asn Gly Ala Thr Glu Glu Asp Leu
        115                 120                 125

Ala Gly Ile Tyr Arg Pro Arg Pro Gly Leu Pro Phe Thr His Tyr Lys
    130                 135                 140

Phe Ala Gly Lys Thr Arg Leu Val Trp Val Ser Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ala Ala Ser His Val Ser Tyr Ile Arg Leu Asp
            180                 185                 190

Ala Val Gly Tyr Gly Ala Lys Glu Ala Gly Thr Ser Cys Phe Met Thr
        195                 200                 205

Pro Lys Thr Phe Lys Leu Ile Ser Arg Leu Arg Glu Glu Gly Val Lys
    210                 215                 220

Arg Gly Leu Glu Ile Leu Ile Glu Val His Ser Tyr Tyr Lys Lys Gln
225                 230                 235                 240
```

```
Val Glu Ile Ala Ser Lys Val Asp Arg Val Tyr Asp Phe Ala Leu Pro
            245                 250                 255

Pro Leu Leu Leu His Ala Leu Ser Thr Gly His Val Glu Pro Val Ala
        260                 265                 270

His Trp Thr Asp Ile Arg Pro Asn Asn Ala Val Thr Val Leu Asp Thr
        275                 280                 285

His Asp Gly Ile Gly Val Ile Asp Ile Gly Ser Asp Gln Leu Asp Arg
        290                 295                 300

Ser Leu Lys Gly Leu Val Pro Asp Glu Asp Val Asp Asn Leu Val Asn
305                 310                 315                 320

Thr Ile His Ala Asn Thr His Gly Glu Ser Gln Ala Ala Thr Gly Ala
                325                 330                 335

Ala Ala Ser Asn Leu Asp Leu Tyr Gln Val Asn Ser Thr Tyr Tyr Ser
            340                 345                 350

Ala Leu Gly Cys Asn Asp Gln His Tyr Ile Ala Ala Arg Ala Val Gln
        355                 360                 365

Phe Phe Leu Pro Gly Val Pro Gln Val Tyr Tyr Val Gly Ala Leu Ala
        370                 375                 380

Gly Lys Asn Asp Met Glu Leu Leu Arg Lys Thr Asn Asn Gly Arg Asp
385                 390                 395                 400

Ile Asn Arg His Tyr Tyr Ser Thr Ala Glu Ile Asp Glu Asn Leu Lys
                405                 410                 415

Arg Pro Val Val Lys Ala Leu Asn Ala Leu Ala Lys Phe Arg Asn Glu
            420                 425                 430

Leu Asp Ala Phe Asp Gly Thr Phe Ser Tyr Thr Thr Asp Asp Thr
        435                 440                 445

Ser Ile Ser Phe Thr Trp Arg Gly Thr Ser Gln Ala Thr Leu Thr
        450                 455                 460

Phe Glu Pro Lys Arg Gly Leu Gly Val Asp Thr Thr Pro Val Ala
465                 470                 475                 480

Met Leu Glu Trp Glu Asp Ser Ala Gly Asp His Arg Ser Asp Asp Leu
                485                 490                 495

Ile Ala Asn Pro Pro Val Val Ala
            500

<210> SEQ ID NO 41
<211> LENGTH: 927
<212> TYPE: DNA
<213> ORGANISM: Agrobacterium tumefaciens

<400> SEQUENCE: 41
atgatcctgt gttgtggtga agccctgatc gacatgctgc cccggcagac gacgctgggt    60
gaggcgggct ttgccccta cgcaggcgga gcggtcttca acacggcaat tgcgctgggg   120
cgtcttggcg tcccttcagc cttttttacc ggtctttccg acgacatgat gggcgatatc   180
ctgcgggaga ccctgcgggc cagcaaggtg gatttcagct attgcgccac cctgtcgcgc   240
cccaccacca ttgcgttcgt taagctggtt gatggccatg cgacctacgc ttttttacgac   300 gagaacaccg ccggccggat gatcaccgag gccgaacttc cggccttggg agcggattgc   360
gaagcgctgc atttcggcgc catcagcctt attcccgaac cctgcggcag cacctatgag   420
gcgctgatga cgcgcgagca tgagaccgc gtcatctcgc tcgatccgaa cattcgtccc   480
ggcttcatcc agaacaagca gtcgcacatg cccgcatcc gccgcatggc ggcgatgtct   540
gacatcgtca agttctcgga tgaggacctg gcgtggttcg gtctggaagg cgacgaggac   600
acgcttgccc gccactggct gcaccacggt gcaaaactcg tcgttgtcac ccgtggcgcc   660
```

```
aagggtgccg tgggttacag cgccaatctc aaggtggaag tggcctccga gcgcgtcgaa    720
gtggtcgata cggtcggcgc cggcgatacg ttcgatgccg gcattcttgc ttcgctgaaa    780
atgcagggcc tgctgaccaa agcgcaggtg gcttcgctga gcgaagagca gatcagaaaa    840
gctttggcgc ttggcgcgaa agccgctgcg gtcactgtct cgcgggctgg cgcaaatccg    900
cctttcgcgc atgaaatcgg tttgtga                                        927
```

<210> SEQ ID NO 42
<211> LENGTH: 308
<212> TYPE: PRT
<213> ORGANISM: Agrobacterium tumefaciens

<400> SEQUENCE: 42

```
Met Ile Leu Cys Cys Gly Glu Ala Leu Ile Asp Met Leu Pro Arg Gln
1               5                   10                  15

Thr Thr Leu Gly Glu Ala Gly Phe Ala Pro Tyr Ala Gly Gly Ala Val
            20                  25                  30

Phe Asn Thr Ala Ile Ala Leu Gly Arg Leu Gly Val Pro Ser Ala Phe
        35                  40                  45

Phe Thr Gly Leu Ser Asp Asp Met Met Gly Asp Ile Leu Arg Glu Thr
    50                  55                  60

Leu Arg Ala Ser Lys Val Asp Phe Ser Tyr Cys Ala Thr Leu Ser Arg
65                  70                  75                  80

Pro Thr Thr Ile Ala Phe Val Lys Leu Val Asp Gly His Ala Thr Tyr
                85                  90                  95

Ala Phe Tyr Asp Glu Asn Thr Ala Gly Arg Met Ile Thr Glu Ala Glu
            100                 105                 110

Leu Pro Ala Leu Gly Ala Asp Cys Glu Ala Leu His Phe Gly Ala Ile
        115                 120                 125

Ser Leu Ile Pro Glu Pro Cys Gly Ser Thr Tyr Glu Ala Leu Met Thr
    130                 135                 140

Arg Glu His Glu Thr Arg Val Ile Ser Leu Asp Pro Asn Ile Arg Pro
145                 150                 155                 160

Gly Phe Ile Gln Asn Lys Gln Ser His Met Ala Arg Ile Arg Arg Met
                165                 170                 175

Ala Ala Met Ser Asp Ile Val Lys Phe Ser Asp Glu Asp Leu Ala Trp
            180                 185                 190

Phe Gly Leu Glu Gly Asp Glu Asp Thr Leu Ala Arg His Trp Leu His
        195                 200                 205

His Gly Ala Lys Leu Val Val Thr Arg Gly Ala Lys Gly Ala Val
    210                 215                 220

Gly Tyr Ser Ala Asn Leu Lys Val Glu Val Ala Ser Glu Arg Val Glu
225                 230                 235                 240

Val Val Asp Thr Val Gly Ala Gly Asp Thr Phe Asp Ala Gly Ile Leu
                245                 250                 255

Ala Ser Leu Lys Met Gln Gly Leu Leu Thr Lys Ala Gln Val Ala Ser
            260                 265                 270

Leu Ser Glu Glu Gln Ile Arg Lys Ala Leu Ala Leu Gly Ala Lys Ala
        275                 280                 285

Ala Ala Val Thr Val Ser Arg Ala Gly Ala Asn Pro Pro Phe Ala His
    290                 295                 300

Glu Ile Gly Leu
305
```

<210> SEQ ID NO 43
<211> LENGTH: 1404
<212> TYPE: DNA
<213> ORGANISM: Streptococcus mutans

<400> SEQUENCE: 43

| | | | | | |
|---|---|---|---|---|---|
| cagctgatta | tgcgtcagtt | gaaaccctcg | cttcttcagg | aactgttgct | gtaggtgata | 60 |
| gcttacttga | agttaaaaaa | taagaaatat | tatcagaaag | accgtaaggt | cttttttgact | 120 |
| gcttaaaaga | ttcagtaaca | atagtattaa | agccttttgg | ctaactaata | cttgaaattt | 180 |
| agcaaattat | gatataatgt | taagtagtcc | ttaagggtag | attaagggta | ttcaaatcca | 240 |
| aaaattgatt | tggtaagtta | agtaaaatat | aagaggttta | ttatgtctaa | attatatggc | 300 |
| agcatcgaag | ctggcggaac | aaaatttgtc | tgtgctgtag | gtgatgaaaa | ttttcaaatt | 360 |
| ttagaaaaag | ttcagttccc | aacaacaaca | cctatgaaa | caatagaaaa | aacagttgct | 420 |
| ttctttaaaa | aatttgaagc | tgatttagcc | agtgttgcca | ttggttcttt | tggccctatt | 480 |
| gatattgatc | aaaattcaga | cacttatggt | tacattactt | caacaccaaa | gccaaactgg | 540 |
| gctaacgttg | attttgtcgg | cttaatttct | aaagatttta | aaattccatt | ttactttacg | 600 |
| acagatgtta | attcttctgc | ttatggggaa | acaattgctc | gttcaaatgt | taaaagtctg | 660 |
| gtttattata | ctattggaac | aggcattgga | gcaggggcta | ttcaaaatgg | cgaattcatt | 720 |
| ggcggtatgg | gacatacgga | agctggacac | gtttacatgg | ctccgcatcc | caatgatgtt | 780 |
| catcatggtt | ttgtaggcac | ctgtcctttc | cataaaggct | gtttagaagg | acttgcagcg | 840 |
| ggtcctagct | tagaggctcg | tactggtatt | cgtggtgagt | taattgagca | aaactcagaa | 900 |
| gtttgggata | ttcaggcata | ctacattgct | caggcggcta | ttcaagcgac | tgtcctttat | 960 |
| cgtccgcaag | tcattgtatt | tggcggaggc | gttatggcac | aagaacatat | gctcaatcgg | 1020 |
| gttcgtgaaa | aatttacttc | acttttgaat | gactatcttc | cagttccaga | tgttaaagat | 1080 |
| tatattgtga | caccagctgt | tgcagaaaat | ggttcagcaa | cattgggaaa | tctcgcttta | 1140 |
| gctaaaaaga | tagcagcgcg | ttaattaaaa | atgaattgga | agattaaagc | accttctaat | 1200 |
| attcaatatt | aaactgttag | aatttacgtg | aacgaaattt | tcattttatg | aggataatga | 1260 |
| agtgaatata | attactcttg | atttcctctg | aaactagata | gtggtatatt | gaaaaacaga | 1320 |
| aaggagaaca | ctatggaagg | acctttgttt | ttacaatcac | aaatgcataa | aaaaatctgg | 1380 |
| ggcggcaatc | ggctcagaaa | agaa | | | | 1404 |

<210> SEQ ID NO 44
<211> LENGTH: 293
<212> TYPE: PRT
<213> ORGANISM: Streptococcus mutans

<400> SEQUENCE: 44

Met Ser Lys Leu Tyr Gly Ser Ile Glu Ala Gly Gly Thr Lys Phe Val
1               5                   10                  15

Cys Ala Val Gly Asp Glu Asn Phe Gln Ile Leu Glu Lys Val Gln Phe
                20                  25                  30

Pro Thr Thr Thr Pro Tyr Glu Thr Ile Glu Lys Thr Val Ala Phe Phe
            35                  40                  45

Lys Lys Phe Glu Ala Asp Leu Ala Ser Val Ala Ile Gly Ser Phe Gly
        50                  55                  60

Pro Ile Asp Ile Asp Gln Asn Ser Asp Thr Tyr Gly Tyr Ile Thr Ser
65                  70                  75                  80

Thr Pro Lys Pro Asn Trp Ala Asn Val Asp Phe Val Gly Leu Ile Ser
                85                  90                  95

| | | | | | | | | | | | |
|---|---|---|---|---|---|---|---|---|---|---|---|
| Lys | Asp | Phe | Lys | Ile | Pro | Phe | Tyr | Phe | Thr | Thr | Asp | Val | Asn | Ser | Ser |
| | | | 100 | | | | 105 | | | | 110 | | | | |
| Ala | Tyr | Gly | Glu | Thr | Ile | Ala | Arg | Ser | Asn | Val | Lys | Ser | Leu | Val | Tyr |
| | | | 115 | | | | 120 | | | | 125 | | | | |
| Tyr | Thr | Ile | Gly | Thr | Gly | Ile | Gly | Ala | Gly | Ala | Ile | Gln | Asn | Gly | Glu |
| | | | 130 | | | | 135 | | | | 140 | | | | |
| Phe | Ile | Gly | Gly | Met | Gly | His | Thr | Glu | Ala | Gly | His | Val | Tyr | Met | Ala |
| 145 | | | | | 150 | | | | 155 | | | | | | 160 |
| Pro | His | Pro | Asn | Asp | Val | His | His | Gly | Phe | Val | Gly | Thr | Cys | Pro | Phe |
| | | | | 165 | | | | | 170 | | | | 175 | | |
| His | Lys | Gly | Cys | Leu | Glu | Gly | Leu | Ala | Ala | Gly | Pro | Ser | Leu | Glu | Ala |
| | | | | 180 | | | | 185 | | | | 190 | | | |
| Arg | Thr | Gly | Ile | Arg | Gly | Glu | Leu | Ile | Glu | Gln | Asn | Ser | Glu | Val | Trp |
| | | | | 195 | | | | 200 | | | | 205 | | | |
| Asp | Ile | Gln | Ala | Tyr | Tyr | Ile | Ala | Gln | Ala | Ala | Ile | Gln | Ala | Thr | Val |
| | | | 210 | | | | 215 | | | | 220 | | | | |
| Leu | Tyr | Arg | Pro | Gln | Val | Ile | Val | Phe | Gly | Gly | Val | Met | Ala | Gln |
| 225 | | | | 230 | | | | 235 | | | | | | 240 |
| Glu | His | Met | Leu | Asn | Arg | Val | Arg | Glu | Lys | Phe | Thr | Ser | Leu | Leu | Asn |
| | | | | 245 | | | | 250 | | | | 255 | | | |
| Asp | Tyr | Leu | Pro | Val | Pro | Asp | Val | Lys | Asp | Tyr | Ile | Val | Thr | Pro | Ala |
| | | | 260 | | | | 265 | | | | 270 | | | | |
| Val | Ala | Glu | Asn | Gly | Ser | Ala | Thr | Leu | Gly | Asn | Leu | Ala | Leu | Ala | Lys |
| | | | 275 | | | | 280 | | | | 285 | | | | |
| Lys | Ile | Ala | Ala | Arg |
| | | | 290 | |

<210> SEQ ID NO 45
<211> LENGTH: 915
<212> TYPE: DNA
<213> ORGANISM: Escherichia coli

<400> SEQUENCE: 45

```
atgtcagcca aagtatgggt tttaggggat gcggtcgtag atctcttgcc agaatcagac      60
gggcgcctac tgccttgtcc tggcggcgcg ccagctaacg ttgcggtggg aatcgccaga     120
ttaggcggaa caagtgggtt tataggtcgg gtggggatg atccttttgg tgcgttaatg      180
caaagaacgc tgctaactga gggagtcgat atcacgtatc tgaagcaaga tgaatggcac     240
cggacatcca cggtgcttgt cgatctgaac gatcaagggg aacgttcatt tacgtttatg     300
gtccgcccca gtgccgatct ttttttagag acgacagact tgccctgctg gcacatggc      360
gaatggttac atctctgttc aattgcgttg tctgccgagc cttcgcgtac cagcgcattt     420
actgcgatga cggcgatccg gcatgccgga ggttttgtca gcttcgatcc taatattcgt     480
gaagatctat ggcaagacga gcatttgctc cgcttgtgtt tgcggcaggc gctacaactg     540
gcggatgtcg tcaagctctc ggaagaagaa tggcgactta tcagtggaaa acacagaac      600
gatcaggata tatgcgccct ggcaaaagag tatgagatcg ccatgctgtt ggtgactaaa     660
ggtgcagaag gggtggtggt ctgttatcga ggacaagttc accattttgc tggaatgtct     720
gtgaattgtg tcgatagcac gggggcggga gatgcgttcg ttgccgggtt actcacaggt     780
ctgtcctcta cgggattatc tacagatgag agaaaatgc gacgaattat cgatctcgct      840
caacgttgcg gagcgcttgc agtaacggcg aaggggcaa tgacagcgct gccatgtcga     900
caagaactgg aatag                                                      915
```

<210> SEQ ID NO 46
<211> LENGTH: 304
<212> TYPE: PRT
<213> ORGANISM: Escherichia coli

<400> SEQUENCE: 46

```
Met Ser Ala Lys Val Trp Val Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30

Asn Val Ala Val Gly Ile Ala Arg Leu Gly Gly Thr Ser Gly Phe Ile
        35                  40                  45

Gly Arg Val Gly Asp Asp Pro Phe Gly Ala Leu Met Gln Arg Thr Leu
    50                  55                  60

Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
            100                 105                 110

Asp Leu Pro Cys Trp Arg His Gly Glu Trp Leu His Leu Cys Ser Ile
        115                 120                 125

Ala Leu Ser Ala Glu Pro Ser Arg Thr Ser Ala Phe Thr Ala Met Thr
    130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Leu Arg Leu Cys Leu Arg Gln
                165                 170                 175

Ala Leu Gln Leu Ala Asp Val Val Lys Leu Ser Glu Glu Glu Trp Arg
            180                 185                 190

Leu Ile Ser Gly Lys Thr Gln Asn Asp Gln Asp Ile Cys Ala Leu Ala
        195                 200                 205

Lys Glu Tyr Glu Ile Ala Met Leu Leu Val Thr Lys Gly Ala Glu Gly
    210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
                245                 250                 255

Leu Leu Thr Gly Leu Ser Ser Thr Gly Leu Ser Thr Glu Arg Glu
            260                 265                 270

Met Arg Arg Ile Ile Asp Leu Ala Gln Arg Cys Gly Ala Leu Ala Val
        275                 280                 285

Thr Ala Lys Gly Ala Met Thr Ala Leu Pro Cys Arg Gln Glu Leu Glu
    290                 295                 300
```

<210> SEQ ID NO 47
<211> LENGTH: 924
<212> TYPE: DNA
<213> ORGANISM: Klebsiella pneumoniae

<400> SEQUENCE: 47

```
atgaatggaa aaatctgggt actcggcgat gcggtcgtcg atctcctgcc cgatggagag      60
ggccgcctgc tgcaatgccc cggcggcgcg ccggccaacg tggcggtcgg cgtggcgcgg     120
ctcggcggtg acagcgggtt tatcggccgc gtcggcgacg atcccttcgg ccgtttttatg    180 cgtcacaccc tggcgcagga gcaagtggat gtgaactata tgcgcctcga tgcggcgcag     240
```

```
cgcacctcca cggtggtggt cgatctcgat agccacgggg agcgcacctt tacctttatg    300
gtccgtccga gcgccgacct gttccttcag cccgaggatc tcccgccgtt tgccgccggt    360
cagtggctgc acgtctgctc catcgctctc agcgcggagc cgagccgcag cacgacattc    420
gcggcgatgg aggcgataaa gcgcgccggg ggctatgtca gcttcgaccc caatatccgc    480
agcgacctgt ggcaggatcc gcaggacctt cgcgactgtc tcgaccgggc gctggccctc    540
gccgacgcca taaaactttc ggaagaggag ctggcgttta tcagcggcag cgacgacatc    600
gtcagcggca ccgcccggct gaacgcccgc ttccagccga cgctactgct ggtgacccag    660
ggtaaagcgg gggtccaggc cgccctgcgc gggcaggtta gccacttccc tgcccgcccg    720
gtggtggccg tcgataccac cggcgccggc gatgcctttg tcgccgggct actcgccggc    780
ctcgccgccc acggtatccc ggacaacctc gcagccctgg ctcccgacct cgcgctggcg    840
caaacctgcg gcgccctggc caccaccgcc aaaggcgcca tgaccgccct gccctacagg    900
gacgatcttc agcgctcgct gtga                                           924
```

<210> SEQ ID NO 48
<211> LENGTH: 307
<212> TYPE: PRT
<213> ORGANISM: Klebsiella pneumoniae

<400> SEQUENCE: 48

```
Met Asn Gly Lys Ile Trp Val Leu Gly Asp Ala Val Val Asp Leu Leu
1               5                   10                  15

Pro Asp Gly Glu Gly Arg Leu Leu Gln Cys Pro Gly Gly Ala Pro Ala
            20                  25                  30

Asn Val Ala Val Gly Val Ala Arg Leu Gly Gly Asp Ser Gly Phe Ile
        35                  40                  45

Gly Arg Val Gly Asp Asp Pro Phe Gly Arg Phe Met Arg His Thr Leu
    50                  55                  60

Ala Gln Glu Gln Val Asp Val Asn Tyr Met Arg Leu Asp Ala Ala Gln
65                  70                  75                  80

Arg Thr Ser Thr Val Val Asp Leu Asp Ser His Gly Glu Arg Thr
                85                  90                  95

Phe Thr Phe Met Val Arg Pro Ser Ala Asp Leu Phe Leu Gln Pro Glu
            100                 105                 110

Asp Leu Pro Pro Phe Ala Ala Gly Gln Trp Leu His Val Cys Ser Ile
        115                 120                 125

Ala Leu Ser Ala Glu Pro Ser Arg Ser Thr Thr Phe Ala Ala Met Glu
130                 135                 140

Ala Ile Lys Arg Ala Gly Gly Tyr Val Ser Phe Asp Pro Asn Ile Arg
145                 150                 155                 160

Ser Asp Leu Trp Gln Asp Pro Gln Asp Leu Arg Asp Cys Leu Asp Arg
                165                 170                 175

Ala Leu Ala Leu Ala Asp Ala Ile Lys Leu Ser Glu Glu Glu Leu Ala
            180                 185                 190

Phe Ile Ser Gly Ser Asp Asp Ile Val Ser Gly Thr Ala Arg Leu Asn
        195                 200                 205

Ala Arg Phe Gln Pro Thr Leu Leu Leu Val Thr Gln Gly Lys Ala Gly
    210                 215                 220

Val Gln Ala Ala Leu Arg Gly Gln Val Ser His Phe Pro Ala Arg Pro
225                 230                 235                 240

Val Val Ala Val Asp Thr Thr Gly Ala Gly Asp Ala Phe Val Ala Gly
                245                 250                 255
```

```
Leu Leu Ala Gly Leu Ala Ala His Gly Ile Pro Asp Asn Leu Ala Ala
            260                 265                 270

Leu Ala Pro Asp Leu Ala Leu Ala Gln Thr Cys Gly Ala Leu Ala Thr
        275                 280                 285

Thr Ala Lys Gly Ala Met Thr Ala Leu Pro Tyr Arg Asp Asp Leu Gln
    290                 295                 300

Arg Ser Leu
305

<210> SEQ ID NO 49
<211> LENGTH: 915
<212> TYPE: DNA
<213> ORGANISM: Escherichia coli

<400> SEQUENCE: 49
atgtcagcca aagtatgggt tttaggggat gcggtcgtag atctcttgcc agaatcagac      60
gggcgcctac tgccttgtcc tggcggcgcg ccagctaacg ttgcggtggg aatcgccaga     120
ttaggcggaa caagtgggtt tataggtcgg gtggggatg atccttttgg tgcgttaatg      180
caaagaacgc tgctaactga gggagtcgat atcacgtatc tgaagcaaga tgaatggcac     240
cggacatcca cggtgcttgt cgatctgaac gatcaagggg aacgttcatt tacgtttatg     300
gtccgcccca gtgccgatct tttttagag acgacagact tgccctgctg gcacatggc      360 gaatggttac atctctgttc aattgcgttg tctgccgagc cttcgcgtac cagcgcattt     420
actgcgatga cggcgatccg gcatgccgga ggttttgtca gcttcgatcc taatattcgt     480
gaagatctat ggcaagacga gcatttgctc cgcttgtgtt tgcggcaggc gctacaactg     540
gcggatgtcg tcaagctctc ggaagaagaa tggcgactta cagtggaaa acacagaac      600 gatcaggata tatgcgccct ggcaaaagag tatgagatcg ccatgctgtt ggtgactaaa     660
ggtgcagaag gggtggtggt ctgttatcga ggacaagttc accattttgc tggaatgtct    720
gtgaattgtg tcgatagcac ggggggggga gatgcgttcg ttgccgggtt actcacaggt    780
ctgtcctcta cgggattatc tacagatgag agagaaatgc gacgaattat cgatctcgct    840
caacgttgcg gagcgcttgc agtaacggcg aaaggggcaa tgacagcgct gccatgtcga    900
caagaactgg aatag                                                    915

<210> SEQ ID NO 50
<211> LENGTH: 304
<212> TYPE: PRT
<213> ORGANISM: Escherichia coli

<400> SEQUENCE: 50

Met Ser Ala Lys Val Trp Val Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30

Asn Val Ala Val Gly Ile Ala Arg Leu Gly Gly Thr Ser Gly Phe Ile
        35                  40                  45

Gly Arg Val Gly Asp Asp Pro Phe Gly Ala Leu Met Gln Arg Thr Leu
    50                  55                  60

Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
```

```
                  100                 105                 110
Asp Leu Pro Cys Trp Arg His Gly Glu Trp Leu His Leu Cys Ser Ile
            115                 120                 125

Ala Leu Ser Ala Glu Pro Ser Arg Thr Ser Ala Phe Thr Ala Met Thr
        130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Leu Arg Leu Cys Leu Arg Gln
            165                 170                 175

Ala Leu Gln Leu Ala Asp Val Val Lys Leu Ser Glu Glu Trp Arg
        180                 185                 190

Leu Ile Ser Gly Lys Thr Gln Asn Asp Gln Asp Ile Cys Ala Leu Ala
            195                 200                 205

Lys Glu Tyr Glu Ile Ala Met Leu Leu Val Thr Lys Gly Ala Glu Gly
        210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
                245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
            275                 280                 285

Thr Ala Lys Gly Ala Met Thr Ala Leu Pro Cys Arg Gln Glu Leu Glu
        290                 295                 300

<210> SEQ ID NO 51
<211> LENGTH: 879
<212> TYPE: DNA
<213> ORGANISM: Enterococcus faecalis

<400> SEQUENCE: 51
atgacagaaa aacttttagg aagtatcgaa gccggtggca caaaatttgt atgtggcgtt      60
gggacagatg atttgaccat cgtagaacgt gtcagttttc ccacaacaac cccagaagaa     120
acaatgaaaa agtaataga attttttccaa caatatcctt taaaagcgat tgggattggt     180
tcatttggtc cgattgatat tcacgttgat tctcctacgt atggttatat cacttctaca     240
ccaaaattag cttggcgtaa ctttgacttg ttaggaacta tgaaacaaca ttttgatgtg     300
ccaatggctt ggacaacgga tgtgaatgct gcggcatatg tgagtatgt tgctggaaat     360 gggcaacata catctagttg tgtatattat acaattggaa ctggtgttgg cgctggagcg     420
attcaaaacg gtgagtttat tgaaggcttt agccacccag aaatggggca tgcgttagtt     480
cgtcgtcatc ctgaagatac gtatgcagga aattgtcctt atcatggaga ttgtttagaa     540
gggattgcag caggaccagc agttgaaggt cgttctggta aaaaaggaca tttattggaa     600
gaggatcata aaacttggga attagaagct tattatttag cgcaagcggc gtacaatacg     660 acttttattat tagcgccaga agtgatcatt ttaggtggcg gcgtcatgaa caacgtcat      720 ttgatgccga aagttcgtga aaaatttgct gaattagtca atggatatgt ggaaacaccg     780
cctttagaaa aatacttggt gacgcctctt ttagaagata atccaggaac aatcggttgc     840
tttgccttgg caaaaaaagc tttaatggct caaaaataa                            879

<210> SEQ ID NO 52
<211> LENGTH: 292
<212> TYPE: PRT
```

-continued

<213> ORGANISM: Enterococcus faecalis

<400> SEQUENCE: 52

```
Met Thr Glu Lys Leu Leu Gly Ser Ile Glu Ala Gly Thr Lys Phe
1               5                   10                  15
Val Cys Gly Val Gly Thr Asp Asp Leu Thr Ile Val Glu Arg Val Ser
            20                  25                  30
Phe Pro Thr Thr Thr Pro Glu Glu Thr Met Lys Lys Val Ile Glu Phe
        35                  40                  45
Phe Gln Gln Tyr Pro Leu Lys Ala Ile Gly Ile Gly Ser Phe Gly Pro
    50                  55                  60
Ile Asp Ile His Val Asp Ser Pro Thr Tyr Gly Tyr Ile Thr Ser Thr
65              70                  75                  80
Pro Lys Leu Ala Trp Arg Asn Phe Asp Leu Leu Gly Thr Met Lys Gln
                85                  90                  95
His Phe Asp Val Pro Met Ala Trp Thr Thr Asp Val Asn Ala Ala Ala
            100                 105                 110
Tyr Gly Glu Tyr Val Ala Gly Asn Gly Gln His Thr Ser Ser Cys Val
        115                 120                 125
Tyr Tyr Thr Ile Gly Thr Gly Val Gly Ala Gly Ala Ile Gln Asn Gly
    130                 135                 140
Glu Phe Ile Glu Gly Phe Ser His Pro Glu Met Gly His Ala Leu Val
145                 150                 155                 160
Arg Arg His Pro Glu Asp Thr Tyr Ala Gly Asn Cys Pro Tyr His Gly
                165                 170                 175
Asp Cys Leu Glu Gly Ile Ala Ala Gly Pro Ala Val Glu Gly Arg Ser
            180                 185                 190
Gly Lys Lys Gly His Leu Leu Glu Glu Asp His Lys Thr Trp Glu Leu
        195                 200                 205
Glu Ala Tyr Tyr Leu Ala Gln Ala Ala Tyr Asn Thr Thr Leu Leu Leu
    210                 215                 220
Ala Pro Glu Val Ile Ile Leu Gly Gly Gly Val Met Lys Gln Arg His
225                 230                 235                 240
Leu Met Pro Lys Val Arg Glu Lys Phe Ala Glu Leu Val Asn Gly Tyr
                245                 250                 255
Val Glu Thr Pro Pro Leu Glu Lys Tyr Leu Val Thr Pro Leu Leu Glu
            260                 265                 270
Asp Asn Pro Gly Thr Ile Gly Cys Phe Ala Leu Ala Lys Lys Ala Leu
        275                 280                 285
Met Ala Gln Lys
    290
```

<210> SEQ ID NO 53
<211> LENGTH: 1458
<212> TYPE: DNA
<213> ORGANISM: Saccharomyces cerevisiae

<400> SEQUENCE: 53

```
atggttcatt taggtccaaa gaaaccacag gctagaaagg gttccatggc tgatgtgccc      60
aaggaattga tggatgaaat tcatcagttg gaagatatgt ttacagttga cagcgagacc     120
ttgagaaagg ttgttaagca ctttatcgac gaattgaata aggtttttgac aaagaaggga     180 ggtaacattc caatgattcc cggttgggtc atggaattcc aacaggtaa agaatctggt      240 aactatttgg ccattgattt gggtggtact aacttaagag tcgtgttggt caagttgagc     300
ggtaaccata cctttgacac cactcaatcc aagtataaac taccacatga catgagaacc     360
```

```
actaagcacc aagaggagtt atggtccttt attgccgact ctttgaagga ctttatggtc    420
gagcaagaat tgctaaacac caaggacacc ttaccattag gtttcacctt ctcgtaccca    480
gcttcccaaa acaagattaa cgaaggtatt ttgcaaagat ggaccaaggg tttcgatatt    540
ccaaatgtcg aaggccacga tgtcgtccca ttgctacaaa acgaaatttc caagagagag    600
ttgcctattg aaattgtagc attgattaat gatactgttg gtactttaat tgcctcatac    660
tacactgacc cagagactaa gatgggtgtg attttcggta ctggtgtcaa cggtgctttc    720
tatgatgttg tttccgatat cgaaaagttg gagggcaaat tagcagacga tattccaagt    780
aactctccaa tggctatcaa ttgtgaatat ggttccttcg ataatgaaca tttggtcttg    840
ccaagaacca agtacgatgt tgctgtcgac gaacaatctc caagacctgg tcaacaagct    900
tttgaaaaga tgacctccgg ttactacttg ggtgaattgt tgcgtctagt gttacttgaa    960
ttaaacgaga agggcttgat gttgaaggat caagatctaa gcaagttgaa acaaccatac   1020
atcatggata cctcctaccc agcaagaatc gaggatgatc catttgaaaa cttggaagat   1080
actgatgaca tcttccaaaa ggactttggt gtcaagacca ctctgccaga acgtaagttg   1140
attagaagac tttgtgaatt gatcggtacc agagctgcta gattagctgt ttgtggtatt   1200
gccgctattt gccaaaagag aggttacaag actggtcaca ttgccgctga cggttctgtc   1260
tataacaaat acccaggttt caaggaagcc gccgctaagg gtttgagaga tatctatgga   1320
tggactggtg acgcaagcaa agatccaatt acgattgttc cagctgagga tggttcaggt   1380
gcaggtgctc tgttattgc tgcattgtcc gaaaaaagaa ttgccgaagg taagtctctt   1440
ggtatcattg gcgcttaa                                                 1458
```

<210> SEQ ID NO 54
<211> LENGTH: 485
<212> TYPE: PRT
<213> ORGANISM: Saccharomyces cerevisiae

<400> SEQUENCE: 54

```
Met Val His Leu Gly Pro Lys Lys Pro Gln Ala Arg Lys Gly Ser Met
1               5                   10                  15

Ala Asp Val Pro Lys Glu Leu Met Asp Glu Ile His Gln Leu Glu Asp
                20                  25                  30

Met Phe Thr Val Asp Ser Glu Thr Leu Arg Lys Val Lys His Phe
            35                  40                  45

Ile Asp Glu Leu Asn Lys Gly Leu Thr Lys Lys Gly Gly Asn Ile Pro
        50                  55                  60

Met Ile Pro Gly Trp Val Met Glu Phe Pro Thr Gly Lys Glu Ser Gly
65                  70                  75                  80

Asn Tyr Leu Ala Ile Asp Leu Gly Gly Thr Asn Leu Arg Val Val Leu
                85                  90                  95

Val Lys Leu Ser Gly Asn His Thr Phe Asp Thr Gln Ser Lys Tyr
            100                 105                 110

Lys Leu Pro His Asp Met Arg Thr Thr Lys His Gln Glu Glu Leu Trp
        115                 120                 125

Ser Phe Ile Ala Asp Ser Leu Lys Asp Phe Met Val Glu Gln Glu Leu
    130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175
```

Gly Phe Asp Ile Pro Asn Val Glu Gly His Asp Val Val Pro Leu Leu
              180                 185                 190

Gln Asn Glu Ile Ser Lys Arg Glu Leu Pro Ile Glu Ile Val Ala Leu
          195                 200                 205

Ile Asn Asp Thr Val Gly Thr Leu Ile Ala Ser Tyr Tyr Thr Asp Pro
      210                 215                 220

Glu Thr Lys Met Gly Val Ile Phe Gly Thr Gly Val Asn Gly Ala Phe
225                 230                 235                 240

Tyr Asp Val Val Ser Asp Ile Glu Lys Leu Glu Gly Lys Leu Ala Asp
              245                 250                 255

Asp Ile Pro Ser Asn Ser Pro Met Ala Ile Asn Cys Glu Tyr Gly Ser
          260                 265                 270

Phe Asp Asn Glu His Leu Val Leu Pro Arg Thr Lys Tyr Asp Val Ala
      275                 280                 285

Val Asp Glu Gln Ser Pro Arg Pro Gly Gln Gln Ala Phe Glu Lys Met
290                 295                 300

Thr Ser Gly Tyr Tyr Leu Gly Glu Leu Leu Arg Leu Val Leu Leu Glu
305                 310                 315                 320

Leu Asn Glu Lys Gly Leu Met Leu Lys Asp Gln Asp Leu Ser Lys Leu
              325                 330                 335

Lys Gln Pro Tyr Ile Met Asp Thr Ser Tyr Pro Ala Arg Ile Glu Asp
          340                 345                 350

Asp Pro Phe Glu Asn Leu Glu Asp Thr Asp Ile Phe Gln Lys Asp
      355                 360                 365

Phe Gly Val Lys Thr Thr Leu Pro Glu Arg Lys Leu Ile Arg Arg Leu
370                 375                 380

Cys Glu Leu Ile Gly Thr Arg Ala Ala Arg Leu Ala Val Cys Gly Ile
385                 390                 395                 400

Ala Ala Ile Cys Gln Lys Arg Gly Tyr Lys Thr Gly His Ile Ala Ala
              405                 410                 415

Asp Gly Ser Val Tyr Asn Lys Tyr Pro Gly Phe Lys Glu Ala Ala Ala
          420                 425                 430

Lys Gly Leu Arg Asp Ile Tyr Gly Trp Thr Gly Asp Ala Ser Lys Asp
      435                 440                 445

Pro Ile Thr Ile Val Pro Ala Glu Asp Gly Ser Gly Ala Gly Ala Ala
450                 455                 460

Val Ile Ala Ala Leu Ser Glu Lys Arg Ile Ala Glu Gly Lys Ser Leu
465                 470                 475                 480

Gly Ile Ile Gly Ala
              485

<210> SEQ ID NO 55
<211> LENGTH: 1461
<212> TYPE: DNA
<213> ORGANISM: Saccharomyces cerevisiae

<400> SEQUENCE: 55
atggttcatt taggtccaaa aaaaccacaa gccagaaagg gttccatggc cgatgtgcca      60
aaggaattga tgcaacaaat tgagaatttt gaaaaaattt tcactgttcc aactgaaact     120
ttacaagccg ttaccaagca cttcatttcc gaattggaaa agggtttgtc caagaagggt     180
ggtaacattc caatgattcc aggttgggtt atggatttcc caactggtaa ggaatccggt     240
gatttcttgg ccattgattt gggtggtacc aacttgagag ttgtcttagt caagttgggc     300
ggtgaccgta cctttgacac cactcaatct aagtacagat accagatgc tatgagaact     360

-continued

```
actcaaaatc cagacgaatt gtgggaattt attgccgact ctttgaaagc ttttattgat    420
gagcaattcc cacaaggtat ctctgagcca attccattgg gtttcacctt tctttcccca    480
gcttctcaaa acaaaatcaa tgaaggtatc ttgcaaagat ggactaaagg ttttgatatt    540
ccaaacattg aaaccacga tgttgttcca atgttgcaaa agcaaatcac taagaggaat    600
atcccaattg aagttgttgc tttgataaac gacactaccg gtactttggt tgcttcttac    660
tacactgacc cagaaactaa gatgggtgtt atcttcggta ctggtgtcaa tggtgcttac    720
tacgatgttt gttccgatat cgaaaagcta caaggaaaac tatctgatga cattccacca    780
tctgctccaa tggccatcaa ctgtgaatac ggttccttcg ataatgaaca tgtcgttttg    840
ccaagaacta aatacgatat caccattgat gaagaatctc caagaccagg ccaacaaacc    900
tttgaaaaaa tgtcttctgg ttactactta ggtgaaattt gcgtttggc cttgatggac    960
atgtacaaac aaggtttcat cttcaagaac caagacttgt ctaagttcga caagcctttc   1020
gtcatggaca cttcttaccc agccagaatc gaggaagatc cattcgagaa cctagaagat   1080
accgatgact tgttccaaaa tgagttcggt atcaacacta ctgttcaaga acgtaaattg   1140
atcagacgtt tatctgaatt gattggtgct agagctgcta gattgtccgt ttgtggtatt   1200
gctgctatct gtcaaaagag aggttacaag accggtcaca tcgctgcaga cggttccgtt   1260
tacaacagat acccaggttt caagaaaaag gctgccaatg ctttgaagga catttacggc   1320
tggactcaaa cctcactaga cgactaccca atcaagattg ttcctgctga agatggttcc   1380
ggtgctggtg ccgctgttat tgctgctttg gcccaaaaaa gaattgctga aggtaagtcc   1440
gttggtatca tcggtgctta a                                             1461
```

<210> SEQ ID NO 56
<211> LENGTH: 486
<212> TYPE: PRT
<213> ORGANISM: Saccharomyces cerevisiae

<400> SEQUENCE: 56

Met Val His Leu Gly Pro Lys Lys Pro Gln Ala Arg Lys Gly Ser Met
1               5                   10                  15

Ala Asp Val Pro Lys Glu Leu Met Gln Gln Ile Glu Asn Phe Glu Lys
                20                  25                  30

Ile Phe Thr Val Pro Thr Glu Thr Leu Gln Ala Val Thr Lys His Phe
            35                  40                  45

Ile Ser Glu Leu Glu Lys Gly Leu Ser Lys Lys Gly Gly Asn Ile Pro
        50                  55                  60

Met Ile Pro Gly Trp Val Met Asp Phe Pro Thr Gly Lys Glu Ser Gly
65                  70                  75                  80

Asp Phe Leu Ala Ile Asp Leu Gly Gly Thr Asn Leu Arg Val Val Leu
                85                  90                  95

Val Lys Leu Gly Gly Asp Arg Thr Phe Asp Thr Thr Gln Ser Lys Tyr
            100                 105                 110

Arg Leu Pro Asp Ala Met Arg Thr Thr Gln Asn Pro Asp Glu Leu Trp
        115                 120                 125

Glu Phe Ile Ala Asp Ser Leu Lys Ala Phe Ile Asp Glu Gln Phe Pro
    130                 135                 140

Gln Gly Ile Ser Glu Pro Ile Pro Leu Gly Phe Thr Phe Ser Phe Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu 180                 185                 190
Gln Lys Gln Ile Thr Lys Arg Asn Ile Pro Ile Glu Val Val Ala Leu
            195                 200                 205
Ile Asn Asp Thr Thr Gly Thr Leu Val Ala Ser Tyr Tyr Thr Asp Pro
        210                 215                 220
Glu Thr Lys Met Gly Val Ile Phe Gly Thr Gly Val Asn Gly Ala Tyr
225                 230                 235                 240
Tyr Asp Val Cys Ser Asp Ile Glu Lys Leu Gln Gly Lys Leu Ser Asp
                245                 250                 255
Asp Ile Pro Pro Ser Ala Pro Met Ala Ile Asn Cys Glu Tyr Gly Ser
            260                 265                 270
Phe Asp Asn Glu His Val Val Leu Pro Arg Thr Lys Tyr Asp Ile Thr
        275                 280                 285
Ile Asp Glu Glu Ser Pro Arg Pro Gly Gln Gln Thr Phe Glu Lys Met
    290                 295                 300
Ser Ser Gly Tyr Tyr Leu Gly Glu Ile Leu Arg Leu Ala Leu Met Asp
305                 310                 315                 320
Met Tyr Lys Gln Gly Phe Ile Phe Lys Asn Gln Asp Leu Ser Lys Phe
                325                 330                 335
Asp Lys Pro Phe Val Met Asp Thr Ser Tyr Pro Ala Arg Ile Glu Glu
            340                 345                 350
Asp Pro Phe Glu Asn Leu Glu Asp Thr Asp Leu Phe Gln Asn Glu
        355                 360                 365
Phe Gly Ile Asn Thr Thr Val Gln Glu Arg Lys Leu Ile Arg Arg Leu
    370                 375                 380
Ser Glu Leu Ile Gly Ala Arg Ala Ala Arg Leu Ser Val Cys Gly Ile
385                 390                 395                 400
Ala Ala Ile Cys Gln Lys Arg Gly Tyr Lys Thr Gly His Ile Ala Ala
                405                 410                 415
Asp Gly Ser Val Tyr Asn Arg Tyr Pro Gly Phe Lys Glu Lys Ala Ala
            420                 425                 430
Asn Ala Leu Lys Asp Ile Tyr Gly Trp Thr Gln Thr Ser Leu Asp Asp
        435                 440                 445
Tyr Pro Ile Lys Ile Val Pro Ala Glu Asp Gly Ser Gly Ala Gly Ala
    450                 455                 460
Ala Val Ile Ala Ala Leu Ala Gln Lys Arg Ile Ala Glu Gly Lys Ser
465                 470                 475                 480
Val Gly Ile Ile Gly Ala
            485

<210> SEQ ID NO 57
<211> LENGTH: 1164
<212> TYPE: DNA
<213> ORGANISM: Klebsiella pneumoniae

<400> SEQUENCE: 57
atgagctatc gtatgtttga ttatctggtg ccaaacgtta actttttttgg ccccaacgcc      60 atttccgtag tcggcgaacg ctgccagctg ctggggggga aaaagccct gctggtcacc       120 gacaaaggcc tgcgggcaat taagatggc gcagtggaca aaccctgca ttatctgcgg        180 gaggccggga tcgaggtggc gatctttgac ggcgtcgagc cgaacccgaa agacaccaac      240
gtgcgcgacg gcctcgccgt gtttcgccgc gaacagtgcg acatcatcgt caccgtgggc     300
ggcggcagcc gcacgattg cggcaaaggc atcggcatcg ccgccaccca tgagggcgat       360
ctgtaccagt atgccggaat cgagaccctg accaacccgc tgccgcctat cgtcgcggtc      420

```
aataccaccg ccggcaccgc cagcgaggtc acccgccact gcgtcctgac caacaccgaa    480
accaaagtga agtttgtgat cgtcagctgg cgcaacctgc cgtcggtctc tatcaacgat    540
ccgctgctga tgatcggtaa accggccgcc ctgaccgcgg cgaccgggat ggatgccctg    600
acccacgccg tagaggccta tatctccaaa gacgctaacc cggtgacgga cgccgccgcc    660
atgcaggcga tccgcctcat cgcccgcaac ctgcgccagg ccgtggccct cggcagcaat    720
ctgcaggcgc gggaaaacat ggcctatgcc tctctgctgg ccgggatggc tttcaataac    780
gccaacctcg gctacgtgca cgccatggcg caccagctgg cggcctgta cgacatgccg     840 cacggcgtgg ccaacgctgt cctgctgccg catgtggccc gctacaacct gatcgccaac    900
ccggagaaat tcgccgatat cgctgaactg atgggcgaaa atatcaccgg actgtccact    960
ctcgacgcgg cggaaaaagc catcgccgct atcacgcgtc tgtcgatgga tatcggtatt   1020
ccgcagcatc tgcgcgatct gggagtaaaa gaggccgact tcccctacat ggcggagatg   1080
gctctgaaag acggcaatgc gttctcgaac ccgcgtaaag caacgagca ggagattgcc    1140 gcgattttcc gccaggcatt ctga                                          1164
```

<210> SEQ ID NO 58
<211> LENGTH: 387
<212> TYPE: PRT
<213> ORGANISM: Klebsiella pneumoniae

<400> SEQUENCE: 58

```
Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Gln Leu Leu Gly
                20                  25                  30

Gly Lys Lys Ala Leu Leu Val Thr Asp Lys Gly Leu Arg Ala Ile Lys
            35                  40                  45

Asp Gly Ala Val Asp Lys Thr Leu His Tyr Leu Arg Glu Ala Gly Ile
        50                  55                  60

Glu Val Ala Ile Phe Asp Gly Val Glu Pro Asn Pro Lys Asp Thr Asn
65                  70                  75                  80

Val Arg Asp Gly Leu Ala Val Phe Arg Arg Glu Gln Cys Asp Ile Ile
                85                  90                  95

Val Thr Val Gly Gly Ser Pro His Asp Cys Gly Lys Gly Ile Gly
                100                 105                 110

Ile Ala Ala Thr His Glu Gly Asp Leu Tyr Gln Tyr Ala Gly Ile Glu
            115                 120                 125

Thr Leu Thr Asn Pro Leu Pro Pro Ile Val Ala Val Asn Thr Thr Ala
        130                 135                 140

Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Ala Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ala Met Gln Ala Ile
    210                 215                 220

Arg Leu Ile Ala Arg Asn Leu Arg Gln Ala Val Ala Leu Gly Ser Asn
225                 230                 235                 240
```

```
Leu Gln Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Pro His Gly Val Ala Asn Ala Val Leu
        275                 280                 285

Leu Pro His Val Ala Arg Tyr Asn Leu Ile Ala Asn Pro Glu Lys Phe
    290                 295                 300

Ala Asp Ile Ala Glu Leu Met Gly Glu Asn Ile Thr Gly Leu Ser Thr
305                 310                 315                 320

Leu Asp Ala Ala Glu Lys Ala Ile Ala Ile Thr Arg Leu Ser Met
                325                 330                 335

Asp Ile Gly Ile Pro Gln His Leu Arg Asp Leu Gly Val Lys Glu Ala
                340                 345                 350

Asp Phe Pro Tyr Met Ala Glu Met Ala Leu Lys Asp Gly Asn Ala Phe
            355                 360                 365

Ser Asn Pro Arg Lys Gly Asn Glu Gln Glu Ile Ala Ala Ile Phe Arg
        370                 375                 380

Gln Ala Phe
385

<210> SEQ ID NO 59
<211> LENGTH: 1824
<212> TYPE: DNA
<213> ORGANISM: Klebsiella pneumoniae
<220> FEATURE:
<221> NAME/KEY: CDS
<222> LOCATION: (1)..(1824)

<400> SEQUENCE: 59 atg ccg tta ata gcc ggg att gat atc ggc aac gcc acc acc gag gtg      48
Met Pro Leu Ile Ala Gly Ile Asp Ile Gly Asn Ala Thr Thr Glu Val
1               5                   10                  15 gcg ctg gcg tcc gac tac ccg cag gcg agg gcg ttt gtt gcc agc ggg      96
Ala Leu Ala Ser Asp Tyr Pro Gln Ala Arg Ala Phe Val Ala Ser Gly
            20                  25                  30 atc gtc gcg acg acg ggc atg aaa ggg acg cgg gac aat atc gcc ggg     144
Ile Val Ala Thr Thr Gly Met Lys Gly Thr Arg Asp Asn Ile Ala Gly
        35                  40                  45 acc ctc gcc gcg ctg gag cag gcc ctg gcg aaa aca ccg tgg tcg atg     192
Thr Leu Ala Ala Leu Glu Gln Ala Leu Ala Lys Thr Pro Trp Ser Met
    50                  55                  60 agc gat gtc tct cgc atc tat ctt aac gaa gcc gcg ccg gtg att ggc     240
Ser Asp Val Ser Arg Ile Tyr Leu Asn Glu Ala Ala Pro Val Ile Gly
65                  70                  75                  80 gat gtg gcg atg gag acc atc acc gag acc att atc acc gaa tcg acc     288
Asp Val Ala Met Glu Thr Ile Thr Glu Thr Ile Ile Thr Glu Ser Thr
                85                  90                  95 atg atc ggt cat aac ccg cag acg ccg ggc ggg gtg ggc gtt ggc gtg     336
Met Ile Gly His Asn Pro Gln Thr Pro Gly Gly Val Gly Val Gly Val
            100                 105                 110 ggg acg act atc gcc ctc ggg cgg ctg gcg acg ctg ccg gcg gcg cag     384
Gly Thr Thr Ile Ala Leu Gly Arg Leu Ala Thr Leu Pro Ala Ala Gln
        115                 120                 125 tat gcc gag ggg tgg atc gta ctg att gac gac gcc gtc gat ttc ctt     432
Tyr Ala Glu Gly Trp Ile Val Leu Ile Asp Asp Ala Val Asp Phe Leu
    130                 135                 140 gac gcc gtg tgg tgg ctc aat gag gcg ctc gac cgg ggg atc aac gtg     480
Asp Ala Val Trp Trp Leu Asn Glu Ala Leu Asp Arg Gly Ile Asn Val
145                 150                 155                 160
```

-continued

| | |
|---|---|
| gtg gcg gcg atc ctc aaa aag gac gac ggc gtg ctg gtg aac aac cgc<br>Val Ala Ala Ile Leu Lys Lys Asp Asp Gly Val Leu Val Asn Asn Arg<br>                165                      170                  175 | 528 |
| ctg cgt aaa acc ctg ccg gtg gtg gat gaa gtg acg ctg ctg gag cag<br>Leu Arg Lys Thr Leu Pro Val Val Asp Glu Val Thr Leu Leu Glu Gln<br>        180                      185                      190 | 576 |
| gtc ccc gag ggg gta atg gcg gcg gtg gaa gtg gcc gcg ccg ggc cag<br>Val Pro Glu Gly Val Met Ala Ala Val Glu Val Ala Ala Pro Gly Gln<br>                195                      200                      205 | 624 |
| gtg gtg cgg atc ctg tcg aat ccc tac ggg atc gcc acc ttc ttc ggg<br>Val Val Arg Ile Leu Ser Asn Pro Tyr Gly Ile Ala Thr Phe Phe Gly<br>        210                      215                      220 | 672 |
| cta agc ccg gaa gag acc cag gcc atc gtc ccc atc gcc cgc gcc ctg<br>Leu Ser Pro Glu Glu Thr Gln Ala Ile Val Pro Ile Ala Arg Ala Leu<br>225                      230                      235                      240 | 720 |
| att ggc aac cgt tcc gcg gtg gtg ctc aag acc ccg cag ggg gat gtg<br>Ile Gly Asn Arg Ser Ala Val Val Leu Lys Thr Pro Gln Gly Asp Val<br>                245                      250                      255 | 768 |
| cag tcg cgg gtg atc ccg gcg ggc aac ctc tac att agc ggc gaa aag<br>Gln Ser Arg Val Ile Pro Ala Gly Asn Leu Tyr Ile Ser Gly Glu Lys<br>        260                      265                      270 | 816 |
| cgc cgc gga gag gcc gat gtc gcc gag ggc gcg gaa gcc atc atg cag<br>Arg Arg Gly Glu Ala Asp Val Ala Glu Gly Ala Glu Ala Ile Met Gln<br>                275                      280                      285 | 864 |
| gcg atg agc gcc tgc gct ccg gta cgc gac atc cgc ggc gaa ccg ggc<br>Ala Met Ser Ala Cys Ala Pro Val Arg Asp Ile Arg Gly Glu Pro Gly<br>        290                      295                      300 | 912 |
| acc cac gcc ggc ggc atg ctt gag cgg gtg cgc aag gta atg gcg tcc<br>Thr His Ala Gly Gly Met Leu Glu Arg Val Arg Lys Val Met Ala Ser<br>305                      310                      315                      320 | 960 |
| ctg acc ggc cat gag atg agc gcg ata tac atc cag gat ctg ctg gcg<br>Leu Thr Gly His Glu Met Ser Ala Ile Tyr Ile Gln Asp Leu Leu Ala<br>                325                      330                      335 | 1008 |
| gtg gat acg ttt att ccg cgc aag gtg cag ggc ggg atg gcc ggc gag<br>Val Asp Thr Phe Ile Pro Arg Lys Val Gln Gly Gly Met Ala Gly Glu<br>        340                      345                      350 | 1056 |
| tgc gcc atg gag aat gcc gtc ggg atg gcg gcg atg gtg aaa gcg gat<br>Cys Ala Met Glu Asn Ala Val Gly Met Ala Ala Met Val Lys Ala Asp<br>                355                      360                      365 | 1104 |
| cgt ctg caa atg cag gtt atc gcc cgc gaa ctg agc gcc cga ctg cag<br>Arg Leu Gln Met Gln Val Ile Ala Arg Glu Leu Ser Ala Arg Leu Gln<br>        370                      375                      380 | 1152 |
| acc gag gtg gtg gtg ggc ggc gtg gag gcc aac atg gcc atc gcc ggg<br>Thr Glu Val Val Val Gly Gly Val Glu Ala Asn Met Ala Ile Ala Gly<br>385                      390                      395                      400 | 1200 |
| gcg tta acc act ccc ggc tgt gcg gcg ccg ctg gcg atc ctc gac ctc<br>Ala Leu Thr Thr Pro Gly Cys Ala Ala Pro Leu Ala Ile Leu Asp Leu<br>                405                      410                      415 | 1248 |
| ggc gcc ggc tcg acg gat gcg gcg atc gtc aac gcg gag ggg cag ata<br>Gly Ala Gly Ser Thr Asp Ala Ala Ile Val Asn Ala Glu Gly Gln Ile<br>        420                      425                      430 | 1296 |
| acg gcg gtc cat ctc gcc ggg gcg ggg aat atg gtc agc ctg ttg att<br>Thr Ala Val His Leu Ala Gly Ala Gly Asn Met Val Ser Leu Leu Ile<br>                435                      440                      445 | 1344 |
| aaa acc gag ctg ggc ctc gag gat ctt tcg ctg gcg gaa gcg ata aaa<br>Lys Thr Glu Leu Gly Leu Glu Asp Leu Ser Leu Ala Glu Ala Ile Lys<br>        450                      455                      460 | 1392 |
| aaa tac ccg ctg gcc aaa gtg gaa agc ctg ttc agt att cgt cac gag<br>Lys Tyr Pro Leu Ala Lys Val Glu Ser Leu Phe Ser Ile Arg His Glu<br>465                      470                      475                  480 | 1440 |

```
aat ggc gcg gtg gag ttc ttt cgg gaa gcc ctc agc ccg gcg gtg ttc      1488
Asn Gly Ala Val Glu Phe Phe Arg Glu Ala Leu Ser Pro Ala Val Phe
            485                 490                 495 gcc aaa gtg gtg tac atc aag gag ggc gaa ctg gtg ccg atc gat aac      1536
Ala Lys Val Val Tyr Ile Lys Glu Gly Glu Leu Val Pro Ile Asp Asn
        500                 505                 510 gcc agc ccg ctg gaa aaa att cgt ctc gtg cgc cgg cag gcg aaa gag      1584
Ala Ser Pro Leu Glu Lys Ile Arg Leu Val Arg Arg Gln Ala Lys Glu
    515                 520                 525 aaa gtg ttt gtc acc aac tgc ctg cgc gcg ctg cgc cag gtc tca ccc      1632
Lys Val Phe Val Thr Asn Cys Leu Arg Ala Leu Arg Gln Val Ser Pro
530                 535                 540 ggc ggt tcc att cgc gat atc gcc ttt gtg gtg ctg gtg ggc ggc tca      1680
Gly Gly Ser Ile Arg Asp Ile Ala Phe Val Val Leu Val Gly Gly Ser
545                 550                 555                 560 tcg ctg gac ttt gag atc ccg cag ctt atc acg gaa gcc ttg tcg cac      1728
Ser Leu Asp Phe Glu Ile Pro Gln Leu Ile Thr Glu Ala Leu Ser His
                565                 570                 575 tat ggc gtg gtc gcc ggg cag ggc aat att cgg gga aca gaa ggg ccg      1776
Tyr Gly Val Val Ala Gly Gln Gly Asn Ile Arg Gly Thr Glu Gly Pro
            580                 585                 590 cgc aat gcg gtc gcc acc ggg ctg cta ctg gcc ggt cag gcg aat taa      1824
Arg Asn Ala Val Ala Thr Gly Leu Leu Leu Ala Gly Gln Ala Asn
        595                 600                 605

<210> SEQ ID NO 60
<211> LENGTH: 607
<212> TYPE: PRT
<213> ORGANISM: Klebsiella pneumoniae

<400> SEQUENCE: 60

Met Pro Leu Ile Ala Gly Ile Asp Ile Gly Asn Ala Thr Thr Glu Val
1               5                   10                  15

Ala Leu Ala Ser Asp Tyr Pro Gln Ala Arg Ala Phe Val Ala Ser Gly
            20                  25                  30

Ile Val Ala Thr Thr Gly Met Lys Gly Thr Arg Asp Asn Ile Ala Gly
        35                  40                  45

Thr Leu Ala Ala Leu Glu Gln Ala Leu Ala Lys Thr Pro Trp Ser Met
    50                  55                  60

Ser Asp Val Ser Arg Ile Tyr Leu Asn Glu Ala Ala Pro Val Ile Gly
65                  70                  75                  80

Asp Val Ala Met Glu Thr Ile Thr Glu Thr Ile Ile Thr Glu Ser Thr
                85                  90                  95

Met Ile Gly His Asn Pro Gln Thr Pro Gly Gly Val Gly Val Gly Val
            100                 105                 110

Gly Thr Thr Ile Ala Leu Gly Arg Leu Ala Thr Leu Pro Ala Ala Gln
        115                 120                 125

Tyr Ala Glu Gly Trp Ile Val Leu Ile Asp Ala Val Asp Phe Leu
    130                 135                 140

Asp Ala Val Trp Trp Leu Asn Glu Ala Leu Asp Arg Gly Ile Asn Val
145                 150                 155                 160

Val Ala Ala Ile Leu Lys Lys Asp Asp Gly Val Leu Val Asn Asn Arg
                165                 170                 175

Leu Arg Lys Thr Leu Pro Val Val Asp Glu Val Thr Leu Leu Glu Gln
            180                 185                 190

Val Pro Glu Gly Val Met Ala Ala Val Glu Val Ala Ala Pro Gly Gln
        195                 200                 205
```

Val Val Arg Ile Leu Ser Asn Pro Tyr Gly Ile Ala Thr Phe Phe Gly
            210                 215                 220

Leu Ser Pro Glu Glu Thr Gln Ala Ile Val Pro Ile Ala Arg Ala Leu
225                 230                 235                 240

Ile Gly Asn Arg Ser Ala Val Val Leu Lys Thr Pro Gln Gly Asp Val
            245                 250                 255

Gln Ser Arg Val Ile Pro Ala Gly Asn Leu Tyr Ile Ser Gly Glu Lys
            260                 265                 270

Arg Arg Gly Glu Ala Asp Val Ala Glu Gly Ala Glu Ala Ile Met Gln
            275                 280                 285

Ala Met Ser Ala Cys Ala Pro Val Arg Asp Ile Arg Gly Glu Pro Gly
290                 295                 300

Thr His Ala Gly Gly Met Leu Glu Arg Val Arg Lys Val Met Ala Ser
305                 310                 315                 320

Leu Thr Gly His Glu Met Ser Ala Ile Tyr Ile Gln Asp Leu Leu Ala
            325                 330                 335

Val Asp Thr Phe Ile Pro Arg Lys Val Gln Gly Gly Met Ala Gly Glu
            340                 345                 350

Cys Ala Met Glu Asn Ala Val Gly Met Ala Ala Met Val Lys Ala Asp
355                 360                 365

Arg Leu Gln Met Gln Val Ile Ala Arg Glu Leu Ser Ala Arg Leu Gln
370                 375                 380

Thr Glu Val Val Gly Gly Val Glu Ala Asn Met Ala Ile Ala Gly
385                 390                 395                 400

Ala Leu Thr Thr Pro Gly Cys Ala Ala Pro Leu Ala Ile Leu Asp Leu
            405                 410                 415

Gly Ala Gly Ser Thr Asp Ala Ala Ile Val Asn Ala Glu Gly Gln Ile
            420                 425                 430

Thr Ala Val His Leu Ala Gly Ala Gly Asn Met Val Ser Leu Leu Ile
            435                 440                 445

Lys Thr Glu Leu Gly Leu Glu Asp Leu Ser Leu Ala Glu Ala Ile Lys
450                 455                 460

Lys Tyr Pro Leu Ala Lys Val Glu Ser Leu Phe Ser Ile Arg His Glu
465                 470                 475                 480

Asn Gly Ala Val Glu Phe Phe Arg Glu Ala Leu Ser Pro Ala Val Phe
            485                 490                 495

Ala Lys Val Val Tyr Ile Lys Glu Gly Glu Leu Val Pro Ile Asp Asn
            500                 505                 510

Ala Ser Pro Leu Glu Lys Ile Arg Leu Val Arg Arg Gln Ala Lys Glu
            515                 520                 525

Lys Val Phe Val Thr Asn Cys Leu Arg Ala Leu Arg Gln Val Ser Pro
530                 535                 540

Gly Gly Ser Ile Arg Asp Ile Ala Phe Val Val Leu Val Gly Gly Ser
545                 550                 555                 560

Ser Leu Asp Phe Glu Ile Pro Gln Leu Ile Thr Glu Ala Leu Ser His
            565                 570                 575

Tyr Gly Val Val Ala Gly Gln Gly Asn Ile Arg Gly Thr Glu Gly Pro
            580                 585                 590

Arg Asn Ala Val Ala Thr Gly Leu Leu Leu Ala Gly Gln Ala Asn
            595                 600                 605

<210> SEQ ID NO 61
<211> LENGTH: 4146
<212> TYPE: DNA
<213> ORGANISM: Escherichia coli

<400> SEQUENCE: 61

```
ggatcccttg cccgctgttg atccgttgtt ccacctgata ttatgttaac ccagtagcca    60
gagtgctcca tgttgcagca cagccactcc gtgggaggca taaagcgaca gttcccgttc   120
ttctggctgc ggatagattc gactactcat caccgcttcc ccgtcgttaa taaatacttc   180
cacggatgat gtatcgataa atatccttag ggcgagcgtg tcacgctgcg ggaggggaat   240
actacggtag ccgtctaaat tctcgtgtgg gtaataccgc cacaaaacaa gtcgctcaga   300
ttggttatca atatacagcc gcattccagt gccgagctgt aatccgtaat gttcggcatc   360
actgttcttc agcgcccact gcaactgaat ctcaactgct tgcgcgtttt cctgcaaaac   420
atatttattg ctgattgtgc ggggagagac agattgatgc tgctggcgta acgactcagc   480
ttcgtgtacc gggcgttgta gaagtttgcc attgctctct gatagctcgc gcgccagcgt   540
catgcagcct gcccatcctt cacgttttga gggcattggc gattcccaca tatccatcca   600
gccgataaca atacgccgac catccttcgc taaaaagctt tgtggtgcat aaaagtcatg   660
cccgttatca agttcagtaa aatgcccgga ttgtgcaaaa agtcgtcctg gcgaccacat   720
tccgggtatt acgccacttt gaaagcgatt tcggtaactg tatccctcgg cattcattcc   780
ctgcggggaa aacatcagat aatgctgatc gccaaggctg aaaaagtccg gacattccca   840
catatagctt tcacccgcat cagcgtgggc cagtacgcga tcgaaggtcc attcacgcaa   900
cgaactgccg cgataaagca ggatctgccc cgtgttgcct ggatctttcg ccccgactac   960
catccaccat gtgtcggctt cacgccacac tttaggatcg cggaagtgca tgattccttc  1020
tggtggagtg aggatcacac cctgtttctc gaaatgaata ccatcccgac tggtagccag  1080
acattgtact tcgcgaattg catcgtcatt acctgcacca tcgagccaga cgtgtccggt  1140
gtagataagt gagaggacac cattgtcatc gacagcacta cctgaaaaac acccgtcttt  1200
gtcattatcg tctcctggcg ctagcgcaat aggctcatgc tgccagtgga tcatatcgtc  1260
gctggtggca tgtccccagt gcattggccc ccagtgttcg ctcatcggat gatgttgata  1320
aaacgcgtga taacgatcgt taaaccagat caggccgttt ggatcgttca tccacccggc  1380
aggaggcgcg aggtgaaaat ggggatagaa agtgttaccc cggtgctcat gaagttttgc  1440
tagggcgttt tgcgccgcat gcaatcgaga ttgcgtcatt ttaatcatcc tggttaagca  1500
aatttggtga attgttaacg ttaacttta taaaaataaa gtcccttact ttcataaatg  1560
cgatgaatat cacaaatgtt aacgttaact atgacgtttt gtgatcgaat atgcatgttt  1620
tagtaaatcc atgacgattt tgcgaaaaag aggtttatca ctatgcgtaa ctcagatgaa  1680
tttaagggaa aaaaatgtca gccaaagtat gggttttagg ggatgcggtc gtagatctct  1740
tgccagaatc agacgggcgc ctactgcctt gtcctggcgg cgcgccagct aacgttgcgg  1800
tgggaatcgc cagattaggc ggaacaagtg ggtttatagg tcgggtgggg gatgatcctt  1860
ttggtgcgtt aatgcaaaga acgctgctaa ctgagggagt cgatatcacg tatctgaagc  1920
aagatgaatg gcaccggaca tccacggtgc ttgtcgatct gaacgatcaa ggggaacgtt  1980
catttacgtt tatggtccgc cccagtgccg atcttttttt agagacgaca gacttgccct  2040
gctggcgaca tggcgaatgg ttacatctct gttcaattgc gttgtctgcc gagccttcgc  2100
gtaccagcgc atttactgcg atgacggcga tccggcatgc cggaggtttt gtcagcttcg  2160
atcctaatat tcgtgaagat ctatggcaag acgagcattt gctccgcttg tgtttgcggc  2220
aggcgctaca actggcggat gtcgtcaagc tctcggaaga agaatggcga cttatcagtg  2280
gaaaaacaca gaacgatcag gatatatgcg ccctggcaaa agagtatgag atcgccatgc  2340
```

```
tgttggtgac taaaggtgca gaagggtgg tggtctgtta tcgaggacaa gttcaccatt      2400
ttgctggaat gtctgtgaat tgtgtcgata gcacggggc gggagatgcg ttcgttgccg      2460
ggttactcac aggtctgtcc tctacgggat tatctacaga tgagagaa atgcgacgaa       2520 ttatcgatct cgctcaacgt tgcggagcgc ttgcagtaac ggcgaaggg gcaatgacag      2580 cgctgccatg tcgacaagaa ctggaatagt gagaagtaaa cggcgaagtc gctcttatct    2640
ctaaatagga cgtgaatttt ttaacgacag gcaggtaatt atggcactga atattccatt    2700
cagaaatgcg tactatcgtt ttgcatccag ttactcattt ctcttttta tttcctggtc     2760 gctgtggtgg tcgttatacg ctatttggct gaaaggacat ctagggttga cagggacgga    2820
attaggtaca ctttattcgg tcaaccagtt taccagcatt ctatttatga tgttctacgg    2880
catcgttcag gataaactcg gtctgaagaa accgctcatc tggtgtatga gtttcatcct   2940
ggtcttgacc ggaccgttta tgatttacgt ttatgaaccg ttactgcaaa gcaattttc    3000 tgtaggtcta attctggggg cgctattttt tggcttgggg tatctggcgg gatgcggttt   3060
gcttgatagc ttcaccgaaa aaatggcgcg aaattttcat ttcgaatatg aacagcgcg    3120 cgcctgggga tcttttggct atgctattgg cgcgttcttt gccggcatat tttttagtat   3180
cagtccccat atcaacttct ggttggtctc gctatttggc gctgtattta tgatgatcaa   3240
catgcgtttt aaagataagg atcaccagtg cgtagcggca gatgcgggag gggtaaaaaa   3300
agaggatttt atcgcagttt tcaaggatcg aaacttctgg gttttcgtca tatttattgt   3360
ggggacgtgg tctttctata acattttga tcaacaactt tttcctgtct tttattcagg   3420
tttattcgaa tcacacgatg taggaacgcg cctgtatggt tatctcaact cattccaggt   3480
ggtactcgaa gcgctgtgca tggcgattat tcctttcttt gtgaatcggg tagggccaaa   3540
aaatgcatta cttatcggag ttgtgattat ggcgttgcgt atcctttcct gcgcgctgtt   3600 cgttaaccc tggattattt cattagtgaa gttgttacat gccattgagg ttccactttg    3660
tgtcatatcc gtcttcaaat acagcgtggc aaactttgat aagcgcctgt cgtcgacgat   3720 cttttctgatt ggttttcaaa ttgccagttc gcttgggatt tgctgctttt caacgccgac   3780
tgggatactc tttgaccacg caggctacca gacagttttc ttcgcaattt cgggtattgt   3840
ctgcctgatg ttgctatttg gcattttctt cttgagtaaa aaacgcgagc aaatagttat   3900
ggaaacgcct gtaccttcag caatatagac gtaaacttt tccggttgtt gtcgatagct    3960
ctatatccct caaccggaaa ataataatag taaaatgctt agccctgcta ataatcgcct   4020
aatccaaacg cctcattcat gttctggtac agtcgctcaa atgtacttca gatgcgcggt   4080
tcgctgattt ccaggacatt gtcgtcattc agtgacctgt cccgtgtatc acggtcctgc   4140
gaattc                                                              4146

<210> SEQ ID NO 62
<211> LENGTH: 13669
<212> TYPE: DNA
<213> ORGANISM: Artificial Sequence
<220> FEATURE:
<223> OTHER INFORMATION: Plasmid

<400> SEQUENCE: 62
tagtaaagcc ctcgctagat tttaatgcgg atgttgcgat tacttcgcca actattgcga     60
taacaagaaa aagccagcct ttcatgatat atctcccaat ttgtgtaggg cttattatgc    120
acgcttaaaa ataataaaag cagacttgac ctgatagttt ggctgtgagc aattatgtgc    180
ttagtgcatc taacgcttga gttaagccgc gccgcgaagc ggcgtcggct tgaacgaatt   240
```

```
gttagacatt atttgccgac taccttggtg atctcgcctt tcacgtagtg gacaaattct      300
tccaactgat ctgcgcgcga ggccaagcga tcttcttctt gtccaagata agcctgtcta      360
gcttcaagta tgacgggctg atactgggcc ggcaggcgct ccattgccca gtcggcagcg      420
acatccttcg gcgcgatttt gccggttact gcgctgtacc aaatgcggga caacgtaagc      480
actacatttc gctcatcgcc agcccagtcg ggcggcgagt tccatagcgt taaggtttca      540
tttagcgcct caaatagatc ctgttcagga accggatcaa agagttcctc cgccgctgga      600
cctaccaagg caacgctatg ttctcttgct tttgtcagca agatagccag atcaatgtcg      660
atcgtggctg gctcgaagat acctgcaaga atgtcattgc gctgccattc tccaaattgc      720
agttcgcgct tagctggata cgccacggga atgatgtcgt cgtgcacaac aatggtgact      780
tctacagcgc ggagaatctc gctctctcca ggggaagccg aagtttccaa aaggtcgttg      840
atcaaagctc gccgcgttgt ttcatcaagc cttacggtca ccgtaaccag caaatcaata      900
tcactgtgtg gcttcaggcc gccatccact gcggagccg acaaatgtac ggccagcaac      960
gtcggttcga gatggcgctc gatgacgcca actacctctg atagttgagt cgatacttcg     1020
gcgatcaccg cttccctcat gatgtttaac tttgttttag ggcgactgcc ctgctgcgta     1080
acatcgttgc tgctccataa catcaaacat cgacccacgg cgtaacgcgc ttgctgcttg     1140
gatgcccgag gcatagactg taccccaaaa aaacagtcat aacaagccat gaaaaccgcc     1200
actgcgccgt taccaccgct gcgttcggtc aaggttctgg accagttgcg tgagcgcata     1260
cgctacttgc attacagctt acgaaccgaa caggcttatg tccactgggt tcgtgccttc     1320
atccgtttcc acggtgtgcg tcacccggca accttgggca gcagcgaagt cgaggcattt     1380
ctgtcctggc tggcgaacga gcgcaaggtt tcggtctcca cgcatcgtca ggcattggcg     1440
gccttgctgt tcttctacgg caaggtgctg tgcacggatc tgccctggct tcaggagatc     1500
ggaagacctc ggccgtcgcg gcgcttgccg gtggtgctga ccccggatga agtggttcgc     1560
atcctcggtt ttctggaagg cgagcatcgt ttgttcgccc agcttctgta tggaacgggc     1620
atgcggatca gtgagggttt gcaactgcgg gtcaaggatc tggatttcga tcacggcacg     1680
atcatcgtgc gggagggcaa gggctccaag gatcgggcct tgatgttacc cgagagcttg     1740
gcacccagcc tgcgcgagca ggggaattaa ttcccacggg ttttgctgcc cgcaaacggg     1800
ctgttctggt gttgctagtt tgttatcaga atcgcagatc cggcttcagc cggtttgccg     1860
gctgaaagcg ctatttcttc cagaattgcc atgattttt ccccacggga ggcgtcactg     1920
gctcccgtgt tgtcggcagc tttgattcga taagcagcat cgcctgtttc aggctgtcta     1980
tgtgtgactg ttgagctgta acaagttgtc tcaggtgttc aatttcatgt tctagttgct     2040 ttgtttact ggtttcacct gttctattag gtgttacatg ctgttcatct gttacattgt     2100
cgatctgttc atggtgaaca gctttgaatg caccaaaaac tcgtaaaagc tctgatgtat     2160
ctatcttttt tacaccgttt tcatctgtgc atatggacag ttttccctt gatatgtaac     2220 ggtgaacagt tgttctactt ttgtttgtta gtcttgatgc ttcactgata gatacaagag     2280
ccataagaac ctcagatcct tccgtattta gccagtatgt tctctagtgt ggttcgttgt     2340
ttttgcgtga gccatgagaa cgaaccattg agatcatact tactttgcat gtcactcaaa     2400
aattttgcct caaaactggt gagctgaatt tttgcagtta aagcatcgtg tagtgttttt     2460
cttagtccgt tatgtaggta ggaatctgat gtaatggttg ttggtatttt gtcaccattc     2520 attttttatct ggttgttctc aagttcggtt acgagatcca tttgtctatc tagttcaact     2580
tggaaaatca acgtatcagt cgggcggcct cgcttatcaa ccaccaattt catattgctg     2640
```

```
taagtgttta aatctttact tattggtttc aaaacccatt ggttaagcct tttaaactca    2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta atttttcgct tgagaacttg    2940
gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg gctagtcaa    3300 tgataattac tagtcctttt cctttgagtt gtgggtatct gtaaattctg ctagacctttt    3360 gctggaaaac ttgtaaattc tgctagaccc tctgtaaatt ccgctagacc tttgtgtgtt    3420
ttttttgttt atattcaagt ggttataatt tatagaataa agaaagaata aaaaaagata    3480 aaagaatag atcccagccc tgtgtataac tcactacttt agtcagttcc gcagtattac    3540 aaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc ttttttcgtga cattcagttc gctgcgctca cggctctggc    3720
agtgaatggg ggtaaatggc actacaggcg ccttttatgg attcatgcaa ggaaactacc    3780
cataatacaa gaaaagcccg tcacgggctt ctcagggcgt tttatggcgg gtctgctatg    3840
tggtgctatc tgacttttttg ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta ttttttaatga gcaggtaatt ggcgccgtcg gcgttagcgg cggtacggtc    4620
gagcaggatc aattattagc ccagtgcgcc ctgattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga    4860 ccataaccta tgacggaggc ggtgacgccg ctgcgctggg cgccctggcg gccagaagct    4920 cgccctgcg ggtgggtatc gggctcagcg cgtccggcga gatagccctc actcatgccc    4980
agctgccggc ggacgcgccg ctggctaccg gacacgtcac cgatagcgac gatcaactgc    5040
```

```
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagg aatctcgcct   5460
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc tttttttttc ctaggcgatc   5700
tgtgctgttt gccacggtat gcagcaccag cgcgagatta tgggctcgca cgctcgactg   5760
tcggacgggg gcactggaac gagaagtcag gcgagccgtc acgcccttga caatgccaca   5820
tcctgagcaa ataattcaac cactaaacaa atcaaccgcg tttcccggag gtaaccaagc   5880
ttcacctttt gagccgatga acaatgaaaa gatcaaaacg atttgcagta ctggcccagc   5940
gccccgtcaa tcaggacggg ctgattggcg agtggcctga agaggggctg atcgccatgg   6000
acagccccct tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgccggcca   6240
aagcggtcga ggtgatggcg cagatgaacg tggtggagat gatgatggcg ctgcagaaga   6300
tgcgtgcccg ccgaccccc tccaaccagt gccacgtcac caatctcaaa gataatccgg   6360
tgcagattgc cgctgacgcc gccgaggccg ggatccgcgg cttctcagaa caggagacca   6420
cggtcggtat cgcgcgctac gcgccgttta cgcccctggc gctgttggtc ggttcgcagt   6480
gcggccgccc cggcgtgttg acgcagtgct cggtggaaga ggccaccgag ctggagctgg   6540
gcatgcgtgg cttaaccagc tacgccgaga cggtgtcggt ctacggcacc gaagcggtat   6600
ttaccgacgg cgatgatacg ccgtggtcaa aggcgttcct cgcctcggcc tacgcctccc   6660
gcgggttgaa aatgcgctac acctccggca ccggatccga agcgctgatg ggctattcgg   6720
agagcaagtc gatgctctac ctcgaatcgc gctgcatctt cattactaaa ggcgccgggg   6780
ttcagggact gcaaaacggc gcggtgagct gtatcggcat gaccggcgct gtgccgtcgg   6840
gcattcgggc ggtgctggcg gaaaacctga tcgcctctat gctcgacctc gaagtggcgt   6900
ccgccaacga ccagactttc tcccactcgg atattcgccg caccgcgcgc acctgatgc   6960 agatgctgcc gggcaccgac tttatttttct ccggctacag cgcggtgccg aactacgaca   7020
acatgttcgc cggctcgaac ttcgatgcgg aagattttga tgattacaac atcctgcagc   7080
gtgacctgat ggttgacggc ggcctgcgtc cggtgaccga ggcggaaacc attgccattc   7140
gccagaaagc ggcgcgggcg atccaggcgg ttttccgcga gctggggctg ccgccaatcg   7200
ccgacgagga ggtggaggcc gccacctacg cgcacgcag caacgagatg ccgccgcgta   7260
acgtggtgga ggatctgagt gcggtggaag agatgatgaa gcgcaacatc accggcctcg   7320
atattgtcgg cgcgctgagc cgcagcggct ttgaggatat cgccagcaat attctcaata   7380
tgctgcgcca gcgggtcacc ggcgattacc tgcagacctc ggccattctc gatcggcagt   7440
```

```
tcgaggtggt gagtgcggtc aacgacatca atgactatca ggggccgggc accggctatc    7500
gcatctctgc cgaacgctgg gcggagatca aaatattcc gggcgtggtt cagcccgaca     7560
ccattgaata aggcggtatt cctgtgcaac agcaaccca aattcagccc tcttttaccc     7620
tgaaacccg cgagggcggg gtagcttctg ccgatgaacg cgccgatgaa gtggtgatcg     7680
gcgtcggccc tgccttcgat aaacaccagc atcacactct gatcgatatg ccccatggcg    7740
cgatcctcaa agagctgatt gccggggtgg aagaagaggg gcttcacgcc cgggtggtgc    7800
gcattctgcg cacgtccgac gtctccttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg gagacctacc    7980
ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220
cccgagcat atcctgacgc ctaccggcaa accattgacc gatattaccc tcgagaaggt     8280
gctctctggc gaggtgggcc cgcaggatgt gcggatctcc cgccagaccc ttgagtacca    8340
ggcgcagatt gccgagcaga tgcagcgcca tgcggtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgcctttg tccgggagtc ggcggaagtg tatcagcagc ggcataagct    8580
gcgtaaagga agctaagcgg aggtcagcat gccgttaata gccgggattg atatcggcaa    8640
cgccaccacc gaggtggcgc tggcgtccga ctacccgcag gcgagggcgt tgttgccag     8700
cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccgggcgggg tgggcgttgg    8940
cgtggggacg actatcgccc tcgggcggct ggcgacgctg ccggcggcgc agtatgccga    9000
ggggtggatc gtactgattg acgacgccgt cgatttcctt gacgccgtgt ggtggctcaa    9060
tgaggcgctc gaccggggga tcaacgtggt ggcggcgatc ctcaaaaagg acgacggcgt    9120
gctggtgaac aaccgcctgc gtaaaaccct gccggtggtg gatgaagtga cgctgctgga    9180
gcaggtcccc gaggggtaa tggcggcggt ggaagtggcc cgcgccgggcc aggtggtgcg     9240
gatcctgtcg aatccctacg ggatcgccac cttcttcggg ctaagcccgg aagagaccca    9300
ggccatcgtc cccatcgccc gcgccctgat tggcaaccgt tccgcggtgg tgctcaagac    9360
cccgcagggg gatgtgcagt cgcgggtgat cccgcgggc aacctctaca ttagcggcga    9420
aaagcgccgc ggagaggccg atgtcgccga gggcgcggaa gccatcatgc aggcgatgag    9480
cgcctgcgct ccggtacgcg acatccgcgg cgaaccgggc acccacgccg gcggcatgct    9540
tgagcgggtg cgcaaggtaa tggcgtccct gaccggccat gagatgagcg cgatatacat    9600
ccaggatctg ctggcggtgg atacgtttat tccgcgcaag gtgcagggcg ggatggccgg    9660
cgagtgcgcc atggagaatg ccgtcgggat ggcggcgatg gtgaaagcgg atcgtctgca    9720
aatgcaggtt atcgcccgcg aactgagcgc ccgactgcag accgaggtgg tggtgggcgg    9780
cgtggaggcc aacatggcca tcgccggggc gttaaccact cccggctgtg cggcgccgct    9840
```

```
ggcgatcctc gacctcggcg ccggctcgac ggatgcggcg atcgtcaacg cggaggggca   9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctg ttcagtattc gtcacgagaa tggcgcggtg gagttctttc gggaagccct  10080
cagcccggcg gtgttcgcca aagtggtgta catcaaggag ggcgaactgg tgccgatcga  10140
taacgccagc ccgctggaaa aaattcgtct cgtgcgccgg caggcgaaag agaaagtgtt  10200
tgtcaccaac tgcctgcgcg cgctgcgcca ggtctcaccc ggcggttcca ttcgcgatat  10260
cgcctttgtg gtgctggtgg gcggctcatc gctggacttt gagatcccgc agcttatcac  10320
ggaagccttg tcgcactatg gcgtggtcgc cgggcagggc aatattcggg aacagaagg   10380
gccgcgcaat gcggtcgcca ccgggctgct actggccggt caggcgaatt aaacgggcgc  10440
tcgcgccagc ctctaggtac aaataaaaaa ggcacgtcag atgacgtgcc ttttttcttg  10500
tctagagtac tggcgaaagg gggatgtgct gcaaggcgat taagttgggt aacgccaggg  10560
ttttcccagt cacgacgttg taaaacgacg gccagtgaat tcgagctcgg tacccggggc  10620
ggccgcgcta gcgcccgatc cagctggagt ttgtagaaac gcaaaaggc catccgtcag   10680
gatggccttc tgcttaattt gatgcctggc agtttatggc gggcgtcctg cccgccaccc  10740
tccgggccgt tgcttcgcaa cgttcaaatc cgctcccggc ggatttgtcc tactcaggag  10800
agcgttcacc gacaaacaac agataaaacg aaaggcccag tctttcgact gagcctttcg  10860
ttttatttga tgcctggcag ttccctactc tcgcatgggg agaccccaca ctaccatcgg  10920
cgctacggcg tttcacttct gagttcggca tggggtcagg tgggaccacc gcgctactgc  10980
cgccaggcaa attctgtttt atcagaccgc ttctgcgttc tgatttaatc tgtatcaggc  11040
tgaaaatctt ctctcatccg ccaaaacagc caagcttgca tgcctgcagc ccgggttacc  11100
atttcaacag atcgtcctta gcatataagt agtcgtcaaa aatgaattca acttcgtctg  11160
tttcggcatt gtagccgcca actctgatgg attcgtggtt tttgacaatg atgtcacagc  11220
ctttttcctt taggaagtcc aagtcgaaag tagtggcaat accaatgatc ttacaaccgg  11280
cggcttttcc ggcggcaata cctgctggag cgtcttcaaa tactactacc ttagatttgg  11340
aagggtcttg ctcattgatc ggatatccta agccattcct gcccttcaga tatggttctg  11400
gatgaggctt accctgtttg acatcattag cggtaatgaa gtactttggt ctcctgattc  11460
ccagatgctc gaaccatttt tgtgccatat cacgggtacc ggaagttgcc acagcccatt  11520
tctcttttgg tagagcgttc aaagcgttgc acagcttaac tgcacctggg acttcaatgg  11580
atttttcacc gtacttgacc ggaatttcag cttctaattt gttaacatac tcttcattgg  11640
caaagtctgg agcgaactta gcaatggcat caaacgttct ccaaccatgc gagacttgga  11700
taacgtgttc agcatcgaaa taaggtttgt ccttaccgaa atccctccag aatgcagcaa  11760
tggctggttg agagatgata atggtaccgt cgacgtcgaa caaagcggcg ttaactttca  11820
aagatagagg tttagtagtc aatcccataa ttcagtctg tttcctggat ccaataaatc   11880
taatcttcat gtagatctaa ttcttcaatc atgtccggca ggtcttcat tgggtagttg    11940
ttgtaaacga tttggtatac ggcttcaaat aatgggaagt cttcgacaga gccacatgtt  12000
tccaaccatt cgtgaacttc tttgcaggta attaaacctt gagcggattg gccattcaac  12060
aactcctttt cacattccca ggcgtcctta ccagaagtag ccattagcct agcaaccttg  12120
acgtttctac caccagcgca ggtggtgatc aaatcagcaa caccagcaga ctcttggtag  12180
tatgtttctt ctctagattc tgggaaaaac atttgaccga atctgatgat ctcacccaaa  12240
```

```
ccgactcttt ggatggcagc agaagcgttg ttaccccagc ctagaccttc gacgaaacca   12300
caacctaagg caacaacgtt cttcaaagca ccacagatgg agataccagc aacatcttcg   12360
atgacactaa cgtggaagta aggtctgtgg aacaaggcct ttagaacctt atggtcgacg   12420
tccttgccct cgcctctgaa atcctttgga atgtggtaag caactgttgt ttcagaccag   12480
tgttcttgag cgacttcggt ggcaatgtta gcaccagata gagcaccaca ttgaatacct   12540
agttcctcag tgatgtaaga ggatagcaat tggacacctt agcaccaac ttcaaaaccc    12600 tttagacagg agatagctct gacgtgtgaa tcaacatgac ctttcaattg gctacagata   12660
cggggcaaaa attgatgtgg aatgttgaaa acgatgatgt cgacatcctt gactgaatca   12720
atcaagtctg gattagcaac caaattgtcg ggtagagtga tgccaggcaa gtatttcacg   12780
ttttgatgtc tagtatttat gatttcagtc aattttttcac cattgatctc ttcttcgaac   12840
acccacattt gtactattgg agcgaaaact tctgggtatc ccttacaatt ttcggcaacc   12900
accttggcaa tagtagtacc ccagttacca gatccaatca cagtaaccttt gaaaggcttt   12960 tcggcagcct tcaaagaaac agaagaggaa cttctctttc taccagcatt caagtggccg   13020
gaagttaagt ttaatctatc agcagcagca gccatgaat gtcctccttt actagtcatg    13080
gtctgtttcc tgtgtgaaat tgttatccgc tcacaattcc acacattata cgagccggat   13140
gattaattgt caacagctca tttcagaata tttgccagaa ccgttatgat gtcggcgcaa   13200
aaaacattat ccagaacggg agtgcgcctt gagcgacacg aattatgcag tgatttacga   13260
cctgcacagc cataccacag cttccgatgg ctgcctgacg ccagaagcat tggtgcacgc   13320
tagccagtac atttaaatgg taccctctag tcaaggcctt aagtgagtcg tattacggac   13380
tggccgtcgt tttacaacgt cgtgactggg aaaaccctgg cgttacccaa cttaatcgcc   13440
ttgcagcaca tcccccttt c gccagctggc gtaatagcga agaggcccgc accgatcgcc   13500
cttcccaaca gttgcgcagc ctgaatgcg aatggcgcct gatgcggtat tttctcctta    13560
cgcatctgtg cggtatttca caccgcatat ggtgcactct cagtacaatc tgctctgatg   13620
ccgcatagtt aagccagccc cgacacccgc caacacccgc tgacgagct               13669
```

<210> SEQ ID NO 63
<211> LENGTH: 13543
<212> TYPE: DNA
<213> ORGANISM: Artificial Sequence
<220> FEATURE:
<223> OTHER INFORMATION: Plasmid

<400> SEQUENCE: 63

```
tagtaaagcc ctcgctagat tttaatgcgg atgttgcgat tacttcgcca actattgcga     60
taacaagaaa aagccagcct ttcatgatat atctcccaat ttgtgtaggg cttattatgc    120
acgcttaaaa ataataaaag cagacttgac ctgatagttt ggctgtgagc aattatgtgc    180
ttagtgcatc taacgcttga gttaagccgc gccgcgaagc ggcgtcggct tgaacgaatt    240
gttagacatt atttgccgac taccttggtg atctcgcctt tcacgtagtg acaaattct    300 tccaactgat ctgcgcgcga ggccaagcga tcttcttctt gtccaagata agcctgtcta    360
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
```

```
atcgtggctg gctcgaagat acctgcaaga atgtcattgc gctgccattc tccaaattgc    720
agttcgcgct tagctggata acgccacgga atgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caaatcaata    900
tcactgtgtg gcttcaggcc gccatccact cggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg taccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320 atccgttttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgatttttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160 ctatctttt tacaccgttt tcatctgtgc atatggacag ttttccctt gatatgtaac   2220 ggtgaacagt tgttctactt tgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta aatctttact tattggtttc aaaaccccatt ggttaagcct tttaaactca   2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta attttttcgct tgagaacttg   2940 gcatagtttg tccactggaa aatctcaaag cctttaacca aaggattcct gatttccaca   3000
gttctcgtca tcagctctct ggttgcttta gctaatacac cataagcatt ttccctactg   3060
```

```
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtcctttt cctttgagtt gtgggtatct gtaaattctg ctagaccttt    3360
gctggaaaac ttgtaaattc tgctagaccc tctgtaaatt ccgctagacc tttgtgtgtt    3420
ttttttgttt atattcaagt ggttataatt tatagaataa agaaagaata aaaaagata     3480 aaagaatag atcccagccc tgtgtataac tcactacttt agtcagttcc gcagtattac    3540 aaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc tttttcgtga cattcagttc gctgcgctca cggctctggc    3720
agtgaatggg ggtaaatggc actacaggcg cctttatgg attcatgcaa ggaaactacc     3780
cataatacaa gaaaagcccg tcacgggctt ctcagggcgt tttatggcgg gtctgctatg    3840
tggtgctatc tgacttttg ctgttcagca gttcctgccc tctgattttc cagtctgacc     3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga ctatgccaca tcctgagcaa ataattcaac cactaaacaa    4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta tttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga     4860 ccataaccta tgacggaggc ggtgacgccg ctgcgctggg cgccctggcg gccagaagct    4920
cgcccctgcg ggtgggtatc gggctcagcc cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
```

```
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc ttttttttc  ctaggcgatc   5700 tgtgctgttt gccacggtat gcagcaccag cgcgagatta tgggctcgca cgctcgactg   5760
tcggacgggg gcactggaac gagaagtcag gcgagccgtc acgcccttga ctatgccaca   5820
tcctgagcaa ataattcaac cactaaacaa atcaaccgcg tttcccggag gtaaccaagc   5880
ttcacctttt gagccgatga acaatgaaaa gatcaaaacg atttgcagta ctggcccagc   5940
gccccgtcaa tcaggacggg ctgattggcg agtggcctga agaggggctg atcgccatgg   6000
acagcccctt tgacccggtc tcttcagtaa agtggacaa  cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgccggcca   6240
aagcggtcga ggtgatggcg cagatgaacg tggtggagat gatgatggcg ctgcagaaga   6300
tgcgtgcccg ccggaccccc tccaaccagt gccacgtcac caatctcaaa gataatccgg   6360
tgcagattgc cgctgacgcc gccgaggccg gatccgcgg  cttctcagaa caggagacca   6420
cggtcggtat cgcgcgctac gcgccgttta acgccctggc gctgttggtc ggttcgcagt   6480
gcggccgccc cggcgtgttg acgcagtgct cggtggaaga ggccaccgag ctggagctgg   6540
gcatgcgtgg cttaaccagc tacgccgaga cggtgtcggt ctacggcacc gaagcggtat   6600
ttaccgacgg cgatgatacg ccgtggtcaa aggcgttcct cgcctcggcc tacgcctccc   6660
gcgggttgaa aatgcgctac acctccggca ccggatccga agcgctgatg ggctattcgg   6720
agagcaagtc gatgctctac ctcgaatcgc gctgcatctt cattactaaa ggcgccgggg   6780
ttcagggact gcaaaacggc gcggtgagct gtatcggcat gaccggcgct gtgccgtcgg   6840
gcattcgggc ggtgctggcg gaaaacctga tcgcctctat gctcgacctc gaagtggcgt   6900
ccgccaacga ccagactttc tcccactcgg atattcgccg caccgcgcgc accctgatgc   6960
agatgctgcc gggcaccgac tttatttct  ccggctacag cgcggtgccg aactacgaca   7020
acatgttcgc cggctcgaac ttcgatgcgg aagattttga tgattacaac atcctgcagc   7080
gtgacctgat ggttgacggc ggcctgcgtc cggtgaccga gcggaaaacc attgccattc   7140
gccagaaagc ggcgcgggcg atccaggcgg ttttccgcga gctggggctg ccgccaatcg   7200
ccgacgagga ggtggaggcc gccacctacg cgcacggcag caacgagatg ccgccgcgta   7260
acgtggtgga ggatctgagt gcggtggaag agatgatgaa gcgcaacatc accggcctcg   7320
atattgtcgg cgcgctgagc cgcagcggct ttgaggatat cgccagcaat attctcaata   7380
tgctgcgcca gcgggtcacc ggcgattacc tgcagacctc ggccattctc gatcggcagt   7440
tcgaggtggt gagtgcggtc aacgacatca atgactatca ggggccgggc accggctatc   7500
gcatctctgc cgaacgctgg gcggagatca aaaatattcc gggcgtggtt cagcccgaca   7560
ccattgaata aggcggtatt cctgtgcaac agacaaccca aattcagccc tcttttaccc   7620 tgaaacccg  cgagggcggg gtagcttctg ccgatgaacg cgccgatgaa gtggtgatcg   7680
gcgtcggccc tgccttcgat aaacaccagc atcacactct gatcgatatg ccccatggcg   7740
cgatcctcaa agagctgatt gccggggtgg aagaagaggg gcttcacgcc cggtggtgc   7800 gcattctgcg cacgtccgac gtctcccttta tggcctggga tgcggccaac ctgagcggct   7860
```

```
cggggatcgg catcggtatc cagtcgaagg ggaccacggt catccatcag cgcgatctgc   7920
tgccgctcag caacctggag ctgttctccc aggcgccgct gctgacgctg gagacctacc   7980
ggcagattgg caaaaacgct gcgcgctatg cgcgcaaaga gtcaccttcg ccggtgccgg   8040
tggtgaacga tcagatggtg cggccgaaat ttatggccaa agccgcgcta tttcatatca   8100
aagagaccaa acatgtggtg caggacgccg agcccgtcac cctgcacatc gacttagtaa   8160
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgcggtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgcctttg tccgggagtc ggcggaagtg tatcagcagc ggcataagct   8580
gcgtaaagga agctaagcgg aggtcagcat gccgttaata gccgggattg atatcggcaa   8640
cgccaccacc gaggtggcgc tggcgtccga ctacccgcag gcgagggcgt ttgttgccag   8700
cgggatcgtc gcgacgacgg gcatgaaagg gacgcgggac aatatcgccg ggaccctcgc   8760
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccggcggcgc agtatgccga   9000
ggggtggatc gtactgattg acgacgccgt cgatttcctt gacgccgtgt ggtggctcaa   9060
tgaggcgctc gaccggggga tcaacgtggt ggcggcgatc ctcaaaaagg acgacggcgt   9120
gctggtgaac aaccgcctgc gtaaaaccct gccggtggtg gatgaagtga cgctgctgga   9180
gcaggtcccc gaggggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg acatccgcgg cgaaccgggc acccacgccg gcggcatgct   9540
tgagcgggtg cgcaaggtaa tggcgtccct gaccggccat gagatgagcg cgatatacat   9600
ccaggatctg ctggcggtgg atacgtttat tccgcgcaag gtgcagggcg ggatggccgg   9660
cgagtgcgcc atggagaatg ccgtcgggat ggcggcgatg gtgaaagcgg atcgtctgca   9720
aatgcaggtt atcgcccgcg aactgagcgc ccgactgcag accgaggtgg tggtgggcgg   9780
cgtggaggcc aacatggcca tcgccgggc gttaaccact cccggctgtg cggcgccgct   9840
ggcgatcctc gacctcggcg ccggctcgac ggatgcggcg atcgtcaacg cggaggggca   9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctg ttcagtattc gtcacgagaa tggcgcggtg gagttctttc gggaagccct  10080
cagcccggcg gtgttcgcca aagtggtgta catcaaggag ggcgaactgg tgccgatcga  10140
taacgccagc ccgctggaaa aaattcgtct cgtgcgccgg caggcgaaag agaaagtgtt  10200
tgtcaccaac tgcctgcgcg cgctgcgcca ggtctcaccc ggcggttcca ttcgcgatat  10260
```

```
cgcctttgtg gtgctggtgg gcggctcatc gctggacttt gagatcccgc agcttatcac   10320
ggaagccttg tcgcactatg gcgtggtcgc cgggcagggc aatattcggg gaacagaagg   10380
gccgcgcaat gcggtcgcca ccgggctgct actggccggt caggcgaatt aaacgggcgc   10440
tcgcgccagc ctctaggtac aaataaaaaa ggcacgtcag atgacgtgcc ttttttcttg   10500
tctagcgtgc accaatgctt ctggcgtcag gcagccatcg gaagctgtgg tatggctgtg   10560
caggtcgtaa atcactgcat aattcgtgtc gctcaaggcg cactcccgtt ctggataatg   10620 tttttttgcgc cgacatcata acggttctgg caaatattct gaaatgagct gttgacaatt   10680
aatcatccgg ctcgtataat gtgtggaatt gtgagcggat aacaatttca cacaggaaac   10740
agaccatgac tagtaaggag gacaattcca tggctgctgc tgctgataga ttaaacttaa   10800
cttccggcca cttgaatgct ggtagaaaga gaagttcctc ttctgttttct ttgaaggctg   10860 ccgaaaagcc tttcaaggtt actgtgattg gatctggtaa ctggggtact actattgcca   10920
aggtggttgc cgaaaattgt aagggatacc cagaagtttt cgctccaata gtacaaatgt   10980
gggtgttcga agaagagatc aatggtgaaa aattgactga aatcataaat actagacatc   11040
aaaacgtgaa atacttgcct ggcatcactc tacccgacaa tttggttgct aatccagact   11100
tgattgattc agtcaaggat gtcgacatca tcgttttcaa cattccacat caattttttgc   11160 cccgtatctg tagccaattg aaaggtcatg ttgattcaca cgtcagagct atctcctgtc   11220
taagggtttt tgaagttggt gctaaaggtg tccaattgct atcctcttac atcactgagg   11280
aactaggtat tcaatgtggt gctctatctg gtgctaacat tgccaccgaa gtcgctcaag   11340
aacactggtc tgaaacaaca gttgcttacc acattccaaa ggatttcaga ggcgagggca   11400
aggacgtcga ccataaggtt ctaaaggcct tgttccacag accttacttc cacgttagtg   11460
tcatcgaaga tgttgctggt atctccatct gtggtgcttt gaagaacgtt gttgccttag   11520 gttgtgggtttt cgtcgaaggt ctaggctggg gtaacaacgc ttctgctgcc atccaaagag   11580
tcggtttggg tgagatcatc agattcggtc aaatgttttt cccagaatct agagaagaaa   11640
catactacca agagtctgct ggtgttgctg atttgatcac cacctgcgct ggtggtagaa   11700
acgtcaaggt tgctaggcta atggctactt ctggtaagga cgcctgggaa tgtgaaaagg   11760
agttgttgaa tggccaatcc gctcaaggtt taattacctg caaagaagtt cacgaatggt   11820
tggaaacatg tggctctgtc gaagacttcc cattatttga agccgtatac caaatcgttt   11880
acaacaacta cccaatgaag aacctgccgg acatgattga agaattagat ctacatgaag   11940
attagattta ttggatccag gaaacagact agaattatgg gattgactac taaacctcta   12000
tctttgaaag ttaacgccgc tttgttcgac gtcgacggta ccattatcat ctctcaacca   12060
gccattgctg cattctggag ggatttcggt aaggacaaac cttatttcga tgctgaacac   12120
gttatccaag tctcgcatgg ttggagaacg tttgatgcca ttgctaagtt cgctccagac   12180
tttgccaatg aagagtatgt taacaaatta gaagctgaaa ttccggtcaa gtacggtgaa   12240
aaatccattg aagtcccagg tgcagttaag ctgtgcaacg ctttgaacgc tctaccaaaa   12300
gagaaatggg ctgtggcaac ttccggtacc cgtgatatgg cacaaaaatg gttcgagcat   12360
ctgggaatca ggagaccaaa gtacttcatt accgctaatg atgtcaaaca gggtaagcct   12420
catccagaac catatctgaa gggcaggaat ggcttaggat atccgatcaa tgagcaagac   12480
ccttccaaat ctaaggtagt agtatttgaa gacgctccag caggtattgc cgccggaaaa   12540
gccgccggtt gtaagatcat tggtattgcc actactttcg acttggactt cctaaaggaa   12600
aaaggctgtg acatcattgt caaaaaccac gaatccatca gagttggcgg ctacaatgcc   12660
```

| | |
|---|---|
| gaaacagacg aagttgaatt cattttttgac gactacttat atgctaagga cgatctgttg | 12720 |
| aaatggtaac ccgggctgca ggcatgcaag cttggctgtt ttggcggatg agagaagatt | 12780 |
| ttcagcctga tacagattaa atcagaacgc agaagcggtc tgataaaaca gaatttgcct | 12840 |
| ggcggcagta gcgcggtggt cccacctgac cccatgccga actcagaagt gaaacgccgt | 12900 |
| agcgccgatg gtagtgtggg gtctcccccat gcgagagtag ggaactgcca ggcatcaaat | 12960 |
| aaaacgaaag gctcagtcga aagactgggc ctttcgtttt atctgttgtt tgtcggtgaa | 13020 |
| cgctctcctg agtaggacaa atccgccggg agcggatttg aacgttgcga agcaacggcc | 13080 |
| cggagggtgg cgggcaggac gcccgccata aactgccagg catcaaatta agcagaaggc | 13140 |
| catcctgacg gatggccttt ttgcgtttct acaaactcca gctggatcgg cgctagagt | 13200 |
| atacatttaa atggtaccct ctagtcaagg ccttaagtga gtcgtattac ggactggccg | 13260 |
| tcgttttaca acgtcgtgac tgggaaaacc ctggcgttac ccaacttaat cgccttgcag | 13320 |
| cacatccccc tttcgccagc tggcgtaata gcgaagaggc ccgcaccgat cgcccttccc | 13380 |
| aacagttgcg cagcctgaat ggcgaatggc gcctgatgcg gtattttctc cttacgcatc | 13440 |
| tgtgcggtat ttcacaccgc atatggtgca ctctcagtac aatctgctct gatgccgcat | 13500 |
| agttaagcca gccccgacac ccgccaacac ccgctgacga gct | 13543 |

<210> SEQ ID NO 64
<211> LENGTH: 13543
<212> TYPE: DNA
<213> ORGANISM: Artificial Sequence
<220> FEATURE:
<223> OTHER INFORMATION: Plasmid

<400> SEQUENCE: 64

| | |
|---|---|
| tagtaaagcc ctcgctagat tttaatgcgg atgttgcgat tacttcgcca actattgcga | 60 |
| taacaagaaa aagccagcct ttcatgatat atctcccaat ttgtgtaggg cttattatgc | 120 |
| acgcttaaaa ataataaaag cagacttgac ctgatagttt ggctgtgagc aattatgtgc | 180 |
| ttagtgcatc taacgcttga gttaagccgc gccgcgaagc ggcgtcggct tgaacgaatt | 240 |
| gttagacatt atttgccgac taccttggtg atctcgcctt tcacgtagtg gacaaattct | 300 |
| tccaactgat ctgcgcgcga ggccaagcga tcttcttctt gtccaagata agcctgtcta | 360 |
| gcttcaagta tgacgggctg atactgggcc ggcaggcgct ccattgccca gtcggcagcg | 420 |
| acatccttcg gcgcgatttt gccggttact gcgctgtacc aaatgcggga caacgtaagc | 480 |
| actacatttc gctcatcgcc agcccagtcg gcggcgagt tccatagcgt taaggtttca | 540 |
| tttagcgcct caaatagatc ctgttcagga accggatcaa agagttcctc cgccgctgga | 600 |
| cctaccaagg caacgctatg ttctcttgct tttgtcagca agatagccag atcaatgtcg | 660 |
| atcgtggctg gctcgaagat acctgcaaga atgtcattgc gctgccattc tccaaattgc | 720 |
| agttcgcgct tagctggata acgccacgga atgatgtcgt cgtgcacaac aatggtgact | 780 |
| tctacagcgc ggagaatctc gctctctcca ggggaagccg aagtttccaa aaggtcgttg | 840 |
| atcaaagctc gccgcgttgt ttcatcaagc cttacggtca ccgtaaccag caaatcaata | 900 |
| tcactgtgtg gcttcaggcc gccatccact gcggagccgt acaaatgtac ggccagcaac | 960 |
| gtcggttcga gatggcgctc gatgacgcca actacctctg atagttgagt cgatacttcg | 1020 |
| gcgatcaccg cttcccctcat gatgtttaac tttgttttag ggcgactgcc ctgctgcgta | 1080 |
| acatcgttgc tgctccataa catcaaacat cgacccacgg cgtaacgcgc ttgctgcttg | 1140 |
| gatgcccgag gcatagactg taccccaaaa aaacagtcat aacaagccat gaaaaccgcc | 1200 |

```
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgttttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatctttt tacaccgttt tcatctgtgc atatggacag ttttcccttt gatatgtaac   2220
ggtgaacagt tgttctactt tgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
attttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta atctttact tattggtttc aaaacccatt ggttaagcct tttaaactca   2700
tggtagttat tttcaagcat taacatgaac ttaaattcat caaggctaat ctctatattt   2760
gccttgtgag ttttctttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta attttcgct tgagaacttg   2940
gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg gctagtcaa   3300
tgataattac tagtcctttt cctttgagtt gtgggtatct gtaaattctg ctagacctt   3360
gctgaaaaac ttgtaaattc tgctagaccc tctgtaaatt ccgctagacc tttgtgtgtt   3420
tttttgttt atattcaagt ggttataatt tatagaataa agaagaata aaaaagata   3480
aaagaataag atcccagccc tgtgtataac tcactacttt agtcagttcc gcagtattac   3540
aaaaggatgt cgcaaacgct gtttgctcct ctacaaaaca gaccttaaaa ccctaaaggc   3600
```

```
ttaagtagca ccctcgcaag ctcgggcaaa tcgctgaata ttccttttgt ctccgaccat   3660
caggcacctg agtcgctgtc ttttcgtga cattcagttc gctgcgctca cggctctggc   3720
agtgaatggg ggtaaatggc actacaggcg ccttttatgg attcatgcaa ggaaactacc   3780
cataatacaa gaaaagcccg tcacgggctt ctcagggcgt tttatggcgg gtctgctatg   3840
tggtgctatc tgactttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt ccacggtat gcagcaccag    4080 cgcgagatta tgggctcgca cgctcgactg tcggacgggg gcactggaac gagaagtcag   4140
gcgagccgtc acgcccttga caatgccaca tcctgagcaa ataattcaac cactaaacaa   4200
atcaaccgcg tttccggag gtaaccaagc ttgcgggaga gaatgatgaa caagagccaa    4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta ttttaatga gcaggtaatt ggcgccgtcg gcgttagcgg cggtacggtc    4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga cagggggtc ccctgccaga    4860 ccataaccta tgacggaggc ggtgacgccg ctgcgctggg cgccctggcg gccagaagct   4920 cgccctgcg ggtgggtatc gggctcagcg cgtccggcga gatagccctc actcatgccc    4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacgcggca    5160 gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagg aatctcgcct   5460
ctgcccagct gcacgtggcg cgcacccagt cccgtcggct cgaacgcctg ctgacgccca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc tttttttttc ctaggcgatc   5700
tgtgctgttt ccacggtat gcagcaccag cgcgagatta tgggctcgca cgctcgactg    5760
tcggacgggg gcactggaac gagaagtcag gcgagccgtc acgcccttga caatgccaca   5820
tcctgagcaa ataattcaac cactaaacaa atcaaccgcg tttccggag gtaaccaagc    5880 ttcacctttt gagccgatga acaatgaaaa gatcaaaacg atttgcagta ctggcccagc   5940
gccccgtcaa tcaggacggg ctgattggcg agtggcctga agaggggctg atcgccatgg   6000
```

```
acagcccctt tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgccggcca   6240
aagcggtcga ggtgatggcg cagatgaacg tggtggagat gatgatgcgc ctgcagaaga   6300
tgcgtgcccg ccggaccccc tccaaccagt gccacgtcac caatctcaaa gataatccgg   6360
tgcagattgc cgctgacgcc gccgaggccg ggatccgcgg cttctcagaa caggagacca   6420
cggtcggtat cgcgcgctac gcgccgttta acgccctggc gctgttggtc ggttcgcagt   6480
gcggccgccc cggcgtgttg acgcagtgct cggtggaaga ggccaccgag ctggagctgg   6540
gcatgcgtgg cttaaccagc tacgccgaga cggtgtcggt ctacggcacc gaagcggtat   6600
ttaccgacgg cgatgatacg ccgtggtcaa aggcgttcct cgcctcggcc tacgcctccc   6660
gcgggttgaa aatgcgctac acctccggca ccggatccga agcgctgatg ggctattcgg   6720
agagcaagtc gatgctctac ctcgaatcgc gctgcatctt cattactaaa ggcgccgggg   6780
ttcagggact gcaaaacggc gcggtgagct gtatcggcat gaccggcgct gtgccgtcgg   6840
gcattcgggc ggtgctggcg gaaaacctga tcgcctctat gctcgacctc gaagtggcgt   6900
ccgccaacga ccagactttc tcccactcgg atattcgccg caccgcgcgc acctgatgc    6960 agatgctgcc gggcaccgac tttatttct ccggctacag cgcggtgccg aactacgaca    7020
acatgttcgc cggctcgaac ttcgatgcgg aagattttga tgattacaac atcctgcagc   7080
gtgacctgat ggttgacggc ggcctgcgtc cggtgaccga ggcggaaacc attgccattc   7140
gccagaaagc ggcgcgggcg atccaggcgg ttttccgcga gctggggctg ccgccaatcg   7200
ccgacgagga ggtggaggcc gccacctacg cgcacggcag caacgagatg ccgccgcgta   7260
acgtggtgga ggatctgagt gcggtggaag agatgatgaa cgcaacatc accggcctcg    7320 atattgtcgg cgcgctgagc cgcagcggct ttgaggatat cgccagcaat attctcaata   7380
tgctgcgcca gcgggtcacc ggcgattacc tgcagacctc ggccattctc gatcggcagt   7440
tcgaggtggt gagtgcggtc aacgacatca atgactatca ggggccgggc accggctatc   7500
gcatctctgc cgaacgctgg gcggagatca aaaatattcc gggcgtggtt cagcccgaca   7560
ccattgaata aggcggtatt cctgtgcaac agacaaccca aattcagccc tcttttaccc   7620
tgaaaacccg cgagggcggg gtagcttctg ccgatgaacg cgccgatgaa gtggtgatcg   7680
gcgtcggccc tgccttcgat aaacaccagc atcacactct gatcgatatg ccccatggcg   7740
cgatcctcaa agagctgatt gccggggtgg aagaagaggg gcttcacgcc cgggtggtgc   7800
gcattctgcg cacgtccgac gtctccttta tggcctggga tgcggccaac ctgagcggct   7860
cggggatcgg catcggtatc cagtcgaagg ggaccacggt catccatcag cgcgatctgc   7920
tgccgctcag caacctggag ctgttctccc aggcgccgct gctgacgctg agacctacc    7980 ggcagattgg caaaaacgct gcgcgctatg cgcgcaaaga gtcaccttcg ccggtgccgg   8040
tggtgaacga tcagatggtg cggccgaaat ttatggccaa agccgcgcta tttcatatca   8100
aagagaccaa acatgtggtg caggacgccg agcccgtcac cctgcacatc gacttagtaa   8160
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgcggtggcg cgcaatttcc gccgcgcggc   8400
```

| | |
|---|---|
| ggagcttatc gccattcctg acgagcgcat tctggctatc tataacgcgc tgcgcccgtt | 8460 |
| ccgctcctcg caggcggagc tgctggcgat cgccgacgag ctggagcaca cctggcatgc | 8520 |
| gacagtgaat gccgcctttg tccgggagtc ggcggaagtg tatcagcagc ggcataagct | 8580 |
| gcgtaaagga agctaagcgg aggtcagcat gccgttaata gccgggattg atatcggcaa | 8640 |
| cgccaccacc gaggtggcgc tggcgtccga ctacccgcag gcgagggcgt ttgttgccag | 8700 |
| cgggatcgtc gcgacgacgg gcatgaaagg gacgcgggac aatatcgccg ggaccctcgc | 8760 |
| cgcgctggag caggccctgg cgaaaacacc gtggtcgatg agcgatgtct ctcgcatcta | 8820 |
| tcttaacgaa gccgcgccgg tgattggcga tgtggcgatg gagaccatca ccgagaccat | 8880 |
| tatcaccgaa tcgaccatga tcggtcataa cccgcagacg ccgggcgggg tgggcgttgg | 8940 |
| cgtggggacg actatcgccc tcgggcggct ggcgacgctg ccggcggcgc agtatgccga | 9000 |
| ggggtggatc gtactgattg acgacgccgt cgatttcctt gacgccgtgt ggtggctcaa | 9060 |
| tgaggcgctc gaccggggga tcaacgtggt ggcggcgatc ctcaaaaagg acgacggcgt | 9120 |
| gctggtgaac aaccgcctgc gtaaaaccct gccggtggtg gatgaagtga cgctgctgga | 9180 |
| gcaggtcccc gagggggtaa tggcggcggt ggaagtggcc gcgccgggcc aggtggtgcg | 9240 |
| gatcctgtcg aatccctacg ggatcgccac cttcttcggg ctaagcccgg aagagaccca | 9300 |
| ggccatcgtc cccatcgccc gcgccctgat tggcaaccgt tccgcggtgg tgctcaagac | 9360 |
| cccgcagggg gatgtgcagt cgcgggtgat cccggcgggc aacctctaca ttagcggcga | 9420 |
| aaagcgccgc ggagaggccg atgtcgccga gggcgcggaa gccatcatgc aggcgatgag | 9480 |
| cgcctgcgct ccggtacgcg acatccgcgg cgaaccgggc acccacgccg gcggcatgct | 9540 |
| tgagcgggtg cgcaaggtaa tggcgtccct gaccggccat gagatgagcg cgatatacat | 9600 |
| ccaggatctg ctggcggtgg atacgtttat tccgcgcaag gtgcagggcg ggatggccgg | 9660 |
| cgagtgcgcc atggagaatg ccgtcgggat ggcggcgatg gtgaaagcgg atcgtctgca | 9720 |
| aatgcaggtt atcgcccgcg aactgagcgc ccgactgcag accgaggtgg tggtgggcgg | 9780 |
| cgtggaggcc aacatggcca tcgccggggc gttaaccact cccggctgtg cggcgccgct | 9840 |
| ggcgatcctc gacctcggcg ccggctcgac ggatgcggcg atcgtcaacg cggaggggca | 9900 |
| gataacggcg gtccatctcg ccggggcggg gaatatggtc agcctgttga ttaaaaccga | 9960 |
| gctgggcctc gaggatcttt cgctggcgga agcgataaaa aaatacccgc tggccaaagt | 10020 |
| ggaaagcctt ttcagtattc gtcacgagaa tggcgcggtg gagttctttc gggaagccct | 10080 |
| cagcccggcg gtgttcgcca aagtggtgta catcaaggag ggcgaactgg tgccgatcga | 10140 |
| taacgccagc ccgctggaaa aaattcgtct cgtgcgccgg caggcgaaag agaaagtgtt | 10200 |
| tgtcaccaac tgcctgcgcg cgctgcgcca ggtctcaccc ggcggttcca ttcgcgatat | 10260 |
| cgcctttgtg gtgctggtgg gcggctcatc gctggacttt gagatcccgc agcttatcac | 10320 |
| ggaagccttg tcgcactatg gcgtggtcgc cgggcagggc aatattcggg gaacagaagg | 10380 |
| gccgcgcaat gcggtcgcca ccgggctgct actggccggt caggcgaatt aaacgggcgc | 10440 |
| tcgcgccagc ctctaggtac aaataaaaaa ggcacgtcag atgacgtgcc tttttcttg | 10500 |
| tctagcgtgc accaatgctt ctggcgtcag gcagccatcg gaagctgtgg tatggctgtg | 10560 |
| caggtcgtaa atcactgcat aattcgtgtc gctcaaggcg cactcccgtt ctggataatg | 10620 |
| ttttttgcgc cgacatcata acggttctgg caaatattct gaaatgagct gttgacaatt | 10680 |
| aatcatccgg ctcgtataat gtgtggaatt gtgagcggat aacaatttca cacaggaaac | 10740 |
| agaccatgac tagtaaggag gacaattcca tggctgctgc tgctgataga ttaaacttaa | 10800 |

| | | | | | |
|---|---|---|---|---|---|
| cttccggcca | cttgaatgct | ggtagaaaga | gaagttcctc | ttctgtttct | ttgaaggctg | 10860 |
| ccgaaaagcc | tttcaaggtt | actgtgattg | gatctggtaa | ctggggtact | actattgcca | 10920 |
| aggtggttgc | cgaaaattgt | aagggatacc | cagaagtttt | cgctccaata | gtacaaatgt | 10980 |
| gggtgttcga | agaagagatc | aatggtgaaa | aattgactga | aatcataaat | actagacatc | 11040 |
| aaaacgtgaa | atacttgcct | ggcatcactc | tacccgacaa | tttggttgct | aatccagact | 11100 |
| tgattgattc | agtcaaggat | gtcgacatca | tcgttttcaa | cattccacat | caattttttgc | 11160 |
| cccgtatctg | tagccaattg | aaaggtcatg | ttgattcaca | cgtcagagct | atctcctgtc | 11220 |
| taaagggttt | tgaagttggt | gctaaaggtg | tccaattgct | atcctcttac | atcactgagg | 11280 |
| aactaggtat | tcaatgtggt | gctctatctg | gtgctaacat | tgccaccgaa | gtcgctcaag | 11340 |
| aacactggtc | tgaaacaaca | gttgcttacc | acattccaaa | ggatttcaga | ggcgagggca | 11400 |
| aggacgtcga | ccataaggtt | ctaaaggcct | tgttccacag | accttacttc | cacgttagtg | 11460 |
| tcatcgaaga | tgttgctggt | atctccatct | gtggtgcttt | gaagaacgtt | gttgccttag | 11520 |
| gttgtggttt | cgtcgaaggt | ctaggctggg | gtaacaacgc | ttctgctgcc | atccaaagag | 11580 |
| tcggtttggg | tgagatcatc | agattcggtc | aaatgttttt | cccagaatct | agagaagaaa | 11640 |
| catactacca | agagtctgct | ggtgttgctg | atttgatcac | cacctgcgct | ggtggtagaa | 11700 |
| acgtcaaggt | tgctaggcta | atggctactt | ctggtaagga | cgcctgggaa | tgtgaaaagg | 11760 |
| agttgttgaa | tggccaatcc | gctcaaggtt | taattacctg | caaagaagtt | cacgaatggt | 11820 |
| tggaaacatg | tggctctgtc | gaagacttcc | cattatttga | agccgtatac | caaatcgttt | 11880 |
| acaacaacta | cccaatgaag | aacctgccgg | acatgattga | agaattagat | ctacatgaag | 11940 |
| attagattta | ttggatccag | gaaacagact | agaattatgg | gattgactac | taaacctcta | 12000 |
| tctttgaaag | ttaacgccgc | tttgttcgac | gtcgacggta | ccattatcat | ctctcaacca | 12060 |
| gccattgctg | cattctggag | ggatttcggt | aaggacaaac | cttatttcga | tgctgaacac | 12120 |
| gttatccaag | tctcgcatgg | ttggagaacg | tttgatgcca | ttgctaagtt | cgctccagac | 12180 |
| tttgccaatg | aagagtatgt | taacaaatta | gaagctgaaa | ttccggtcaa | gtacggtgaa | 12240 |
| aaatccattg | aagtcccagg | tgcagttaag | ctgtgcaacg | ctttgaacgc | tctaccaaaa | 12300 |
| gagaaatggg | ctgtggcaac | ttccggtacc | cgtgatatgg | cacaaaaatg | gttcgagcat | 12360 |
| ctgggaatca | ggagaccaaa | gtacttcatt | accgctaatg | atgtcaaaca | gggtaagcct | 12420 |
| catccagaac | catatctgaa | gggcaggaat | ggcttaggat | atccgatcaa | tgagcaagac | 12480 |
| ccttccaaat | ctaaggtagt | agtatttgaa | gacgctccag | caggtattgc | cgccggaaaa | 12540 |
| gccgccggtt | gtaagatcat | tggtattgcc | actactttcg | acttggactt | cctaaaggaa | 12600 |
| aaaggctgtg | acatcattgt | caaaaaccac | gaatccatca | gagttggcgg | ctacaatgcc | 12660 |
| gaaacagacg | aagttgaatt | cattttttgac | gactacttat | atgctaagga | cgatctgttg | 12720 |
| aaatggtaac | ccgggctgca | ggcatgcaag | cttggctgtt | ttggcggatg | agagaagatt | 12780 |
| ttcagcctga | tacagattaa | atcagaacgc | agaagcggtc | tgataaaaca | gaatttgcct | 12840 |
| ggcggcagta | gcgcggtggt | cccacctgac | cccatgccga | actcagaagt | gaaacgccgt | 12900 |
| agcgccgatg | gtagtgtggg | gtctccccat | gcgagagtag | ggaactgcca | ggcatcaaat | 12960 |
| aaaacgaaag | gctcagtcga | aagactgggc | ctttcgtttt | atctgttgtt | tgtcggtgaa | 13020 |
| cgctctcctg | agtaggacaa | atccgccggg | agcggatttg | aacgttgcga | agcaacggcc | 13080 |
| cggagggtgg | cgggcaggac | gcccgccata | aactgccagg | catcaaatta | agcagaaggc | 13140 |
| catcctgacg | gatggccttt | ttgcgtttct | acaaactcca | gctggatcgg | cgctagagt | 13200 |

```
atacatttaa atggtaccct ctagtcaagg ccttaagtga gtcgtattac ggactggccg    13260
tcgttttaca acgtcgtgac tgggaaaacc ctggcgttac ccaacttaat cgccttgcag    13320
cacatccccc tttcgccagc tggcgtaata gcgaagaggc ccgcaccgat cgcccttccc    13380
aacagttgcg cagcctgaat ggcgaatggc gcctgatgcg gtattttctc cttacgcatc    13440
tgtgcggtat ttcacaccgc atatggtgca ctctcagtac aatctgctct gatgccgcat    13500
agttaagcca gccccgacac ccgccaacac ccgctgacga gct                      13543

<210> SEQ ID NO 65
<211> LENGTH: 13402
<212> TYPE: DNA
<213> ORGANISM: Artificial Sequence
<220> FEATURE:
<223> OTHER INFORMATION: Plamid

<400> SEQUENCE: 65
tagtaaagcc ctcgctagat tttaatgcgg atgttgcgat tacttcgcca actattgcga      60
taacaagaaa aagccagcct ttcatgatat atctcccaat ttgtgtaggg cttattatgc     120
acgcttaaaa ataataaaag cagacttgac ctgatagttt ggctgtgagc aattatgtgc     180
ttagtgcatc taacgcttga gttaagccgc gccgcgaagc ggcgtcggct tgaacgaatt     240
gttagacatt atttgccgac taccttggtg atctcgcctt tcacgtagtg acaaattct      300 tccaactgat ctgcgcgcga ggccaagcga tcttcttctt gtccaagata agcctgtcta     360
gcttcaagta tgacgggctg atactgggcc ggcaggcgct ccattgccca gtcggcagcg     420
acatccttcg cgcgatttt gccggttact gcgctgtacc aaatgcggga caacgtaagc     480 actcatttc gctcatcgcc agcccagtcg ggcggcgagt tccatagcgt taaggtttca     540
tttagcgcct caaatagatc ctgttcagga accggatcaa agagttcctc cgccgctgga     600
cctaccaagg caacgctatg ttctcttgct tttgtcagca agatagccag atcaatgtcg     660
atcgtggctg gctcgaagat acctgcaaga atgtcattgc gctgccattc tccaaattgc     720
agttcgcgct tagctggata cgccacggaa tgatgtcgt cgtgcacaac aatggtgact     780
tctacagcgc ggagaatctc gctctctcca ggggaagccg aagtttccaa aaggtcgttg     840
atcaaagctc gccgcgttgt ttcatcaagc cttacggtca ccgtaaccag caaatcaata     900
tcactgtgtg gcttcaggcc gccatccact gcggagccgt acaaatgtac ggccagcaac     960
gtcggttcga gatggcgctc gatgacgcca actacctctg atagttgagt cgatacttcg    1020
gcgatcaccg cttccctcat gatgtttaac tttgttttag ggcgactgcc ctgctgcgta    1080
acatcgttgc tgctccataa catcaaacat cgacccacgg cgtaacgcgc ttgctgcttg    1140
gatgcccgag gcatagactg taccccaaaa aaacagtcat aacaagccat gaaaaccgcc    1200
actgcgccgt taccaccgct gcgttcggtc aaggttctgg accagttgcg tgagcgcata    1260
cgctacttgc attacagctt acgaaccgaa caggcttatg tccactgggt tcgtgccttc    1320
atccgtttcc acggtgtgcg tcacccggca accttgggca gcagcgaagt cgaggcattt    1380
ctgtcctggc tggcgaacga gcgcaaggtt tcggtctcca cgcatcgtca ggcattggcg    1440
gccttgctgt tcttctacgg caaggtgctg tgcacggatc tgccctggct tcaggagatc    1500
ggaagacctc ggccgtcgcg gcgcttgccg gtggtgctga cccggatga agtggttcgc    1560 atcctcggtt ttctggaagg cgagcatcgt ttgttcgccc agcttctgta tggaacgggc    1620
atgcggatca gtgagggttt gcaactgcgg gtcaaggatc tggatttcga tcacggcacg    1680
atcatcgtgc gggagggcaa gggctccaag gatcgggcct tgatgttacc cgagagcttg    1740
```

```
gcacccagcc tgcgcgagca ggggaattaa ttcccacggg ttttgctgcc cgcaaacggg    1800
ctgttctggt gttgctagtt tgttatcaga atcgcagatc cggcttcagc cggtttgccg    1860
gctgaaagcg ctatttcttc cagaattgcc atgattttt ccccacggga ggcgtcactg    1920
gctcccgtgt tgtcggcagc tttgattcga taagcagcat cgcctgtttc aggctgtcta    1980
tgtgtgactg ttgagctgta acaagttgtc tcaggtgttc aatttcatgt tctagttgct    2040
ttgttttact ggtttcacct gttctattag gtgttacatg ctgttcatct gttacattgt    2100
cgatctgttc atggtgaaca gctttgaatg caccaaaaac tcgtaaaagc tctgatgtat    2160 ctatctttt tacaccgttt tcatctgtgc atatggacag ttttcccttt gatatgtaac    2220
ggtgaacagt tgttctactt ttgtttgtta gtcttgatgc ttcactgata gatacaagag    2280
ccataagaac ctcagatcct tccgtattta gccagtatgt tctctagtgt ggttcgttgt    2340
ttttgcgtga gccatgagaa cgaaccattg agatcatact tactttgcat gtcactcaaa    2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520 attttatct ggttgttctc aagttcggtt acgagatcca tttgtctatc tagttcaact    2580
tggaaaatca acgtatcagt cgggcggcct cgcttatcaa ccaccaattt catattgctg    2640
taagtgttta aatctttact tattggtttc aaaacccatt ggttaagcct tttaaactca    2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta attttttcgct tgagaacttg    2940 gcatagtttg tccactggaa aatctcaaag cctttaacca aaggattcct gatttccaca    3000
gttctcgtca tcagctctct ggttgcttta gctaatacac cataagcatt tccctactg    3060 atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtcctttt cctttgagtt gtgggtatct gtaaattctg ctagacctt    3360 gctggaaaac ttgtaaattc tgctagaccc tctgtaaatt ccgctagacc tttgtgtgtt    3420
ttttttgttt atattcaagt ggttataatt tatagaataa agaaagaata aaaaagata    3480 aaaagaatag atcccagccc tgtgtataac tcactacttt agtcagttcc gcagtattac    3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc tttttcgtga cattcagttc gctgcgctca cggctctggc    3720
agtgaatggg ggtaaatggc actacaggcg ccttttatgg attcatgcaa ggaaactacc    3780
cataatacaa gaaaagcccg tcacgggctt ctcagggcgt tttatggcgg gtctgctatg    3840
tggtgctatc tgacttttg ctgttcagca gttcctgccc tctgatttc cagtctgacc    3900 acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt ccacggtat gcagcaccag    4080 cgcgagatta tgggctcgca cgctcgactg tcggacgggg gcactggaac gagaagtcag    4140
```

```
gcgagccgtc acgcccttga caatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta tttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcaggggtc ccctgccaga   4860 ccataaccta tgacggaggc ggtgacgccg ctgcgctggg cgccctggcg gccagaagct   4920
cgcccctgcg ggtgggtatc gggctcagcg cgtccggcga gatagccctc actcatgccc   4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaaac agttcgtgat cccggggagg aatctcgcct   5460
ctgcccagct gcaccctgat gcttgcgctt gaactggcct agcaaacaca gaaaaaagcc   5520
cgcacctgac agtgcgggct ttttttttcc taggcgatct gtgctgtttg ccacggtatg   5580
cagcaccagc gcgagattat gggctcgcac gctcgactgt cggacggggg cactggaacg   5640
agaagtcagg cgagccgtca cgcccttgac aatgccacat cctgagcaaa taattcaacc   5700
actaaacaaa tcaaccgcgt ttcccggagg taaccaagct tcaccttttg agccgatgaa   5760
caatgaaaag atcaaaacga tttgcagtac tggcccagcg ccccgtcaat caggacgggc   5820
tgattggcga gtggcctgaa gagggggctga tcgccatgga cagccccttt gacccggtct   5880
cttcagtaaa agtggacaac ggtctgatcg tcgaactgga cggcaaacgc cgggaccagt   5940
ttgacatgat cgaccgattt atcgccgatt acgcgatcaa cgttgagcgc acagagcagg   6000
caatgcgcct ggaggcggtg gaaatagccc gtatgctggt ggatattcac gtcagccggg   6060
aggagatcat tgccatcact accgccatca cgccggccaa agcggtcgag gtgatggcgc   6120
agatgaacgt ggtggagatg atgatggcgc tgcagaagat gcgtgcccgc cggaccccct   6180
ccaaccagtg ccacgtcacc aatctcaaag ataatccggt gcagattgcc gctgacgccg   6240
ccgaggccgg gatccgcggc ttctcagaac aggagaccac ggtcggtatc gcgcgctacg   6300
cgccgtttaa cgccctggcg ctgttggtcg gttcgcagtg cggccgcccc ggcgtgttga   6360
cgcagtgctc ggtggaagag gccaccgagc tggagctggg catgcgtggc ttaaccagct   6420
acgccgagac ggtgtcggtc tacggcaccg aagcggtatt taccgacggc gatgatacgc   6480
cgtggtcaaa ggcgttcctc gcctcggcct acgcctcccg cgggttgaaa atgcgctaca   6540
```

-continued

```
cctccggcac cggatccgaa gcgctgatgg gctattcgga gagcaagtcg atgctctacc    6600
tcgaatcgcg ctgcatcttc attactaaag gcgccggggt tcagggactg caaaacggcg    6660
cggtgagctg tatcggcatg accggcgctg tgccgtcggg cattcgggcg gtgctggcgg    6720
aaaacctgat cgcctctatg ctcgacctcg aagtggcgtc cgccaacgac cagactttct    6780
cccactcgga tattcgccgc accgcgcgca ccctgatgca gatgctgccg ggcaccgact    6840
ttattttctc cggctacagc gcggtgccga actacgacaa catgttcgcc ggctcgaact    6900
tcgatgcgga agattttgat gattacaaca tcctgcagcg tgacctgatg gttgacggcg    6960
gcctgcgtcc ggtgaccgag gcggaaacca ttgccattcg ccagaaagcg gcgcgggcga    7020
tccaggcggt tttccgcgag ctggggctgc cgccaatcgc cgacgaggag gtggaggccg    7080
ccacctacgc gcacggcagc aacgagatgc cgccgcgtaa cgtggtggag gatctgagtg    7140
cggtggaaga gatgatgaag cgcaacatca ccggcctcga tattgtcggc gcgctgagcc    7200
gcagcggctt tgaggatatc gccagcaata ttctcaatat gctgcgccag cgggtcaccg    7260
gcgattacct gcagacctcg gccattctcg atcggcagtt cgaggtggtg agtgcggtca    7320
acgacatcaa tgactatcag gggccgggca ccggctatcg catctctgcc gaacgctggg    7380
cggagatcaa aaatattccg ggcgtggttc agcccgacac cattgaataa ggcggtattc    7440
ctgtgcaaca gacaacccaa attcagccct cttttaccct gaaacccgc gagggcgggg    7500
tagcttctgc cgatgaacgc gccgatgaag tggtgatcgg cgtcggccct gccttcgata    7560
aacaccagca tcacactctg atcgatatgc cccatggcgc gatcctcaaa gagctgattg    7620
ccggggtgga agaagagggg cttcacgccc gggtggtgcg cattctgcgc acgtccgacg    7680
tctcctttat ggcctgggat gcggccaacc tgagcggctc ggggatcggc atcggtatcc    7740
agtcgaaggg gaccacggtc atccatcagc gcgatctgct gccgctcagc aacctggagc    7800
tgttctccca ggcgccgctg ctgacgcggg agacctaccg gcagattggc aaaaacgctg    7860
cgcgctatgc gcgcaaagag tcaccttcgc cggtgccggt ggtgaacgat cagatggtgc    7920
ggccgaaatt tatggccaaa gccgcgctat ttcatatcaa agagaccaaa catgtggtgc    7980
aggacgccga gcccgtcacc ctgcacatcg acttagtaag ggagtgacca tgagcgagaa    8040
aaccatgcgc gtgcaggatt atccgttagc caccccgctgc ccggagcata tcctgacgcc    8100
taccggcaaa ccattgaccg atattaccct cgagaaggtg ctctctggcg aggtgggccc    8160
gcaggatgtg cggatctccc gccagaccct tgagtaccag gcgcagattg ccgagcagat    8220
gcagcgccat gcggtggcgc gcaatttccg ccgcgcggcg gagcttatcg ccattcctga    8280
cgagcgcatt ctggctatct ataacgcgct gcgcccgttc cgctcctcgc aggcggagct    8340
gctggcgatc gccgacgagc tggagcacac ctggcatgcg acagtgaatg ccgcctttgt    8400
ccgggagtcg gcggaagtgt atcagcagcg gcataagctg cgtaaaggaa gctaagcgga    8460
ggtcagcatg ccgttaatag ccgggattga tatcggcaac gccaccaccg aggtggcgct    8520
ggcgtccgac tacccgcagg cgagggcgtt tgttgccagc gggatcgtcg cgacgacggg    8580
catgaaaggg acgcgggaca atatcgccgg gaccctcgcc gcgctggagc aggccctggc    8640
gaaaacaccg tggtcgatga gcgatgtctc tcgcatctat cttaacgaag ccgcgccggt    8700
gattggcgat gtggcgatgg agaccatcac cgagaccatt atcaccgaat cgaccatgat    8760
cggtcataac ccgcagacgc cggcggggt gggcgttggc gtgggacga ctatcgccct    8820
cgggcggctg gcgacgctgc cggcggcgca gtatgccgag gggtggatcg tactgattga    8880
cgacgccgtc gatttccttg acgccgtgtg gtggctcaat gaggcgctcg accgggggat    8940
```

```
caacgtggtg gcggcgatcc tcaaaaagga cgacggcgtg ctggtgaaca accgcctgcg   9000
taaaaccctg ccggtggtgg atgaagtgac gctgctggag caggtccccg aggggggtaat   9060
ggcggcggtg gaagtggccg cgccgggcca ggtggtgcgg atcctgtcga atccctacgg   9120
gatcgccacc ttcttcgggc taagcccgga agagacccag gccatcgtcc ccatcgcccg   9180
cgccctgatt ggcaaccgtt ccgcggtggt gctcaagacc ccgcagggg  atgtgcagtc   9240
gcgggtgatc ccggcgggca acctctacat tagcggcgaa aagcgccgcg gagaggccga   9300
tgtcgccgag ggcgcggaag ccatcatgca ggcgatgagc gcctgcgctc cggtacgcga   9360
catccgcggc gaaccgggca cccacgccgg cggcatgctt gagcgggtgc gcaaggtaat   9420
ggcgtccctg accggccatg agatgagcgc gatatacatc caggatctgc tggcggtgga   9480
tacgtttatt ccgcgcaagg tgcagggcgg gatggccggc gagtgcgcca tggagaatgc   9540
cgtcgggatg gcggcgatgg tgaaagcgga tcgtctgcaa atgcaggtta tcgcccgcga   9600
actgagcgcc cgactgcaga ccgaggtggt ggtgggcggc gtggaggcca acatggccat   9660
cgccggggcg ttaaccactc ccggctgtgc ggcgccgctg gcgatcctcg acctcggcgc   9720
cggctcgacg gatgcggcga tcgtcaacgc ggagggggcag ataacggcgg tccatctcgc   9780
cggggcgggg aatatggtca gcctgttgat taaaaccgag ctgggcctcg aggatctttc   9840
gctggcggaa gcgataaaaa aatacccgct ggccaaagtg gaaagcctgt tcagtattcg   9900
tcacgagaat ggcgcggtgg agttctttcg ggaagccctc agcccggcgg tgttcgccaa   9960
agtggtgtac atcaaggagg cgaactggt  gccgatcgat aacgccagcc cgctggaaaa  10020
aattcgtctc gtgcgccggc aggcgaaaga gaaagtgttt gtcaccaact gcctgcgcgc  10080
gctgcgccag gtctcacccg gcggttccat tcgcgatatc gcctttgtgg tgctggtggg  10140
cggctcatcg ctggactttg agatcccgca gcttatcacg gaagccttgt cgcactatgg  10200
cgtggtcgcc gggcagggca atattcgggg aacagaaggg ccgcgcaatg cggtcgccac  10260
cgggctgcta ctggccggtc aggcgaatta acgggcgct  cgcgccagcc tctaggtaca  10320
aataaaaaag gcacgtcaga tgacgtgcct ttttcttgt  ctagcgtgca ccaatgcttc  10380
tggcgtcagg cagccatcgg aagctgtggt atggctgtgc aggtcgtaaa tcactgcata  10440
attcgtgtcg ctcaaggcgc actcccgttc tggataatgt tttttgcgcc gacatcataa  10500
cggttctggc aaatattctg aaatgagctg ttgacaatta atcatccggc tcgtataatg  10560
tgtggaattg tgagcggata acaatttcac acaggaaaca gaccatgact agtaaggagg  10620
acaattccat ggctgctgct gctgatagat taaacttaac ttccggccac ttgaatgctg  10680
gtagaaagag aagttcctct tctgtttctt tgaaggctgc cgaaaagcct tcaaggtta   10740
ctgtgattgg atctggtaac tggggtacta ctattgccaa ggtggttgcc gaaaattgta  10800
agggataccc agaagttttc gctccaatag tacaaatgtg ggtgttcgaa gaagagatca  10860
atggtgaaaa attgactgaa atcataaata ctagacatca aaacgtgaaa tacttgcctg  10920
gcatcactct acccgacaat ttggttgcta atccagactt gattgattca gtcaaggatg  10980
tcgacatcat cgttttcaac attccacatc aattttttgcc ccgtatctgt agccaattga  11040
aaggtcatgt tgattcacac gtcagagcta tctcctgtct aaagggtttt gaagttggtg  11100
ctaaaggtgt ccaattgcta tcctcttaca tcactgagga actaggtatt caatgtggtg  11160
ctctatctgg tgctaacatt gccaccgaag tcgctcaaga acactggtct gaaacaacag  11220
ttgcttacca cattccaaag gatttcagag gcgagggcaa ggacgtcgac cataaggttc  11280
taaaggcctt gttccacaga ccttacttcc acgttagtgt catcgaagat gttgctggta  11340
```

```
tctccatctg tggtgctttg aagaacgttg ttgccttagg ttgtggtttc gtcgaaggtc    11400
taggctgggg taacaacgct tctgctgcca tccaaagagt cggtttgggt gagatcatca    11460
gattcggtca aatgttttc ccagaatcta gagaagaaac atactaccaa gagtctgctg    11520
gtgttgctga tttgatcacc acctgcgctg gtggtagaaa cgtcaaggtt gctaggctaa    11580
tggctacttc tggtaaggac gcctgggaat gtgaaaagga gttgttgaat ggccaatccg    11640
ctcaaggttt aattacctgc aaagaagttc acgaatggtt ggaaacatgt ggctctgtcg    11700
aagacttccc attatttgaa gccgtatacc aaatcgttta caacaactac ccaatgaaga    11760
acctgccgga catgattgaa gaattagatc tacatgaaga ttagatttat tggatccagg    11820
aaacagacta gaattatggg attgactact aaacctctat ctttgaaagt taacgccgct    11880
ttgttcgacg tcgacggtac cattatcatc tctcaaccag ccattgctgc attctggagg    11940
gatttcggta aggacaaacc ttatttcgat gctgaacacg ttatccaagt ctcgcatggt    12000
tggagaacgt ttgatgccat tgctaagttc gctccagact ttgccaatga agagtatgtt    12060
aacaaattag aagctgaaat tccggtcaag tacggtgaaa aatccattga agtcccaggt    12120
gcagttaagc tgtgcaacgc tttgaacgct ctaccaaaag agaaatgggc tgtggcaact    12180
tccggtaccc gtgatatggc acaaaaatgg ttcgagcatc tgggaatcag gagaccaaag    12240
tacttcatta ccgctaatga tgtcaaacag ggtaagcctc atccagaacc atatctgaag    12300
ggcaggaatg gcttaggata tccgatcaat gagcaagacc cttccaaatc taaggtagta    12360
gtatttgaag acgctccagc aggtattgcc gccggaaaag ccgccggttg taagatcatt    12420
ggtattgcca ctactttcga cttggacttc ctaaaggaaa aaggctgtga catcattgtc    12480
aaaaaccacg aatccatcag agttggcggc tacaatgccg aaacagacga agttgaattc    12540 attttgacg actacttata tgctaaggac gatctgttga aatggtaacc cgggctgcag    12600
gcatgcaagc ttggctgttt tggcggatga gagaagattt tcagcctgat acagattaaa    12660
tcagaacgca gaagcggtct gataaaacag aatttgcctg gcggcagtag cgcggtggtc    12720
ccacctgacc ccatgccgaa ctcagaagtg aaacgccgta cgcgcgatgg tagtgtgggg    12780
tctccccatg cgagagtagg gaactgccag gcatcaaata aaacgaaagg ctcagtcgaa    12840
agactgggcc tttcgtttta tctgttgttt gtcggtgaac gctctcctga gtaggacaaa    12900
tccgccggga gcggatttga acgttgcgaa gcaacggccc ggagggtggc gggcaggacg    12960
cccgccataa actgccaggc atcaaattaa gcagaaggcc atcctgacgg atggccttt    13020 tgcgtttcta caactccag ctggatcggg cgctagagta tacatttaaa tggtaccctc    13080
tagtcaaggc cttaagtgag tcgtattacg gactggccgt cgttttacaa cgtcgtgact    13140
gggaaaaccc tggcgttacc caacttaatc gccttgcagc acatcccct ttcgccagct    13200 ggcgtaatag cgaagaggcc cgcaccgatc gcccttccca acagttgcgc agcctgaatg    13260
gcgaatggcg cctgatgcgg tatttctcc ttacgcatct gtgcggtatt tcacaccgca    13320
tatggtgcac tctcagtaca atctgctctg atgccgcata gttaagccag ccccgacacc    13380
cgccaacacc cgctgacgag ct                                             13402
```

<210> SEQ ID NO 66
<211> LENGTH: 14443
<212> TYPE: DNA
<213> ORGANISM: Artificial Sequence
<220> FEATURE:
<223> OTHER INFORMATION: Plasmid

<400> SEQUENCE: 66

-continued

```
ttctgataac aaactagcaa caccagaaca gcccgtttgc gggcagcaaa acccgtggga     60
attaattccc ctgctcgcgc aggctgggtg ccaagctctc gggtaacatc aaggcccgat    120
ccttggagcc cttcttacag agatgaaaaa caaaccgcga cgccaggcgg catcgcggtc    180
tcagagatat gtttacgtag atcgaagagc accggtgttt aaacgccctt gacgatgcca    240
catcctgagc aaataattca accactaaac aaatcaaccg cgtttcccgg aggtaaccga    300
gctcatgatc ctgtgttgtg gtgaagccct gatcgacatg ctgccccggc agacgacgct    360
gggtgaggcg ggcttttgccc cttacgcagg cggagcggtc ttcaacacgg caattgcgct    420
ggggcgtctt ggcgtccctt cagccttttt taccggtctt tccgacgaca tgatgggcga    480
tatcctgcgg gagaccctgc gggccagcaa ggtggatttc agctattgcg ccaccctgtc    540
gcgccccacc accattgcgt tcgttaagct ggttgatggc catgcgacct acgcttttta    600
cgacgagaac accgccggcc ggatgatcac cgaggccgaa cttccggcct gggagcgga    660
ttgcgaagcg ctgcatttcg gcgccatcag ccttattccc gaaccctgcg gcagcaccta    720
tgaggcgctg atgacgcgcg agcatgagac ccgcgtcatc tcgctcgatc cgaacattcg    780
tcccggcttc atccagaaca gcagtcgca catggcccgc atccgccgca tggcggcgat    840
gtctgacatc gtcaagttct cggatgagga cctggcgtgg ttcggtctgg aaggcgacga    900
ggacacgctt gcccgccact ggctgcacca cggtgcaaaa ctcgtcgttg tcacccgtgg    960
cgccaagggt gccgtgggtt acagcgccaa tctcaaggtg gaagtggcct ccgagcgcgt   1020
cgaagtggtc gatacggtcg cgccggcga tacgttcgat gccggcattc ttgcttcgct   1080
gaaaatgcag ggcctgctga ccaaagcgca ggtggcttcg ctgagcgaag agcagatcag   1140
aaaagctttg gcgcttggcg cgaaagccgc tgcggtcact gtctcgcggg ctggcgcaaa   1200
tccgcctttc gcgcatgaaa tcggtttgtg attaattaaa gcacgcagtc aaacaaaaaa   1260
cccgcgccat tgcgcgggtt tttttatgcc cgaaggcgcg ccagcacgca gtcaaacaaa   1320
aaacccgcgc cattgcgcgg gttttttttat gcccgaacgg ccgaggtctt ccgatctcct   1380
gaagccaggg cagatccgtg cacagcacct tgccgtagaa gaacagcaag gccgccaatg   1440
cctgacgatg cgtggagacc gaaaccttgc gctcgttcgc cagccaggac agaaatgcct   1500
cgacttcgct gctgcccaag gttgccgggt gacgcacacc gtggaaacgg atgaaggcac   1560
gaacccagtg gacataagcc tgttcggttc gtaagctgta atgcaagtag cgtatgcgct   1620
cacgcaactg gtccagaacc ttgaccgaac gcagcgtgg taacggcgca gtggcggttt   1680
tcatggcttg ttatgactgt ttttttgggg tacagtctat gcctcgggca tccaagcagc   1740
aagcgcgtta cgccgtgggt cgatgtttga tgttatggag cagcaacgat gttacgcagc   1800
agggcagtcg ccctaaaaca aagttaaaca tcatgaggga agcggtgatc gccgaagtat   1860
cgactcaact atcagaggta gttggcgtca tcgagcgcca tctcgaaccg acgttgctgg   1920
ccgtacattt gtacggctcc gcagtggatg gcggcctgaa gccacacagt gatattgatt   1980
tgctggttac ggtgaccgta aggcttgatg aaacaacgcg gcgagctttg atcaacgacc   2040
ttttggaaac ttcggcttcc cctggagaga gcgagattct ccgcgctgta gaagtcacca   2100
ttgttgtgca cgacgacatc attccgtggc gttatccagc taagcgcgaa ctgcaatttg   2160
gagaatggca gcgcaatgac attcttgcag gtatcttcga ccagccacg atcgacattg   2220
atctggctat cttgctgaca aaagcaagag aacatagcgt tgccttggta ggtccagcgg   2280
cggaggaact ctttgatccg gttcctgaac aggatctatt tgaggcgcta atgaaacct   2340
taacgctatg gaactcgccg cccgactggg ctggcgatga gcgaaatgta gtgcttacgt   2400
```

```
tgtcccgcat ttggtacagc gcagtaaccg gcaaaatcgc gccgaaggat gtcgctgccg   2460
actgggcaat ggagcgcctg ccggcccagt atcagcccgt catacttgaa gctagacagg   2520
cttatcttgg acaagaagaa gatcgcttgg cctcgcgcgc agatcagttg gaagaatttg   2580
tccactacgt gaaaggcgag atcaccaagg tagtcggcaa ataatgtcta acaattcgtt   2640
caagccgacg ccgcttcgcg gcgcggctta actcaagcgt tagatgcact aagcacataa   2700
ttgctcacag ccaaactatc aggtcaagtc tgcttttatt attttttaagc gtgcataata   2760 agccctacac aaattgggag atatatcatg aaaggctggc tttttcttgt tatcgcaata   2820
gttggcgaag taatcgcaac atccgcatta aaatctagcg agggctttac taagctcgtc   2880
agcgggtgtt ggcgggtgtc ggggctggct taactatgcg gcatcagagc agattgtact   2940
gagagtgcac catatgcggt gtgaaatacc gcacagatgc gtaaggagaa aataccgcat   3000
caggcgccat cgccattcca ggctgcgcaa ctgttgggaa gggcgatcgg tgcgggcctc   3060
ttcgctatta cgccagctgg cgaaaggggg atgtgctgca aggcgattaa gttgggtaac   3120
gccagggttt tcccagtcac gacgttgtaa aacgacggcc agtccgtaat acgactcact   3180
taaggccttg actagagggt accatttaaa tgtatactct agcgcccgat ccagctggag   3240
tttgtagaaa cgcaaaaagg ccatccgtca ggatggcctt ctgcttaatt tgatgcctgg   3300
cagtttatgg cgggcgtcct gcccgccacc ctccgggccg ttgcttcgca acgttcaaat   3360
ccgctcccgg cggatttgtc ctactcagga gagcgttcac cgacaaacaa cagataaaac   3420
gaaaggccca gtctttcgac tgagcctttc gttttatttg atgcctggca gttccctact   3480
ctcgcatggg gagaccccac actaccatcg gcgctacggc gtttcacttc tgagttcggc   3540
atggggtcag gtgggaccac cgcgctactg ccgccaggca aattctgttt tatcagaccg   3600
cttctgcgtt ctgatttaat ctgtatcagg ctgaaaatct tctctcatcc gccaaaacag   3660
ccaagcttgc atgcctgcag cccgggttac catttcaaca gatcgtcctt agcatataag   3720
tagtcgtcaa aaatgaattc aacttcgtct gtttcggcat tgtagccgcc aactctgatg   3780
gattcgtggt ttttgacaat gatgtcacag ccttttttcct ttaggaagtc caagtcgaaa   3840
gtagtggcaa taccaatgat cttacaaccg gcggcttttc cggcggcaat acctgctgga   3900
gcgtcttcaa atactactac cttagatttg gaagggtctt gctcattgat cggatatcct   3960
aagccattcc tgcccttcag atatggttct ggatgaggct taccctgttt gacatcatta   4020
gcggtaatga agtactttgg tctcctgatt cccagatgct cgaaccattt ttgtgccata   4080
tcacgggtac cggaagttgc cacagcccat ttctcttttg gtagagcgtt caaagcgttg   4140
cacagcttaa ctgcacctgg gacttcaatg gattttttcac cgtacttgac cggaatttca   4200
gcttctaatt tgttaacata ctcttcattg gcaaagtctg gagcgaactt agcaatggca   4260
tcaaacgttc tccaaccatg cgagacttgg ataacgtgtt cagcatcgaa ataaggtttg   4320
tccttaccga aatccctcca gaatgcagca atggctggtt gagagatgat aatggtaccg   4380
tcgacgtcga acaaagcggc gttaactttc aaagatagag gtttagtagt caatcccata   4440
attctagtct gtttcctgga tccaataaat ctaatcttca tgtagatcta attcttcaat   4500
catgtccggc aggttcttca ttgggtagtt gttgtaaacg attggtata cggcttcaaa   4560 taatgggaag tcttcgacag agccacatgt ttccaaccat tcgtgaactt ctttgcaggt   4620
aattaaacct tgagcggatt ggccattcaa caactccttt tcacattccc aggcgtcctt   4680
accagaagta gccattagcc tagcaacctt gacgtttcta ccaccagcgc aggtggtgat   4740
caaatcagca acaccagcag actcttggta gtatgttttct tctctagatt ctgggaaaaa   4800
```

| | |
|---|---|
| catttgaccg aatctgatga tctcacccaa accgactctt tggatggcag cagaagcgtt | 4860 |
| gttaccccag cctagacctt cgacgaaacc acaacctaag gcaacaacgt tcttcaaagc | 4920 |
| accacagatg gagataccag caacatcttc gatgacacta acgtggaagt aaggtctgtg | 4980 |
| gaacaaggcc tttagaacct tatggtcgac gtccttgccc tcgcctctga aatcctttgg | 5040 |
| aatgtggtaa gcaactgttg tttcagacca gtgttcttga gcgacttcgg tggcaatgtt | 5100 |
| agcaccagat agagcaccac attgaatacc tagttcctca gtgatgtaag aggatagcaa | 5160 |
| ttggacacct ttagcaccaa cttcaaaacc ctttagacag gagatagctc tgacgtgtga | 5220 |
| atcaacatga cctttcaatt ggctacagat acggggcaaa aattgatgtg gaatgttgaa | 5280 |
| aacgatgatg tcgacatcct tgactgaatc aatcaagtct ggattagcaa ccaaattgtc | 5340 |
| gggtagagtg atgccaggca agtatttcac gttttgatgt ctagtattta tgatttcagt | 5400 |
| caatttttca ccattgatct cttcttcgaa cacccacatt tgtactattg gagcgaaaac | 5460 |
| ttctgggtat cccttacaat tttcggcaac caccttggca atagtagtac cccagttacc | 5520 |
| agatccaatc acagtaacct tgaaaggctt ttcggcagcc ttcaaagaaa cagaagagga | 5580 |
| acttctcttt ctaccagcat tcaagtggcc ggaagttaag tttaatctat cagcagcagc | 5640 |
| agccatggaa ttgtcctcct tactagtcat ggtctgtttc ctgtgtgaaa ttgttatccg | 5700 |
| ctcacaattc cacacattat acgagccgga tgattaattg tcaacagctc atttcagaat | 5760 |
| atttgccaga accgttatga tgtcggcgca aaaaacatta tccagaacgg gagtgcgcct | 5820 |
| tgagcgacac gaattatgca gtgatttacg acctgcacag ccataccaca gcttccgatg | 5880 |
| gctgcctgac gccagaagca ttggtgcacg ctagacaaga aaaaaggcac gtcatctgac | 5940 |
| gtgccttttt tatttgtacc tagaggctgg cgcgagcgcc cgtttaattc gcctgaccgg | 6000 |
| ccagtagcag cccggtggcg accgcattgc gcggcccttc tgttccccga atattgccct | 6060 |
| gcccggcgac cacgccatag tgcgacaagg cttccgtgat aagctgcggg atctcaaagt | 6120 |
| ccagcgatga gccgcccacc agcaccacaa aggcgatatc gcgaatggaa ccgccgggtg | 6180 |
| agacctggcg cagcgcgcgc aggcagttgg tgacaaacac tttctctttc gcctgccggc | 6240 |
| gcacgagacg aattttttcc agcgggctgg cgttatcgat cggcaccagt tcgccctcct | 6300 |
| tgatgtacac cactttggcg aacaccgccg ggctgagggc ttcccgaaag aactccaccg | 6360 |
| cgccattctc gtgacgaata ctgaacaggc tttccacttt ggccagcggg tattttttta | 6420 |
| tcgcttccgc cagcgaaaga tcctcgaggc ccagctcggt tttaatcaac aggctgacca | 6480 |
| tattccccgc cccggcgaga tggaccgccg ttatctgccc ctccgcgttg acgatcgccg | 6540 |
| catccgtcga gccggcgccg aggtcgagga tcgccagcgg cgccgcacag ccgggagtgg | 6600 |
| ttaacgcccc ggcgatggcc atgttggcct ccacgccgcc caccaccacc tcggtctgca | 6660 |
| gtcgggcgct cagttcgcgg gcgataacct gcatttgcag acgatccgct ttcaccatcg | 6720 |
| ccgccatccc gacggcattc tccatggcgc actcgccggc catcccgccc tgcaccttgc | 6780 |
| gcggaataaa cgtatccacc gccagcagat cctggatgta tatcgcgctc atctcatggc | 6840 |
| cggtcaggga cgccattacc ttgcgcaccc gctcaagcat gccgccggcg tgggtgcccg | 6900 |
| gttcgccgcg gatgtcgcgt accggagcgc aggcgctcat cgcctgcatg atggcttccg | 6960 |
| cgccctcggc gacatcggcc tctccgcggc gcttttcgcc gctaatgtag aggttgcccg | 7020 |
| ccgggatcac ccgcgactgc acatccccct gcggggtctt gagcaccacc gcggaacggt | 7080 |
| tgccaatcag ggcgcgggcg atggggacga tggcctgggt ctcttccggg cttagcccga | 7140 |
| agaaggtggc gatcccgtag ggattcgaca ggatccgcac cacctggccc ggcgcggcca | 7200 |

```
cttccaccgc cgccattacc ccctcgggga cctgctccag cagcgtcact tcatccacca    7260
ccggcagggt tttacgcagg cggttgttca ccagcacgcc gtcgtccttt ttgaggatcg    7320
ccgccaccac gttgatcccc cggtcgagcg cctcattgag ccaccacacg gcgtcaagga    7380
aatcgacggc gtcgtcaatc agtacgatcc accccctcgg atactgcgcc gccggcagcg    7440
tcgccagccg cccgagggcg atagtcgtcc ccacgccaac gcccaccccg cccggcgtct    7500
gcgggttatg accgatcatg gtcgattcgg tgataatggt ctcggtgatg gtctccatcg    7560
ccacatcgcc aatcaccggc gcggcttcgt taagatagat gcgagagaca tcgctcatcg    7620
accacggtgt tttcgccagg gcctgctcca gcgcggcgag ggtcccggcg atattgtccc    7680
gcgtcccttt catgcccgtc gtcgcgacga tcccgctggc aacaaacgcc ctcgcctgcg    7740
ggtagtcgga cgccagcgcc acctcggtgg tggcgttgcc gatatcaatc ccggctatta    7800
acggcatgct gacctccgct tagcttcctt tacgcagctt atgccgctgc tgatacactt    7860
ccgccgactc ccggacaaag gcggcattca ctgtcgcatg ccaggtgtgc tccagctcgt    7920
cggcgatcgc cagcagctcc gcctgcgagg agcggaacgg gcgcagcgcg ttatagatag    7980
ccagaatgcg ctcgtcagga atggcgataa gctccgccgc gcggcggaaa ttgcgcgcca    8040
ccgcatggcg ctgcatctgc tcggcaatct gcgcctggta ctcaagggtc tggcgggaga    8100
tccgcacatc ctgcgggccc acctcgccag agagcacctt ctcgagggta atatcggtca    8160
atggtttgcc ggtaggcgtc aggatatgct ccgggcagcg ggtggctaac ggataatcct    8220
gcacgcgcat ggttttctcg ctcatggtca ctcccttact aagtcgatgt gcagggtgac    8280
gggctcggcg tcctgcacca catgtttggt ctctttgata tgaaatagcg cggctttggc    8340
cataaatttc ggccgcacca tctgatcgtt caccaccggc accggcgaag gtgactcttt    8400
gcgcgcatag cgcgcagcgt ttttgccaat ctgccggtag gtctccagcg tcagcagcgg    8460
cgcctgggag aacagctcca ggttgctgag cggcagcaga tcgcgctgat ggatgaccgt    8520
ggtccccttc gactggatac cgatgccgat ccccgagccg ctcaggttgg ccgcatccca    8580
ggccataaag gagacgtcgg acgtgcgcag aatgcgcacc acccgggcgt gaagcccctc    8640
ttcttccacc ccggcaatca gctctttgag gatcgcgcca tggggcatat cgatcagagt    8700
gtgatgctgg tgtttatcga aggcagggcc gacgccgatc accacttcat cggcgcgttc    8760
atcggcagaa gctaccccgc cctcgcgggt tttcagggta aaagagggct gaatttgggt    8820
tgtctgttgc acaggaatac cgccttgttc aatggtgtcg ggctgaacca cgcccggaat    8880 attttttgatc tccgcccagc gttcggcaga gatgcgatag ccggtgcccg gcccctgata    8940
gtcattgatg tcgttgaccg cactcaccac ctcgaactgc cgatcgaaaa tggccgaggt    9000
ctgcaggtaa tcgccggtga cccgctggcg cagcatattg agaatattgc tggcgatatc    9060
ctcaaagccg ctgcggctca gcgcgccgac aatatcgagg ccggtgatgt tgcgcttcat    9120
catctcttcc accgcactca gatcctccac cacgttacgc ggcggcatct cgttgctgcc    9180
gtgcgcgtag gtggcggcct ccacctcctc gtcggcgatt ggcggcagcc ccagctcgcg    9240
gaaaaccgcc tggatcgccc gcgccgcttt ctggcgaatg caatggtttt ccgcctcggt    9300
caccggacgc aggccgccgt caaccatcag gtcacgctgc aggatgttgt aatcatcaaa    9360
atcttccgca tcgaagttcg agccggcgaa catgttgtcg tagttcggca ccgcgctgta    9420
gccggagaaa ataaagtcgg tgcccggcag catctgcatc agggtgcgcg cggtgcggcg    9480
aatatccgag tgggagaaag tctggtcgtt ggcggacgcc acttcgaggt cgagcataga    9540
ggcgatcagg tttccgcca gcaccgcccg aatgcccgac ggcacagcgc cggtcatgcc    9600
```

```
gatacagctc accgcgccgt tttgcagtcc ctgaaccccg gcgcctttag taatgaagat   9660
gcagcgcgat tcgaggtaga gcatcgactt gctctccgaa tagcccatca gcgcttcgga   9720
tccggtgccg gaggtgtagc gcattttcaa cccgcgggag gcgtaggccg aggcgaggaa   9780
cgcctttgac cacggcgtat catcgccgtc ggtaaatacc gcttcggtgc cgtagaccga   9840
caccgtctcg gcgtagctgg ttaagccacg catgcccagc tccagctcgg tggcctcttc   9900
caccgagcac tgcgtcaaca cgccggggcg gccgcactgc gaaccgacca acagcgccag   9960
ggcgttaaac ggcgcgtagc gcgcgatacc gaccgtggtc tcctgttctg agaagccgcg  10020
gatcccggcc tcggcggcgt cagcggcaat ctgcaccgga ttatctttga gattggtgac  10080
gtggcactgg ttggagggggg tccggcgggc acgcatcttc tgcagcgcca tcatcatctc  10140
caccacgttc atctgcgcca tcacctcgac cgctttggcc ggcgtgatgg cggtagtgat  10200
ggcaatgatc tcctcccggc tgacgtgaat atccaccagc atacgggcta tttccaccgc  10260
ctccaggcgc attgcctgct ctgtgcgctc aacgttgatc gcgtaatcgg cgataaatcg  10320
gtcgatcatg tcaaactggt cccggcgttt gccgtccagt tcgacgatca gaccgttgtc  10380
cactttact gaagagaccg ggtcaaaggg gctgtccatg gcgatcagcc cctcttcagg  10440
ccactcgcca atcagcccgt cctgattgac ggggcgctgg gccagtactg caaatcgttt  10500
tgatcttttc attgttcatc ggctcaaaag gtgaagcttg gttacctccg ggaaacgcgg  10560
ttgatttgtt tagtggttga attatttgct caggatgtgg cattgtcaag ggcgtgacgg  10620
ctcgcctgac ttctcgttcc agtgcccccg tccgacagtc gagcgtgcga gcccataatc  10680
tcgcgctggt gctgcatacc gtggcaaaca gcacagatcg cctaggaaaa aaaaagcccg  10740
cactgtcagg tgcgggcttt tttctgtgtt tgctaggcca gttcaagcgc aagcatcagg  10800
gtgcagctgg gcagaggcga gattcctccc cgggatcacg aactgttta acgggccgct  10860
ctcggccata ttgcggtcga taagccgctc cagggcggtg atctcctctt cgccgatcgt  10920
ctggctcagg cgggtcaggc cccgcgcatc gctggccagt tcagccccca gcacgaacag  10980
cgtctgctga atatggtgca ggcttttccg cagcccggcg tcgcgggtcg tggcgtagca  11040
gacgcccagc tgggatatca gttcatcgac ggtgccgtag gcctcgacgc gaatatggtc  11100
tttctcgatg cggctgccgc cgtacagggc ggtggtgcct ttatccccgg tgcgggtata  11160
gatacgatac attcagtttc tctcacttaa cggcaggact ttaaccagct gcccggcgtt  11220
ggcgccgagc gtacgcagtt gatcgtcgct atcggtgacg tgtccggtag ccagcggcgc  11280
gtccgccggc agctgggcat gagtgagggc tatctcgccg gacgcgctga gcccgatacc  11340
cacccgcagg ggcgagcttc tggccgccag ggcgcccagc gcagcggcgt caccgcctcc  11400
gtcataggtt atggtctggc aggggacccc ctgctcctcc agcccccagc acagctcatt  11460
gatggcgccg gcatggtgcc cgcgcggatc gtaaaacagg cgtacgcctg gcggtgaaag  11520
cgacatgacg gtcccctcgt taacactcag aatgcctggc ggaacatacg atagctcata  11580
atataccttc tcgcttcagg ttataatgcg gaaaaacaat ccaggggcgca ctgggctaat  11640
aattgatcct gctcgaccgt accgccgcta acgccgacgg cgccaattac ctgctcatta  11700
aaaataactg gcaggccgcc gccaaaaata taattcgct gttggttggt tagctgcaga  11760
ccgtacagag attgtcctgg ctggaccgct gacgtaattt catgggtacc ttgcttcagg  11820
ctgcaggcgc tccaggcttt attcagggaa atatcgcagc tggagacgaa ggcctcgtcc  11880
atccgctgga taagcagcgt gttgcctccg cggtcaacta cggaaaacac caccgccacg  11940
ttgatctcag tggcttttttt ttccaccgcc gccgccattt gctgggcggc ggccagggtg  12000
```

```
attgtctgaa cttgttggct cttgttcatc attctctccc gcaagcttgg ttacctccgg    12060
gaaacgcggt tgatttgttt agtggttgaa ttatttgctc aggatgtggc attgtcaagg    12120
gcgtgacggc tcgcctgact tctcgttcca gtgcccccgt ccgacagtcg agcgtgcgag    12180
cccataatct cgcgctggtg ctgcataccg tggcaaacag cacagatcgc ctagcagtca    12240
aaagcctccg gtcggaggct tttgactatt taaatgaatt cccgacagta agacgggtaa    12300
gcctgttgat gataccgctg ccttactggg tgcattagcc agtctgaatg acctgtcacg    12360
ggataatccg aagtggtcag actggaaaat cagagggcag gaactgctga acagcaaaaa    12420
gtcagatagc accacatagc agacccgcca taaaacgccc tgagaagccc gtgacgggct    12480
tttcttgtat tatgggtagt ttccttgcat gaatccataa aaggcgcctg tagtgccatt    12540
tacccccatt cactgccaga gccgtgagcg cagcgaactg aatgtcacga aaaagacagc    12600
gactcaggtg cctgatggtc ggagacaaaa ggaatattca gcgatttgcc cgagcttgcg    12660
agggtgctac ttaagccttt agggttttaa ggtctgtttt gtagaggagc aaacagcgtt    12720
tgcgacatcc ttttgtaata ctgcggaact gactaaagta gtgagttata cacagggctg    12780
ggatctattc tttttatctt tttttattct ttctttattc tataaattat aaccacttga    12840
atataaacaa aaaaaacaca caaaggtcta gcggaattta cagagggtct agcagaattt    12900
acaagttttc cagcaaaggt ctagcagaat ttacagatac ccacaactca aggaaaagg    12960 actagtaatt atcattgact agcccatctc aattggtata gtgattaaaa tcacctagac    13020
caattgagat gtatgtctga attagttgtt ttcaaagcaa atgaactagc gattagtcgc    13080
tatgacttaa cggagcatga accaagcta attttatgct gtgtggcact actcaacccc    13140
acgattgaaa accctacaag gaaagaacgg acggtatcgt tcacttataa ccaatacgct    13200
cagatgatga acatcagtag ggaaaatgct tatggtgtat tagctaaagc aaccagagag    13260
ctgatgacga gaactgtgga aatcaggaat cctttggtta aaggctttga gattttccag    13320
tggacaaact atgccaagtt ctcaagcgaa aaattagaat tagttttag tgaagagata    13380 ttgccttatc ttttccagtt aaaaaaattc ataaaatata atctggaaca tgttaagtct    13440
tttgaaaaca aatactctat gaggatttat gagtggttat taaagaact aacacaaaag    13500 aaaactcaca aggcaaatat agagattagc cttgatgaat ttaagttcat gttaatgctt    13560 gaaataact accatgagtt taaaaggctt aaccaatggg ttttgaaacc aataagtaaa    13620
gatttaaaca cttacagcaa tatgaaattg gtggttgata agcgaggccg cccgactgat    13680
acgttgattt tccaagttga actagataga caaatggatc tcgtaaccga acttgagaac    13740
aaccagataa aaatgaatgg tgacaaaata ccaacaacca ttacatcaga ttcctaccta    13800
cataacggac taagaaaaac actacacgat gctttaactg caaaaattca gctcaccagt    13860
tttgaggcaa aattttttgag tgacatgcaa agtaagtatg atctcaatgg ttcgttctca    13920
tggctcacgc aaaaacaacg aaccacacta gagaacatac tggctaaata cggaaggatc    13980
tgaggttctt atggctcttg tatctatcag tgaagcatca agactaacaa acaaagtag    14040 aacaactgtt caccgttaca tatcaaaggg aaaactgtcc atatgcacag atgaaaacgg    14100
tgtaaaaaag atagatacat cagagctttt acgagttttt ggtgcattca agctgttca    14160 ccatgaacag atcgacaatg taacagatga acagcatgta acacctaata gaacaggtga    14220
aaccagtaaa acaaagcaac tagaacatga aattgaacac ctgagacaac ttgttacagc    14280
tcaacagtca cacatagaca gcctgaaaca ggcgatgctg cttatcgaat caaagctgcc    14340
gacaacacgg gagccagtga cgcctcccgt ggggaaaaaa tcatggcaat tctggaagaa    14400
```

```
                                            atagcgcttt cagccggcaa accggctgaa gccggatctg cga        14443

<210> SEQ ID NO 67
<211> LENGTH: 1260
<212> TYPE: DNA
<213> ORGANISM: Citrobacter sp

<400> SEQUENCE: 67
atgaagataa atatgccgtt cagtaatgac aaatatcggt actcgtccgg gtatctgctt       60
tttttctttg ccgcctggtc gttgtggtgg tcttttttatg cgatatggct aaaaaataaa     120
cttggcctgt ccggaacgga gctgggaatg ctgtatgccg taaaccagtt ctttagcatg      180
ctgtttatgc tggtctacgg ttttctgcag gataagctcg gcacccgtaa acaccttatc     240
tggctgatgg ggatagtcat cacgctcagc ggcccgttcc tgatttatgt ttacgaaccg     300
ctgctgacct ccaacttcaa acttggtatg gcgctgggag ccattttctt tggccttggc    360
tacctcgcgg gttgtggtct ggtagaaagc ttcgtcgaaa agtgagccg caaattcaac     420 tttgaattcg gcaccgcccg cttgtgggga tcgcttggct acgccgcagg gacatttgtt    480
ggcggtatct tcttcagcat caacccacac attaacttct ggtgcgtatc ggtaatgggg    540
gtgttattcc tgttgattaa cgtgttgttc aaaaccaact cacccgcccc atcttctgta    600
aaaacgcgtt ctcctgaacc tgacgcgctg acccgaaagg attttctcac tatctttaaa   660
gatacgcagt tctggttttt cgttatctttt gtcgtcggta cctggtcgtt ctatagcatc   720
tacgatcagc agatgttccc ggtgtttttac gccagcttat ttgacgatcc cgaactggca   780
ccacgcgtat acggctacct caactcggta caggtcttta tggaagccgt cggtatggcg    840
ctggttccat tcctgattaa ccgcatcggg cctaaatccg cattgctgct gggtggcaca    900
atcatggcct gtcgaatcct gggttcagca ctgttcaccg atatctatat tatctccttg    960
attaaaatgc ttcatgcgct ggaagtccca ctgtttgtta tttcagtgtt taaattcagc   1020
gtagcgaatt ttgataaacg cctgtcatca acgatatatc tcattggctt caatatcgcc   1080
agttccattg gcattatcgt gctgtcactg cctgtcggta agttgtttga taaagtgggc    1140
tatcaggaaa tcttcctgat tatggccagc attgtgataa taacactaat atttggctat   1200
ttctcgttga gcaaaaagca tcatcagcag aagatgggaa atgaactggt gacagagtag   1260

<210> SEQ ID NO 68
<211> LENGTH: 419
<212> TYPE: PRT
<213> ORGANISM: Citrobacter sp

<400> SEQUENCE: 68

Met Lys Ile Asn Met Pro Phe Ser Asn Asp Lys Tyr Arg Tyr Ser Ser
1               5                   10                  15

Gly Tyr Leu Leu Phe Phe Phe Ala Ala Trp Ser Leu Trp Trp Ser Phe
            20                  25                  30

Tyr Ala Ile Trp Leu Lys Asn Lys Leu Gly Leu Ser Gly Thr Glu Leu
        35                  40                  45

Gly Met Leu Tyr Ala Val Asn Gln Phe Phe Ser Met Leu Phe Met Leu
    50                  55                  60

Val Tyr Gly Phe Leu Gln Asp Lys Leu Gly Thr Arg Lys His Leu Ile
65                  70                  75                  80

Trp Leu Met Gly Ile Val Ile Thr Leu Ser Gly Pro Phe Leu Ile Tyr
                85                  90                  95

Val Tyr Glu Pro Leu Leu Thr Ser Asn Phe Lys Leu Gly Met Ala Leu
```

```
              100                 105                 110
Gly Ala Ile Phe Phe Gly Leu Gly Tyr Leu Ala Gly Cys Gly Leu Val
            115                 120                 125

Glu Ser Phe Val Glu Lys Val Ser Arg Lys Phe Asn Phe Glu Phe Gly
            130                 135                 140

Thr Ala Arg Leu Trp Gly Ser Leu Gly Tyr Ala Ala Gly Thr Phe Val
145                 150                 155                 160

Gly Gly Ile Phe Phe Ser Ile Asn Pro His Ile Asn Phe Trp Cys Val
                165                 170                 175

Ser Val Met Gly Val Leu Phe Leu Leu Ile Asn Val Leu Phe Lys Thr
            180                 185                 190

Asn Ser Pro Ala Pro Ser Ser Val Lys Thr Arg Ser Pro Glu Pro Asp
            195                 200                 205

Ala Leu Thr Arg Lys Asp Phe Leu Thr Ile Phe Lys Asp Thr Gln Phe
            210                 215                 220

Trp Phe Phe Val Ile Phe Val Val Gly Thr Trp Ser Phe Tyr Ser Ile
225                 230                 235                 240

Tyr Asp Gln Gln Met Phe Pro Val Phe Tyr Ala Ser Leu Phe Asp Asp
                245                 250                 255

Pro Glu Leu Ala Pro Arg Val Tyr Gly Tyr Leu Asn Ser Val Gln Val
            260                 265                 270

Phe Met Glu Ala Val Gly Met Ala Leu Val Pro Phe Leu Ile Asn Arg
            275                 280                 285

Ile Gly Pro Lys Ser Ala Leu Leu Leu Gly Gly Thr Ile Met Ala Cys
            290                 295                 300

Arg Ile Leu Gly Ser Ala Leu Phe Thr Asp Ile Tyr Ile Ile Ser Leu
305                 310                 315                 320

Ile Lys Met Leu His Ala Leu Glu Val Pro Leu Phe Val Ile Ser Val
                325                 330                 335

Phe Lys Phe Ser Val Ala Asn Phe Asp Lys Arg Leu Ser Ser Thr Ile
            340                 345                 350

Tyr Leu Ile Gly Phe Asn Ile Ala Ser Ser Ile Gly Ile Ile Val Leu
            355                 360                 365

Ser Leu Pro Val Gly Lys Leu Phe Asp Lys Val Gly Tyr Gln Glu Ile
370                 375                 380

Phe Leu Ile Met Ala Ser Ile Val Ile Ile Thr Leu Ile Phe Gly Tyr
385                 390                 395                 400

Phe Ser Leu Ser Lys Lys His His Gln Gln Lys Met Gly Asn Glu Leu
                405                 410                 415

Val Thr Glu

<210> SEQ ID NO 69
<211> LENGTH: 1314
<212> TYPE: DNA
<213> ORGANISM: Enterococcus faecium

<400> SEQUENCE: 69
atgaaagggg atacaaatat atcgttggag ataaaaata tgtcaaaagt taacgtattt     60
aaaaatcaat cttatttaca aagttcagct acattattac tattttttgc ttcttggggt    120
gtttggtggt cattttttca actttggcta acatctgaat caaatggttt agggttatct    180
ggcagtgctg taggaacagt attctcggca aattcgttag ttaccttaat tttgatgttt    240
atttatggaa cattacaaga taattgtat attaaacgaa atttattaat ttttgcttct    300
gtattagcga cacttgttgg accatttttt atatggatat atgggccatt gctagataac    360
```

```
aattttaatt taggcattat tatgggagcg ctattttgt cagctggata tttagcttct    420
gtaggagttt ttgaagctgt gtcagaaagg tttagtcgtt tatttggctt tgaatatgga    480
caagcaaggg cgtggggatc atttggttat gccttggtag cgcttttggc aggatttta    540 tttgtaaaaa atcctcattt aaactttttgg gcgggatctt tctttggttc tttactattg    600
ttaaatttat tattttggaa ccctaaagtt gaacgggaag caaatcaaaa ttttaatcaa    660
gaacaagctg aatcaaatag tattccttct ttaaaagaaa tgtttgatct aatgaaactg    720
cctcaattat ggacgataat catctttatt gttttttacat ggacatttta acggtattc    780 gatcaacaaa tgtttccggg atttatact ggtttgtttt caacatcagc taatggtgaa    840
aaaatatatg ggacattgaa tgctattcaa gtattttgtg aagcgttaat gatgggaatt    900
gttccaatca ttatgagaaa attaggggtt cgaaatactt tgttattagg tgtaaccatt    960
atgtgtgtac gaattggatt gtgcgggttt gcctcgacac cattatctgt ttcatgcata    1020
aaaatgttgc atgctttaga agtaccatta tttacattac caatgtttcg ctatttaca    1080 cttcattttg atacaaagct atcagcaacc ctctatatga taggatttca gatagctgct    1140
caaattgggc aagtgatttt atcaaccacca ttgggaatat aagagacaa cgttggctat    1200 caaccaacat ttaaaattat ttctcttatt gtattactag caggcatata tgcattcttt    1260
attcttaaac aagatgatag agatgttcaa ggggatccat ttattcgagg ataa    1314
```

<210> SEQ ID NO 70
<211> LENGTH: 437
<212> TYPE: PRT
<213> ORGANISM: Enterococcus faecium

<400> SEQUENCE: 70

Met Lys Gly Asp Thr Asn Ile Ser Leu Glu Asp Lys Asn Met Ser Lys
1               5                   10                  15

Val Asn Val Phe Lys Asn Gln Ser Tyr Leu Gln Ser Ser Ala Thr Leu
            20                  25                  30

Leu Leu Phe Phe Ala Ser Trp Gly Val Trp Trp Ser Phe Phe Gln Leu
        35                  40                  45

Trp Leu Thr Ser Glu Ser Asn Gly Leu Gly Leu Ser Gly Ser Ala Val
    50                  55                  60

Gly Thr Val Phe Ser Ala Asn Ser Leu Val Thr Leu Ile Leu Met Phe
65                  70                  75                  80

Ile Tyr Gly Thr Leu Gln Asp Lys Leu Tyr Ile Lys Arg Asn Leu Leu
                85                  90                  95

Ile Phe Ala Ser Val Leu Ala Thr Leu Val Gly Pro Phe Phe Ile Trp
            100                 105                 110

Ile Tyr Gly Pro Leu Leu Asp Asn Asn Phe Asn Leu Gly Ile Ile Met
        115                 120                 125

Gly Ala Leu Phe Leu Ser Ala Gly Tyr Leu Ala Ser Val Gly Val Phe
    130                 135                 140

Glu Ala Val Ser Glu Arg Phe Ser Arg Leu Phe Gly Phe Glu Tyr Gly
145                 150                 155                 160

Gln Ala Arg Ala Trp Gly Ser Phe Gly Tyr Ala Leu Val Ala Leu Leu
                165                 170                 175

Ala Gly Phe Leu Phe Val Lys Asn Pro His Leu Asn Phe Trp Ala Gly
            180                 185                 190

Ser Phe Phe Gly Ser Leu Leu Leu Leu Asn Leu Leu Phe Trp Asn Pro
        195                 200                 205

```
Lys Val Glu Arg Glu Ala Asn Gln Asn Phe Asn Gln Glu Gln Ala Glu
    210                 215                 220

Ser Asn Ser Ile Pro Ser Leu Lys Glu Met Phe Asp Leu Met Lys Leu
225                 230                 235                 240

Pro Gln Leu Trp Thr Ile Ile Phe Ile Val Phe Thr Trp Thr Phe
                245                 250                 255

Tyr Thr Val Phe Asp Gln Gln Met Phe Pro Gly Phe Tyr Thr Gly Leu
            260                 265                 270

Phe Ser Thr Ser Ala Asn Gly Glu Lys Ile Tyr Gly Thr Leu Asn Ala
        275                 280                 285

Ile Gln Val Phe Cys Glu Ala Leu Met Met Gly Ile Val Pro Ile Ile
    290                 295                 300

Met Arg Lys Leu Gly Val Arg Asn Thr Leu Leu Leu Gly Val Thr Ile
305                 310                 315                 320

Met Cys Val Arg Ile Gly Leu Cys Gly Phe Ala Ser Thr Pro Leu Ser
                325                 330                 335

Val Ser Cys Ile Lys Met Leu His Ala Leu Glu Val Pro Leu Phe Thr
            340                 345                 350

Leu Pro Met Phe Arg Tyr Phe Thr Leu His Phe Asp Thr Lys Leu Ser
        355                 360                 365

Ala Thr Leu Tyr Met Ile Gly Phe Gln Ile Ala Ala Gln Ile Gly Gln
    370                 375                 380

Val Ile Leu Ser Thr Pro Leu Gly Ile Leu Arg Asp Asn Val Gly Tyr
385                 390                 395                 400

Gln Pro Thr Phe Lys Ile Ile Ser Leu Ile Val Leu Leu Ala Gly Ile
                405                 410                 415

Tyr Ala Phe Phe Ile Leu Lys Gln Asp Asp Arg Asp Val Gln Gly Asp
            420                 425                 430

Pro Phe Ile Arg Gly
        435

<210> SEQ ID NO 71
<211> LENGTH: 1299
<212> TYPE: DNA
<213> ORGANISM: Corynebacterium glucuronolyticum

<400> SEQUENCE: 71
atgtcaaaat tcatgcagca gctgaaaaac actgcgtatc agcagtcatc agcgcaactc      60
ctgctcttct tcatgtcctg gggcatctgg tggtccttct ccagctttg gctctccagc     120 gaaaccgcg gtctcggctt caacggcagt gagatcggca ccatctactc ggtgaactcc     180
gccgtcacgc tcgtcctcat gctcgtctac ggaactgccc aagataagct tcgtactcgc     240
cgtaatttgg tgatcggtat tgcagttcta atgagcttga ccggcccgtt cttcatgtgg     300
gtctactggc cactgctgca gagcgagtcg ctctatgtcc tcggtgttgg acttggcgca     360
atcttcatcg gtacggcttt tgtggggtca tgcccgctgt cgaggcgct tgccgagcgc     420 atgtcccgaa acacaacttc gaatatggc caggcccgcg cgtggggttc ctttggctac     480
gccatcgtcg cactcctcgc cggcttcaac ttcaccatca acccggcgat taacttctgg     540
atggcctcgg ccttcggcgt tctgttgctt ctcatcctcg ttttctggaa ggaaccggta     600
gcgcctcgta acgaaattgc agaggaggaa gtggaaaaca ccacacctag cgtcaaggaa     660
atggtgtctg ttctcaaagt gcccgcccctc tgggtcgtca ttgtcctcgt gttcttcacg     720
tggacgttct acacggtctt cgaccagcag atgttcccgc agttctacac ctcactttt      780 agtgactccg ccaccggcga gcgaacctat ggcgtgctca actccgtcca agtgttcgtc     840
```

```
gaggcgttga tgatgggaat cgtgcccatc tacatgcgga aggtcggcgt gaagaacacc    900
ctcatgacgg gcttcgccgt catggcactg cgcatcctag gttgcgcggt cttcgcggac    960
ccagtcacca tctcctttgt caagatgttc cacgctctcg aggtaccact gtgcatcctc   1020
cccatcttcc gctacttcac cctgcacttc cccacgaaga tctcggccac cttgtacatg   1080
gtcggcttcc agattgcctc gcaggtgggt aacgtcgtca tgtccccgat cctcggttcg   1140
ctgcgtgacc gcctcggttt ccagccgacc ttctatgtca tctcgggaat cgtccttgtc   1200
tccgctatct tcgcctggtt ggctctcaag ggcgataagg aacaagtgga gggcgatccc   1260
ttctaccgcg attcggaact taaggagata caccaatga                          1299
```

<210> SEQ ID NO 72
<211> LENGTH: 432
<212> TYPE: PRT
<213> ORGANISM: Corynebacterium glucuronolyticum

<400> SEQUENCE: 72

```
Met Ser Lys Phe Met Gln Gln Leu Lys Asn Thr Ala Tyr Gln Gln Ser
1               5                   10                  15

Ser Ala Gln Leu Leu Phe Phe Met Ser Trp Gly Ile Trp Trp Ser
            20                  25                  30

Phe Phe Gln Leu Trp Leu Ser Ser Glu Thr Arg Gly Leu Gly Phe Asn
        35                  40                  45

Gly Ser Glu Ile Gly Thr Ile Tyr Ser Val Asn Ser Ala Val Thr Leu
    50                  55                  60

Val Leu Met Leu Val Tyr Gly Thr Ala Gln Asp Lys Leu Arg Thr Arg
65                  70                  75                  80

Arg Asn Leu Val Ile Gly Ile Ala Val Leu Met Ser Leu Thr Gly Pro
                85                  90                  95

Phe Phe Met Trp Val Tyr Trp Pro Leu Leu Gln Ser Glu Ser Leu Tyr
            100                 105                 110

Val Leu Gly Val Gly Leu Gly Ala Ile Phe Ile Gly Thr Ala Phe Val
        115                 120                 125

Gly Ser Cys Pro Leu Phe Glu Ala Leu Ala Glu Arg Met Ser Arg Lys
    130                 135                 140

His Asn Phe Glu Tyr Gly Gln Ala Arg Ala Trp Gly Ser Phe Gly Tyr
145                 150                 155                 160

Ala Ile Val Ala Leu Leu Ala Gly Phe Asn Phe Thr Ile Asn Pro Ala
                165                 170                 175

Ile Asn Phe Trp Met Ala Ser Ala Phe Gly Val Leu Leu Leu Ile
            180                 185                 190

Leu Val Phe Trp Lys Glu Pro Val Ala Pro Arg Asn Glu Ile Ala Glu
        195                 200                 205

Glu Glu Val Glu Asn Thr Thr Pro Ser Val Lys Glu Met Val Ser Val
    210                 215                 220

Leu Lys Val Pro Ala Leu Trp Val Val Ile Val Leu Val Phe Thr
225                 230                 235                 240

Trp Thr Phe Tyr Thr Val Phe Asp Gln Gln Met Phe Pro Gln Phe Tyr
                245                 250                 255

Thr Ser Leu Phe Ser Asp Ser Ala Thr Gly Glu Arg Tyr Gly Val
            260                 265                 270

Leu Asn Ser Val Gln Val Phe Val Glu Ala Leu Met Met Gly Ile Val
        275                 280                 285

Pro Ile Tyr Met Arg Lys Val Gly Val Lys Asn Thr Leu Met Thr Gly
```

```
                290                 295                 300
Phe Ala Val Met Ala Leu Arg Ile Leu Gly Cys Ala Val Phe Ala Asp
305                 310                 315                 320

Pro Val Thr Ile Ser Phe Val Lys Met Phe His Ala Leu Glu Val Pro
                325                 330                 335

Leu Cys Ile Leu Pro Ile Phe Arg Tyr Phe Thr Leu His Phe Pro Thr
            340                 345                 350

Lys Ile Ser Ala Thr Leu Tyr Met Val Gly Phe Gln Ile Ala Ser Gln
        355                 360                 365

Val Gly Asn Val Val Met Ser Pro Ile Leu Gly Ser Leu Arg Asp Arg
    370                 375                 380

Leu Gly Phe Gln Pro Thr Phe Tyr Val Ile Ser Gly Ile Val Leu Val
385                 390                 395                 400

Ser Ala Ile Phe Ala Trp Leu Ala Leu Lys Gly Asp Lys Glu Gln Val
                405                 410                 415

Glu Gly Asp Pro Phe Tyr Arg Asp Ser Glu Leu Lys Glu Ile His Gln
            420                 425                 430

<210> SEQ ID NO 73
<211> LENGTH: 1326
<212> TYPE: DNA
<213> ORGANISM: Bifidobacterium animalis

<400> SEQUENCE: 73
atggcaacaa ccacgaaggt gtggaggaac ccctcctacc tgcaaagctc aaccggcatc      60
ttcctgttct tctgctcctg gggcatctgg tggtcgttct tccagcgctg gctcaactcg     120
atgggactca acggcgcgga agtgggcacg atctattcga tcaactcgct ggccacgctc     180
atcctcatgt tcgggtacgg cctcatccag gacaatctcg gactcaagcg ccgtcttgtg     240
ctcgtcatct cggcgatcgc cgcactcgtc ggacccttcg tgcagttcgt gtacgcgccg     300
ctgatgagga cgaacatgat ggccgccgca ctcgtgggct ccgtcgttct ctccgcgggc     360
ttcatggcag gctgctcgct catcgaggcc gtgaccgaac ggtacagccg ccgtttcaac     420
ttcgagtacg gccaatcccg cgcatggggt tccttcggct atgccattgt ggcgcttgtc     480
gccggcttcg tgttcaacat caacccgatg atcaacttct ggctcggctc cgcattcggc     540
gtgggcatgc tcatcgtgta cctcacctgg tatccggccg agcagcgcga agcgctcaag     600
gaagccgccg atccgaatgc cgcgccaact aacccgacca tcaaagacat gctcggcgtg     660
ctcaagatgc ccacgctgtg ggtgctcatc gtgttcatgc tgctcaccaa cacgttctac     720
accgtattcg accagcagat gttccccacc tactacgcct cgctcttccc gaatgaggcc     780
accggcaacg ccgtctacgg cacgctcaac tcggtgcagg tgttctgcga atccgcgatg     840
atgggcgtcg tgccgatcat catgcgcaag gtaggtgtgc gcaacgcgtt gctgctcgga     900
tccacggtga tgttccttcg catcgggctg tgcggcatct ccacgatcc ggtgtccatc     960 tcgatcgtca aaatgttcca cgccattgaa gttccgctgt tctgcctgcc ggcgttccgc    1020
tacttcacgc tccacttcaa tccgaagctc tccgcgacgc tctacatggt cggcttccag    1080
attgcctcac agatcggcca ggtcgtcttc tccaccccgc tcggcatgct gcatgaccgc    1140
atgggcgacc gcacgacgtt cctgacgatc tccgccatcg tgcttgctgc caccgtctac    1200
ggattcttcg tgatcaagcg cgacgacgag caggtggatg gcgatccgtt catccgcgat    1260
tcgaagaagc tgccgtcgct cgccaccgac gaggcgatcc tctccgcgga ttccgaggat    1320
atgtaa                                                               1326
```

<210> SEQ ID NO 74
<211> LENGTH: 441
<212> TYPE: PRT
<213> ORGANISM: Bifidobacterium animalis

<400> SEQUENCE: 74

```
Met Ala Thr Thr Thr Lys Val Trp Arg Asn Pro Ser Tyr Leu Gln Ser
1               5                   10                  15

Ser Thr Gly Ile Phe Leu Phe Cys Ser Trp Gly Ile Trp Trp Ser
            20                  25                  30

Phe Phe Gln Arg Trp Leu Asn Ser Met Gly Leu Asn Gly Ala Glu Val
                35                  40                  45

Gly Thr Ile Tyr Ser Ile Asn Ser Leu Ala Thr Leu Ile Leu Met Phe
    50                  55                  60

Gly Tyr Gly Leu Ile Gln Asp Asn Leu Gly Leu Lys Arg Arg Leu Val
65                  70                  75                  80

Leu Val Ile Ser Ala Ile Ala Ala Leu Val Gly Pro Phe Val Gln Phe
                85                  90                  95

Val Tyr Ala Pro Leu Met Arg Thr Asn Met Met Ala Ala Leu Val
                100                 105                 110

Gly Ser Val Val Leu Ser Ala Gly Phe Met Ala Gly Cys Ser Leu Ile
            115                 120                 125

Glu Ala Val Thr Glu Arg Tyr Ser Arg Arg Phe Asn Phe Glu Tyr Gly
    130                 135                 140

Gln Ser Arg Ala Trp Gly Ser Phe Gly Tyr Ala Ile Val Ala Leu Val
145                 150                 155                 160

Ala Gly Phe Val Phe Asn Ile Asn Pro Met Ile Asn Phe Trp Leu Gly
                165                 170                 175

Ser Ala Phe Gly Val Gly Met Leu Ile Val Tyr Leu Thr Trp Tyr Pro
            180                 185                 190

Ala Glu Gln Arg Glu Ala Leu Lys Glu Ala Ala Asp Pro Asn Ala Ala
    195                 200                 205

Pro Thr Asn Pro Thr Ile Lys Asp Met Leu Gly Val Leu Lys Met Pro
210                 215                 220

Thr Leu Trp Val Leu Ile Val Phe Met Leu Leu Thr Asn Thr Phe Tyr
225                 230                 235                 240

Thr Val Phe Asp Gln Gln Met Phe Pro Thr Tyr Ala Ser Leu Phe
                245                 250                 255

Pro Asn Glu Ala Thr Gly Asn Ala Val Tyr Gly Thr Leu Asn Ser Val
            260                 265                 270

Gln Val Phe Cys Glu Ser Ala Met Met Gly Val Val Pro Ile Ile Met
    275                 280                 285

Arg Lys Val Gly Val Arg Asn Ala Leu Leu Leu Gly Ser Thr Val Met
290                 295                 300

Phe Leu Arg Ile Gly Leu Cys Gly Ile Phe His Asp Pro Val Ser Ile
305                 310                 315                 320

Ser Ile Val Lys Met Phe His Ala Ile Glu Val Pro Leu Phe Cys Leu
                325                 330                 335

Pro Ala Phe Arg Tyr Phe Thr Leu His Phe Asn Pro Lys Leu Ser Ala
            340                 345                 350

Thr Leu Tyr Met Val Gly Phe Gln Ile Ala Ser Gln Ile Gly Gln Val
    355                 360                 365

Val Phe Ser Thr Pro Leu Gly Met Leu His Asp Arg Met Gly Asp Arg
370                 375                 380
```

```
Thr Thr Phe Leu Thr Ile Ser Ala Ile Val Leu Ala Ala Thr Val Tyr
385                 390                 395                 400

Gly Phe Phe Val Ile Lys Arg Asp Asp Glu Gln Val Asp Gly Asp Pro
                405                 410                 415

Phe Ile Arg Asp Ser Lys Lys Leu Pro Ser Leu Ala Thr Asp Glu Ala
            420                 425                 430

Ile Leu Ser Ala Asp Ser Glu Asp Met
        435                 440

<210> SEQ ID NO 75
<211> LENGTH: 1398
<212> TYPE: DNA
<213> ORGANISM: Bifidobacterium gallicum

<400> SEQUENCE: 75
atggtgaata aaccgaagac cgcaaaaatc tggtccaacc cgtcctattt gcagagctcg      60
tttggcattt tcctgttctt ctgctcatgg ggcatctggt ggtccttctt ccagcgctgg     120
ctcaatacca ttggcctgaa cggcgcggaa gtcggcaccg tctattccat caactcgctg     180
gccacgctga tcctcatgtt cggctacggc atcatccagg acaacctggg catcaagcgc     240
cgtctcgtgg tcgtcatcgc caccatcgcg gcactgatcg cccccttcgt ccagttcgtg     300
tacgcgccgc tcatgcagac gaacatcatg gccgccgccc tgatcggctc cgtggtgctc     360
tccgccggct tcatgtccgg atgctcgctg attgaagcgc ttaccgaacg ctacagccgc     420
aagttcggct tcgaatacgg ccagtcccgc gcatggggct ccttcggcta cgccattgtg     480
gccctgatcg ccggcattgt cttcaacatc aacccgatga tcaacttctg gctcggctcc     540
gcattcggcg tgggcatgct catcgtgtac ctcacgtggt acccggccga gcagcgccag     600
gccctcaagg aagcggccga cccgaacgcc gagaagtcca accgtccctt caaggacatg     660
gtcaacgtgc tcaagatgcc gacgctgtgg gtgctcatca tcttcatgct gctgaccaac     720
acgttctaca cggtcttcga ccagcagatg ttcccgacct actacgcctc gctgttcccg     780
agcattgaaa cgggcaacac ggtctacggc gtgctcaact ccatccaggt cttctgcgaa     840
tccgcgatga tgggcgtcgt cccgatcatc atgcgcaaga tcggcgtgcg caacgcgctg     900
ctgctgggcg ccaccgtcat gttcctgcgc atcggcctgt gcggcatctt ccacgacccg     960
gtagccatct ccatcgtcaa gatgttccac gccatcgaag ttccactgtt ctgcctgccg    1020
gcgttccgct acttcacgct gcacttcaac ccgaagctct cggccacgct gtacatggtg    1080
ggcttccaga tcgcctcaca gatcggccag gttatcttct ccaccccgct gggcatgctg    1140
cacgaccgct tcggcgaccg caccaccttc ctgtccatca gcggcatcgt gctgctggca    1200
acgatctacg gcttcttcgt catcaagcgc gacgacgagc acgtggacgg cgatccgttc    1260
ctgcgtgacc gcgaccgcaa ggaaatggaa ctcatcgaag agaacctgca gccagacgcc    1320
gagctggaaa cgagccccgt aggcgtcgca gcacaggtgc cgacaaccgc gcggtccag    1380 ccggaatacg caagctga                                                 1398

<210> SEQ ID NO 76
<211> LENGTH: 465
<212> TYPE: PRT
<213> ORGANISM: Bifidobacterium gallicum

<400> SEQUENCE: 76

Met Val Asn Lys Pro Lys Thr Ala Lys Ile Trp Ser Asn Pro Ser Tyr
1               5                   10                  15

Leu Gln Ser Ser Phe Gly Ile Phe Leu Phe Phe Cys Ser Trp Gly Ile
```

```
                    20                  25                  30
Trp Trp Ser Phe Phe Gln Arg Trp Leu Asn Thr Ile Gly Leu Asn Gly
            35                  40                  45

Ala Glu Val Gly Thr Val Tyr Ser Ile Asn Ser Leu Ala Thr Leu Ile
50                  55                  60

Leu Met Phe Gly Tyr Gly Ile Ile Gln Asp Asn Leu Gly Ile Lys Arg
65                  70                  75                  80

Arg Leu Val Val Val Ile Ala Thr Ile Ala Ala Leu Ile Gly Pro Phe
                85                  90                  95

Val Gln Phe Val Tyr Ala Pro Leu Met Gln Thr Asn Ile Met Ala Ala
            100                 105                 110

Ala Leu Ile Gly Ser Val Val Leu Ser Ala Gly Phe Met Ser Gly Cys
            115                 120                 125

Ser Leu Ile Glu Ala Leu Thr Glu Arg Tyr Ser Arg Lys Phe Gly Phe
            130                 135                 140

Glu Tyr Gly Gln Ser Arg Ala Trp Gly Ser Phe Gly Tyr Ala Ile Val
145                 150                 155                 160

Ala Leu Ile Ala Gly Ile Val Phe Asn Ile Asn Pro Met Ile Asn Phe
                165                 170                 175

Trp Leu Gly Ser Ala Phe Gly Val Gly Met Leu Ile Val Tyr Leu Thr
            180                 185                 190

Trp Tyr Pro Ala Glu Gln Arg Gln Ala Leu Lys Glu Ala Ala Asp Pro
            195                 200                 205

Asn Ala Glu Lys Ser Asn Pro Ser Phe Lys Asp Met Val Asn Val Leu
            210                 215                 220

Lys Met Pro Thr Leu Trp Val Leu Ile Ile Phe Met Leu Leu Thr Asn
225                 230                 235                 240

Thr Phe Tyr Thr Val Phe Asp Gln Gln Met Phe Pro Thr Tyr Tyr Ala
                245                 250                 255

Ser Leu Phe Pro Ser Ile Glu Thr Gly Asn Thr Val Tyr Gly Val Leu
            260                 265                 270

Asn Ser Ile Gln Val Phe Cys Glu Ser Ala Met Met Gly Val Val Pro
            275                 280                 285

Ile Ile Met Arg Lys Ile Gly Val Arg Asn Ala Leu Leu Leu Gly Ala
290                 295                 300

Thr Val Met Phe Leu Arg Ile Gly Leu Cys Gly Ile Phe His Asp Pro
305                 310                 315                 320

Val Ala Ile Ser Ile Val Lys Met Phe His Ala Ile Glu Val Pro Leu
                325                 330                 335

Phe Cys Leu Pro Ala Phe Arg Tyr Phe Thr Leu His Phe Asn Pro Lys
            340                 345                 350

Leu Ser Ala Thr Leu Tyr Met Val Gly Phe Gln Ile Ala Ser Gln Ile
            355                 360                 365

Gly Gln Val Ile Phe Ser Thr Pro Leu Gly Met Leu His Asp Arg Phe
            370                 375                 380

Gly Asp Arg Thr Thr Phe Leu Ser Ile Ser Gly Ile Val Leu Leu Ala
385                 390                 395                 400

Thr Ile Tyr Gly Phe Phe Val Ile Lys Arg Asp Asp Glu His Val Asp
                405                 410                 415

Gly Asp Pro Phe Leu Arg Asp Arg Asp Arg Lys Glu Met Glu Leu Ile
            420                 425                 430

Glu Glu Asn Leu Gln Pro Asp Ala Glu Leu Glu Thr Ser Pro Val Gly
            435                 440                 445
```

Val Ala Ala Gln Val Arg Asp Asn Arg Ala Val Gln Pro Glu Tyr Ala
                450                 455                 460

Ser
465

<210> SEQ ID NO 77
<211> LENGTH: 1338
<212> TYPE: DNA
<213> ORGANISM: Bifidobacterium longum

<400> SEQUENCE: 77

| | | | | | | |
|---|---|---|---|---|---|---|
| atggcaagtg | caaccaagtc | tgcatggaag | aatccttcct | atctgcagag | ctctttcggc | 60 |
| atcttcatgt | tcttctgctc | ctgggcatc | tggtggtcct | tcttccagcg | ctggctcatc | 120 |
| tcaggcgttg | gattgaccaa | tgctgaagtc | ggcaccatct | actccatcaa | ctcgctggcc | 180 |
| accctggtca | tcatgtttgt | gtacggcgtg | attcaggatc | agctcggcat | caagcgcaag | 240 |
| ctcgtcatcg | tagtctcggt | aatcgccgcc | tgcgttggcc | cattcgtcca | attcgtttac | 300 |
| gccccgatga | tcctcgccgg | tggcaccacc | cgctggatcg | gcgcactcat | cggctccatc | 360 |
| gttctgtctg | ccggcttcat | gtccggctgc | tccctgttcg | aggccgtcac | cgaacgctac | 420 |
| tcccgtaaat | tcggtttcga | atatggccag | tcccgtgctt | ggggctcctt | cggttacgcc | 480 |
| atcgtggcgc | tgtgcgccgg | cttcctgttc | aacatcaacc | cgctgatcaa | cttctgggtc | 540 |
| ggctccgcat | tcggccctgg | catgctcctc | gtgtacgcct | ctgggtccc | ggccgagcag | 600 |
| aaggaagagc | tcaagaagga | aaccgacccg | aacgcagccc | ccaccaaccc | gtccctcaag | 660 |
| gaaatggtcg | ccgttctcaa | gatgccgacc | ctgtgggtgc | tcatcgtctt | catgctgctg | 720 |
| accaacacct | tctacaccgt | gttcgatcag | cagatgttcc | cgacctacta | cgccaacctc | 780 |
| ttccccactg | aagaaatcgg | caacgccacc | tacggcaccc | tgaacggttt | ccaggtcttc | 840 |
| cttgagtccg | caatgatggg | cgtggtcccg | atcatcatga | agaagatcgg | cgtgcgcaac | 900 |
| gctctgctgc | tcggcgctac | cgtgatgttc | ctgcgcatcg | gcttgtgcgg | cgtgttccac | 960 |
| gacccggtca | ccatctccat | cgtcaagctg | ttccactcca | tcgaagtgcc | gctgttctgc | 1020 |
| ctgccggcat | tccgctactt | cactctgcac | ttcgacacca | agctctctgc | cacgctgtac | 1080 |
| atggtgggct | tccagatcgc | ttcccaagtg | ggtcaggtca | tcttctcgac | ccctctgggt | 1140 |
| gccttccacg | acaagatggc | tcagattctg | ccgaacaacg | acatgggatc | cgcgtgacc | 1200 |
| ttctgggtca | tctctgccat | cgtgctgtgc | gcactgattt | acggcttctt | cgtcatcaag | 1260 |
| catgatgatc | aggaagtcgg | cggcgacccg | ttctacaccg | acaagcagct | tcgccagatg | 1320 |
| gaagccgcca | aggcctga | | | | | 1338 |

<210> SEQ ID NO 78
<211> LENGTH: 445
<212> TYPE: PRT
<213> ORGANISM: Bifidobacterium longum

<400> SEQUENCE: 78

Met Ala Ser Ala Thr Lys Ser Ala Trp Lys Asn Pro Ser Tyr Leu Gln
1               5                   10                  15

Ser Ser Phe Gly Ile Phe Met Phe Phe Cys Ser Trp Gly Ile Trp Trp
                20                  25                  30

Ser Phe Phe Gln Arg Trp Leu Ile Ser Gly Val Gly Leu Thr Asn Ala
            35                  40                  45

Glu Val Gly Thr Ile Tyr Ser Ile Asn Ser Leu Ala Thr Leu Val Ile
        50                  55                  60

```
Met Phe Val Tyr Gly Val Ile Gln Asp Gln Leu Gly Ile Lys Arg Lys
 65                  70                  75                  80

Leu Val Ile Val Val Ser Val Ile Ala Ala Cys Val Gly Pro Phe Val
                 85                  90                  95

Gln Phe Val Tyr Ala Pro Met Ile Leu Ala Gly Gly Thr Thr Arg Trp
            100                 105                 110

Ile Gly Ala Leu Ile Gly Ser Ile Val Leu Ser Ala Gly Phe Met Ser
        115                 120                 125

Gly Cys Ser Leu Phe Glu Ala Val Thr Glu Arg Tyr Ser Arg Lys Phe
130                 135                 140

Gly Phe Glu Tyr Gly Gln Ser Arg Ala Trp Gly Ser Phe Gly Tyr Ala
145                 150                 155                 160

Ile Val Ala Leu Cys Ala Gly Phe Leu Phe Asn Ile Asn Pro Leu Ile
                165                 170                 175

Asn Phe Trp Val Gly Ser Ala Phe Gly Pro Gly Met Leu Leu Val Tyr
            180                 185                 190

Ala Phe Trp Val Pro Ala Glu Gln Lys Glu Leu Lys Lys Glu Thr
        195                 200                 205

Asp Pro Asn Ala Ala Pro Thr Asn Pro Ser Leu Lys Glu Met Val Ala
210                 215                 220

Val Leu Lys Met Pro Thr Leu Trp Val Leu Ile Val Phe Met Leu Leu
225                 230                 235                 240

Thr Asn Thr Phe Tyr Thr Val Phe Asp Gln Met Phe Pro Thr Tyr
                245                 250                 255

Tyr Ala Asn Leu Phe Pro Thr Glu Glu Ile Gly Asn Ala Thr Tyr Gly
            260                 265                 270

Thr Leu Asn Gly Phe Gln Val Phe Leu Glu Ser Ala Met Met Gly Val
        275                 280                 285

Val Pro Ile Ile Met Lys Lys Ile Gly Val Arg Asn Ala Leu Leu Leu
290                 295                 300

Gly Ala Thr Val Met Phe Leu Arg Ile Gly Leu Cys Gly Val Phe His
305                 310                 315                 320

Asp Pro Val Thr Ile Ser Ile Val Lys Leu Phe His Ser Ile Glu Val
                325                 330                 335

Pro Leu Phe Cys Leu Pro Ala Phe Arg Tyr Phe Thr Leu His Phe Asp
            340                 345                 350

Thr Lys Leu Ser Ala Thr Leu Tyr Met Val Gly Phe Gln Ile Ala Ser
        355                 360                 365

Gln Val Gly Gln Val Ile Phe Ser Thr Pro Leu Gly Ala Phe His Asp
370                 375                 380

Lys Met Ala Gln Ile Leu Pro Asn Asn Asp Met Gly Ser Arg Val Thr
385                 390                 395                 400

Phe Trp Val Ile Ser Ala Ile Val Leu Cys Ala Leu Ile Tyr Gly Phe
                405                 410                 415

Phe Val Ile Lys His Asp Asp Gln Glu Val Gly Gly Asp Pro Phe Tyr
            420                 425                 430

Thr Asp Lys Gln Leu Arg Gln Met Glu Ala Ala Lys Ala
        435                 440                 445

<210> SEQ ID NO 79
<211> LENGTH: 1422
<212> TYPE: DNA
<213> ORGANISM: Bifidobacterium adolescentis

<400> SEQUENCE: 79
```

-continued

```
ctgaaatcag agcaggcgca agccaaaaca acatcggaag cgatcgctgc cgcgcggcag      60
cggcagcgcg aagagaaaaa gagaatcaaa atggcaagca aaacacgttc tgtatggaag     120
aatccttcct atctgcagag ctccttcggc attttcatgt tcttctgttc ctggggcatc     180
tggtggtcct tcttctcccg ctggctcact gacccgaccc acggtctggg catgagctcc     240
gcggaacagg gccagatcta ctccatcaac tccttggcca ccctggtcat catgttcgtt     300
tacggcacca ttcaggacca gctgggcatt aagcgtaagc tcgtgatctt catctctgcg     360
gtcgctgcat gcgttggccc gttcgtgcag ttcgtgtacc agccgatgct gaccgccggc     420
ggcaccaccc gattcatcgg cgtgcttctc ggctccatcg tgctgtccgc aggcttcatg     480
gccggctgct ccctgttcga agccatcacc gaacgttact cccgtaagtt cggcttcgaa     540
tacgccagt cccgcgcttg gggctccttc ggctacgctg tcgtggcact gtgcgcaggc     600
ttcctgttca acatcaaccc gctgctgaac ttctggggttg gttccatctg cggcctcagc     660
atgctgtgcg tctatgcttt ctgggttccg gccgagcaga aggaagaact caagaaggaa     720
gctgatccga acgcaactcc gaccaacccg tccttcaagg aaatggtctc cgtcctgaag     780
atgccgaccc tgtgggtgct catcgtcttc atgctgttca ccaacacctt ctacaccgtg     840
ttcgatcagc agatgttccc gaactactac gcctccctct cccgaccac cgaaatcggc     900
aacgccacct acggcaccct gaactccttc caggtgttcc ttgagtccgc catgatgggc     960
gtcgtcccga tcatcatgaa aagatcggc gtgcgtaact ccctgctgct cggcgccacc    1020
gtgatgttcg cccgtatcgg tctgtgcggc gtgttccatg acccggtctc cgtctccatc    1080
gtcaagctgt ccactccat cgaggtaccg ctgttctgcc tgccggcgtt ccgctacttc    1140
accctgcact cgacacgaa gctgtctgcc accctgtaca tggttggttt ccagatcgct    1200
tcccaggtcg gccaggtgat tttctccacc ccgatgggtg ctctgcatga tgccatgggc    1260
gaccgtccga ccttcttcac catctctgcc atcgtgtttg cggctctggt ctacggcttc    1320
ttcgtcatca agaaggatga tcaggaagtc ggcggcgatc cgttctacac tgacaagcag    1380
ctcaaggcca tgaaggccgc tgatgcggaa gtgaaggcct ga                       1422
```

<210> SEQ ID NO 80
<211> LENGTH: 473
<212> TYPE: PRT
<213> ORGANISM: Bifidobacterium adolescentis

<400> SEQUENCE: 80

```
Met Lys Ser Glu Gln Ala Gln Ala Lys Thr Thr Ser Glu Ala Ile Ala
1               5                   10                  15

Ala Ala Arg Gln Arg Gln Arg Glu Glu Lys Lys Arg Ile Lys Met Ala
                20                  25                  30

Ser Lys Thr Arg Ser Val Trp Lys Asn Pro Ser Tyr Leu Gln Ser Ser
            35                  40                  45

Phe Gly Ile Phe Met Phe Phe Cys Ser Trp Gly Ile Trp Trp Ser Phe
        50                  55                  60

Phe Ser Arg Trp Leu Thr Asp Pro Thr His Gly Leu Gly Met Ser Ser
65                  70                  75                  80

Ala Glu Gln Gly Gln Ile Tyr Ser Ile Asn Ser Leu Ala Thr Leu Val
                85                  90                  95

Ile Met Phe Val Tyr Gly Thr Ile Gln Asp Gln Leu Gly Ile Lys Arg
                100                 105                 110

Lys Leu Val Ile Phe Ile Ser Ala Val Ala Ala Cys Val Gly Pro Phe
            115                 120                 125
```

-continued

Val Gln Phe Val Tyr Gln Pro Met Leu Thr Ala Gly Gly Thr Thr Arg
130                 135                 140

Phe Ile Gly Val Leu Leu Gly Ser Ile Val Leu Ser Ala Gly Phe Met
145                 150                 155                 160

Ala Gly Cys Ser Leu Phe Glu Ala Ile Thr Glu Arg Tyr Ser Arg Lys
            165                 170                 175

Phe Gly Phe Glu Tyr Gly Gln Ser Arg Ala Trp Gly Ser Phe Gly Tyr
            180                 185                 190

Ala Val Val Ala Leu Cys Ala Gly Phe Leu Phe Asn Ile Asn Pro Leu
        195                 200                 205

Leu Asn Phe Trp Val Gly Ser Ile Cys Gly Leu Ser Met Leu Cys Val
210                 215                 220

Tyr Ala Phe Trp Val Pro Ala Glu Gln Lys Glu Glu Leu Lys Lys Glu
225                 230                 235                 240

Ala Asp Pro Asn Ala Thr Pro Thr Asn Pro Ser Phe Lys Glu Met Val
                245                 250                 255

Ser Val Leu Lys Met Pro Thr Leu Trp Val Leu Ile Val Phe Met Leu
            260                 265                 270

Phe Thr Asn Thr Phe Tyr Thr Val Phe Asp Gln Gln Met Phe Pro Asn
275                 280                 285

Tyr Tyr Ala Ser Leu Phe Pro Thr Thr Glu Ile Gly Asn Ala Thr Tyr
290                 295                 300

Gly Thr Leu Asn Ser Phe Gln Val Phe Leu Glu Ser Ala Met Met Gly
305                 310                 315                 320

Val Val Pro Ile Ile Met Lys Lys Ile Gly Val Arg Asn Ser Leu Leu
                325                 330                 335

Leu Gly Ala Thr Val Met Phe Ala Arg Ile Gly Leu Cys Gly Val Phe
            340                 345                 350

His Asp Pro Val Ser Val Ser Ile Val Lys Leu Phe His Ser Ile Glu
            355                 360                 365

Val Pro Leu Phe Cys Leu Pro Ala Phe Arg Tyr Phe Thr Leu His Phe
        370                 375                 380

Asp Thr Lys Leu Ser Ala Thr Leu Tyr Met Val Gly Phe Gln Ile Ala
385                 390                 395                 400

Ser Gln Val Gly Gln Val Ile Phe Ser Thr Pro Met Gly Ala Leu His
            405                 410                 415

Asp Ala Met Gly Asp Arg Pro Thr Phe Phe Thr Ile Ser Ala Ile Val
            420                 425                 430

Phe Ala Ala Leu Val Tyr Gly Phe Phe Val Ile Lys Lys Asp Asp Gln
        435                 440                 445

Glu Val Gly Gly Asp Pro Phe Tyr Thr Asp Lys Gln Leu Lys Ala Met
450                 455                 460

Lys Ala Ala Asp Ala Glu Val Lys Ala
465                 470

<210> SEQ ID NO 81
<211> LENGTH: 1503
<212> TYPE: DNA
<213> ORGANISM: Bifidobacterium longum

<400> SEQUENCE: 81
ttgcgtgtcg aacaggtacg acacgccgat ttacgtcaat cgattgacgt aaatcgattg      60
acgtcgcata ataattacta cataacaact tctacaaagg cacggccgcc cgagcagaag     120
cgttacataa ccaataacca accaagtagt aatcaaagga tgattatggc aagtgcaacc     180

```
aagtctgcat ggaagaatcc ttcctatctg cagagctctt tcggcatctt catgttcttc    240
tgctcctggg gcatctggtg gtccttcttc agcgctggc tcatctcagg cgttggattg     300
accaatgctg aagtcggcac catctactcc atcaactcgc tggccaccct ggtcatcatg    360
tttgtgtacg gcgtgattca ggatcagctc ggcatcaagc gcaagctcgt catcgtagtc    420
tcggtaatcg ccgcctgcgt tggcccattc gtccaattcg tttacgcccc gatgatcctc    480
gccggtggca ccaccgctg atcggcgca ctcatcggct ccatcgttct gtctgccggc      540
ttcatgtccg gctgctccct gttcgaggcc gtcaccgaac gctactcccg taaattcggt    600
ttcgaatatg ccagtcccg tgcttgggc tccttcggtt acgccatcgt ggcgctgtgc      660
gccggcttcc tgttcaacat caacccgctg atcaacttct gggtcggctc cgcattcggc    720
cctggcatgc tcctcgtgta cgccttctgg gtcccggccg agcagaagga agagctcaag    780
aaggaaaccg acccgaacgc agcccccacc aacccgtccc tcaaggaaat ggtcgccgtt    840
ctcaagatgc cgaccctgtg ggtgctcatc gtcttcatgc tgctgaccaa caccttctac    900
accgtgttcg atcagcagat gttcccgacc tactacgcca acctcttccc cactgaagaa    960
atcggcaacg ccacctacgg caccctgaac ggtttccagg tcttccttga gtccgcaatg   1020
atgggcgtgg tcccgatcat catgaagaag atcggcgtgc gcaacgctct gctgctcggc   1080
gctaccgtga tgttcctgcg catcggcttg tgcggcgtgt ccacgaccc ggtcaccatc    1140
tccatcgtca agctgttcca ctccatcgaa gtgccgctgt tctgcctgcc ggcattccgc   1200
tacttcactc tgcacttcga caccaagctc tctgccacgc tgtacatggt gggcttccag   1260
atcgcttccc aagtgggtca ggtcatcttc tcgacccctc tgggtgcctt ccacgacaag   1320
atggctcaga ttctgccgaa caacgacatg ggatcccgcg tgaccttctg ggtcatctct   1380
gccatcgtgc tgtgcgcact gatttacggc ttcttcgtca tcaagcatga tgatcaggaa   1440
gtcggcggcg acccgttcta caccgacaag cagcttcgcc agatggaagc cgccaaggcc   1500
tga                                                                  1503
```

<210> SEQ ID NO 82  
<211> LENGTH: 500  
<212> TYPE: PRT  
<213> ORGANISM: Bifidobacterium longum

<400> SEQUENCE: 82

```
Met Arg Val Glu Gln Val Arg His Ala Asp Leu Arg Gln Ser Ile Asp
1               5                   10                  15

Val Asn Arg Leu Thr Ser His Asn Asn Tyr Tyr Ile Thr Thr Ser Thr
            20                  25                  30

Lys Ala Arg Pro Pro Glu Gln Lys Arg Tyr Ile Thr Asn Asn Gln Pro
        35                  40                  45

Ser Ser Asn Gln Arg Met Ile Met Ala Ser Ala Thr Lys Ser Ala Trp
    50                  55                  60

Lys Asn Pro Ser Tyr Leu Gln Ser Ser Phe Gly Ile Phe Met Phe Phe
65                  70                  75                  80

Cys Ser Trp Gly Ile Trp Trp Ser Phe Phe Gln Arg Trp Leu Ile Ser
                85                  90                  95

Gly Val Gly Leu Thr Asn Ala Glu Val Gly Thr Ile Tyr Ser Ile Asn
            100                 105                 110

Ser Leu Ala Thr Leu Val Ile Met Phe Val Tyr Gly Val Ile Gln Asp
        115                 120                 125

Gln Leu Gly Ile Lys Arg Lys Leu Val Ile Val Ser Val Ile Ala
    130                 135                 140
```

Ala Cys Val Gly Pro Phe Val Gln Phe Val Tyr Ala Pro Met Ile Leu
145                 150                 155                 160

Ala Gly Gly Thr Thr Arg Trp Ile Gly Ala Leu Ile Gly Ser Ile Val
            165                 170                 175

Leu Ser Ala Gly Phe Met Ser Gly Cys Ser Leu Phe Glu Ala Val Thr
        180                 185                 190

Glu Arg Tyr Ser Arg Lys Phe Gly Phe Glu Tyr Gly Gln Ser Arg Ala
            195                 200                 205

Trp Gly Ser Phe Gly Tyr Ala Ile Val Ala Leu Cys Ala Gly Phe Leu
        210                 215                 220

Phe Asn Ile Asn Pro Leu Ile Asn Phe Trp Val Gly Ser Ala Phe Gly
225                 230                 235                 240

Pro Gly Met Leu Leu Val Tyr Ala Phe Trp Pro Ala Glu Gln Lys
            245                 250                 255

Glu Glu Leu Lys Lys Glu Thr Asp Pro Asn Ala Ala Pro Thr Asn Pro
            260                 265                 270

Ser Leu Lys Glu Met Val Ala Val Leu Lys Met Pro Thr Leu Trp Val
        275                 280                 285

Leu Ile Val Phe Met Leu Leu Thr Asn Thr Phe Tyr Thr Val Phe Asp
    290                 295                 300

Gln Gln Met Phe Pro Thr Tyr Tyr Ala Asn Leu Phe Pro Thr Glu Glu
305                 310                 315                 320

Ile Gly Asn Ala Thr Tyr Gly Thr Leu Asn Gly Phe Gln Val Phe Leu
            325                 330                 335

Glu Ser Ala Met Met Gly Val Val Pro Ile Ile Met Lys Lys Ile Gly
        340                 345                 350

Val Arg Asn Ala Leu Leu Leu Gly Ala Thr Val Met Phe Leu Arg Ile
            355                 360                 365

Gly Leu Cys Gly Val Phe His Asp Pro Val Thr Ile Ser Ile Val Lys
    370                 375                 380

Leu Phe His Ser Ile Glu Val Pro Leu Phe Cys Leu Pro Ala Phe Arg
385                 390                 395                 400

Tyr Phe Thr Leu His Phe Asp Thr Lys Leu Ser Ala Thr Leu Tyr Met
            405                 410                 415

Val Gly Phe Gln Ile Ala Ser Gln Val Gly Gln Val Ile Phe Ser Thr
        420                 425                 430

Pro Leu Gly Ala Phe His Asp Lys Met Ala Gln Ile Leu Pro Asn Asn
            435                 440                 445

Asp Met Gly Ser Arg Val Thr Phe Trp Val Ile Ser Ala Ile Val Leu
    450                 455                 460

Cys Ala Leu Ile Tyr Gly Phe Phe Val Ile Lys His Asp Asp Gln Glu
465                 470                 475                 480

Val Gly Gly Asp Pro Phe Tyr Thr Asp Lys Gln Leu Arg Gln Met Glu
            485                 490                 495

Ala Ala Lys Ala
        500

<210> SEQ ID NO 83
<211> LENGTH: 1266
<212> TYPE: DNA
<213> ORGANISM: Mitsuokella multacida

<400> SEQUENCE: 83
atgggaaatc tcttgaaggc attttcgaat ccgttctaca ggacgagctc gcttgagatc      60

```
ctgctgttct tcgcgggctg gggcatctgg tggtcgttct ttcagatctg gctgacgacg    120
aagcagggct tcacgggcgc gcaggtcggc acgatttact ccttcggcag cgcggtcgcg    180
ctcgtcctga tgttcgtcta cggctccctg caggacaagc tcggcatgaa gaagacgatg    240
ctgaagttct tcgccgtctg ccagatcctc gtcggcccgt tcttcacctg gtctacgtg     300
ccgatgctcg ccgcgaactt ctacgtcggc gctgtcgtcg gtgccgtcta cctcgcggtg    360
gcgttcctcg cggcctgccc tgtctttgag gcggtcacag agcgcctgag ccgccgctac    420
tcctttgagt acggccaggc cagagcctgg ggctcgttcg gctatgccgt ggcagcgctc    480
tgcgcaggct cctcttcac gatgaacccg aacctgatct tctggacggg ctccgctgtg     540
gcggcggtgc agcttatcgt cttggtctcg atgacgccgg agaacgacgc ttcgcttacg    600
gcgcagtacg aggtcaaggc agagagcatc aaggagagca agacgccgtc gttcggcgag    660
atcgtcggcg tgttcaagct catcgaggtc tggaagatga tcgtcttcgt catcatgagc    720
tggacgttct acaccgtctt tgaccagcag atgttcccgg agttcttcac gcgcttcttc    780
gcgacgccag aagcaggcca gcaggcttac ggcgtgctca actccatcga agtcttcctc    840
gaattcctca tgatgggcct cgtgccgatc ctcatgcgcc gtatcggcgt tcgcaaggcc    900
atcctgctcg gctgcgccat catgatcgtc cgcatcggcg gctgcggcct cgtcacgaat    960
cctcttggcg tcgccgtcat caagctcttg cacgcaccgg aaacggcgct cttcatcctc   1020
gctgtcttcc gctacttcac gctgcacttt gacacgcgca tctcggcgac gctctacatg   1080
gtcggtttcc agatcgctgc acaggtcggc cagattatct tctcgacgcc gctcggcgcc   1140
ctgcatgaca gcatcggcta ccagagcact ttcctcgtca tctccggcat cgtctgtgtg   1200
gccagcctct acgctttcgt catcctcaag aaagacgacc agcaggtcga cggccagccg   1260
ctttga                                                               1266
```

<210> SEQ ID NO 84
<211> LENGTH: 421
<212> TYPE: PRT
<213> ORGANISM: Mitsuokella multacida

<400> SEQUENCE: 84

```
Met Gly Asn Leu Leu Lys Ala Phe Ser Asn Pro Phe Tyr Arg Thr Ser
1               5                   10                  15

Ser Leu Glu Ile Leu Leu Phe Phe Ala Gly Trp Gly Ile Trp Trp Ser
            20                  25                  30

Phe Phe Gln Ile Trp Leu Thr Thr Lys Gln Gly Phe Thr Gly Ala Gln
        35                  40                  45

Val Gly Thr Ile Tyr Ser Phe Gly Ser Ala Val Ala Leu Val Leu Met
    50                  55                  60

Phe Val Tyr Gly Ser Leu Gln Asp Lys Leu Gly Met Lys Lys Thr Met
65                  70                  75                  80

Leu Lys Phe Phe Ala Val Cys Gln Ile Leu Val Gly Pro Phe Phe Thr
                85                  90                  95

Trp Val Tyr Val Pro Met Leu Ala Ala Asn Phe Tyr Val Gly Ala Val
            100                 105                 110

Val Gly Ala Val Tyr Leu Ala Val Ala Phe Leu Ala Ala Cys Pro Val
        115                 120                 125

Phe Glu Ala Val Thr Glu Arg Leu Ser Arg Arg Tyr Ser Phe Glu Tyr
    130                 135                 140

Gly Gln Ala Arg Ala Trp Gly Ser Phe Gly Tyr Ala Val Ala Ala Leu
145                 150                 155                 160
```

-continued

```
Cys Ala Gly Phe Leu Phe Thr Met Asn Pro Asn Leu Ile Phe Trp Thr
            165                 170                 175
Gly Ser Ala Val Ala Ala Val Gln Leu Ile Val Leu Val Ser Met Thr
        180                 185                 190
Pro Glu Asn Asp Ala Ser Leu Thr Ala Gln Tyr Glu Val Lys Ala Glu
    195                 200                 205
Ser Ile Lys Glu Ser Lys Thr Pro Ser Phe Gly Glu Ile Val Gly Val
210                 215                 220
Phe Lys Leu Ile Glu Val Trp Lys Met Ile Val Phe Val Ile Met Ser
225                 230                 235                 240
Trp Thr Phe Tyr Thr Val Phe Asp Gln Gln Met Phe Pro Glu Phe Phe
            245                 250                 255
Thr Arg Phe Phe Ala Thr Pro Glu Ala Gly Gln Gln Ala Tyr Gly Val
        260                 265                 270
Leu Asn Ser Ile Glu Val Phe Leu Glu Phe Leu Met Met Gly Leu Val
    275                 280                 285
Pro Ile Leu Met Arg Arg Ile Gly Val Arg Lys Ala Ile Leu Leu Gly
290                 295                 300
Cys Ala Ile Met Ile Val Arg Ile Gly Gly Cys Gly Leu Val Thr Asn
305                 310                 315                 320
Pro Leu Gly Val Ala Val Ile Lys Leu Leu His Ala Pro Glu Thr Ala
            325                 330                 335
Leu Phe Ile Leu Ala Val Phe Arg Tyr Phe Thr Leu His Phe Asp Thr
        340                 345                 350
Arg Ile Ser Ala Thr Leu Tyr Met Val Gly Phe Gln Ile Ala Ala Gln
    355                 360                 365
Val Gly Gln Ile Ile Phe Ser Thr Pro Leu Gly Ala Leu His Asp Ser
370                 375                 380
Ile Gly Tyr Gln Ser Thr Phe Leu Val Ile Ser Gly Ile Val Cys Val
385                 390                 395                 400
Ala Ser Leu Tyr Ala Phe Val Ile Leu Lys Lys Asp Asp Gln Gln Val
            405                 410                 415
Asp Gly Gln Pro Leu
            420
```

<210> SEQ ID NO 85
<211> LENGTH: 1275
<212> TYPE: DNA
<213> ORGANISM: Lactobacillus antri

<400> SEQUENCE: 85

| | | | | |
|---|---|---|---|---|
| atgaaaaata gcaagttatc agcgtttaaa aacagctttt acctggagag ttcgcttagt | 60 |
| ctgctgctgt tcttcgccgc gtggggaatc tggtggtcgt tcttccaaat ctggctcacc | 120 |
| aatgacctcg gcttctctgg ggccaaggtc gggatgatct atactttcga ttcgcaatt | 180 |
| acgctggtct taatgttcat ctacgggtca gtgcaagaca agctcggcat taaacgccgg | 240 |
| ctgctgattg gggttaccat cctggaaatg ctccttgggc ccttctttac ctggatttac | 300 |
| gcgccactgc tgcactctaa ctttatcctc ggcgccttct taggttccct ctacctctcc | 360 |
| tttgccttc tggcggcgtc cccgaccttc gaggccctcg cagaacggat gagccggcgg | 420 |
| tacagctttg aatacggtcg ggcccgggcc tgggggtcat tggttacgc cgtttcggca | 480 |
| ttgtgtgccg gctacctctt caccatcagt ccctacatcg tcttttggct cagcagcggg | 540 |
| attagcttgc taaccttcct cctgctctgc tttggccgga ctaagagccc cacacaggtt | 600 |
| gcccgttacg agaataaggc cgaggaagaa cacgacgcgg ataagccgag tttcaaagag | 660 |

```
atcatcagtg ttttcaagct caagcagttg tgggaattgg ttttcttcat tattttcagc    720 gggtccttt  acacggtctt tgaccagcag atgtttcccc agttctttac ccaattttc     780 aagacggcgg cccagggaaa cacggcctac ggaatcctca attcgattga agtcttcctc    840
gaagcaatta tgatggcgat tgttccctgg attatgaaga agatcggggt ccgcaagacc    900
ctcttgattg gggtcaccat tatgttcttg cggatcggcc tctgcggcct ggtcgtcagc    960
ccggtcggga tctcgattgt gaagctcttt cacgccccgg aaacgccat  ctttgccctg   1020 gcgatgttcc gctatttgac cctccacttt gacacccggc atcggcgac  gatgtacatg   1080 gtggttgggc agattgccgg tcaaatcggc cagatcatcc tgtcgacgcc cctgggaatg   1140
ctccacgacc ggatcggcta ccgggcgacc ttcctggtta tttcgctgat tgtgatttgc   1200
gctgcggtat acgcattcgt catttgcgc  aaggataacc aggaggttga cggtcaacca   1260
ctagaaaaca actaa                                                    1275

<210> SEQ ID NO 86
<211> LENGTH: 424
<212> TYPE: PRT
<213> ORGANISM: Lactobacillus antri

<400> SEQUENCE: 86

Met Lys Asn Ser Lys Leu Ser Ala Phe Lys Asn Ser Phe Tyr Leu Glu
1               5                   10                  15

Ser Ser Leu Ser Leu Leu Leu Phe Phe Ala Ala Trp Gly Ile Trp Trp
            20                  25                  30

Ser Phe Phe Gln Ile Trp Leu Thr Asn Asp Leu Gly Phe Ser Gly Ala
        35                  40                  45

Lys Val Gly Met Ile Tyr Thr Phe Asp Ser Ala Ile Thr Leu Val Leu
    50                  55                  60

Met Phe Ile Tyr Gly Ser Val Gln Asp Lys Leu Gly Ile Lys Arg Arg
65                  70                  75                  80

Leu Leu Ile Gly Val Thr Ile Leu Glu Met Leu Leu Gly Pro Phe Phe
                85                  90                  95

Thr Trp Ile Tyr Ala Pro Leu Leu His Ser Asn Phe Ile Leu Gly Ala
            100                 105                 110

Phe Leu Gly Ser Leu Tyr Leu Ser Phe Ala Phe Leu Ala Ala Ser Pro
        115                 120                 125

Thr Phe Glu Ala Leu Ala Glu Arg Met Ser Arg Arg Tyr Ser Phe Glu
    130                 135                 140

Tyr Gly Arg Ala Arg Ala Trp Gly Ser Phe Gly Tyr Ala Val Ser Ala
145                 150                 155                 160

Leu Cys Ala Gly Tyr Leu Phe Thr Ile Ser Pro Tyr Ile Val Phe Trp
                165                 170                 175

Leu Ser Ser Gly Ile Ser Leu Leu Thr Phe Leu Leu Leu Cys Phe Gly
            180                 185                 190

Arg Thr Lys Ser Pro Thr Gln Val Ala Arg Tyr Glu Asn Lys Ala Glu
        195                 200                 205

Glu Glu His Asp Ala Asp Lys Pro Ser Phe Lys Glu Ile Ile Ser Val
    210                 215                 220

Phe Lys Leu Lys Gln Leu Trp Glu Leu Val Phe Ile Ile Phe Ser
225                 230                 235                 240

Gly Ser Phe Tyr Thr Val Phe Asp Gln Gln Met Phe Pro Gln Phe Phe
                245                 250                 255

Thr Gln Phe Phe Lys Thr Ala Ala Gln Gly Asn Thr Ala Tyr Gly Ile
```

```
                        260                 265                 270
Leu Asn Ser Ile Glu Val Phe Leu Glu Ala Ile Met Met Ala Ile Val
                275                 280                 285

Pro Trp Ile Met Lys Lys Ile Gly Val Arg Lys Thr Leu Leu Ile Gly
            290                 295                 300

Val Thr Ile Met Phe Leu Arg Ile Gly Leu Cys Gly Leu Val Val Ser
305                 310                 315                 320

Pro Val Gly Ile Ser Ile Val Lys Leu Phe His Ala Pro Glu Thr Ala
                325                 330                 335

Ile Phe Ala Leu Ala Met Phe Arg Tyr Leu Thr Leu His Phe Asp Thr
            340                 345                 350

Arg Leu Ser Ala Thr Met Tyr Met Val Val Gly Gln Ile Ala Gly Gln
                355                 360                 365

Ile Gly Gln Ile Ile Leu Ser Thr Pro Leu Gly Met Leu His Asp Arg
            370                 375                 380

Ile Gly Tyr Arg Ala Thr Phe Leu Val Ile Ser Leu Ile Val Ile Cys
385                 390                 395                 400

Ala Ala Val Tyr Ala Phe Val Ile Leu Arg Lys Asp Asn Gln Glu Val
                405                 410                 415

Asp Gly Gln Pro Leu Glu Asn Asn
            420
```

<210> SEQ ID NO 87
<211> LENGTH: 1323
<212> TYPE: DNA
<213> ORGANISM: Lactobacillus ruminis

<400> SEQUENCE: 87

```
atgatgccga tttctgacaa ttggaaagga attttattta tgaacgatat gaataaaagc     60
ggacggatgt cacaactgaa gaatccgttc tttacaagca atgcgacaaa tattctcatg    120
ttctttgctg gctggggcat ctggtggtca ttcttccaga tctggctgac aaccaagcag    180
gggttcaccg gagcccaggt tggcgagata tactccttca actcggcgtt ctcactgatt    240
gccaaccttg tttacagcaa cattcaggac aggctcggcc tcaaacgcaa ccttttgatc    300
ttctgcgcct gctgcaggt gttcctcggg cccttcttca cgttcctctt cgtgccgatg    360
cttcatgcca accttgaact cggcgctctg atcggttcat gctacctgac gcttgcctat    420
cttttccgcat ccccgatgtt cgaggcactg acggaacgtg caagccgccg cttcaactat    480
cagtatgggt cagcgcgtgc ctggggctcg ttcggatatg ccgtatccgc cttgcttgca    540
ggattcgtct tcacaatcaa tccgtcgctg ctgttctgga tcggctctgc catcgctgtt    600
gtccttcttc tcctgctttt gttctggaac cctgtccgca acaaggagac ggttgccaga    660
tttgaaaatg aaatggtcag ggaacgtgag aactccaagc tgggtcaagg gacttcctc    720
aatgtcttca aggttcgcag cctttgggaa atcgccattt tccttgtctt cagcggtaca    780
ttctacacga ttttcgatca gcagatgttt cctcagttct tcactcagtt cttcaagacc    840
caggcaatgg cgatcacat gtatgggatc ctgaactcgg ttgaggtgtt cctcgaagca    900
ctcatgatgg gcctggttcc gcttctcatg aagaagatcg gcgtccgccg cacgattctt    960
gtcggcgtga cgttcatgtt catcagaatc ggtggctgcg gtctgattac gaaccctctt   1020
ggcgtttcaa tgatcaagct tctccatgcg cctgaaacgg ccattttctg cgtcgtaatg   1080
ttccgttact acactctgca ctacgatccg cgagtatcag ccacgatcaa tatcgtaacg   1140
ggcattgcgg gttcgttcgg ccagatactt ctctcaacgc cgcttggact tctgcgtgac   1200
```

```
cacatcggct atcagccgac cttcctggta atcgccggca tcgtattctg cgccggcatc    1260
tacggcttat tcatcattcg aaggatgat caggaagtaa acggagagag gctgtctgaa    1320
taa                                                                 1323
```

<210> SEQ ID NO 88
<211> LENGTH: 440
<212> TYPE: PRT
<213> ORGANISM: Lactobacillus ruminis

<400> SEQUENCE: 88

```
Met Met Pro Ile Ser Asp Asn Trp Lys Gly Ile Leu Phe Met Asn Asp
1               5                   10                  15

Met Asn Lys Ser Gly Arg Met Ser Gln Leu Lys Asn Pro Phe Phe Thr
            20                  25                  30

Ser Asn Ala Thr Asn Ile Leu Met Phe Phe Ala Gly Trp Gly Ile Trp
        35                  40                  45

Trp Ser Phe Phe Gln Ile Trp Leu Thr Thr Lys Gln Gly Phe Thr Gly
    50                  55                  60

Ala Gln Val Gly Glu Ile Tyr Ser Phe Asn Ser Ala Phe Ser Leu Ile
65                  70                  75                  80

Ala Asn Leu Val Tyr Ser Asn Ile Gln Asp Arg Leu Gly Leu Lys Arg
                85                  90                  95

Asn Leu Leu Ile Phe Cys Ala Cys Leu Gln Val Phe Leu Gly Pro Phe
            100                 105                 110

Phe Thr Phe Leu Phe Val Pro Met Leu His Ala Asn Leu Glu Leu Gly
        115                 120                 125

Ala Leu Ile Gly Ser Cys Tyr Leu Thr Leu Ala Tyr Leu Ser Ala Ser
    130                 135                 140

Pro Met Phe Glu Ala Leu Thr Glu Arg Ala Ser Arg Arg Phe Asn Tyr
145                 150                 155                 160

Gln Tyr Gly Ser Ala Arg Ala Trp Gly Ser Phe Gly Tyr Ala Val Ser
                165                 170                 175

Ala Leu Leu Ala Gly Phe Val Phe Thr Ile Asn Pro Ser Leu Leu Phe
            180                 185                 190

Trp Ile Gly Ser Ala Ile Ala Val Val Leu Leu Leu Leu Leu Leu Phe
        195                 200                 205

Trp Asn Pro Val Arg Asn Lys Glu Thr Val Ala Arg Phe Glu Asn Glu
    210                 215                 220

Met Val Arg Glu Arg Glu Asn Ser Lys Pro Gly Ser Arg Asp Phe Leu
225                 230                 235                 240

Asn Val Phe Lys Val Arg Ser Leu Trp Glu Ile Ala Ile Phe Leu Val
                245                 250                 255

Phe Ser Gly Thr Phe Tyr Thr Ile Phe Asp Gln Gln Met Phe Pro Gln
            260                 265                 270

Phe Phe Thr Gln Phe Phe Lys Thr Gln Ala Met Gly Asp His Met Tyr
        275                 280                 285

Gly Ile Leu Asn Ser Val Glu Val Phe Leu Glu Ala Leu Met Met Gly
    290                 295                 300

Leu Val Pro Leu Leu Met Lys Lys Ile Gly Val Arg Arg Thr Ile Leu
305                 310                 315                 320

Val Gly Val Thr Phe Met Phe Ile Arg Ile Gly Gly Cys Gly Leu Ile
                325                 330                 335

Thr Asn Pro Leu Gly Val Ser Met Ile Lys Leu Leu His Ala Pro Glu
            340                 345                 350
```

```
Thr Ala Ile Phe Cys Val Val Met Phe Arg Tyr Tyr Thr Leu His Tyr
        355                 360                 365

Asp Pro Arg Val Ser Ala Thr Ile Asn Ile Val Thr Gly Ile Ala Gly
        370                 375                 380

Ser Phe Gly Gln Ile Leu Leu Ser Thr Pro Leu Gly Leu Leu Arg Asp
385                 390                 395                 400

His Ile Gly Tyr Gln Pro Thr Phe Leu Val Ile Ala Gly Ile Val Phe
                405                 410                 415

Cys Ala Gly Ile Tyr Gly Leu Phe Ile Ile Arg Arg Asp Asp Gln Glu
                420                 425                 430

Val Asn Gly Glu Arg Leu Ser Glu
        435                 440

<210> SEQ ID NO 89
<211> LENGTH: 1242
<212> TYPE: DNA
<213> ORGANISM: Yersinia frederiksenii

<400> SEQUENCE: 89
atgaaacatt ctgtccgtaa tcaatatctg atcttaagtg gcttattgtt tacgttttc      60 tttacttggt catcggcatt ctctttattc tccatatggc tcaatcaata tgtaggatta    120
aaaggtaccg aaacaggggc gacttttttcc gccattgcct aacggcact ttgcgctcaa    180 ccgcttatg gcgtgataca agataagttg gggctaaaaa acatctttt atgggccatt      240 ggtattttgc tgctgatcag tggcccttt tttatttatg tttatgcccc tttattgcgt    300
gtcaacatgc tggttggtgc cgttaccggt ggcttatata tggggatgac gttctttgcc    360
ggtattggtg cgcttgagtc ttataccgaa cgagtgagcc gtattagtgg gtttgagttt    420
ggtaaagccc gtatgtgggg atcgctgggg tgggcgggtg caacctttt tgctggcatg    480 ttgtttaata ttaatcccaa cattaatttc tggatggcat cggcatcggc gcgatattt    540 ttactgttgt tgtggcactt acatgaagtt aaaacagcgg ctatggggca gttggaatac    600
ggtaagaata gtgccctgac actgagtgat acattgtcac tgtttcgtat gccgcgtttc    660
tgggcgctgg tggtatttgt caccggtgtg agcgtttata acgtctatga ccagcaattt    720
ccggtctatt tctcctctct atttactgac cgacgccacg gcaatgaaat gtacggcttt    780
cttaattcac tacaggtatt cctagaggct ggtggtatgt cctcgcgcc ttttctggtt    840 aaccgtattg gcgcgaaaaa gggcttactg ctgagcggat taatcatggc aatgcgcata    900
ttgggttcag ggttggcaca agatgcagtc accatctcat tgatgaagtt attacatgca    960
gtggagttgc ctatttttgct cattgcgatg tttaagtata tcgccgccaa tttcgacccg   1020
cgtttgtcag ccacgcttta tctggtggga tttcagttta ttacccaagt ctatgccagc   1080 gtatttttcgc cgttggcagg taaaggctat gacctgatcg ggttcgctga tacctatctg   1140
atcatgggag gcattgtcct cggattaaca gcaatttctt gttttatgct gcgcggcgag   1200
tcgcgtacgg atgatccttc cctacaatta accactaagt ga                       1242

<210> SEQ ID NO 90
<211> LENGTH: 413
<212> TYPE: PRT
<213> ORGANISM: Yersinia frederiksenii

<400> SEQUENCE: 90

Met Lys His Ser Val Arg Asn Gln Tyr Leu Ile Leu Ser Gly Leu Leu
1               5                   10                  15

Phe Thr Phe Phe Phe Thr Trp Ser Ser Ala Phe Ser Leu Phe Ser Ile
```

|   |   |   | 20 |   |   | 25 |   |   | 30 |   |   |
|---|---|---|---|---|---|---|---|---|---|---|---|

Trp Leu Asn Gln Tyr Val Gly Leu Lys Gly Thr Glu Thr Gly Ala Thr
            35                    40                    45

Phe Ser Ala Ile Ala Leu Thr Ala Leu Cys Ala Gln Pro Leu Tyr Gly
    50                    55                    60

Val Ile Gln Asp Lys Leu Gly Leu Lys Lys His Leu Leu Trp Ala Ile
65                    70                    75                    80

Gly Ile Leu Leu Leu Ile Ser Gly Pro Phe Phe Ile Tyr Val Tyr Ala
                  85                    90                    95

Pro Leu Leu Arg Val Asn Met Leu Val Gly Ala Val Thr Gly Gly Leu
            100                    105                    110

Tyr Met Gly Met Thr Phe Phe Ala Gly Ile Gly Ala Leu Glu Ser Tyr
                115                    120                    125

Thr Glu Arg Val Ser Arg Ile Ser Gly Phe Glu Phe Gly Lys Ala Arg
        130                    135                    140

Met Trp Gly Ser Leu Gly Trp Ala Gly Ala Thr Phe Phe Ala Gly Met
145                    150                    155                    160

Leu Phe Asn Ile Asn Pro Asn Ile Asn Phe Trp Met Ala Ser Ala Ser
                165                    170                    175

Ala Ala Ile Phe Leu Leu Leu Trp His Leu His Glu Val Lys Thr
        180                    185                    190

Ala Ala Met Gly Gln Leu Glu Tyr Gly Lys Asn Ser Ala Leu Thr Leu
            195                    200                    205

Ser Asp Thr Leu Ser Leu Phe Arg Met Pro Arg Phe Trp Ala Leu Val
    210                    215                    220

Val Phe Val Thr Gly Val Ser Val Tyr Asn Val Tyr Asp Gln Gln Phe
225                    230                    235                    240

Pro Val Tyr Phe Ser Ser Leu Phe Thr Asp Arg Arg His Gly Asn Glu
                  245                    250                    255

Met Tyr Gly Phe Leu Asn Ser Leu Gln Val Phe Leu Glu Ala Gly Gly
            260                    265                    270

Met Phe Leu Ala Pro Phe Leu Val Asn Arg Ile Gly Ala Lys Lys Gly
                275                    280                    285

Leu Leu Leu Ser Gly Leu Ile Met Ala Met Arg Ile Leu Gly Ser Gly
        290                    295                    300

Leu Ala Gln Asp Ala Val Thr Ile Ser Leu Met Lys Leu Leu His Ala
305                    310                    315                    320

Val Glu Leu Pro Ile Leu Leu Ile Ala Met Phe Lys Tyr Ile Ala Ala
                325                    330                    335

Asn Phe Asp Pro Arg Leu Ser Ala Thr Leu Tyr Leu Val Gly Phe Gln
            340                    345                    350

Phe Ile Thr Gln Val Tyr Ala Ser Val Phe Ser Pro Leu Ala Gly Lys
                355                    360                    365

Gly Tyr Asp Leu Ile Gly Phe Ala Asp Thr Tyr Leu Ile Met Gly Gly
        370                    375                    380

Ile Val Leu Gly Leu Thr Ala Ile Ser Cys Phe Met Leu Arg Gly Glu
385                    390                    395                    400

Ser Arg Thr Asp Asp Pro Ser Leu Gln Leu Thr Thr Lys
                  405                    410

<210> SEQ ID NO 91
<211> LENGTH: 1260
<212> TYPE: DNA
<213> ORGANISM: Serratia proteamaculans

<400> SEQUENCE: 91

```
atgaaccgcg aaacaaaaaa atattatgtg cttctcagcg gcctgttgtt tttcttcttc      60
tttacctggt catccagctt ttcactgatc tccatctggc tgaaccagaa aatcggcctg     120
aaagggactg aaaccgggct gatcttcgcg gcaatgtcga tcatggcgtt gtgcgcccaa     180
ccgctgtacg gctttattca ggacaaactt gggctgcgta agcacctgct gctgtttgtc     240
ggcgtgctgc tgttgctcac cggcccgttc tttatctatg tctacgcccc gctgctgcag     300
agcaaccttg tggtcggcgc actggtgggc ggcgtgtttg tcagcctggc gttcaatgcc     360
ggtattggcg cgctggaatc ctataccgaa cgagtcagcc gatcgtcgg tttcgaattc      420
ggccgggcgc gtatgtgggg gtcattgggc tgggccagcg ccaccttctt tgccggcttt     480
aactacaata tcgaccccaa tatcaacttc tggatcgctt cggcctcggc ggcagtgttt     540
ctgctgttgc tgtggcaagt gcgtgagctg aaacccaacg ccatggccgg tctggaatac     600
ggcaagccgg aaaacctgaa gctgcaggac gcattggccc tgctgcgcct gccggggttc     660
tgggcgctgg tggtgtttgt gctgggcacc agcatctacg gcgtgtttga ccagcagttc     720
ccggtgtatt tcgcctcgca gttccccacc cacgaagaag caaccgcat gtacggtttc      780
cttaattcgc tgcaggtgtt tctggaggcc ggtggcatgt tcctggcccc gctgctggtt     840
aaccgcattg gcataaagca aagcctgttg ctggccagca gcgtgatggc gctgcgcatg     900
gtcggttccg gctttgccag cggcgccctg atgatttccg ccatgaaact gctgcacgcc     960
gtagaattgc caatcctgct ggtggcgatg ttcaagtaca tcaccacccg tttcgacagc    1020
cgcctgtcct ccacgctgta cctggtgggc ttccagttta tcagccaaat tgtcgccggt    1080
tttctggcac cgctggccgg ttatggttac gaccgcatcg gctttgccga cacctatttg    1140
ctgatgggtt gcgcggtggc cgggaccacg ctgatttcct gcttcctgct gcgcggcgag    1200
accgtcgcca gtgcgcctca atttcaatcc acgttaaaat caagtgagcc aacccaatga    1260
```

<210> SEQ ID NO 92
<211> LENGTH: 419
<212> TYPE: PRT
<213> ORGANISM: Serratia proteamaculans

<400> SEQUENCE: 92

```
Met Asn Arg Glu Thr Lys Lys Tyr Tyr Val Leu Leu Ser Gly Leu Leu
  1               5                  10                  15

Phe Phe Phe Phe Phe Thr Trp Ser Ser Ser Phe Ser Leu Ile Ser Ile
                 20                  25                  30

Trp Leu Asn Gln Lys Ile Gly Leu Lys Gly Thr Glu Thr Gly Leu Ile
             35                  40                  45

Phe Ala Ala Met Ser Ile Met Ala Leu Cys Ala Gln Pro Leu Tyr Gly
         50                  55                  60

Phe Ile Gln Asp Lys Leu Gly Leu Arg Lys His Leu Leu Leu Phe Val
 65                  70                  75                  80

Gly Val Leu Leu Leu Leu Thr Gly Pro Phe Phe Ile Tyr Val Tyr Ala
                 85                  90                  95

Pro Leu Leu Gln Ser Asn Leu Val Val Gly Ala Leu Val Gly Val
                100                 105                 110

Phe Val Ser Leu Ala Phe Asn Ala Gly Ile Gly Ala Leu Glu Ser Tyr
            115                 120                 125

Thr Glu Arg Val Ser Arg Ile Val Gly Phe Glu Phe Gly Arg Ala Arg
        130                 135                 140

Met Trp Gly Ser Leu Gly Trp Ala Ser Ala Thr Phe Phe Ala Gly Phe
```

```
                145                 150                 155                 160
Asn Tyr Asn Ile Asp Pro Asn Ile Asn Phe Trp Ile Ala Ser Ala Ser
                    165                 170                 175
Ala Ala Val Phe Leu Leu Leu Leu Trp Gln Val Arg Glu Leu Lys Pro
                    180                 185                 190
Asn Ala Met Ala Gly Leu Glu Tyr Gly Lys Pro Glu Asn Leu Lys Leu
                    195                 200                 205
Gln Asp Ala Leu Ala Leu Leu Arg Leu Pro Gly Phe Trp Ala Leu Val
                    210                 215                 220
Val Phe Val Leu Gly Thr Ser Ile Tyr Gly Val Phe Asp Gln Gln Phe
225                 230                 235                 240
Pro Val Tyr Phe Ala Ser Gln Phe Pro Thr His Glu Glu Gly Asn Arg
                    245                 250                 255
Met Tyr Gly Phe Leu Asn Ser Leu Gln Val Phe Leu Glu Ala Gly Gly
                    260                 265                 270
Met Phe Leu Ala Pro Leu Leu Val Asn Arg Ile Gly Ile Lys Gln Ser
                    275                 280                 285
Leu Leu Leu Ala Ser Ser Val Met Ala Leu Arg Met Val Gly Ser Gly
    290                 295                 300
Phe Ala Ser Gly Ala Leu Met Ile Ser Ala Met Lys Leu Leu His Ala
305                 310                 315                 320
Val Glu Leu Pro Ile Leu Leu Val Ala Met Phe Lys Tyr Ile Thr Thr
                    325                 330                 335
Arg Phe Asp Ser Arg Leu Ser Ser Thr Leu Tyr Leu Val Gly Phe Gln
                    340                 345                 350
Phe Ile Ser Gln Ile Val Ala Gly Phe Leu Pro Leu Ala Gly Tyr
                    355                 360                 365
Gly Tyr Asp Arg Ile Gly Phe Ala Asp Thr Tyr Leu Leu Met Gly Cys
    370                 375                 380
Ala Val Ala Gly Thr Thr Leu Ile Ser Cys Phe Leu Leu Arg Gly Glu
385                 390                 395                 400
Thr Val Ala Ser Ala Pro Gln Phe Gln Ser Thr Leu Lys Ser Ser Glu
                    405                 410                 415
Pro Thr Gln

<210> SEQ ID NO 93
<211> LENGTH: 1239
<212> TYPE: DNA
<213> ORGANISM: Escherichia coli

<400> SEQUENCE: 93
atgaaaaaac ggcctactcg aagttacatg ctgctcagcg ctctgctgtt cttttttctt     60
gtgacctggt cctcatcaag ttcactgctc tcaatctggc ttcaccagga agtgggcta    120 aaagcatcgg aaaccggcat tattttttca gtattatccg tctccgcgct cttcgcgcag    180
gtctgttatg gctttattca ggaccgactt ggtctgcgca acatttgtt atggtttatc    240 accgcgttgt tgatcctctc cggcccggct tatctgcttt ttagttattt gctgagcgtt    300
aatattctgc tgggcagcgt attcggggc ttatttatcg ggctgacgtt taatggggt    360 atcggcgttc tggagtccta taccgagcgc gtcgcgcgtc aaagtacctt tgagtttggg    420
cgggcacgca tgtggggggtc tctgggctgg gcagttgcca cgttttttgc cgggttactg    480
tttaatatca accctgacct taacttcctg gtggcttcat gctcagggtt aatcttcttc    540
tgcctcctgg cccgattaaa ggtggccgcg ccggcaagca tggagaaact cgaaattggc    600
```

```
gctaaaaaag tttctctgga agacgccctg cgtctgctta ctctgccgcg cttctgggca    660
ctgatattct tcgtggtcgg aacctgcatt tacggcgtat acgatcagca attcccggtc    720
tatttctcat cacagttccc gacattacgc gaagggaacg agatgtttgg ctatttaaac    780
tctttccagg tctttctcga ggccgcaggt atgttttgtg cgccgtggct ggttaatcgc    840
attggtgcta aaaatggtct gatattcgca ggaatggtga tggcgctgcg catgattact    900
tcagggctgg tggaaggccc cctgcttatc tccattacca aactgcttca cgcggtcgaa    960
ctgccaatat tgttagtcgc catatttaaa tacaacagtc tgaatttcga caaacgtctc   1020
tcctccacca tttatctggt gggatttgcc tgcaccagct ccgtcattgg taccgtattg   1080
tccccgctgg caggctttag ctatgagaga tttggcttcg cccaatccta tctgatcatg   1140
ggcatcatgg tgttcagcac cacgtttatt tccattttcc ttttgcgctc aactaaatcc   1200
tcatctgagc catctttttct gcagcaaaaa gctgtgtaa                         1239
```

<210> SEQ ID NO 94
<211> LENGTH: 412
<212> TYPE: PRT
<213> ORGANISM: Escherichia coli

<400> SEQUENCE: 94

```
Met Lys Lys Arg Pro Thr Arg Ser Tyr Met Leu Leu Ser Ala Leu Leu
1               5                   10                  15

Phe Phe Phe Phe Val Thr Trp Ser Ser Ser Ser Leu Leu Ser Ile
            20                  25                  30

Trp Leu His Gln Glu Val Gly Leu Lys Ala Ser Glu Thr Gly Ile Ile
        35                  40                  45

Phe Ser Val Leu Ser Val Ser Ala Leu Phe Ala Gln Val Cys Tyr Gly
    50                  55                  60

Phe Ile Gln Asp Arg Leu Gly Leu Arg Lys His Leu Leu Trp Phe Ile
65                  70                  75                  80

Thr Ala Leu Leu Ile Leu Ser Gly Pro Ala Tyr Leu Leu Phe Ser Tyr
                85                  90                  95

Leu Leu Ser Val Asn Ile Leu Leu Gly Ser Val Phe Gly Gly Leu Phe
            100                 105                 110

Ile Gly Leu Thr Phe Asn Gly Gly Ile Gly Val Leu Glu Ser Tyr Thr
        115                 120                 125

Glu Arg Val Ala Arg Gln Ser Thr Phe Glu Phe Gly Arg Ala Arg Met
    130                 135                 140

Trp Gly Ser Leu Gly Trp Ala Val Ala Thr Phe Ala Gly Leu Leu
145                 150                 155                 160

Phe Asn Ile Asn Pro Asp Leu Asn Phe Leu Val Ala Ser Cys Ser Gly
                165                 170                 175

Leu Ile Phe Phe Cys Leu Leu Ala Arg Leu Lys Val Ala Ala Pro Ala
            180                 185                 190

Ser Met Glu Lys Leu Glu Ile Gly Ala Lys Lys Val Ser Leu Glu Asp
        195                 200                 205

Ala Leu Arg Leu Leu Thr Leu Pro Arg Phe Trp Ala Leu Ile Phe Phe
    210                 215                 220

Val Val Gly Thr Cys Ile Tyr Gly Val Tyr Asp Gln Gln Phe Pro Val
225                 230                 235                 240

Tyr Phe Ser Ser Gln Phe Pro Thr Leu Arg Glu Gly Asn Glu Met Phe
                245                 250                 255

Gly Tyr Leu Asn Ser Phe Gln Val Phe Leu Glu Ala Ala Gly Met Phe
            260                 265                 270
```

Cys Ala Pro Trp Leu Val Asn Arg Ile Gly Ala Lys Asn Gly Leu Ile
            275                 280                 285

Phe Ala Gly Met Val Met Ala Leu Arg Met Ile Thr Ser Gly Leu Val
            290                 295                 300

Glu Gly Pro Leu Leu Ile Ser Ile Thr Lys Leu Leu His Ala Val Glu
305                 310                 315                 320

Leu Pro Ile Leu Leu Val Ala Ile Phe Lys Tyr Asn Ser Leu Asn Phe
                325                 330                 335

Asp Lys Arg Leu Ser Ser Thr Ile Tyr Leu Val Gly Phe Ala Cys Thr
            340                 345                 350

Ser Ser Val Ile Gly Thr Val Leu Ser Pro Leu Ala Gly Phe Ser Tyr
            355                 360                 365

Glu Arg Phe Gly Phe Ala Gln Ser Tyr Leu Ile Met Gly Ile Met Val
            370                 375                 380

Phe Ser Thr Thr Phe Ile Ser Ile Phe Leu Leu Arg Ser Thr Lys Ser
385                 390                 395                 400

Ser Ser Glu Pro Ser Phe Leu Gln Gln Lys Ala Val
            405                 410

<210> SEQ ID NO 95
<211> LENGTH: 1236
<212> TYPE: DNA
<213> ORGANISM: Bacillus licheniformis

<400> SEQUENCE: 95

```
atgaaaagct caaacagtct gtattggaaa ctaagcgcct attttttctt tttcttttt      60
acttggtctt ccagctattc tttatttgcg atttggttag ggcaagaaat caatttgaac    120
gggtccgcga cgggcattat cttttctgta acgctatctt tactttgtg catgcagcct     180
ttgtacggtt ttatctccga taagctcggg ctgaagaaaa acatattatt tatgatcagt    240
ttgctgctcg tatttacggg tccctttat atttttcgtct acggaccgct tttgcaatac    300
aacgtctttc ttggggctat cgtcggggga atttattgg gaactgcttt tctcgccgga    360
atcggtgcga ttgaaacctt tattgaaaag gtcagccgca aatatcaatt tgaatatgga    420
agaacaagga tgtgggggtc cctcggctgg gctgcggcga cattttttgc aggtcagctg    480
ttcaatatcg atccgaatat caacttctgg gttgcgtccg cctcagcaat catattggtg    540
gccattattg tttccgtaaa aattgagatg acagatgatg aaaaggaaag agcagactcg    600
gtcggattaa aagacgtagg agggcttttt ctcttaaaag attctggtt tttgatgctg     660
tacgtgatcg gcgtaacatg cgtgtacggc gtctatgacc agcagttccc gctttactac    720
gcttccttat ttccgactgc ggccttgggg aaccaaatat tggatacct taattcattc     780
caagtattta ttgaagcggg catgatgttt cttgcgcctt tcatcgtcaa taagctcggt    840
cctaaaaaaa gcttgatttt agcggggctg ttaatggctt tccggattat cggttccgga    900
cttgtcagcg gaccggtcgg aatttcatcg atgaaactca ttcatgcttt agaattgccg    960
attatgctga ttgcgatgtt taaatatttg gcgactaatt ttgataatcg tctttcatcc   1020
gtactttatc ttgtcggctt tcaattcgca tcccaggtag gcacgtcgat ttttttcgccg  1080
cttgcgggag gttatacgga cagcatcgga tttcgccaca cttatctcat catgggagca   1140
atggtccttt gttttaccat tatttcgatt tttaccttgc tagactcaaa gaaagatgtt   1200
gaatttgctc aaaatctaca aagcaatcat atatag                            1236
```

<210> SEQ ID NO 96

```
<211> LENGTH: 411
<212> TYPE: PRT
<213> ORGANISM: Bacillus licheniformis

<400> SEQUENCE: 96

Met Lys Ser Ser Asn Ser Leu Tyr Trp Lys Leu Ser Ala Tyr Phe Phe
1               5                   10                  15

Phe Phe Phe Phe Thr Trp Ser Ser Tyr Ser Leu Phe Ala Ile Trp
            20                  25                  30

Leu Gly Gln Glu Ile Asn Leu Asn Gly Ser Ala Thr Gly Ile Ile Phe
            35                  40                  45

Ser Val Asn Ala Ile Phe Thr Leu Cys Met Gln Pro Leu Tyr Gly Phe
50                  55                  60

Ile Ser Asp Lys Leu Gly Leu Lys Lys Asn Ile Leu Phe Met Ile Ser
65                  70                  75                  80

Leu Leu Leu Val Phe Thr Gly Pro Phe Tyr Ile Phe Val Tyr Gly Pro
                85                  90                  95

Leu Leu Gln Tyr Asn Val Phe Leu Gly Ala Ile Val Gly Gly Ile Tyr
            100                 105                 110

Leu Gly Thr Ala Phe Leu Ala Gly Ile Gly Ala Ile Glu Thr Phe Ile
            115                 120                 125

Glu Lys Val Ser Arg Lys Tyr Gln Phe Glu Tyr Gly Arg Thr Arg Met
130                 135                 140

Trp Gly Ser Leu Gly Trp Ala Ala Thr Phe Phe Ala Gly Gln Leu
145                 150                 155                 160

Phe Asn Ile Asp Pro Asn Ile Asn Phe Trp Val Ala Ser Ala Ser Ala
            165                 170                 175

Ile Ile Leu Val Ala Ile Ile Val Ser Val Lys Ile Glu Met Thr Asp
            180                 185                 190

Asp Glu Lys Glu Arg Ala Asp Ser Val Gly Leu Lys Asp Val Gly Gly
            195                 200                 205

Leu Phe Leu Leu Lys Asp Phe Trp Phe Leu Met Leu Tyr Val Ile Gly
210                 215                 220

Val Thr Cys Val Tyr Gly Val Tyr Asp Gln Gln Phe Pro Leu Tyr Tyr
225                 230                 235                 240

Ala Ser Leu Phe Pro Thr Ala Ala Leu Gly Asn Gln Ile Phe Gly Tyr
            245                 250                 255

Leu Asn Ser Phe Gln Val Phe Ile Glu Ala Gly Met Met Phe Leu Ala
            260                 265                 270

Pro Phe Ile Val Asn Lys Leu Gly Pro Lys Lys Ser Leu Ile Leu Ala
            275                 280                 285

Gly Leu Leu Met Ala Phe Arg Ile Ile Gly Ser Gly Leu Val Ser Gly
            290                 295                 300

Pro Val Gly Ile Ser Ser Met Lys Leu Ile His Ala Leu Glu Leu Pro
305                 310                 315                 320

Ile Met Leu Ile Ala Met Phe Lys Tyr Leu Ala Thr Asn Phe Asp Asn
            325                 330                 335

Arg Leu Ser Ser Val Leu Tyr Leu Val Gly Phe Gln Phe Ala Ser Gln
            340                 345                 350

Val Gly Thr Ser Ile Phe Ser Pro Leu Ala Gly Gly Leu Tyr Asp Ser
            355                 360                 365

Ile Gly Phe Arg His Thr Tyr Leu Ile Met Gly Ala Met Val Leu Cys
            370                 375                 380

Phe Thr Ile Ile Ser Ile Phe Thr Leu Leu Asp Ser Lys Lys Asp Val
385                 390                 395                 400
```

Glu Phe Ala Gln Asn Leu Gln Ser Asn His Ile
            405                 410

<210> SEQ ID NO 97
<211> LENGTH: 1290
<212> TYPE: DNA
<213> ORGANISM: Pseudomonas fluorescens

<400> SEQUENCE: 97

| | | | | | |
|---|---|---|---|---|---|
| atgcagtttg | ccgccaaacg | cgagtactgg | cttatcagtg | gtttgttgtt | tttcttcttc | 60 |
| ttttcgtggt | catccagcta | ttcattgttt | tctatctggc | tgcatcgagt | cattggcttg | 120 |
| aatggcacgg | aaaccggctt | cattttcgcc | gccaacgcta | ttgcggcgct | gctggttcaa | 180 |
| cccttctacg | gcgcccttca | agaccgcctc | gggctgtcca | aaaagcttct | ggtgtggatt | 240 |
| ggcatcctgc | tgtgtgccgc | ggccccgttt | gcaatttatg | tctacgccgg | cctgttggcg | 300 |
| cagaacgtga | tgctcggcgc | gttggtcggt | gcggcgttcc | tggcgctggc | gatgctggca | 360 |
| ggcgttgggg | tgatcgagtc | gtacaccgag | cgcttgtcgc | ggcatgcagg | attcgagttt | 420 |
| ggaaccaccc | gaatgtgggg | gtcgttgggc | tgggccagcg | cgacgggcgt | ggtcggcgtg | 480 |
| gtgttcaaca | tcgatcctga | cattgcgttt | tacatgagca | gcctcgccgg | catcgtgttt | 540 |
| ttgctgatcc | tgttccgtct | ggacctcgac | cggttggccc | agccggcagt | gcaggcgggc | 600 |
| gcggttgtcc | accccgtgcg | cctgaacgat | ctctggaagt | tgctggcact | cccgcggttc | 660 |
| tgggctttca | gcctttacct | gacggggta | tgcgggatct | acatgatcta | cgagcaacag | 720 |
| tttccggtgt | atttctcctc | gttttcccg | accccggagg | aggggacccg | tgcctatggc | 780 |
| tacctgaact | cgtctcaggt | actggtcgag | gcggtcctga | tgctgcttgc | acctggggtg | 840 |
| gtcagccgca | caggcgccaa | atacgggctg | attctggccg | gcagcatcat | gttcgtgcgc | 900 |
| atccttgggt | cggggctggt | aacgcaggct | tgggccatcg | ccgcctgcaa | gatgttgcac | 960 |
| gccttggaag | tgcccatctt | gctggtctcg | atattcaaat | acatttcgct | caactttgac | 1020 |
| tctcggctgt | ccgcctcgat | ctacttggtg | gggttccagt | tcgcccagca | actgaccgcc | 1080 |
| atgttgctgt | caccgctggt | gggctacggc | tacgaccatt | tcggtttctc | cagcgtctac | 1140 |
| gtactgatgg | caggcctggt | cggcgcttgc | ctgctgcttt | catggaccttt | gttgcgcaag | 1200 |
| gaccccgtgc | gtgacgcctc | tcaagtcggg | gctggcgatt | cacggcagct | tcccgccatc | 1260 |
| gcgccatccg | cccctcgtta | tgaaccctag | | | | 1290 |

<210> SEQ ID NO 98
<211> LENGTH: 429
<212> TYPE: PRT
<213> ORGANISM: Pseudomonas fluorescens

<400> SEQUENCE: 98

Met Gln Phe Ala Ala Lys Arg Glu Tyr Trp Leu Ile Ser Gly Leu Leu
1               5                   10                  15

Phe Phe Phe Phe Phe Ser Trp Ser Ser Ser Tyr Ser Leu Phe Ser Ile
                20                  25                  30

Trp Leu His Arg Val Ile Gly Leu Asn Gly Thr Glu Thr Gly Phe Ile
            35                  40                  45

Phe Ala Ala Asn Ala Ile Ala Ala Leu Leu Val Gln Pro Phe Tyr Gly
        50                  55                  60

Ala Leu Gln Asp Arg Leu Gly Leu Ser Lys Lys Leu Leu Val Trp Ile
65                  70                  75                  80

Gly Ile Leu Leu Cys Ala Ala Ala Pro Phe Ala Ile Tyr Val Tyr Ala

```
                    85                  90                  95
Gly Leu Leu Ala Gln Asn Val Met Leu Gly Ala Leu Val Gly Ala Ala
                100                 105                 110

Phe Leu Ala Leu Ala Met Leu Ala Gly Val Gly Val Ile Glu Ser Tyr
            115                 120                 125

Thr Glu Arg Leu Ser Arg His Ala Gly Phe Glu Phe Gly Thr Thr Arg
        130                 135                 140

Met Trp Gly Ser Leu Gly Trp Ala Ser Ala Thr Gly Val Val Gly Val
145                 150                 155                 160

Val Phe Asn Ile Asp Pro Asp Ile Ala Phe Tyr Met Ser Ser Leu Ala
                165                 170                 175

Gly Ile Val Phe Leu Leu Ile Leu Phe Arg Leu Asp Leu Asp Arg Leu
            180                 185                 190

Ala Gln Pro Ala Val Gln Ala Gly Ala Val Val His Pro Val Arg Leu
        195                 200                 205

Asn Asp Leu Trp Lys Leu Leu Ala Leu Pro Arg Phe Trp Ala Phe Ser
210                 215                 220

Leu Tyr Leu Thr Gly Val Cys Gly Ile Tyr Met Ile Tyr Glu Gln Gln
225                 230                 235                 240

Phe Pro Val Tyr Phe Ser Ser Phe Pro Thr Pro Glu Gly Thr
                245                 250                 255

Arg Ala Tyr Gly Tyr Leu Asn Ser Ser Gln Val Leu Val Glu Ala Val
            260                 265                 270

Leu Met Leu Leu Ala Pro Trp Val Val Ser Arg Thr Gly Ala Lys Tyr
        275                 280                 285

Gly Leu Ile Leu Ala Gly Ser Ile Met Phe Val Arg Ile Leu Gly Ser
    290                 295                 300

Gly Leu Val Thr Gln Ala Trp Ala Ile Ala Ala Cys Lys Met Leu His
305                 310                 315                 320

Ala Leu Glu Val Pro Ile Leu Leu Val Ser Ile Phe Lys Tyr Ile Ser
                325                 330                 335

Leu Asn Phe Asp Ser Arg Leu Ser Ala Ser Ile Tyr Leu Val Gly Phe
            340                 345                 350

Gln Phe Ala Gln Gln Leu Thr Ala Met Leu Leu Ser Pro Leu Val Gly
        355                 360                 365

Tyr Gly Tyr Asp His Phe Gly Phe Ser Ser Val Tyr Val Leu Met Ala
    370                 375                 380

Gly Leu Val Gly Ala Cys Leu Leu Leu Ser Trp Thr Leu Leu Arg Lys
385                 390                 395                 400

Asp Pro Val Arg Asp Ala Ser Gln Val Gly Ala Gly Asp Ser Arg Gln
                405                 410                 415

Leu Pro Ala Ile Ala Pro Ser Ala Pro Arg Tyr Glu Pro
            420                 425

<210> SEQ ID NO 99
<211> LENGTH: 1248
<212> TYPE: DNA
<213> ORGANISM: Artificial Sequence
<220> FEATURE:
<223> OTHER INFORMATION: Coding sequence for variant sucrose transporter

<400> SEQUENCE: 99
atggcactga atattccatt cagaaatgcg tactatcgtt ttgcatccag ttactcattt    60
ctctttttta tttcctggtc gctgtggtgg tcgttatacg ctatttggct gaaaggacat   120
ctagggttga cagggacgga attaggtaca ctttattcgg tcaaccagtt taccagcatt   180
```

```
ctatttatga tgttctacgg catcgttcag gataaactcg gtctgaagaa accgctcatc      240
tggtgtatga gtttcatcct ggtcttgacc ggaccgttta tgatttacgt ttatgaaccg      300
ttactgcaaa gcaattttc tgtaggtcta attctggggg cgctattttt tggcttgggg      360
tatctggcgg gatgcggttt gcttgatagc ttcaccgaaa aaatggcgcg aaattttcat      420
ttcgaatatg gaacagcgcg cgcctgggga tcttttggct atgctattgg cgcgttcttt      480
gccggcatat ttttagtat cagtcccccat atcaacttct ggttggtctc gctatttggc      540
gctgtattta tgatgatcaa catgcgtttt aaagataagg atcaccagtg cgtagcggca      600
gatgcgggag gggtaaaaaa agaggatttt atcgcagttt caaggatcg aaacttctgg      660 gttttcgtca tatttattgt ggggacgtgg tctttctata acatttttga tcaacaactt      720
tttcctgtct tttattcagg tttattcgaa tcacacgatg taggaacgcg cctgtatggt      780
tatctcaact cattccaggt ggtactcgaa gcgctgtgca tggcgattat tccttctctt      840
gtgaatcggg tagggccaaa aaatgcatta cttatcggag ttgtgattat ggcgttggcg      900 atccttttcct gcgcgctgtt cgttaaccccc tggattattt cattagtgaa gttgttacat      960
gccattgagg ttccactttg tgtcatatcc gtcttcaaat acagcgtggc aaactttgat      1020
aagcgcctgt cgtcgacgat ctttctgatt ggttttcaaa ttgccagttc gcttgggatt      1080
gtgctgcttt caacgccgac tgggatactc tttgaccacg caggctacca gacagttttc      1140
ttcgcaattt cgggtattgt ctgcctgatg ttgctatttg gcattttctt cttgagtaaa      1200
aaacgcgagc aaatagttat ggaaacgcct gtaccttcag caatatag                  1248
```

<210> SEQ ID NO 100  
<211> LENGTH: 415  
<212> TYPE: PRT  
<213> ORGANISM: Artificial Sequence  
<220> FEATURE:  
<223> OTHER INFORMATION: Variant sucrose transporter

<400> SEQUENCE: 100

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175
```

| Ser | Leu | Phe | Gly | Ala | Val | Phe | Met | Met | Ile | Asn | Met | Arg | Phe | Lys | Asp |
| --- | --- | --- | --- | --- | --- | --- | --- | --- | --- | --- | --- | --- | --- | --- | --- |
| | | | 180 | | | | 185 | | | | | 190 | | | |

| Lys | Asp | His | Gln | Cys | Val | Ala | Ala | Asp | Ala | Gly | Gly | Val | Lys | Lys | Glu |
| --- | --- | --- | --- | --- | --- | --- | --- | --- | --- | --- | --- | --- | --- | --- | --- |
| | | | 195 | | | | 200 | | | | 205 | | | | |

| Asp | Phe | Ile | Ala | Val | Phe | Lys | Asp | Arg | Asn | Phe | Trp | Val | Phe | Val | Ile |
| --- | --- | --- | --- | --- | --- | --- | --- | --- | --- | --- | --- | --- | --- | --- | --- |
| | 210 | | | | | 215 | | | | | 220 | | | | |

| Phe | Ile | Val | Gly | Thr | Trp | Ser | Phe | Tyr | Asn | Ile | Phe | Asp | Gln | Gln | Leu |
| --- | --- | --- | --- | --- | --- | --- | --- | --- | --- | --- | --- | --- | --- | --- | --- |
| 225 | | | | | 230 | | | | | 235 | | | | | 240 |

| Phe | Pro | Val | Phe | Tyr | Ser | Gly | Leu | Phe | Glu | Ser | His | Asp | Val | Gly | Thr |
| --- | --- | --- | --- | --- | --- | --- | --- | --- | --- | --- | --- | --- | --- | --- | --- |
| | | | | 245 | | | | | 250 | | | | | 255 | |

| Arg | Leu | Tyr | Gly | Tyr | Leu | Asn | Ser | Phe | Gln | Val | Val | Leu | Glu | Ala | Leu |
| --- | --- | --- | --- | --- | --- | --- | --- | --- | --- | --- | --- | --- | --- | --- | --- |
| | | | 260 | | | | | 265 | | | | | 270 | | |

| Cys | Met | Ala | Ile | Ile | Pro | Phe | Phe | Val | Asn | Arg | Val | Gly | Pro | Lys | Asn |
| --- | --- | --- | --- | --- | --- | --- | --- | --- | --- | --- | --- | --- | --- | --- | --- |
| | | 275 | | | | | 280 | | | | | 285 | | | |

| Ala | Leu | Leu | Ile | Gly | Val | Val | Ile | Met | Ala | Leu | Ala | Ile | Leu | Ser | Cys |
| --- | --- | --- | --- | --- | --- | --- | --- | --- | --- | --- | --- | --- | --- | --- | --- |
| | 290 | | | | | 295 | | | | | 300 | | | | |

| Ala | Leu | Phe | Val | Asn | Pro | Trp | Ile | Ile | Ser | Leu | Val | Lys | Leu | Leu | His |
| --- | --- | --- | --- | --- | --- | --- | --- | --- | --- | --- | --- | --- | --- | --- | --- |
| 305 | | | | | 310 | | | | | 315 | | | | | 320 |

| Ala | Ile | Glu | Val | Pro | Leu | Cys | Val | Ile | Ser | Val | Phe | Lys | Tyr | Ser | Val |
| --- | --- | --- | --- | --- | --- | --- | --- | --- | --- | --- | --- | --- | --- | --- | --- |
| | | | | 325 | | | | | 330 | | | | | 335 | |

| Ala | Asn | Phe | Asp | Lys | Arg | Leu | Ser | Ser | Thr | Ile | Phe | Leu | Ile | Gly | Phe |
| --- | --- | --- | --- | --- | --- | --- | --- | --- | --- | --- | --- | --- | --- | --- | --- |
| | | | 340 | | | | | 345 | | | | | 350 | | |

| Gln | Ile | Ala | Ser | Ser | Leu | Gly | Ile | Val | Leu | Leu | Ser | Thr | Pro | Thr | Gly |
| --- | --- | --- | --- | --- | --- | --- | --- | --- | --- | --- | --- | --- | --- | --- | --- |
| | 355 | | | | | 360 | | | | | 365 | | | | |

| Ile | Leu | Phe | Asp | His | Ala | Gly | Tyr | Gln | Thr | Val | Phe | Phe | Ala | Ile | Ser |
| --- | --- | --- | --- | --- | --- | --- | --- | --- | --- | --- | --- | --- | --- | --- | --- |
| 370 | | | | | 375 | | | | | 380 | | | | | |

| Gly | Ile | Val | Cys | Leu | Met | Leu | Leu | Phe | Gly | Ile | Phe | Phe | Leu | Ser | Lys |
| --- | --- | --- | --- | --- | --- | --- | --- | --- | --- | --- | --- | --- | --- | --- | --- |
| 385 | | | | | 390 | | | | | 395 | | | | | 400 |

| Lys | Arg | Glu | Gln | Ile | Val | Met | Glu | Thr | Pro | Val | Pro | Ser | Ala | Ile | |
| --- | --- | --- | --- | --- | --- | --- | --- | --- | --- | --- | --- | --- | --- | --- | --- |
| | | | 405 | | | | | 410 | | | | | 415 | | |

<210> SEQ ID NO 101
<211> LENGTH: 1248
<212> TYPE: DNA
<213> ORGANISM: Artificial Sequence
<220> FEATURE:
<223> OTHER INFORMATION: coding squence for variant sucrose transporter

<400> SEQUENCE: 101

```
atggcactga atattccatt cagaaatgcg tactatcgtt ttgcatccag ttactcattt      60
ctcttttta tttcctggtc gctgtggtgg tcgttatacg ctatttggct gaaaggacat     120
ctagggttga cagggacgga attaggtaca ctttattcgg tcaaccagtt taccagcatt    180
ctatttatga tgttctacgg catcgttcag gataaactcg gtctgaagaa accgctcatc    240
tggtgtatga gtttcatcct ggtcttgacc ggaccgttta tgatttacgt ttatgaaccg    300
ttactgcaaa gcaattttc tgtaggtcta attctgggggg cgctattttt tggcttgggg    360
tatctggcgg gatgcggttt gcttgatagc ttcaccgaaa aaatggcgcg aaattttcat    420
ttcgaatatg aacagcgcg cgcctgggga tcttttggct atgctattgg cgcgttcttt    480
gccggcatat tttttagtat cagtccccat atcaacttct ggttggtctc gctatttggc    540
gctgtattta tgatgatcaa catgcgtttt aaagataagg atcaccagtg cgtagcggca    600
gatgcgggag ggtaaaaaaa agaggatttt atcgcagttt tcaaggatcg aaacttctgg    660
gttttcgtca tatttattgt ggggacgtgg tctttctata acatttttga tcaacaactt    720
tttcctgtct tttattcagg tttattcgaa tcacacgatg taggaacgcg cctgtatggt    780
```

-continued

```
tatctcaact cattccaggt ggtactcgaa gcgctgtgca tggcgattat tcctttcttt    840
gtgaatcggg tagggccaaa aaatgcatta cttatcggag ttgtgattat ggcgttgctg    900
atcctttcct gcgcgctgtt cgttaacccc tggattattt cattagtgaa gttgttacat    960
gccattgagg ttccactttg tgtcatatcc gtcttcaaat acagcgtggc aaactttgat   1020
aagcgcctgt cgtcgacgat ctttctgatt ggttttcaaa ttgccagttc gcttgggatt   1080
gtgctgcttt caacgccgac tgggatactc tttgaccacg caggctacca gacagttttc   1140
ttcgcaattt cgggtattgt ctgcctgatg ttgctatttg gcattttctt cttgagtaaa   1200
aaacgcgagc aaatagttat ggaaacgcct gtaccttcag caatatag               1248
```

<210> SEQ ID NO 102
<211> LENGTH: 415
<212> TYPE: PRT
<213> ORGANISM: Artificial Sequence
<220> FEATURE:
<223> OTHER INFORMATION: Variant sucrose transporter

<400> SEQUENCE: 102

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Val Asn Arg Val Gly Pro Lys Asn
        275                 280                 285
```

Ala Leu Leu Ile Gly Val Val Ile Met Ala Leu Leu Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 103
<211> LENGTH: 1248
<212> TYPE: DNA
<213> ORGANISM: Artificial Sequence
<220> FEATURE:
<223> OTHER INFORMATION: Coding sequence for variant sucrose transporter

<400> SEQUENCE: 103
atggcactga atattccatt cagaaatgcg tactatcgtt ttgcatccag ttactcattt      60
ctcttttta tttcctggtc gctgtggtgg tcgttatacg ctatttggct gaaaggacat     120
ctagggttga cagggacgga attaggtaca ctttattcgg tcaaccagtt taccagcatt     180
ctatttatga tgttctacgg catcgttcag gataaactcg gtctgaagaa accgctcatc     240
tggtgtatga gtttcatcct ggtcttgacc ggaccgttta tgatttacgt ttatgaaccg     300
ttactgcaaa gcaattttc tgtaggtcta attctggggg cgctatttt tggcttgggg     360
tatctggcgg gatgcggttt gcttgatagc ttcaccgaaa aaatggcgcg aaatttcat     420
ttcgaatatg aacagcgcg cgcctgggga tcttttggct atgctattgg cgcgttcttt     480
gccggcatat tttttagtat cagtccccat atcaacttct ggttggtctc gctatttggc     540
gctgtattta tgatgatcaa catgcgtttt aaagataagg atcaccagtg cgtagcggca     600
gatgcgggag gggtaaaaaa agaggatttt atcgcagttt tcaaggatcg aaacttctgg     660
gtttcgtca tatttattgt ggggacgtgg tctttctata acattttga tcaacaactt     720
tttcctgtct tttattcagg tttattcgaa tcacacgatg taggaacgcg cctgtatggt     780
tatctcaact cattccaggt ggtactcgaa gcgctgtgca tggcgattat tcctttcttt     840
gtgaatcggg tagggccaaa aaatgcatta cttatcggag ttgtgattat ggcgttggcg     900
atcctttcct gcgcgctgtt cgttaaccc tggattattt cattagtgaa gttgttacat     960
gccattgagg ttccactttg tgtcatatcc gtcttcaaat acagcgtggc aaactttgat    1020
aagcgcctgt cgtcgacgat ctttctgatt ggttttcaca ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg gcattttctt cttgagtaaa    1200
aaacgcgagc aaatagttat ggaaacgcct gtaccttcag caatatag              1248

<210> SEQ ID NO 104
<211> LENGTH: 415

<212> TYPE: PRT
<213> ORGANISM: Artificial Sequence
<220> FEATURE:
<223> OTHER INFORMATION: Variant sucrose transporter

<400> SEQUENCE: 104

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Ala Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

His Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
```

```
                385                 390                 395                 400

Lys Arg Glu Gln Ile Val Met Glu Thr Pro Val Pro Ser Ala Ile
                405                 410                 415

<210> SEQ ID NO 105
<211> LENGTH: 1248
<212> TYPE: DNA
<213> ORGANISM: Artificial Sequence
<220> FEATURE:
<223> OTHER INFORMATION: Coding sequence for variant sucrose transporter

<400> SEQUENCE: 105
atggcactga atattccatt cagaaatgcg tactatcgtt ttgcatccag ttactcattt       60
ctctttttta tttcctggtc gctgtggtgg tcgttatacg ctatttggct gaaaggacat      120
ctagggttga cagggacgga attaggtaca ctttattcgg tcaaccagtt taccagcatt      180
ccatttatga tgttctacgg catcgttcag gataaactcg gtctgaagaa accgctcatc      240
tggtgtatga gtttcatcct ggtcttgacc ggaccgttta tgatttacgt ttatgaaccg      300
ttactgcaaa gcaattttc tgtaggtcta attctggggg cgctattttt tggcttgggg      360
tatctggcgg gatgcggttt gcttgatagc ttcaccgaaa aaatggcgcg aaattttcat      420
ttcgaatatg aacagcgcg cgcctgggga tcttttggct atgctattgg cgcgttcttt      480
gccggcatat tttttagtat cagtccccat atcaacttct ggttggtctc gctatttggc      540
gctgtattta tgatgatcaa catgcgtttt aaagataagg atcaccagtg cgtagcggca      600
gatgcgggag gggtaaaaaa agaggatttt atcgcagttt tcaaggatcg aaacttctgg      660
gttttcgtca tatttattgt ggggacgtgg tctttctata cattttttga tcaacaactt      720
tttcctgtct tttattcagg tttattcgaa tcacacgatg taggaacgcg cctgtatggt      780
tatctcaact cattccaggt ggtactcgaa gcgctgtgca tggcgattat cctttctttt      840
gtgaatcggg tagggccaaa aaatgcatta cttatcggag ttgtgattat ggcgttggcg      900
atcctttcct gcgcgctgtt cgttaacccc tggattattt cattagtgaa gttgttacat      960
gccattgcgg ttccactttg tgtcatatcc gtcttcaaat acagcgtggc aaactttgat     1020
aagcgcctgt cgtcgacgat ctttctgatt ggttttcaca ttgccagttc gcttgggatt     1080
gtgctgcttt caacgccgac tgggatactc tttgaccacg caggctacca gacagttttc     1140
ttcgcaattt cgggtattgt ctgcctgatg ttgctatttg gcattttctt cttgagtaaa     1200
aaacgcgagc aaatagttat ggaaacgcct gtaccttcag caatatag                  1248

<210> SEQ ID NO 106
<211> LENGTH: 415
<212> TYPE: PRT
<213> ORGANISM: Artificial Sequence
<220> FEATURE:
<223> OTHER INFORMATION: Variant sucrose transporter

<400> SEQUENCE: 106

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
                20                  25                  30

Tyr Ala Ile Trp Leu Lys Gly His Leu Gly Leu Thr Gly Thr Glu Leu
            35                  40                  45

Gly Thr Leu Tyr Ser Val Asn Gln Phe Thr Ser Ile Pro Phe Met Met
        50                  55                  60

Phe Tyr Gly Ile Val Gln Asp Lys Leu Gly Leu Lys Lys Pro Leu Ile
```

|   |   |   |   |   |   |   |   |   |   |   |   |   |   |   |
|---|---|---|---|---|---|---|---|---|---|---|---|---|---|---|
| | | | | 65 | | | | | 70 | | | | | 75 | | | | | 80 |

Trp Cys Met Ser Phe Ile Leu Val Leu Thr Gly Pro Phe Met Ile Tyr
                    85                  90                  95

Val Tyr Glu Pro Leu Leu Gln Ser Asn Phe Ser Val Gly Leu Ile Leu
                    100                 105                 110

Gly Ala Leu Phe Phe Gly Leu Gly Tyr Leu Ala Gly Cys Gly Leu Leu
                    115                 120                 125

Asp Ser Phe Thr Glu Lys Met Ala Arg Asn Phe His Phe Glu Tyr Gly
                    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                    165                 170                 175

Ser Leu Phe Gly Ala Val Phe Met Met Ile Asn Met Arg Phe Lys Asp
                    180                 185                 190

Lys Asp His Gln Cys Val Ala Ala Asp Ala Gly Gly Val Lys Lys Glu
                    195                 200                 205

Asp Phe Ile Ala Val Phe Lys Asp Arg Asn Phe Trp Val Phe Val Ile
                    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                    245                 250                 255

Arg Leu Tyr Gly Tyr Leu Asn Ser Phe Gln Val Val Leu Glu Ala Leu
                    260                 265                 270

Cys Met Ala Ile Ile Pro Phe Phe Val Asn Arg Val Gly Pro Lys Asn
                    275                 280                 285

Ala Leu Leu Ile Gly Val Val Ile Met Ala Leu Ala Ile Leu Ser Cys
                    290                 295                 300

Ala Leu Phe Val Asn Pro Trp Ile Ile Ser Leu Val Lys Leu Leu His
305                 310                 315                 320

Ala Ile Ala Val Pro Leu Cys Val Ile Ser Val Phe Lys Tyr Ser Val
                    325                 330                 335

Ala Asn Phe Asp Lys Arg Leu Ser Ser Thr Ile Phe Leu Ile Gly Phe
                    340                 345                 350

His Ile Ala Ser Ser Leu Gly Ile Val Leu Leu Ser Thr Pro Thr Gly
                    355                 360                 365

Ile Leu Phe Asp His Ala Gly Tyr Gln Thr Val Phe Phe Ala Ile Ser
                    370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                    405                 410                 415

<210> SEQ ID NO 107
<211> LENGTH: 1261
<212> TYPE: DNA
<213> ORGANISM: Artificial Sequence
<220> FEATURE:
<223> OTHER INFORMATION: Coding sequence for variant sucrose transporter

<400> SEQUENCE: 107
atgaaaatca atatgccgtt ctccaatgac aaataccgtt atagttcggg ctacctgctg      60
ttcttcttcg ctgcgtggtc cctgtggtgg agtttctacg caatctggct gaaaaacaaa     120
ctgggcctgt ccggcaccga actgggcatg ctgtatgctg ttaatcagtt tttctccatg     180

-continued

```
ctgttcatgc tggtctacgg ctttctgcaa gataaactgg gcacccgtaa acatctgatt    240
tggctgatgg gcattgtgat cacgctgtca ggtccgttcc tgatctatgt ttacgaaccg    300
ctgctgacct cgaactttaa actgggcatg gcactgggtg ctattttctt tggtctgggt    360
tatctggcag gttgcggcct ggtggaatct tttgtggaaa aagtttctcg taaattcaac    420
ttcgaatttg gcaccgcacg tctgtggggc tctctgggtt acgcggccgg tacgttcgtt    480
ggcggtattt tctttagcat caacccgcac attaattttt ggtgtgtctc tgtgatgggc    540
gtcctgttcc tgctgatcaa cgtgctgttt aaaaccaata gtccggcacc gagctctgtg    600
aaaacccgtt ccccggaacc ggatgctctg acgcgcaaag acttcctgac catctttaaa    660
gatacgcagt tctggttttt cgttattttt gtggttggca cgtggagttt ctattccatc    720
tacgaccagc aaatgttccc ggtgttttat gcgagcctgt tgatgaccc ggaactggcc    780 ccgcgtgttt atggttacct gaactctgtt caagtcttca tggaagcggt tggcatggcc    840
ctggtcccgt ttctgattaa tcgtatcggt ccgaaaagcg cactgctgct gggcggcacc    900
atcatggcat gcgcgattct gggttcagct ctgtttacgg atatctacat catctcgctg    960
atcaaaatgc tgcatgcgct ggaagtcccg ctgttcgtca tttcagtgtt caaattttcg   1020
gtggccaact ttgacaaacg cctgagttcc accatttacc tgatcggctt taatatcgcg   1080
tcatcgattg gtattatcgt gctgagtctg ccggttggca aactgttcga taaagttggt   1140
tatcaggaaa ttttctgat catggccagc atcgtcatta tcaccctgat tttcggctac   1200
tttagcctgt ctaaaaaaca tcaccagcaa aaaatgggta cgaactggt gacggaataa   1260 c                                                                   1261
```

<210> SEQ ID NO 108
<211> LENGTH: 419
<212> TYPE: PRT
<213> ORGANISM: Artificial Sequence
<220> FEATURE:
<223> OTHER INFORMATION: Variant sucrose transporter

<400> SEQUENCE: 108

```
Met Lys Ile Asn Met Pro Phe Ser Asn Asp Lys Tyr Arg Tyr Ser Ser
1               5                   10                  15

Gly Tyr Leu Leu Phe Phe Phe Ala Ala Trp Ser Leu Trp Trp Ser Phe
            20                  25                  30

Tyr Ala Ile Trp Leu Lys Asn Lys Leu Gly Leu Ser Gly Thr Glu Leu
        35                  40                  45

Gly Met Leu Tyr Ala Val Asn Gln Phe Phe Ser Met Leu Phe Met Leu
    50                  55                  60

Val Tyr Gly Phe Leu Gln Asp Lys Leu Gly Thr Arg Lys His Leu Ile
65                  70                  75                  80

Trp Leu Met Gly Ile Val Ile Thr Leu Ser Gly Pro Phe Leu Ile Tyr
                85                  90                  95

Val Tyr Glu Pro Leu Leu Thr Ser Asn Phe Lys Leu Gly Met Ala Leu
            100                 105                 110

Gly Ala Ile Phe Phe Gly Leu Gly Tyr Leu Ala Gly Cys Gly Leu Val
        115                 120                 125

Glu Ser Phe Val Glu Lys Val Ser Arg Lys Phe Asn Phe Glu Phe Gly
    130                 135                 140

Thr Ala Arg Leu Trp Gly Ser Leu Gly Tyr Ala Ala Gly Thr Phe Val
145                 150                 155                 160

Gly Gly Ile Phe Phe Ser Ile Asn Pro His Ile Asn Phe Trp Cys Val
```

```
                165                 170                 175
Ser Val Met Gly Val Leu Phe Leu Ile Asn Val Leu Phe Lys Thr
            180                 185                 190
Asn Ser Pro Ala Pro Ser Ser Val Lys Thr Arg Ser Pro Glu Pro Asp
            195                 200                 205
Ala Leu Thr Arg Lys Asp Phe Leu Thr Ile Phe Lys Asp Thr Gln Phe
    210                 215                 220
Trp Phe Phe Val Ile Phe Val Val Gly Thr Trp Ser Phe Tyr Ser Ile
225                 230                 235                 240
Tyr Asp Gln Gln Met Phe Pro Val Phe Tyr Ala Ser Leu Phe Asp Asp
                245                 250                 255
Pro Glu Leu Ala Pro Arg Val Tyr Gly Tyr Leu Asn Ser Val Gln Val
            260                 265                 270
Phe Met Glu Ala Val Gly Met Ala Leu Val Pro Phe Leu Ile Asn Arg
        275                 280                 285
Ile Gly Pro Lys Ser Ala Leu Leu Leu Gly Gly Thr Ile Met Ala Cys
    290                 295                 300
Ala Ile Leu Gly Ser Ala Leu Phe Thr Asp Ile Tyr Ile Ile Ser Leu
305                 310                 315                 320
Ile Lys Met Leu His Ala Leu Glu Val Pro Leu Phe Val Ile Ser Val
                325                 330                 335
Phe Lys Phe Ser Val Ala Asn Phe Asp Lys Arg Leu Ser Thr Ile
            340                 345                 350
Tyr Leu Ile Gly Phe Asn Ile Ala Ser Ser Ile Gly Ile Val Leu
        355                 360                 365
Ser Leu Pro Val Gly Lys Leu Phe Asp Lys Val Gly Tyr Gln Glu Ile
    370                 375                 380
Phe Leu Ile Met Ala Ser Ile Val Ile Ile Thr Leu Ile Phe Gly Tyr
385                 390                 395                 400
Phe Ser Leu Ser Lys Lys His His Gln Gln Lys Met Gly Asn Glu Leu
                405                 410                 415
Val Thr Glu

<210> SEQ ID NO 109
<211> LENGTH: 1261
<212> TYPE: DNA
<213> ORGANISM: Artificial Sequence
<220> FEATURE:
<223> OTHER INFORMATION: Coding sequence for variant sucrose transporter

<400> SEQUENCE: 109
atgaaaatca atatgccgtt ctccaatgac aaataccgtt atagttcggg ctacctgctg      60
ttcttcttcg ctgcgtggtc cctgtggtgg agtttctacg caatctggct gaaaaacaaa     120
ctgggcctgt ccggcaccga actgggcatg ctgtatgctg ttaatcagtt tttctccatg     180
ctgttcatgc tggtctacgg cttctgcaa gataaactgg gcacccgtaa acatctgatt     240
tggctgatgg gcattgtgat cacgctgtca ggtccgttcc tgatctatgt ttacgaaccg     300
ctgctgacct cgaactttaa actgggcatg gcactgggtg ctattttctt tggtctgggt     360
tatctggcag gttgcggcct ggtggaatct tttgtggaaa agtttctcg taaattcaac     420 ttcgaatttg gcaccgcacg tctgtgggc tctctggggtt acgcggccgg tacgttcgtt     480
ggcggtattt tctttagcat caaccccgcac attaattttt ggtgtgtctc tgtgatgggc     540
gtcctgttcc tgctgatcaa cgtgctgttt aaaaccaata gtccggcacc gagctctgtg     600
aaaacccgtt ccccggaacc ggatgctctg acgcgcaaag acttcctgac catctttaaa     660
```

```
gatacgcagt tctggttttt cgttattttt gtggttggca cgtggagttt ctattccatc      720
tacgaccagc aaatgttccc ggtgttttat gcgagcctgt ttgatgaccc ggaactggcc      780
ccgcgtgttt atggttacct gaactctgtt caagtcttca tggaagcggt tggcatggcc      840
ctggtcccgt ttctgattaa tcgtatcggt ccgaaaagcg cactgctgct gggcggcacc      900
atcatggcat gcctgattct gggttcagct ctgtttacgg atatctacat catctcgctg      960
atcaaaatgc tgcatgcgct ggaagtcccg ctgttcgtca tttcagtgtt caaattttcg     1020
gtggccaact ttgacaaacg cctgagttcc accatttacc tgatcggctt taatatcgcg     1080
tcatcgattg gtattatcgt gctgagtctg ccggttggca aactgttcga taaagttggt     1140
tatcaggaaa ttttctgat catggccagc atcgtcatta tcaccctgat tttcggctac      1200
tttagcctgt ctaaaaaaca tcaccagcaa aaatgggta acgaactggt gacggaataa      1260
c                                                                    1261
```

<210> SEQ ID NO 110
<211> LENGTH: 419
<212> TYPE: PRT
<213> ORGANISM: Artificial Sequence
<220> FEATURE:
<223> OTHER INFORMATION: Variant sucrose transporter

<400> SEQUENCE: 110

```
Met Lys Ile Asn Met Pro Phe Ser Asn Asp Lys Tyr Arg Tyr Ser Ser
1               5                   10                  15

Gly Tyr Leu Leu Phe Phe Phe Ala Ala Trp Ser Leu Trp Trp Ser Phe
            20                  25                  30

Tyr Ala Ile Trp Leu Lys Asn Lys Leu Gly Leu Ser Gly Thr Glu Leu
        35                  40                  45

Gly Met Leu Tyr Ala Val Asn Gln Phe Phe Ser Met Leu Phe Met Leu
    50                  55                  60

Val Tyr Gly Phe Leu Gln Asp Lys Leu Gly Thr Arg Lys His Leu Ile
65                  70                  75                  80

Trp Leu Met Gly Ile Val Ile Thr Leu Ser Gly Pro Phe Leu Ile Tyr
                85                  90                  95

Val Tyr Glu Pro Leu Leu Thr Ser Asn Phe Lys Leu Gly Met Ala Leu
            100                 105                 110

Gly Ala Ile Phe Phe Gly Leu Gly Tyr Leu Ala Gly Cys Gly Leu Val
        115                 120                 125

Glu Ser Phe Val Glu Lys Val Ser Arg Lys Phe Asn Phe Glu Phe Gly
    130                 135                 140

Thr Ala Arg Leu Trp Gly Ser Leu Gly Tyr Ala Ala Gly Thr Phe Val
145                 150                 155                 160

Gly Gly Ile Phe Phe Ser Ile Asn Pro His Ile Asn Phe Trp Cys Val
                165                 170                 175

Ser Val Met Gly Val Leu Phe Leu Leu Ile Asn Val Leu Phe Lys Thr
            180                 185                 190

Asn Ser Pro Ala Pro Ser Ser Val Lys Thr Arg Ser Pro Glu Pro Asp
        195                 200                 205

Ala Leu Thr Arg Lys Asp Phe Leu Thr Ile Phe Lys Asp Thr Gln Phe
    210                 215                 220

Trp Phe Phe Val Ile Phe Val Val Gly Thr Trp Ser Phe Tyr Ser Ile
225                 230                 235                 240

Tyr Asp Gln Gln Met Phe Pro Val Phe Tyr Ala Ser Leu Phe Asp Asp
                245                 250                 255
```

```
Pro Glu Leu Ala Pro Arg Val Tyr Gly Tyr Leu Asn Ser Val Gln Val
        260                 265                 270

Phe Met Glu Ala Val Gly Met Ala Leu Val Pro Phe Leu Ile Asn Arg
        275                 280                 285

Ile Gly Pro Lys Ser Ala Leu Leu Gly Gly Thr Ile Met Ala Cys
290                 295                 300

Leu Ile Leu Gly Ser Ala Leu Phe Thr Asp Ile Tyr Ile Ile Ser Leu
305                 310                 315                 320

Ile Lys Met Leu His Ala Leu Glu Val Pro Leu Phe Val Ile Ser Val
            325                 330                 335

Phe Lys Phe Ser Val Ala Asn Phe Asp Lys Arg Leu Ser Ser Thr Ile
            340                 345                 350

Tyr Leu Ile Gly Phe Asn Ile Ala Ser Ser Ile Gly Ile Ile Val Leu
            355                 360                 365

Ser Leu Pro Val Gly Lys Leu Phe Asp Lys Val Gly Tyr Gln Glu Ile
370                 375                 380

Phe Leu Ile Met Ala Ser Ile Val Ile Ile Thr Leu Ile Phe Gly Tyr
385                 390                 395                 400

Phe Ser Leu Ser Lys Lys His His Gln Gln Lys Met Gly Asn Glu Leu
                    405                 410                 415

Val Thr Glu

<210> SEQ ID NO 111
<211> LENGTH: 1339
<212> TYPE: DNA
<213> ORGANISM: Artificial Sequence
<220> FEATURE:
<223> OTHER INFORMATION: Coding sequence for variant sucrose transporter

<400> SEQUENCE: 111
atggcgtcag cgaccaaatc ggcgtggaaa aacccgtcct atctgcaatc ctcattcggc      60
atcttcatgt tcttctgttc gtggggcatt tggtggtcat ttttccagcg ttggctgatc     120
tcgggcgtgg gtctgacgaa cgccgaagtt ggcaccattt atagcatcaa ttctctggca     180
accctggtga ttatgtttgt gtacggcgtt attcaggatc aactgggtat caaacgtaaa     240
ctggttattg tggttagcgt catcgcggcc tgcgtgggtc cgtttgtcca gttcgtgtat     300
gcaccgatga ttctggcggg cggcaccacg cgttggatcg gtgctctgat ggttcaatc      360
gtgctgtcgg cgggctttat gagtggttgc tccctgttcg aagctgttac cgaacgttat     420
tctcgcaaat ttggcttcga atacggtcag agccgcgcct ggggctcttt tggttatgca     480
attgtggctc tgtgtgcggg ctttctgttc aacattaatc cgctgatcaa ctttttgggt     540
ggttcagcat tcggtccggg catgctgctg gtttacgctt tgggtccc ggcggaacaa      600
aaagaagaac tgaaaaaaga aacggatccg aacgcagctc cgaccaatcc gtcgctgaaa     660
gaaatggttg cggtcctgaa aatgccgacg ctgtgggttc tgattgtctt tatgctgctg     720
accaacacgt tttataccgt gttcgaccag caaatgtttc gacgtatta cgctaacctg     780
tttccgaccg aagaaatcgg caacgcgacc tacggcacgc tgaatggttt tcaggttttc     840
ctggaaagcg ccatgatggg tgtcgtgccg attatcatga agaaaattgg cgttcgtaat     900
gccctgctgc tgggtgcaac ggtcatgttt ctggcgatcg gcctgtgcgg tgtgttccat     960
gatccggtta ccattagtat cgtcaaactg tttcactcca tgaagtgcc gctgttctgt    1020
ctgccggcgt tcgttatttt cacccctgcat tttgacacga aactgagcgc cacccctgtac    1080
atggttggct tccagattgc aagccaagtg ggtcaagtta tctttctctac gccgctgggc    1140
```

-continued

```
gccttccacg ataaaatggc acaaatcctg ccgaacaatg acatgggtag tcgtgtcacc   1200
ttttgggtga tttccgctat cgtgctgtgt gcgctgattt atggcttttt cgtcatcaaa   1260
catgatgacc aggaagtggg cggtgatccg ttctacaccg acaaacaact gcgccaaatg   1320
gaagcggcca aagcgtaac                                                1339
```

<210> SEQ ID NO 112
<211> LENGTH: 445
<212> TYPE: PRT
<213> ORGANISM: Artificial Sequence
<220> FEATURE:
<223> OTHER INFORMATION: Variant sucrose transporter

<400> SEQUENCE: 112

```
Met Ala Ser Ala Thr Lys Ser Ala Trp Lys Asn Pro Ser Tyr Leu Gln
1               5                   10                  15

Ser Ser Phe Gly Ile Phe Met Phe Phe Cys Ser Trp Gly Ile Trp Trp
            20                  25                  30

Ser Phe Phe Gln Arg Trp Leu Ile Ser Gly Val Gly Leu Thr Asn Ala
        35                  40                  45

Glu Val Gly Thr Ile Tyr Ser Ile Asn Ser Leu Ala Thr Leu Val Ile
    50                  55                  60

Met Phe Val Tyr Gly Val Ile Gln Asp Gln Leu Gly Ile Lys Arg Lys
65                  70                  75                  80

Leu Val Ile Val Val Ser Val Ile Ala Ala Cys Val Gly Pro Phe Val
                85                  90                  95

Gln Phe Val Tyr Ala Pro Met Ile Leu Ala Gly Gly Thr Thr Arg Trp
            100                 105                 110

Ile Gly Ala Leu Ile Gly Ser Ile Val Leu Ser Ala Gly Phe Met Ser
        115                 120                 125

Gly Cys Ser Leu Phe Glu Ala Val Thr Glu Arg Tyr Ser Arg Lys Phe
    130                 135                 140

Gly Phe Glu Tyr Gly Gln Ser Arg Ala Trp Gly Ser Phe Gly Tyr Ala
145                 150                 155                 160

Ile Val Ala Leu Cys Ala Gly Phe Leu Phe Asn Ile Asn Pro Leu Ile
                165                 170                 175

Asn Phe Trp Val Gly Ser Ala Phe Gly Pro Gly Met Leu Leu Val Tyr
            180                 185                 190

Ala Phe Trp Val Pro Ala Glu Gln Lys Glu Glu Leu Lys Lys Glu Thr
        195                 200                 205

Asp Pro Asn Ala Ala Pro Thr Asn Pro Ser Leu Lys Glu Met Val Ala
    210                 215                 220

Val Leu Lys Met Pro Thr Leu Trp Val Leu Ile Val Phe Met Leu Leu
225                 230                 235                 240

Thr Asn Thr Phe Tyr Thr Val Phe Asp Gln Gln Met Phe Pro Thr Tyr
                245                 250                 255

Tyr Ala Asn Leu Phe Pro Thr Glu Glu Ile Gly Asn Ala Thr Tyr Gly
            260                 265                 270

Thr Leu Asn Gly Phe Gln Val Phe Leu Glu Ser Ala Met Met Gly Val
        275                 280                 285

Val Pro Ile Ile Met Lys Lys Ile Gly Val Arg Asn Ala Leu Leu Leu
    290                 295                 300

Gly Ala Thr Val Met Phe Leu Ala Ile Gly Leu Cys Gly Val Phe His
305                 310                 315                 320

Asp Pro Val Thr Ile Ser Ile Val Lys Leu Phe His Ser Ile Glu Val
```

|  | 325 | 330 | 335 |  |
|---|---|---|---|---|

Pro Leu Phe Cys Leu Pro Ala Phe Arg Tyr Phe Thr Leu His Phe Asp
              340                 345                 350

Thr Lys Leu Ser Ala Thr Leu Tyr Met Val Gly Phe Gln Ile Ala Ser
              355                 360                 365

Gln Val Gly Gln Val Ile Phe Ser Thr Pro Leu Gly Ala Phe His Asp
          370                 375                 380

Lys Met Ala Gln Ile Leu Pro Asn Asn Asp Met Gly Ser Arg Val Thr
385                 390                 395                 400

Phe Trp Val Ile Ser Ala Ile Val Leu Cys Ala Leu Ile Tyr Gly Phe
                405                 410                 415

Phe Val Ile Lys His Asp Asp Gln Glu Val Gly Gly Asp Pro Phe Tyr
                420                 425                 430

Thr Asp Lys Gln Leu Arg Gln Met Glu Ala Ala Lys Ala
              435                 440                 445

<210> SEQ ID NO 113
<211> LENGTH: 447
<212> TYPE: DNA
<213> ORGANISM: Artificial Sequence
<220> FEATURE:
<223> OTHER INFORMATION: Plasmid

<400> SEQUENCE: 113
aggaattccc taggcgatct gtgctgtttg ccacggtatg cagcaccagc gcgagattat      60
gggctcgcac gctcgactgt cggacggggg cactggaacg agaagtcagg cgagccgtca     120
cgcccttgac tatgccacat cctgagcaaa taattcaacc actaaacaaa tcaaccgcgt     180
ttcccggagg taaccaagct tgcccggatc cgcatgcgcg gccgcgtcga ctctagttta     240
aaccccgggt gatcgatag ctcttaatta agttgtttgc aatgtaatg ccgctgcacc      300 caggcatcaa ataaaacgaa aggctcagtc gaaagactgg gcctttcgtt ttatctgttg    360
tttgtcggtg aacgctctct actagagtca cactggctca ccttcgggtg gcctttctg     420 cgtttataca gctgtcggta ccgccag                                         447

<210> SEQ ID NO 114
<211> LENGTH: 447
<212> TYPE: DNA
<213> ORGANISM: Artificial Sequence
<220> FEATURE:
<223> OTHER INFORMATION: Plasmid

<400> SEQUENCE: 114
aggaattccc taggcgatct gtgctgtttg ccacggtatg cagcaccagc gcgagattat      60
gggctcgcac gctcgactgt cggacggggg cactggaacg agaagtcagg cgagccgtca     120
cgcccttgac gatgccacat cctgagcaaa taattcaacc actaaacaaa tcaaccgcgt     180
ttcccggagg taaccaagct tgcccggatc cgcatgcgcg gccgcgtcga ctctagttta     240
aaccccgggt gatcgatag ctcttaatta agttgtttgc aatgtaatg ccgctgcacc      300 caggcatcaa ataaaacgaa aggctcagtc gaaagactgg gcctttcgtt ttatctgttg    360
tttgtcggtg aacgctctct actagagtca cactggctca ccttcgggtg gcctttctg     420 cgtttataca gctgtcggta ccgccag                                         447

<210> SEQ ID NO 115
<211> LENGTH: 39
<212> TYPE: DNA
<213> ORGANISM: Artificial Sequence

```
<220> FEATURE:
<223> OTHER INFORMATION: Primer

<400> SEQUENCE: 115
gttgtgatta tggcgttggc gatcctttcc tgcgcgctg                              39

<210> SEQ ID NO 116
<211> LENGTH: 39
<212> TYPE: DNA
<213> ORGANISM: Artificial Sequence
<220> FEATURE:
<223> OTHER INFORMATION: Primer

<400> SEQUENCE: 116
cagcgcgcag gaaaggatcg ccaacgccat aatcacaac                              39

<210> SEQ ID NO 117
<211> LENGTH: 27
<212> TYPE: DNA
<213> ORGANISM: Artificial Sequence
<220> FEATURE:
<223> OTHER INFORMATION: Primer

<400> SEQUENCE: 117
aagcttatgg cactgaatat tccattc                                           27

<210> SEQ ID NO 118
<211> LENGTH: 26
<212> TYPE: DNA
<213> ORGANISM: Artificial Sequence
<220> FEATURE:
<223> OTHER INFORMATION: Primer

<400> SEQUENCE: 118
atcgatctat attgctgaag gtacag                                            26

<210> SEQ ID NO 119
<211> LENGTH: 9317
<212> TYPE: DNA
<213> ORGANISM: Artificial Sequence
<220> FEATURE:
<223> OTHER INFORMATION: Plasmid

<400> SEQUENCE: 119
tcgaggaatt cgcaggaccg tgatacacgg gacaggtcac tgaatgacga caatgtcctg       60
gaaatcagcg aaccgcgcat ctgaagtaca tttgagcgac tgtaccgaaa catgaatgag      120
gcgtttggat taggcgatta ttagcagggc taagcatttt actattatta ttttccggtt      180
gagggatata gagctatcga caacaaccgg aaaaagttta cgtctatatt gctgaaggta      240
caggcgtttc cataactatt tgctcgcgtt ttttactcaa gaagaaaatg ccaaatagca      300
acatcaggca gacaataccc gaaattgcga agaaaactgt ctggtagcct gcgtggtcaa      360
agagtatccc agtcggcgtt gaaagcagca caatcccaag cgaactggca atttgaaaac      420
caatcagaaa gatcgtcgac gacaggcgct tatcaaagtt tgccacgctg tatttgaaga      480
cggatatgac acaaagtgga acctcaatgg catgtaacaa cttcactaat gaaataatcc      540
aggggttaac gaacagcgcg caggaaagga tacgcaacgc cataatcaca actccgataa      600
gtaatgcatt ttttggccct acccgattca caaagaaagg aataatcgcc atgcacagcg      660
cttcgagtac cacctggaat gagttgagat aaccatacag gcgcgttcct acatcgtgtg      720
attcgaataa acctgaataa aagacaggaa aaagttgttg atcaaaaatg ttatagaaag      780
accacgtccc cacaataaat atgacgaaaa cccagaagtt tcgatccttg aaaactgcga      840
```

```
taaaatcctc ttttttttacc cctcccgcat ctgccgctac gcactggtga tccttatctt    900
taaaacgcat gttgatcatc ataaatacag cgccaaatag cgagaccaac cagaagttga    960
tatggggact gatactaaaa aatatgccgg caaagaacgc gccaatagca tagccaaaag   1020
atccccaggc gcgcgctgtt ccatattcga aatgaaaatt tcgcgccatt ttttcggtga   1080
agctatcaag caaaccgcat cccgccagat accccaagcc aaaaaatagc gccccagaa   1140
ttagacctac agaaaaattg ctttgcagta acggttcata aacgtaaatc ataaacggtc   1200
cggtcaagac caggatgaaa ctcatacacc agatgagcgg tttcttcaga ccgagtttat   1260
cctgaacgat gccgtagaac atcataaata gaatgctggt aaactggttg accgaataaa   1320
gtgtacctaa ttccgtccct gtcaaccta gatgtccttt cagccaaata gcgtataacg   1380
accaccacag cgaccaggaa ataaaaaga gaaatgagta actggatgca aaacgatagt   1440
acgcatttct gaatgaaata ttcagtgcca taattacctg cctgtcgtta aaaaattcac   1500
gtcctattta gagataagag cgacttcgcc gtttacttct cactattcca gttcttgtcg   1560
acatggcagc gctgtcattg ccccttcgc cgttactgca agcgctccgc aacgttgagc   1620
gagatcgata attcgtcgca tttctctctc atctgtagat aatcccgtag aggacagacc   1680
tgtgagtaac ccggcaacga acgcatctcc cgcccccgtg ctatcgacac aattcacaga   1740
cattccagca aaatggtgaa cttgtcctcg ataacagacc accacccctt ctgcaccttt   1800
agtcaccaac agcatggcga tctcatactc ttttgccagg gcgcatatat cctgatcgtt   1860
ctgtgttttt ccactgataa gtcgccattc ttcttccgag agcttgacga catccgccag   1920
ttgtagcgcc tgccgcaaac acaagcggag caaatgctcg tcttgccata gatcttcacg   1980
aatattagga tcgaagctga caaaacctcc ggcatgccgg atcgccgtca tcgcagtaaa   2040
tgcgctggta cgcgaaggct cggcagacaa cgcaattgaa cagagatgta accattcgcc   2100
atgtcgccag cagggcaagt ctgtcgtctc taaaaaaaga tcggcactgg ggcggaccat   2160
aaacgtaaat gaacgttccc cttgatcgtt cagatcgaca agcaccgtgg atgtccggtg   2220
ccattcatct tgcttcagat acgtgatatc gactccctca gttagcagcg ttcttttgcat   2280
taacgcacca aaaggatcat ccccaacccg acctataaac ccacttgttc cgcctaatct   2340
ggcgattccc accgcaacgt tagctggcgc gccgccagga caaggcagta ggcgcccgtc   2400
tgattctggc aagagatcta cgaccgcatc ccctaaaacc catactttgg ctgacatttt   2460
tttcccttaa attcatctga gttacgcata gtgataaacc tcttttttcgc aaaatcgtca   2520
tggatttact aaaacatgca tattcgatca caaaacgtca tagttaacgt taacatttgt   2580
gatattcatc gcatttatga aagtaaggga ctttatttt ataaaagtta acgttaacaa   2640
ttcaccaaat ttgcttaacc aggatgatta aaatgacgca atctcgattg catgcggcgc   2700
aaaacgccct agcaaaactt catgagcacc ggggtaacac tttctatccc cattttcacc   2760
tcgcgcctcc tgccgggtgg atgaacgatc caaacggcct gatctggttt aacgatcgtt   2820
atcacgcgtt ttatcaacat catccgatga gcgaacactg ggggccaatg cactggggac   2880
atgccaccag cgacgatatg atccactggc agcatgagcc tattgcgcta gcgccaggag   2940
acgataatga caaagacggg tgttttcag gtagtgctgt cgatgacaat ggtgtcctct   3000
cacttatcta caccggacac gtctggctcg atggtgcagg taatgacgat gcaattcgcg   3060
aagtacaatg tctggctacc agtcgggatg gtattcattt cgagaaacag ggtgtgatcc   3120
tcactccacc agaaggaatc atgcacttcc gcgatcctaa agtgtggcgt gaagccgaca   3180
catggtggat ggtagtcggg gcgaaagatc caggcaacac ggggcagatc ctgctttatc   3240
```

```
gcggcagttc gttgcgtgaa tggaccttcg atcgcgtact ggcccacgct gatgcgggtg   3300
aaagctatat gtgggaatgt ccggactttt tcagccttgg cgatcagcat tatctgatgt   3360
tttccccgca gggaatgaat gccgagggat acagttaccg aaatcgcttt caaagtggcg   3420
taatacccgg aatgtggtcg ccaggacgac tttttgcaca atccgggcat tttactgaac   3480
ttgataacgg gcatgacttt tatgcaccac aaagcttttt agcgaaggat ggtcggcgta   3540
ttgttatcgg ctggatggat atgtgggaat cgccaatgcc ctcaaaacgt gaaggatggg   3600
caggctgcat gacgctggcg cgcgagctat cagagagcaa tggcaaactt ctacaacgcc   3660
cggtacacga agctgagtcg ttacgccagc agcatcaatc tgtctctccc cgcacaatca   3720
gcaataaata tgttttgcag gaaaacgcgc aagcagttga gattcagttg cagtgggcgc   3780
tgaagaacag tgatgccgaa cattacggat tacagctcgg cactggaatg cggctgtata   3840
ttgataacca atctgagcga cttgttttgt ggcggtatta cccacacgag aatttagacg   3900
gctaccgtag tattcccctc ccgcagcgtg acacgctcgc cctaaggata tttatcgata   3960
catcatccgt ggaagtattt attaacgacg gggaagcggt gatgagtagt cgaatctatc   4020
cgcagccaga agaacgggaa ctgtcgcttt atgcctccca cggagtggct gtgctgcaac   4080
atggagcact ctggctactg ggttaacata atatcaggtg gaacaacgga tcaacagcgg   4140
gcaagggatc cacgaagctt cccatggtga cgtcaccggt aaaccagcaa tagacataag   4200
cggctattta acgaccctgc cctgaaccga cgaccgggtc gaatttgctt tcgaatttct   4260
gccattcatc cgcttattat acttattcag gcgtagcacc aggcgtttaa gggcaccaat   4320
aactgcctta aaaaaattac gccccgccct gccactcatc gcagtactgt tgtaattcat   4380
taagcattct gccgacatgg aagccatcac agacggcatg atgaacctga atcgccagcg   4440
gcatcagcac cttgtcgcct tgcgtataat atttgcccat ggtgaaaacg ggggcgaaga   4500
agttgtccat attggccacg tttaaatcaa aactggtgaa actcacccag ggattggctg   4560
agacgaaaaa catattctca ataaacccct tagggaaata ggccaggttt tcaccgtaac   4620
acgccacatc ttgcgaatat atgtgtagaa actgccggaa atcgtcgtgg tattcactcc   4680
agagcgatga aaacgtttca gtttgctcat ggaaaacggt gtaacaaggg tgaacactat   4740
cccatatcac cagctcaccg tctttcattg ccatacggaa ttccggatga gcattcatca   4800
ggcgggcaag aatgtgaata aaggccggat aaaacttgtg cttattttc tttacggtct   4860
ttaaaaaggc cgtaatatcc agctgaacgg tctggttata ggtacattga caactgact   4920
gaaatgcctc aaaatgttct ttacgatgcc attgggatat atcaacggtg gtatatccag   4980
tgatttttttt ctccatttta gcttccttag ctccctgaaaa tctcgataac tcaaaaaata   5040
cgcccggtag tgatcttatt tcattatggt gaaagttgga acctcttacg tgccgatcaa   5100
cgtctcattt tcgccaaaag ttgggccagg gcttcccggt atcaacaggg acaccaggat   5160
ttatttattc tgcgaagtga tcttccgtca caggtatttta ttcggcgcaa agggcctcgt   5220
gatacgccta tttttatagg ttaatgtcat gataataatg gtttcttaga cgtcaggtgg   5280
cactttttcgg ggaaatgtgc gcgcccgcgt tcctgctggc gctgggcctg tttctggcgc   5340
tggacttccc gctgttccgt cagcagcttt tcgcccacgg ccttgatgat cgcggcggcc   5400
ttggcctgca tatcccgatt caacggcccc agggcgtcca gaacgggctt caggcgctcc   5460
cgaaggtctc gggccgtctc ttgggcttga tcggccttct tgcgcatctc acgcgctcct   5520
gcggcggcct gtagggcagg ctcatacccc tgccgaaccg cttttgtcag ccggtcggcc   5580
acggcttccg gcgtctcaac gcgctttgag attcccagct tttcggccaa tccctgcggt   5640
```

```
gcataggcgc gtggctcgac cgcttgcggg ctgatggtga cgtggcccac tggtggccgc   5700
tccagggcct cgtagaacgc ctgaatgcgc gtgtgacgtg ccttgctgcc ctcgatgccc   5760
cgttgcagcc ctagatcggc cacagcggcc gcaaacgtgg tctggtcgcg ggtcatctgc   5820
gctttgttgc cgatgaactc cttggccgac agcctgccgt cctgcgtcag cggcaccacg   5880
aacgcggtca tgtgcgggct ggtttcgtca cggtggatgc tggccgtcac gatgcgatcc   5940
gccccgtact tgtccgccag ccacttgtgc gccttctcga gaacgccgc ctgctgttct    6000 tggctggccg acttccacca ttccgggctg gccgtcatga cgtactcgac cgccaacaca   6060
gcgtccttgc gccgcttctc tggcagcaac tcgcgcagtc ggcccatcgc ttcatcggtg   6120
ctgctggccg cccagtgctc gttctctggc gtcctgctgg cgtcagcgtt gggcgtctcg   6180
cgctcgcggt aggcgtgctt gagactggcc gccacgttgc ccattttcgc cagcttcttg   6240
catcgcatga tcgcgtatgc cgccatgcct gcccctccct tttggtgtcc aaccggctcg   6300 acggggcag cgcaaggcgg tgcctccggc gggccactca atgcttgagt atactcacta    6360
gactttgctt cgcaaagtcg tgaccgccta cggcggctgc ggcgccctac gggcttgctc   6420
tccgggcttc gccctgcgcg gtcgctgcgc tcccttgcca gcccgtggat atgtggacga   6480
tggccgcgag cggccaccgg ctggctcgct tcgctcggcc cgtggacaac cctgctggac   6540
aagctgatgg acaggctgcg cctgcccacg agcttgacca cagggattgc ccaccggcta   6600
cccagccttc gaccacatac ccaccggctc caactgcgcg gcctgcggcc ttgccccatc   6660
aattttttta attttctctg gggaaaagcc tccggcctgc ggcctgcgcg cttcgcttgc   6720
cggttggaca ccaagtggaa ggcgggtcaa ggctcgcgca gcgaccgcgc agcggcttgg   6780
ccttgacgcg cctggaacga cccaagccta tgcgagtggg ggcagtcgaa ggcgaagccc   6840
gcccgcctgc ccccgagac ctgcagggg ggggggcgc tgaggtctgc ctcgtgaaga      6900
aggtgttgct gactcatacc aggcctgaat cgcccatca tccagccaga aagtgaggga    6960
gccacggttg atgagagctt tgttgtaggt ggaccagttg gtgattttga acttttgctt   7020
tgccacggaa cggtctgcgt tgtcgggaag atgcgtgatc tgatccttca actcagcaaa   7080
agttcgattt attcaacaaa gccgccgtcc cgtcaagtca gcgtaatgct ctgccagtgt   7140
tacaaccaat taaccaattc tgattagaaa aactcatcga gcatcaaatg aaactgcaat   7200
ttattcatat caggattatc aataccatat ttttgaaaaa gccgtttctg taatgaagga   7260
gaaaactcac cgaggcagtt ccataggatg gcaagatcct ggtatcggtc tgcgattccg   7320
actcgtccaa catcaataca acctattaat ttcccctcgt caaaaataag gttatcaagt   7380
gagaaatcac catgagtgac gactgaatcc ggtgagaatg gcaaaagctt atgcatttct   7440
ttccagactt gttcaacagg ccagccatta cgctcgtcat caaaatcact cgcatcaacc   7500
aaaccgttat tcattcgtga ttgcgcctga gcgagacgaa atacgcgatc gctgttaaaa   7560
ggacaattac aaacaggaat cgaatgcaac ggcgcagga acactgccag cgcatcaaca     7620
atattttcac ctgaatcagg atattcttct aatacctgga atgctgtttt cccggggatc    7680
gcagtggtga gtaaccatgc atcatcagga gtacggataa aatgcttgat ggtcggaaga    7740
ggcataaatt ccgtcagcca gtttagtctg accatctcat ctgtaacatc attggcaacg   7800
ctacctttgc catgtttcag aaacaactct ggcgcatcgg gcttcccata caatcgatag   7860
attgtcgcac ctgattgccc gacattatcg cgagcccatt tatacccata taaatcagca   7920
tccatgttgg aatttaatcg cggcctcgag caagacgttt cccgttgaat atggctcata   7980
acaccccttg tattactgtt tatgtaagca gacagtttta ttgttcatga tgatatattt   8040
```

```
ttatcttgtg caatgtaaca tcagagattt tgagacacaa cgtggctttc cccccccccc    8100
ctgcaggtcc cgagcctcac ggcggcgagt gcggggttc caagggggca gcgccacctt    8160
gggcaaggcc gaaggccgcg cagtcgatca acaagcccg gaggggccac ttttttgccgg    8220 agggggagcc gcgccgaagg cgtgggggaa ccccgcaggg gtgcccttct ttgggcacca    8280
aagaactaga tatagggcga aatgcgaaag acttaaaaat caacaactta aaaaaggggg    8340
gtacgcaaca gctcattgcg gcaccccccg caatagctca ttgcgtaggt taaagaaaat    8400
ctgtaattga ctgccacttt tacgcaacgc ataattgttg tcgcgctgcc gaaaagttgc    8460
agctgattgc gcatggtgcc gcaaccgtgc ggcaccctac cgcatggaga taagcatggc    8520
cacgcagtcc agagaaatcg gcattcaagc caagaacaag cccggtcact gggtgcaaac    8580
ggaacgcaaa gcgcatgagg cgtgggccgg gcttattgcg aggaaaccca cggcggcaat    8640
gctgctgcat cacctcgtgg cgcagatggg ccaccagaac gccgtggtgg tcagccagaa    8700
gacactttcc aagctcatcg gacgttcttt gcggacggtc caatacgcag tcaaggactt    8760
ggtggccgag cgctggatct ccgtcgtgaa gctcaacggc cccggcaccg tgtcggccta    8820
cgtggtcaat gaccgcgtgg cgtggggcca gccccgcgac cagttgcgcc tgtcggtgtt    8880
cagtgccgcc gtggtggttg atcacgacga ccaggacgaa tcgctgttgg ggcatggcga    8940
cctgcgccgc atcccgaccc tgtatccggg cgagcagcaa ctaccgaccg gccccggcga    9000
ggagccgccc agccagcccg gcattccggg catggaacca gacctgccag ccttgaccga    9060
aacggaggaa tgggaacggc gcgggcagca gcgcctgccg atgcccgatg agccgtgttt    9120
tctggacgat ggcgagccgt tggagccgcc gacacgggtc acgctgccgc gccggtagca    9180
cttgggttgc gcagcaaccc gtaagtgcgc tgttccagac tatcggctgt agccgcctcg    9240
ccgccctata ccttgtctgc ctccccgcgt tgcgtcgcgg tgcatggagc cgggccacct    9300
cgacctgaat ggaagcc                                                9317

<210> SEQ ID NO 120
<211> LENGTH: 60
<212> TYPE: DNA
<213> ORGANISM: Artificial Sequence
<220> FEATURE:
<223> OTHER INFORMATION: Primer

<400> SEQUENCE: 120
accattgtgg cgatgggttg cttctacagc ctgaacgaga ggatcccttg cccgctgttg    60

<210> SEQ ID NO 121
<211> LENGTH: 60
<212> TYPE: DNA
<213> ORGANISM: Artificial Sequence
<220> FEATURE:
<223> OTHER INFORMATION: Primer

<400> SEQUENCE: 121
ttacgggctt ctatctcttc cacaatgcgg acatacatct gaattcgcag gaccgtgata    60

<210> SEQ ID NO 122
<211> LENGTH: 41
<212> TYPE: DNA
<213> ORGANISM: Artificial Sequence
<220> FEATURE:
<223> OTHER INFORMATION: Primer

<400> SEQUENCE: 122
caaccagttt accagcattc catttatgat gttctacggc a                      41
```

<210> SEQ ID NO 123
<211> LENGTH: 41
<212> TYPE: DNA
<213> ORGANISM: Artificial Sequence
<220> FEATURE:
<223> OTHER INFORMATION: Primer

<400> SEQUENCE: 123
tgccgtagaa catcataaat ggaatgctgg taaactggtt g         41

<210> SEQ ID NO 124
<211> LENGTH: 447
<212> TYPE: DNA
<213> ORGANISM: Artificial Sequence
<220> FEATURE:
<223> OTHER INFORMATION: Promoter/MCS/terminator insert

<400> SEQUENCE: 124
aggaattccc taggcgatct gtgctgtttg ccacggtatg cagcaccagc gcgagattat    60
gggctcgcac gctcgactgt cggacggggg cactggaacg agaagtcagg cgagccgtca   120
cgcccttgac gatgccacat cctgagcaaa taattcaacc actaaacaaa tcaaccgcgt   180
ttcccggagg taaccaagct tgcccggatc cgcatgcgcg gccgcgtcga ctctagttta   240
aaccccaggg tgatcgatag ctcttaatta agttgtttgc caatgtaatg ccgctgcacc   300
caggcatcaa ataaaacgaa aggctcagtc gaaagactgg gcctttcgtt ttatctgttg   360
tttgtcggtg aacgctctct actagagtca cactggctca ccttcgggtg ggcctttctg   420
cgtttataca gctgtcggta ccgccag                                      447

<210> SEQ ID NO 125
<211> LENGTH: 1260
<212> TYPE: DNA
<213> ORGANISM: Artificial Sequence
<220> FEATURE:
<223> OTHER INFORMATION: codon optimized CDS from Citrobacter sp

<400> SEQUENCE: 125
atgaaaatca atatgccgtt ctccaatgac aaataccgtt atagttcggg ctacctgctg    60
ttcttcttcg ctgcgtggtc cctgtggtgg agtttctacg caatctggct gaaaaacaaa   120
ctgggcctgt ccggcaccga actgggcatg ctgtatgctg ttaatcagtt tttctccatg   180
ctgttcatgc tggtctacgg ctttctgcaa gataaactgg gcacccgtaa acatctgatt   240
tggctgatgg gcattgtgat cacgctgtca ggtccgttcc tgatctatgt ttacgaaccg   300
ctgctgacct cgaactttaa actgggcatg gcactgggtg ctattttctt ggtctgggt    360 tatctggcag gttgcggcct ggtggaatct tttgtggaaa agtttctcg taaattcaac   420 ttcgaatttg gcaccgcacg tctgtggggc tctctgggtt acgcggccgg tacgttcgtt   480
ggcggtattt tctttagcat caacccgcac attaattttt ggtgtgtctc tgtgatgggc   540
gtcctgttcc tgctgatcaa cgtgctgttt aaaaccaata gtccggcacc gagctctgtg   600
aaaacccgtt ccccggaacc ggatgctctg acgcgcaaag acttcctgac catctttaaa   660
gatacgcagt tctggttttt cgttattttt gtggttggca cgtggagttt ctattccatc   720
tacgaccagc aaatgttccc ggtgtttat gcgagcctgt tgatgaccc ggaactggcc   780 ccgcgtgttt atggttacct gaactctgtt caagtcttca tggaagcggt tggcatggcc   840
ctggtcccgg ttctgattaa tcgtatcggt ccgaaaagcg cactgctgct gggcggcacc   900
atcatggcat gccgcattct gggttcagct ctgtttacgg atatctacat catctcgctg   960

```
atcaaaatgc tgcatgcgct ggaagtcccg ctgttcgtca tttcagtgtt caaattttcg   1020
gtggccaact ttgacaaacg cctgagttcc accatttacc tgatcggctt taatatcgcg   1080
tcatcgattg gtattatcgt gctgagtctg ccggttggca aactgttcga taaagttggt   1140
tatcaggaaa ttttctgat catggccagc atcgtcatta tcaccctgat tttcggctac    1200
tttagcctgt ctaaaaaaca tcaccagcaa aaaatgggta acgaactggt gacggaataa   1260
```

<210> SEQ ID NO 126
<211> LENGTH: 1338
<212> TYPE: DNA
<213> ORGANISM: Artificial Sequence
<220> FEATURE:
<223> OTHER INFORMATION: codon optimized CDS from Bifidobacterium longum

<400> SEQUENCE: 126

```
atggcgtcag cgaccaaatc ggcgtggaaa aacccgtcct atctgcaatc ctcattcggc    60
atcttcatgt tcttctgttc gtggggcatt tggtggtcat ttttccagcg ttggctgatc   120
tcgggcgtgg gtctgacgaa cgccgaagtt ggcaccattt atagcatcaa ttctctggca   180
accctggtga ttatgtttgt gtacggcgtt attcaggatc aactgggtat caaacgtaaa   240
ctggttattg tggttagcgt catcgcggcc tgcgtgggtc cgtttgtcca gttcgtgtat   300
gcaccgatga ttctggcggg cggcaccacg cgttggatcg tgctctgat ggttcaatc    360 gtgctgtcgg cgggctttat gagtggttgc tccctgttcg aagctgttac cgaacgttat   420
tctcgcaaat ttggcttcga atacggtcag agccgcgcct ggggctcttt tggttatgca   480
attgtggctc tgtgtgcggg ctttctgttc aacattaatc cgctgatcaa cttttgggtt   540
ggttcagcat tcggtccggg catgctgctg gtttacgctt ttgggtccc ggcggaacaa   600 aaagaagaac tgaaaaaaga aacggatccg aacgcagctc cgaccaatcc gtcgctgaaa   660
gaaatggttg cggtcctgaa aatgccgacg ctgtgggttc tgattgtctt tatgctgctg   720
accaacacgt tttatacccgt gttcgaccag caaatgtttc cgacgtatta cgctaacctg   780
tttccgaccg aagaaatcgg caacgcgacc tacggcacgc tgaatggttt tcaggtttc    840 ctggaaagcg ccatgatggg tgtcgtgccg attatcatga agaaaattgg cgttcgtaat   900
gccctgctgc tgggtgcaac ggtcatgttt ctgcgcatcg gcctgtgcgg tgtgttccat   960
gatccggtta ccattagtat cgtcaaactg tttcactcca ttgaagtgcc gctgttctgt   1020
ctgccggcgt tcgttatttt caccctgcat tttgacacga aactgagcgc caccctgtac   1080
atggttggct tccagattgc aagccaagtg ggtcaagtta tcttttctac gccgctgggc   1140
gccttccacg ataaaatggc acaaatcctg ccgaacaatg acatgggtag tcgtgtcacc   1200
ttttgggtga tttccgctat cgtgctgtgt gcgctgattt atggcttttt cgtcatcaaa   1260
catgatgacc aggaagtggg cggtgatccg ttctacaccg acaaacaact gcgccaaatg   1320
gaagcggcca aagcgtaa                                                  1338
```

<210> SEQ ID NO 127
<211> LENGTH: 37
<212> TYPE: DNA
<213> ORGANISM: Artificial Sequence
<220> FEATURE:
<223> OTHER INFORMATION: Primer

<400> SEQUENCE: 127

```
gcaccatcat ggcatgcgcg attctgggtt cagctct                              37
```

```
<210> SEQ ID NO 128
<211> LENGTH: 37
<212> TYPE: DNA
<213> ORGANISM: Artificial Sequence
<220> FEATURE:
<223> OTHER INFORMATION: Primer

<400> SEQUENCE: 128
agagctgaac ccagaatcgc gcatgccatg atggtgc                         37

<210> SEQ ID NO 129
<211> LENGTH: 36
<212> TYPE: DNA
<213> ORGANISM: Artificial Sequence
<220> FEATURE:
<223> OTHER INFORMATION: Primer

<400> SEQUENCE: 129
caccatcatg gcatgcctga ttctgggttc agctct                          36

<210> SEQ ID NO 130
<211> LENGTH: 36
<212> TYPE: DNA
<213> ORGANISM: Artificial Sequence
<220> FEATURE:
<223> OTHER INFORMATION: Primer

<400> SEQUENCE: 130
agagctgaac ccagaatcag gcatgccatg atggtg                          36

<210> SEQ ID NO 131
<211> LENGTH: 35
<212> TYPE: DNA
<213> ORGANISM: Artificial Sequence
<220> FEATURE:
<223> OTHER INFORMATION: Primer

<400> SEQUENCE: 131
aacggtcatg tttctggcga tcggcctgtg cggtg                           35

<210> SEQ ID NO 132
<211> LENGTH: 35
<212> TYPE: DNA
<213> ORGANISM: Artificial Sequence
<220> FEATURE:
<223> OTHER INFORMATION: Primer

<400> SEQUENCE: 132
caccgcacag gccgatcgcc agaaacatga ccgtt                           35

<210> SEQ ID NO 133
<211> LENGTH: 1476
<212> TYPE: DNA
<213> ORGANISM: Pseudomonas fluorescens

<400> SEQUENCE: 133
atgcacgctg cactgttaga gcaagcgcat cgcgctattg aaaaaaaact gcctgggcgg      60
ggtgatgtct atcgcctggc ctatcatctt gcgccgccgg tggggtggat gaatgacccg     120
aacggtctgg tttatttttcg cggcgagtac catgtgttct accaacatca tccctattcg    180
gctcagtggg ggccgatgca ctggggccat gccaagagcc gtgacctggt gcactgggag    240
cacctgccca tcgcgctggc gccgggcgag gcctatgacc gcgacggttg cttttcaggg    300 tctgcgcgtgg tcatggacga cgtgttgtac ctgatttaca ccgggcatac ctggctgggt    360
gcgcccggtg acgagcggag cattcgccag gttcagtgcc tggccagcag caccgacggg    420
```

```
gttgcgttca gcaagcacgg gccggtgatc gatagggcgc ctgaaccggg catcatgcat   480
tttcgcgacc ccaaggtatg gcggcgagga gagcaatggt ggatggccct ggggggcgcgc  540 caaggcgacg cccctcagct cctgctctat cgctcaggcg acctgcatca ctggacgtac   600
ctcaggtgcg cactgcaagg gcaacgagag tcggacggct atatgtggga gtgtcctgac   660
ctgttcgaac tcgatggctg tgatgtgttt ctctattcgc tcaaggcttg aaccccagc   720 ggttatgaca actggaacaa gttccagaac agctatcgga tgggcctgct ggacgatcgc   780
ggatacttca gcgagggcgg tgagctgcgt gaactggatc atggtcacga tttctatgcg   840
gcgcagacct tgctggcgcc agacgggcga cgcctgttgt gggcttggat ggacatgtgg   900
gacagcccga tgccgagtca ggcgcaacac tggtgcggtg cgctgtcgct acctcgtgaa   960
ctgagccgca atggcgaacg gctacgcatg cggccggccc gcgagttggc agcgctacgc  1020
cagtcgcaac ggacactggc gatcggcgtg gtcgaatccg gcaattgcat actcgctgag  1080 cgagggcgc tgctggaatt cgaactgacc ctggacctgg ctggtagcac ggctgagcgt  1140
ttcgggttgg cgctgcgttt agtgaggat cggcaagagc ggaccctggt gtacttcgat  1200
gcgatggcgc ggcgtctggt gctggacagg caacactcgg gagcggggt aagcggtgcg  1260 cgcagcgtgc cgatagccaa gggccaaatg cagatagcct tgcggatttt ccttgatcga  1320
tcctccattg aggtgtttgt cgatgacgga gcctatagct tgagcagtcg gatctaccct  1380
agccccgaca gcgtggcggt catggcgttt gcggtcaatg gtagcggtgg ttttggccaa  1440
gcgtcggtct ggcacctggc cgatctgcac ctgtga                           1476
```

<210> SEQ ID NO 134
<211> LENGTH: 491
<212> TYPE: PRT
<213> ORGANISM: Pseudomonas fluorescens

<400> SEQUENCE: 134

```
Met His Ala Ala Leu Leu Glu Gln Ala His Arg Ala Ile Glu Lys Lys
1               5                   10                  15

Leu Pro Gly Arg Gly Asp Val Tyr Arg Leu Ala Tyr His Leu Ala Pro
            20                  25                  30

Pro Val Gly Trp Met Asn Asp Pro Asn Gly Leu Val Tyr Phe Arg Gly
        35                  40                  45

Glu Tyr His Val Phe Tyr Gln His His Pro Tyr Ser Ala Gln Trp Gly
    50                  55                  60

Pro Met His Trp Gly His Ala Lys Ser Arg Asp Leu Val His Trp Glu
65                  70                  75                  80

His Leu Pro Ile Ala Leu Ala Pro Gly Glu Ala Tyr Asp Arg Asp Gly
                85                  90                  95

Cys Phe Ser Gly Ser Ala Val Val Met Asp Asp Val Leu Tyr Leu Ile
            100                 105                 110

Tyr Thr Gly His Thr Trp Leu Gly Ala Pro Gly Asp Glu Arg Ser Ile
        115                 120                 125

Arg Gln Val Gln Cys Leu Ala Ser Ser Thr Asp Gly Val Ala Phe Ser
    130                 135                 140

Lys His Gly Pro Val Ile Asp Arg Ala Pro Glu Pro Gly Ile Met His
145                 150                 155                 160

Phe Arg Asp Pro Lys Val Trp Arg Arg Gly Glu Gln Trp Trp Met Ala
                165                 170                 175

Leu Gly Ala Arg Gln Gly Asp Ala Pro Gln Leu Leu Leu Tyr Arg Ser
            180                 185                 190
```

Gly Asp Leu His His Trp Thr Tyr Leu Arg Cys Ala Leu Gln Gly Gln
            195                 200                 205

Arg Glu Ser Asp Gly Tyr Met Trp Glu Cys Pro Asp Leu Phe Glu Leu
        210                 215                 220

Asp Gly Cys Asp Val Phe Leu Tyr Ser Pro Gln Gly Leu Asn Pro Ser
225                 230                 235                 240

Gly Tyr Asp Asn Trp Asn Lys Phe Gln Asn Ser Tyr Arg Met Gly Leu
                245                 250                 255

Leu Asp Asp Arg Gly Tyr Phe Ser Glu Gly Gly Glu Leu Arg Glu Leu
            260                 265                 270

Asp His Gly His Asp Phe Tyr Ala Ala Gln Thr Leu Leu Ala Pro Asp
        275                 280                 285

Gly Arg Arg Leu Leu Trp Ala Trp Met Asp Met Trp Asp Ser Pro Met
290                 295                 300

Pro Ser Gln Ala Gln His Trp Cys Gly Ala Leu Ser Leu Pro Arg Glu
305                 310                 315                 320

Leu Ser Arg Asn Gly Glu Arg Leu Arg Met Arg Pro Ala Arg Glu Leu
                325                 330                 335

Ala Ala Leu Arg Gln Ser Gln Arg Thr Leu Ala Ile Gly Val Val Glu
            340                 345                 350

Ser Gly Asn Cys Ile Leu Ala Glu Arg Gly Ala Leu Leu Glu Phe Glu
        355                 360                 365

Leu Thr Leu Asp Leu Ala Gly Ser Thr Ala Glu Arg Phe Gly Leu Ala
    370                 375                 380

Leu Arg Cys Ser Glu Asp Arg Gln Glu Arg Thr Leu Val Tyr Phe Asp
385                 390                 395                 400

Ala Met Ala Arg Arg Leu Val Leu Asp Arg Gln His Ser Gly Ala Gly
                405                 410                 415

Val Ser Gly Ala Arg Ser Val Pro Ile Ala Lys Gly Gln Met Gln Ile
            420                 425                 430

Ala Leu Arg Ile Phe Leu Asp Arg Ser Ser Ile Glu Val Phe Val Asp
        435                 440                 445

Asp Gly Ala Tyr Ser Leu Ser Ser Arg Ile Tyr Pro Ser Pro Asp Ser
    450                 455                 460

Val Ala Val Met Ala Phe Ala Val Asn Gly Ser Gly Phe Gly Gln
465                 470                 475                 480

Ala Ser Val Trp His Leu Ala Asp Leu His Leu
                485                 490

<210> SEQ ID NO 135
<211> LENGTH: 1479
<212> TYPE: DNA
<213> ORGANISM: Bacillus licheniformis

<400> SEQUENCE: 135
atgaacagaa ttcagcaggc agaagaagca ttaaagaaag ccgggaaaaa agtgaatcgc        60
cgttaccgaa tgggctatca catgatgccc cgggcaaact ggataaatga tccaaacgga       120
cttattcaat ataaggggga gtatcatgtc ttttatcaac atcatccgta tgatgagaat       180 tggggggccga tgcattgggg ccatttgaag agcaaggatc ttattcactg ggagcacttg       240
ccggttgctt tagcgccggg agacgaattt gatgagagcg gctgtttctc aggaagcgca       300
gtcgaatata acggcgacct cgctttaatc tatactgggc ataatatgat agatgaagag       360
aaagacgatt tctaccaaac tcagaatata gcagtcagca aagacggtat cgtctttgaa       420

```
aaactgaaag aaaaccctgt tattgcagag ccgccggaag acagcgcacg tcactttcgc    480
gatccaaaag tatggaagca tcgtgagaac tggtatatgg tggtcggaaa ctcctcaaaa    540
gagaacgtcg ggcgggtcat cttataccgc tcgcctaact ttgtagattg ggagtacgta    600
ggcgttctcg cccaaagcga cggaaatctc ggctttatgt gggaatgtcc ggatttcttt    660
gaactagacg gcaaacacat tttgctgatt tcccctcagg gtatagaggc tgatggtgaa    720
tcatatcaaa atctgtatca aacaggctat ttgattggag actatgatga agaaacgaat    780
gagtttgtac atggctcctt taaagagttg gatcacggcc acgactttta tgccgtgcaa    840
actttattgg atgacaaagg ccgcagaatt gcgattggct ggatggatat gtgggagtca    900
gagatgccga cgaaagcaga cggatggtgc ggggcattaa cttttgccgcg tgaattgacg    960
ttgaaggatg gtcacaaaat tttaatgaat cccgtcgagg agactaaatt acttcgtgga   1020
tcggaacatc atgagtgtga caatcaatcg atttccggca gctatttat aaagacagcc   1080
gaaaagcttc ttgaagtggt ggccgttttt gatttgacaa tttgcagtgc cgaaacggtt   1140
ggcttaaaga tccggggaat tgaacaggaa gaaacaacca tcaagtacag cttgattgat   1200
caaaagctga cgctcgactg ttcaaagtcc ggcaaagcga gggacggtgt gagaaacgta   1260
cggcttgaag cggatgagaa gctcactttg catctgtttc tcgacagatc gtctattgaa   1320
gtatttgcaa atcatggtga agcgacaatg acaagccgca tatatccgaa ggaaggaaga   1380
gcggggattg agctgttttc tgagaaaggc aacgtacggg ttgaagaatt cacttactgg   1440
acgttgaaag atatttggaa aggtgatgaa gccaaatga                          1479
```

<210> SEQ ID NO 136
<211> LENGTH: 492
<212> TYPE: PRT
<213> ORGANISM: Bacillus licheniformis

<400> SEQUENCE: 136

```
Met Asn Arg Ile Gln Gln Ala Glu Glu Ala Leu Lys Lys Ala Gly Lys
1               5                   10                  15

Lys Val Asn Arg Arg Tyr Arg Met Gly Tyr His Met Met Pro Arg Ala
            20                  25                  30

Asn Trp Ile Asn Asp Pro Asn Gly Leu Ile Gln Tyr Lys Gly Glu Tyr
        35                  40                  45

His Val Phe Tyr Gln His Pro Tyr Asp Glu Asn Trp Gly Pro Met
    50                  55                  60

His Trp Gly His Leu Lys Ser Lys Asp Leu Ile His Trp Glu His Leu
65                  70                  75                  80

Pro Val Ala Leu Ala Pro Gly Asp Glu Phe Asp Glu Ser Gly Cys Phe
                85                  90                  95

Ser Gly Ser Ala Val Glu Tyr Asn Gly Asp Leu Ala Leu Ile Tyr Thr
            100                 105                 110

Gly His Asn Met Ile Asp Glu Glu Lys Asp Asp Phe Tyr Gln Thr Gln
        115                 120                 125

Asn Ile Ala Val Ser Lys Asp Gly Ile Val Phe Glu Lys Leu Lys Glu
    130                 135                 140

Asn Pro Val Ile Ala Glu Pro Pro Glu Asp Ser Ala Arg His Phe Arg
145                 150                 155                 160

Asp Pro Lys Val Trp Lys His Arg Glu Asn Trp Tyr Met Val Val Gly
                165                 170                 175

Asn Ser Ser Lys Glu Asn Val Gly Arg Val Ile Leu Tyr Arg Ser Pro
            180                 185                 190
```

-continued

```
Asn Phe Val Asp Trp Glu Tyr Val Gly Val Leu Ala Gln Ser Asp Gly
        195                 200                 205

Asn Leu Gly Phe Met Trp Glu Cys Pro Asp Phe Phe Glu Leu Asp Gly
        210                 215                 220

Lys His Ile Leu Leu Ile Ser Pro Gln Gly Ile Glu Ala Asp Gly Glu
225                 230                 235                 240

Ser Tyr Gln Asn Leu Tyr Gln Thr Gly Tyr Leu Ile Gly Asp Tyr Asp
                245                 250                 255

Glu Glu Thr Asn Glu Phe Val His Gly Ser Phe Lys Glu Leu Asp His
                260                 265                 270

Gly His Asp Phe Tyr Ala Val Gln Thr Leu Leu Asp Asp Lys Gly Arg
            275                 280                 285

Arg Ile Ala Ile Gly Trp Met Asp Met Trp Glu Ser Glu Met Pro Thr
        290                 295                 300

Lys Ala Asp Gly Trp Cys Gly Ala Leu Thr Leu Pro Arg Glu Leu Thr
305                 310                 315                 320

Leu Lys Asp Gly His Lys Ile Leu Met Asn Pro Val Glu Glu Thr Lys
                325                 330                 335

Leu Leu Arg Gly Ser Glu His His Glu Cys Asp Asn Gln Ser Ile Ser
                340                 345                 350

Gly Ser Tyr Phe Ile Lys Thr Ala Glu Lys Leu Leu Glu Val Val Ala
                355                 360                 365

Val Phe Asp Leu Thr Ile Cys Ser Ala Glu Thr Val Gly Leu Lys Ile
        370                 375                 380

Arg Gly Ile Glu Gln Glu Thr Thr Ile Lys Tyr Ser Leu Ile Asp
385                 390                 395                 400

Gln Lys Leu Thr Leu Asp Cys Ser Lys Ser Gly Lys Ala Arg Asp Gly
                405                 410                 415

Val Arg Asn Val Arg Leu Glu Ala Asp Glu Lys Leu Thr Leu His Leu
                420                 425                 430

Phe Leu Asp Arg Ser Ser Ile Glu Val Phe Ala Asn His Gly Glu Ala
            435                 440                 445

Thr Met Thr Ser Arg Ile Tyr Pro Lys Glu Gly Arg Ala Gly Ile Glu
        450                 455                 460

Leu Phe Ser Glu Lys Gly Asn Val Arg Val Glu Glu Phe Thr Tyr Trp
465                 470                 475                 480

Thr Leu Lys Asp Ile Trp Lys Gly Asp Glu Ala Lys
                485                 490
```

US 8,686,114 B2

VARIANT SUCROSE TRANSPORTER POLYPEPTIDES

FIELD OF THE INVENTION

The invention relates to the fields of microbiology and molecular biology. More specifically, variant sucrose transporter polypeptides that enable bacterial growth over a wide range of gene expression levels and sucrose concentrations, recombinant bacteria comprising these variant sucrose transporter polypeptides, and methods of utilizing such bacteria to produce products such as glycerol and glycerol-derived products are provided.

BACKGROUND OF THE INVENTION

Many commercially useful microorganisms use glucose as their main carbohydrate source. However, a disadvantage of the use of glucose by microorganisms developed for production of commercially desirable products is the high cost of glucose. The use of sucrose and mixed feedstocks containing sucrose and other sugars as carbohydrate sources for microbial production systems would be more commercially desirable because these materials are usually readily available at a lower cost.

A production microorganism can function more efficiently when it can utilize any sucrose present in a mixed feedstock. Therefore, when a production microorganism does not have the ability to utilize sucrose efficiently as a major carbon source, it cannot operate as efficiently. For example, bacterial cells typically show preferential sugar use, with glucose being the most preferred. In artificial media containing mixtures of sugars, glucose is typically metabolized to its entirety ahead of other sugars. Moreover, many bacteria lack the ability to utilize sucrose. For example, less than 50% of *Escherichia coli* (*E. coli*) strains have the ability to utilize sucrose. Thus, when a production microorganism cannot utilize sucrose as a carbohydrate source, it is desirable to engineer the microorganism so that it can utilize sucrose.

Recombinant bacteria that have been engineered to utilize sucrose by incorporation of sucrose utilization genes have been reported. For example, Livshits et al. (U.S. Pat. No. 6,960,455) describe the production of amino acids using *Escherichia coli* strains containing genes encoding a metabolic pathway for sucrose utilization. Additionally, Olson et al. (*Appl. Microbiol. Biotechnol.* 74:1031-1040, 2007) describe *Escherichia coli* strains carrying genes responsible for sucrose to degradation, which produce L-tyrosine or L-phenylalanine using sucrose as a carbon source. Eliot et al. (U.S. Patent Application No. 2011/0136190 A1) describe recombinant bacteria that produce glycerol and glycerol-derived products from sucrose.

However, problems remain in engineering production microorganisms so that they can utilize sucrose effectively. Specifically, high levels of expression of sucrose transport genes result in poor growth on sucrose because excess sucrose transport is inhibitory. On the other hand, low levels of sucrose transport also result in sub-optimal growth on sucrose. Therefore, it is difficult to obtain the proper sucrose transporter gene expression level. Additionally, expression of sucrose transport genes under conditions at which sucrose transport is in excess, such as at high sucrose concentrations, may inhibit growth even at gene expression levels at which growth is not inhibited at lower sucrose concentrations. Therefore, a need also exists for a sucrose transporter that can enable growth on sucrose over a broad range of sucrose concentrations.

SUMMARY OF THE INVENTION

One embodiment provides a variant sucrose transporter polypeptide having an amino acid sequence that has at least 95% identity to an amino acid sequence as set forth in SEQ ID NO:26 based on a Clustal W method of alignment and having an amino acid change from arginine to alanine or arginine to leucine at position 300, and comprising:
 (a) at least one additional amino acid change selected from the group consisting of:
  (i) glutamine to histidine at position 353;
  (ii) leucine to proline at position 61;
  (iii) phenylalanine to leucine at position 159;
  (iv) glycine to cysteine at position 162;
  (v) proline to histidine at position 169;
  (vi) leucine to tryptophan at position 61;
  (vii) leucine to histidine at position 61;
  (viii) leucine to phenylalanine at position 61; and
  (ix) leucine to tyrosine at position 61; or
 (b) a length of 402 to 407 amino acids from the N-terminus; or
 (c) a length of 402 to 407 amino acids from the N-terminus, and having at least one of the amino acid changes of (a).

Another embodiment provides a variant sucrose transporter polypeptide having an amino acid sequence that has at least 95% identity based on a Clustal W method of alignment to an amino acid sequence selected from the group consisting of SEQ ID NOs: 68, 70, 72, 74, 76, 78, 80, 82, 84, 86, 88, 90, 92, 94, 96, and 98, and comprising an amino acid at an equivalent position when compared with a reference amino acid sequence of SEQ ID NO:26 selected from the group consisting of:
 (a) alanine at a position equivalent to position 300; and
 (b) leucine at a position equivalent to position 300.

Another embodiment provides a recombinant bacterium comprising in its genome or on at least one recombinant construct:
 (a) a nucleotide sequence encoding a variant sucrose transporter polypeptide having an amino acid sequence that has at least 95% identity based on a Clustal W method of alignment to an amino acid sequence selected from the group consisting of SEQ ID NOs:26, 68, 70, 72, 74, 76, 78, 80, 82, 84, 86, 88, 90, 92, 94, 96, and 98, and an amino acid at an equivalent position when compared with a reference amino acid sequence of SEQ ID NO:26 selected from the group consisting of:
  (i) alanine at a position equivalent to position 300; and
  (ii) leucine at a position equivalent to position 300; and
 (b) a nucleotide sequence encoding a polypeptide having sucrose hydrolase activity;
wherein (a) and (b) are each operably linked to the same or a different promoter, further wherein said recombinant bacterium is capable of metabolizing sucrose.

In one embodiment, the recombinant bacterium produces 1,3-propanediol, glycerol, and/or 3-hydroxypropionic acid.

Another embodiment provides a process for making glycerol, 1,3-propanediol and/or 3-hydroxypropionic acid from sucrose comprising:
 a) culturing the recombinant bacterium that produces 1,3-propanediol, glycerol, and/or 3-hydroxypropionic acid, disclosed herein, in the presence of sucrose; and b) optionally, recovering the glycerol, 1,3-propanediol and/or 3-hydroxypropionic acid produced.

BRIEF SEQUENCE DESCRIPTIONS

The following sequences conform with 37 C.F.R. 1.821 1.825 ("Requirements for Patent Applications Containing Nucleotide Sequences and/or Amino Acid Sequence Disclosures—the Sequence Rules") and consistent with World Intellectual Property Organization (WIPO) Standard ST.25 (2009) and the sequence listing requirements of the EPO and PCT (Rules 5.2 and 49.5(a bis), and Section 208 and Annex C of the Administrative Instructions). The symbols and format used for nucleotide and amino acid sequence data comply with the rules set forth in 37 C.F.R. §1.822.

TABLE 1

Summary of Gene and Protein SEQ ID Numbers

| Gene | Coding Sequence SEQ ID NO: | Encoded Protein SEQ ID NO: |
| --- | --- | --- |
| GPD1 from *Saccharomyces cerevisiae* | 1 | 2 |
| GPD2 from *Saccharomyces cerevisiae* | 3 | 4 |
| GPP1 from *Saccharomyces cerevisiae* | 5 | 6 |
| GPP2 from *Saccharomyces cerevisiae* | 7 | 8 |
| dhaB1 from *Klebsiella pneumoniae* | 9 | 10 |
| dhaB2 from *Klebsiella pneumoniae* | 11 | 12 |
| dhaB3 from *Klebsiella pneumoniae* | 13 | 14 |
| aldB from *Escherichia coli* | 15 | 16 |
| aldA from *Escherichia coli* | 17 | 18 |
| aldH from *Escherichia coli* | 19 | 20 |
| galP from *Escherichia coli* | 21 | 22 |
| cscB from *Escherichia coli* EC3132 | 23 | 24 |
| cscB from *Escherichia coli* ATCC ® 13281 | 25 | 26 |
| cscA from *Escherichia coli* EC3132 | 27 | 28 |
| cscA from *Escherichia coli* ATCC13281 | 29 | 30 |
| bfrA from *Bifidobacterium lactis* strain DSM 10140$^T$ | 31 | 32 |
| SUC2 from *Saccharomyces cerevisiae* | 33 | 34 |
| scrB from *Corynebacterium glutamicum* | 35 | 36 |
| sucrose phosphorylase gene from *Leuconostoc mesenteroides* DSM 20193 | 37 | 38 |
| sucP *Bifidobacterium adolescentis* DSM 20083 | 39 | 40 |
| scrK from *Agrobacterium tumefaciens* | 41 | 42 |
| scrK from *Streptococcus mutans* | 43 | 44 |
| scrK From *Escherichia coli* | 45 | 46 |
| scrK from *Klebsiella pneumoniae* | 47 | 48 |
| cscK from *Escherichia coli* | 49 | 50 |
| cscK from *Enterococcus faecalis* | 51 | 52 |
| HXK1 from *Saccharomyces cerevisiae* | 53 | 54 |
| HXK2 from *Saccharomyces cerevisiae* | 55 | 56 |
| dhaT from *Klebsiella pneumoniae* | 57 | 58 |
| dhaX from *Klebsiella pneumoniae* | 59 | 60 |
| scrT1 from *Citrobacter* sp | 67 | 68 |
| scrT3 from *Enterococcus faecium* | 69 | 70 |
| scrT4 from *Corynebacterium glucuronolyticum* | 71 | 72 |
| scrT5 from *Bifidobacterium animalis* subsp. *lactis* | 73 | 74 |
| scrT6 from *Bifidobacterium gallicum* | 75 | 76 |
| scrT7 from *Bifidobacterium longum* | 77 | 78 |
| scrT8 from *Bifidobacterium adolescentis* | 79 | 80 |
| scrT9 from *Bifidobacterium longum* | 81 | 82 |
| scrT12 from *Mitsuokella multacida* | 83 | 84 |
| scrT13 from *Lactobacillus antri* | 85 | 86 |
| scrT14 from *Lactobacillus ruminis* | 87 | 88 |
| scrT21 from *Yersinia frederiksenii* | 89 | 90 |
| scrT25 from *Serratia proteamaculans* | 91 | 92 |
| scrT26 from *Escherichia coli* | 93 | 94 |
| fruP from *Bacillus licheniformis* 14580 | 95 | 96 |
| lacY from *Pseudomonas fluorescens* Pf5 | 97 | 98 |
| cscB from *Escherichia coli* ATCC ® 13281 with R300A mutation | 99 | 100 |

TABLE 1-continued

Summary of Gene and Protein SEQ ID Numbers

| Gene | Coding Sequence SEQ ID NO: | Encoded Protein SEQ ID NO: |
| --- | --- | --- |
| cscB from *Escherichia coli* ATCC ® 13281 with R300L mutation | 101 | 102 |
| cscB from *Escherichia coli* ATCC ® 13281 with R300A and Q353H mutations | 103 | 104 |
| cscB from *Escherichia coli* ATCC ® 13281 with R300A, Q353H, L61P mutations | 105 | 106 |
| scrT1 from *Citrobacter* sp with R305A mutation | 107 | 108 |
| scrT1 from *Citrobacter* sp with R305L mutation | 109 | 110 |
| scrT7 from *Bifidobacterium longum* with R312A mutation | 111 | 112 |
| scrB from *Pseudomonas fluorescens* Pf5 | 133 | 134 |
| fruA from *Bacillus licheniformis* 14580 | 135 | 136 |

SEQ ID NO:61 is the nucleotide sequence of the cscAKB gene cluster from *Escherichia coli* ATCC®13281.

SEQ ID NO:62 is the nucleotide sequence of plasmid pSYCO101.

SEQ ID NO:63 is the nucleotide sequence of plasmid pSYCO103.

SEQ ID NO:64 is the nucleotide sequence of plasmid pSYCO106.

SEQ ID NO:65 is the nucleotide sequence of plasmid pSYCO109.

SEQ ID NO:66 is the nucleotide sequence of plasmid pSYCO400/AGRO.

SEQ ID NO:113 is the nucleotide sequence of plasmid pDMWP1.

SEQ ID NO:114 is the nucleotide sequence of plasmid pDMWP3.

SEQ ID NO:119 is the nucleotide sequence of plasmid pBHR-cscBKA.

SEQ ID NO:124 is the nucleotide sequence of the promoter/MCS/double terminator insert described in Examples 22-24.

SEQ ID NO:125 is the codon optimized nucleotide sequence of the coding region of scrT1 for expression in *E. coli*.

SEQ ID NO:130 is the codon optimized nucleotide sequence of the coding region of scrT7 for expression in *E. coli*.

SEQ ID NOs:115-118, 120-123, 126-129 and 131-132 are the nucleotide sequences of primers used in the Examples herein.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a cell" includes one or more cells and equivalents thereof known to those skilled in the art, and so forth.

In the context of this disclosure, a number of terms and abbreviations are used. The following definitions are provided.

"Open reading frame" is abbreviated as "ORF".

"Polymerase chain reaction" is abbreviated as "PCR".

"American Type Culture Collection" is abbreviated as "ATCC".

The term "recombinant glycerol-producing bacterium" refers to a bacterium that has been genetically engineered to be capable of producing glycerol and/or glycerol-derived products.

The term "polypeptide having sucrose transporter activity" refers to a polypeptide that is capable of mediating the transport of sucrose into microbial cells.

The term "polypeptide having fructokinase activity" refers to a polypeptide that has the ability to catalyze the conversion of D-fructose+ATP to fructose-phosphate+ADP. Typical of fructokinase is EC 2.7.1.4. Enzymes that have some ability to phosphorylate fructose, whether or not this activity is their predominant activity, may be referred to as a fructokinase. Abbreviations used for genes encoding fructokinases and proteins having fructokinase activity include, for example, "Frk", "scrK", "cscK", "FK", and "KHK". Fructokinase is encoded by the scrK gene in *Agrobacterium tumefaciens* and *Streptococcus mutans*; and by the cscK gene in certain *Escherichia coli* strains.

The term "polypeptide having sucrose hydrolase activity" refers to a polypeptide that has the ability to catalyze the hydrolysis of sucrose to produce glucose and fructose. Such polypeptides are often referred to as "invertases" or "β-fructofuranosidases".

The terms "glycerol derivative" and "glycerol-derived products" are used interchangeably herein and refer to a compound that is synthesized from glycerol or in a pathway that includes glycerol. Examples of such products include 3-hydroxypropionic acid, methylglyoxal, 1,2-propanediol, and 1,3-propanediol.

The term "microbial product" refers to a product that is microbially produced, i.e., the result of a microorganism metabolizing a substance. The product may be naturally produced by the microorganism, or the microorganism may be genetically engineered to produce the product.

The terms "phosphoenolpyruvate-sugar phosphotransferase system", "PTS system", and "PTS" are used interchangeably herein and refer to the phosphoenolpyruvate-dependent sugar uptake system.

The terms "phosphocarrier protein HPr" and "PtsH" refer to the phosphocarrier protein encoded by ptsH in *E. coli*. The terms "phosphoenolpyruvate-protein phosphotransferase" and "PtsI" refer to the phosphotransferase, EC 2.7.3.9, encoded by ptsI in *E. coli*. The terms "glucose-specific IIA component", and "Crr" refer to enzymes designated as EC 2.7.1.69, encoded by crr in *E. coli*. PtsH, PtsI, and Crr comprise the PTS system.

The term "PTS minus" refers to a microorganism that does not contain a PTS system in its native state or a microorganism in which the PTS system has been inactivated through the inactivation of a PTS gene.

The terms "glycerol-3-phosphate dehydrogenase" and "G3PDH" refer to a polypeptide responsible for an enzyme activity that catalyzes the conversion of dihydroxyacetone phosphate (DHAP) to glycerol 3-phosphate (G3P). In vivo G3PDH may be NAD- or NADP-dependent. When specifically referring to a cofactor specific glycerol-3-phosphate dehydrogenase, the terms "NAD-dependent glycerol-3-phosphate dehydrogenase" and "NADP-dependent glycerol-3-phosphate dehydrogenase" will be used. As it is generally the case that NAD-dependent and NADP-dependent glycerol-3-phosphate dehydrogenases are able to use NAD and NADP interchangeably (for example by the enzyme encoded by gpsA), the terms NAD-dependent and NADP-dependent glycerol-3-phosphate dehydrogenase will be used interchangeably. The NAD-dependent enzyme (EC 1.1.1.8) is encoded, for example, by several genes including GPD1, also referred to herein as DAR1 (coding sequence set forth in SEQ ID NO:1; encoded protein sequence set forth in SEQ ID NO:2), or GPD2 (coding sequence set forth in SEQ ID NO:3; encoded protein sequence set forth in SEQ ID NO:4), or GPD3. The NADP-dependent enzyme (EC 1.1.1.94) is encoded, for example, by gpsA.

The terms "glycerol 3-phosphatase", "sn-glycerol 3-phosphatase", "D,L-glycerol phosphatase", and "G3P phosphatase" refer to a polypeptide having an enzymatic activity that is capable of catalyzing the conversion of glycerol 3-phosphate and water to glycerol and inorganic phosphate. G3P phosphatase is encoded, for example, by GPP1 (coding sequence set forth in SEQ ID NO:5; encoded protein sequence set forth in SEQ ID NO:6), or GPP2 (coding sequence set forth in SEQ ID NO:7; encoded protein sequence set forth in SEQ ID NO:8).

The term "glycerol dehydratase" or "dehydratase enzyme" refers to a polypeptide having enzyme activity that is capable of catalyzing the conversion of a glycerol molecule to the product, 3-hydroxypropionaldehyde (3-HPA).

For the purposes of the present invention the dehydratase enzymes include a glycerol dehydratase (E.C. 4.2.1.30) and a diol dehydratase (E.C. 4.2.1.28) having preferred substrates of glycerol and 1,2-propanediol, respectively. Genes for dehydratase enzymes have been identified in *Klebsiella pneumoniae, Citrobacter freundii, Clostridium pasteurianum, Salmonella typhimurium, Klebsiella oxytoca*, and *Lactobacillus reuteri*, among others. In each case, the dehydratase is composed of three subunits: the large or "α" subunit, the medium or "β" subunit, and the small or "γ" subunit. The genes are also described in, for example, Daniel et al. (*FEMS Microbiol. Rev.* 22, 553 (1999)) and Toraya and Mori (*J. Biol. Chem.* 274, 3372 (1999)). Genes encoding the large or "α" (alpha) subunit of glycerol dehydratase include dhaB1 (coding sequence set forth in SEQ ID NO:9, encoded protein sequence set forth in SEQ ID NO:10), gldA and dhaB; genes encoding the medium or "n" (beta) subunit include dhaB2 (coding sequence set forth in SEQ ID NO:11, encoded protein sequence set forth in SEQ ID NO:12), gldB, and dhaC; genes encoding the small or "γ" (gamma) subunit include dhaB3 (coding sequence set forth in SEQ ID NO:13, encoded protein sequence set forth in SEQ ID NO:14), gldC, and dhaE. Other genes encoding the large or "α" subunit of diol dehydratase include pduC and pddA; other genes encoding the medium or "β" subunit include pduD and pddB; and other genes encoding the small or "γ" subunit include pduE and pddC.

Glycerol and diol dehydratases are subject to mechanism-based suicide inactivation by glycerol and some other substrates (Daniel et al., *FEMS Microbiol. Rev.* 22, 553 (1999)). The term "dehydratase reactivation factor" refers to those proteins responsible for reactivating the dehydratase activity. The terms "dehydratase reactivating activity", "reactivating the dehydratase activity" and "regenerating the dehydratase activity" are used interchangeably and refer to the phenomenon of converting a dehydratase not capable of catalysis of a reaction to one capable of catalysis of a reaction or to the phenomenon of inhibiting the inactivation of a dehydratase or the phenomenon of extending the useful half-life of the dehydratase enzyme in vivo. Two proteins have been identified as being involved as the dehydratase reactivation factor (see, e.g., U.S. Pat. No. 6,013,494 and references therein; Daniel et al., supra; Toraya and Mori, *J. Biol. Chem.* 274, 3372 (1999); and Tobimatsu et al., *J. Bacteriol.* 181, 4110 (1999)). Genes encoding one of the proteins include, for example, orfZ, dhaB4, gdrA, pduG and ddrA. Genes encoding the second of the two proteins include, for example, orfX, orf2b, gdrB, pduH and ddrB.

The terms "1,3-propanediol oxidoreductase", "1,3-propanediol dehydrogenase" and "DhaT" are used interchangeably herein and refer to the polypeptide(s) having an enzymatic activity that is capable of catalyzing the interconversion of 3-HPA and 1,3-propanediol provided the gene(s) encoding such activity is found to be physically or transcriptionally linked to a dehydratase enzyme in its natural (i.e., wild type) setting; for example, the gene is found within a dha regulon as is the case with dhaT from *Klebsiella pneumoniae*. Genes encoding a 1,3-propanediol oxidoreductase include, but are not limited to, dhaT from *Klebsiella pneumoniae*, *Citrobacter freundii*, and *Clostridium pasteurianum*. Each of these genes encode a polypeptide belonging to the family of type III alcohol dehydrogenases, which exhibits a conserved iron-binding motif, and has a preference for the NAD$^+$/NADH linked interconversion of 3-HPA and 1,3-propanediol (Johnson and Lin, *J. Bacteriol*. 169, 2050 (1987); Daniel et al., *J. Bacteriol*. 177, 2151 (1995); and Leurs et al., *FEMS Microbiol. Lett*. 154, 337 (1997)). Enzymes with similar physical properties have been isolated from *Lactobacillus brevis* and *Lactobacillus buchneri* (Veiga da Dunha and Foster, *Appl. Environ. Microbiol*. 58, 2005 (1992)).

The term "dha regulon" refers to a set of associated polynucleotides or open reading frames encoding polypeptides having various biological activities, including but not limited to a dehydratase activity, a reactivation activity, and a 1,3-propanediol oxidoreductase. Typically a dha regulon comprises the open reading frames dhaR, orfY, dhaT, orfX, orfW, dhaB1, dhaB2, dhaB3, and orfZ as described in U.S. Pat. No. 7,371,558.

The terms "aldehyde dehydrogenase" and "Ald" refer to a polypeptide that catalyzes the conversion of an aldehyde to a carboxylic acid. Aldehyde dehydrogenases may use a redox cofactor such as NAD, NADP, FAD, or PQQ. Typical of aldehyde dehydrogenases is EC 1.2, 1.3 (NAD-dependent); EC 1.2.1.4 (NADP-dependent); EC 1.2.99.3 (PQQ-dependent); or EC 1.2.99.7 (FAD-dependent). An example of an NADP-dependent aldehyde dehydrogenase is AldB (SEQ ID NO:16), encoded by the *E. coli* gene aldB (coding sequence set forth in SEQ ID NO:15). Examples of NAD-dependent aldehyde dehydrogenases include AldA (SEQ ID NO:18), encoded by the *E. coli* gene aldA (coding sequence set forth in SEQ ID NO:17); and AldH (SEQ ID NO:20), encoded by the *E. coli* gene aldH (coding sequence set forth in SEQ ID NO:19).

The terms "glucokinase" and "Glk" are used interchangeably herein and refer to a protein that catalyzes the conversion of D-glucose+ATP to glucose 6-phosphate+ADP. Typical of glucokinase is EC 2.7.1.2. Glucokinase is encoded by glk in *E. coli*.

The terms "phosphoenolpyruvate carboxylase" and "Ppc" are used interchangeably herein and refer to a protein that catalyzes the conversion of phosphoenolpyruvate+$H_2O$+$CO_2$ to phosphate+oxaloacetic acid. Typical of phosphoenolpyruvate carboxylase is EC 4.1.1.31. Phosphoenolpyruvate carboxylase is encoded by ppc in *E. coli*.

The terms "glyceraldehyde-3-phosphate dehydrogenase" and "GapA" are used interchangeably herein and refer to a protein having an enzymatic activity capable of catalyzing the conversion of glyceraldehyde 3-phosphate+phosphate+NAD$^+$ to 3-phospho-D-glyceroyl-phosphate+NADH+H. Typical of glyceraldehyde-3-phosphate dehydrogenase is EC 1.2, 1.12. Glyceraldehyde-3-phosphate dehydrogenase is encoded by gapA in *E. coli*.

The terms "aerobic respiration control protein" and "ArcA" are used interchangeably herein and refer to a global regulatory protein. The aerobic respiration control protein is encoded by arcA in *E. coli*.

The terms "methylglyoxal synthase" and "MgsA" are used interchangeably herein and refer to a protein having an enzymatic activity capable of catalyzing the conversion of dihydroxyacetone phosphate to methylglyoxal+phosphate. Typical of methylglyoxal synthase is EC 4.2.3.3. Methylglyoxal synthase is encoded by mgsA in *E. coli*.

The terms "phosphogluconate dehydratase" and "Edd" are used interchangeably herein and refer to a protein having an enzymatic activity capable of catalyzing the conversion of 6-phospho-gluconate to 2-keto-3-deoxy-6-phospho-gluconate+$H_2O$. Typical of phosphogluconate dehydratase is EC 4.2.1.12. Phosphogluconate dehydratase is encoded by edd in *E. coli*.

The term "YciK" refers to a putative enzyme encoded by yciK which is translationally coupled to btuR, the gene encoding Cob(I)alamin adenosyltransferase in *E. coli*.

The term "cob(I)alamin adenosyltransferase" refers to an enzyme capable of transferring a deoxyadenosyl moiety from ATP to the reduced corrinoid. Typical of cob(I)alamin adenosyltransferase is EC 2.5.1.17. Cob(I)alamin adenosyltransferase is encoded by the gene "btuR" in *E. coli*, "cobA" in *Salmonella typhimurium*, and "cobO" in *Pseudomonas denitrificans*.

The terms "galactose-proton symporter" and "GalP" are used interchangeably herein and refer to a protein having an enzymatic activity capable of transporting a sugar and a proton from the periplasm to the cytoplasm. D-glucose is a preferred substrate for GalP. Galactose-proton symporter is encoded by galP in *Escherichia coli* (coding sequence set forth in SEQ ID NO:21, encoded protein sequence set forth in SEQ ID NO:22).

The term "non-specific catalytic activity" refers to the polypeptide(s) having an enzymatic activity capable of catalyzing the interconversion of 3-HPA and 1,3-propanediol and specifically excludes 1,3-propanediol oxidoreductase(s). Typically these enzymes are alcohol dehydrogenases. Such enzymes may utilize cofactors other than NAD$^+$/NADH, including but not limited to flavins such as FAD or FMN. A gene for a non-specific alcohol dehydrogenase (yqhD) is found, for example, to be endogenously encoded and functionally expressed within *E. coli* K-12 strains.

The terms "1.6 long GI promoter", "1.20 short/long GI Promoter", "1.5 long GI promoter", "P1.6", "P1.5" and "P1.20" refer to polynucleotides or fragments containing a promoter from the *Streptomyces lividans* glucose isomerase gene as described in U.S. Pat. No. 7,132,527. These promoter fragments include a mutation which decreases their activities as compared to the wild type *Streptomyces lividans* glucose isomerase gene promoter.

The terms "function" and "enzyme function" are used interchangeably herein and refer to the catalytic activity of an enzyme in altering the rate at which a specific chemical reaction occurs without itself being consumed by the reaction. It is understood that such an activity may apply to a reaction in equilibrium where the production of either product or substrate may be accomplished under suitable conditions.

The terms "polypeptide" and "protein" are used interchangeably herein.

The terms "carbon substrate" and "carbon source" are used interchangeably herein and refer to a carbon source capable of being metabolized by the recombinant bacteria disclosed herein and, particularly, carbon sources comprising sucrose. The carbon source may further comprise other monosaccharides, disaccharides, oligosaccharides; or polysaccharides.

The terms "host cell" and "host bacterium" are used interchangeably herein and refer to a bacterium capable of receiving foreign or heterologous genes and capable of expressing those genes to produce an active gene product.

The term "production microorganism" as used herein refers to a microorganism, including, but not limited to, those that are recombinant, used to make a specific product such as 1,3-propanediol, glycerol, 3-hydroxypropionic acid, polyunsaturated fatty acids, and the like.

As used herein, "nucleic acid" means a polynucleotide and includes a single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably herein and refer to a polymer of RNA or DNA that is single- or double-stranded, optionally containing synthetic, non-natural to or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise genes inserted into a non-native organism, genes introduced into a new location within the native host, or chimeric genes.

The term "native nucleotide sequence" refers to a nucleotide sequence that is normally found in the host microorganism.

The term "non-native nucleotide sequence" refers to a nucleotide sequence that is not normally found in the host microorganism.

The term "native polypeptide" refers to a polypeptide that is normally found in the host microorganism.

The term "non-native polypeptide" refers to a polypeptide that is not normally found in the host microorganism.

The terms "encoding" and "coding" are used interchangeably herein and refer to the process by which a gene, through the mechanisms of transcription and translation, produces an amino acid sequence.

The term "coding sequence" refers to a nucleotide sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., ORF) and, 3) a 3' untranslated region (e.g., a terminator) that, in eukaryotes, usually contains a polyadenylation site. The expression cassette(s) is usually included within a vector, to facilitate cloning and transformation.

Different organisms, including bacteria, yeast, and fungi, can be transformed with different expression cassettes as long as the correct regulatory sequences are used for each host.

"Transformation" refers to the transfer of a nucleic acid molecule into a host organism, resulting in genetically stable inheritance. The nucleic acid molecule may be a plasmid that replicates autonomously, for example, or it may integrate into the genome of the host organism. Host organisms transformed with the nucleic acid fragments are referred to as "recombinant" or "transformed" organisms or "transformants". "Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. Chimeric genes can be designed for use in suppression by linking a nucleic acid fragment or subfragment thereof, whether or not it encodes an active enzyme, in the sense or antisense orientation relative to a promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein.

The terms "substantially similar" and "corresponds substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. Moreover, the skilled artisan recognizes that substantially similar nucleic acid sequences encompassed by this invention are also defined by their ability to hybridize (under moderately stringent conditions, e.g., 0.5×SSC (standard sodium citrate), 0.1% SDS (sodium dodecyl sulfate), 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences are two nucleotide sequences wherein the complement of one of the nucleotide sequences typically has about at least 80% sequence identity, or 90% sequence identity, up to and including 100% sequence identity (i.e., fully complementary) to the other nucleotide sequence.

The term "stringent conditions" or "stringent hybridization conditions" includes reference to conditions under which a probe will selectively hybridize to its target sequence. Probes are typically single stranded nucleic acid sequences which are complementary to the nucleic acid sequences to be detected. Probes are "hybridizable" to the nucleic acid sequence to be detected. Generally, a probe is less than about 1000 nucleotides in length, optionally less than 500 nucleotides in length.

Hybridization methods are well defined. Typically the probe and sample are mixed under conditions which will permit nucleic acid hybridization. This involves contacting the probe and sample in the presence of an inorganic or organic salt under the proper concentration and temperature conditions. Optionally a chaotropic agent may be added. Nucleic acid hybridization is adaptable to a variety of assay formats. One of the most suitable is the sandwich assay format. A primary component of a sandwich-type assay is a solid support. The solid support has adsorbed to it or covalently coupled to it an immobilized nucleic acid probe that is unlabeled and complementary to one portion of the sequence.

Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of to destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the thermal melting point ($T_m$) can be approximated from the equation of Meinkoth et al., *Anal. Biochem.* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS.* 5:151-153 (1989); Higgins, D. G. et al., *Comput. Appl. Biosci.* 8:189-191 (1992)) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, supra; Higgins, D. G. et al., supra) and found in the MegAlign™ v6.1 program of the LASERGENE bioinformatics computing suite (DNASTAR Inc., Madison, Wis.). Default parameters for multiple alignment correspond to GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB. After alignment of the sequences using the Clustal W program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters. The "BLASTP method of alignment" is an algorithm provided by the NCBI to compare protein sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Thus, the invention encompasses more than the specific exemplary nucleotide sequences disclosed herein. For example, alterations in the gene sequence which reflect the degeneracy of the genetic code are contemplated. Also, it is well known in the art that alterations in a gene which result in the production of a chemically equivalent amino acid at a given site, but do not affect the functional properties of the encoded protein are common. Substitutions are defined for the discussion herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may is be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize under stringent conditions, as defined above.

Preferred substantially similar nucleic acid fragments of the instant invention are those nucleic acid fragments whose nucleotide sequences are at least 70% identical to the nucleotide sequence of the nucleic acid fragments reported herein. More preferred nucleic acid fragments are at least 90% identical to the nucleotide sequence of the nucleic acid fragments reported herein. Most preferred are nucleic acid fragments that are at least 95% identical to the nucleotide sequence of the nucleic acid fragments reported herein.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.,* 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art.

The term "complementary" describes the relationship between two sequences of nucleotide bases that are capable of Watson-Crick base-pairing when aligned in an anti-parallel orientation. For example, with respect to DNA, adenosine is capable of base-pairing with thymine and cytosine is capable of base-pairing with guanine. Accordingly, the instant invention may make use of isolated nucleic acid molecules that are complementary to the complete sequences as reported in the accompanying Sequence Listing and the specification as well as those substantially similar nucleic acid sequences.

The term "isolated" refers to a polypeptide or nucleotide sequence that is removed from at least one component with which it is naturally associated.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

"3' non-coding sequences", "transcription terminator" and "termination sequences" are used interchangeably herein and refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used is herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

A "plasmid" or "vector" is an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "genetically altered" refers to the process of changing hereditary material by genetic engineering, transformation and/or mutation.

The term "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation, natural transduction, natural transposition) such as those occurring without deliberate human intervention.

The terms "recombinant construct", "expression construct", "chimeric construct", "construct", and "recombinant DNA construct", are used interchangeably herein. A recombinant construct comprises an artificial combination of nucleic acid fragments, e.g., regulatory and coding sequences that are not found together in nature. For example, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events may result in different levels and patterns of expression (Jones et al., *EMBO J.* 4:2411-2418 (1985); De Almeida et al., *Mol. Gen. Genetics* 218:78-86 (1989)), and thus that multiple events may need be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., an mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "homologous" refers to proteins or polypeptides of common evolutionary origin with similar catalytic function. The invention may include bacteria producing homologous proteins via recombinant technology.

Disclosed herein are variant sucrose transporter polypeptides that enable bacterial growth over a wide range of gene expression levels and sucrose concentrations. Sucrose transporter polypeptides are polypeptides that are capable of mediating the transport of sucrose into microbial cells. Sucrose transporters known in the art, such as CscB from E. coli, function as H$^+$/sucrose symporters, which transport one proton for every sucrose molecule transported, thereby coupling the energy of the proton motive force to sucrose transport. Such active transport allows accumulation of sucrose against a concentration gradient. Mutations which change certain amino acids in CscB that result in polypeptides unable to catalyze active uptake of sucrose, but are able to catalyze equilibrium exchange across a membrane have been described by Vadyvaloo et al. (J. Mol. Biol. 358:1051-1059, 2006). The sucrose transporter polypeptides disclosed herein are novel variants that have lost the ability to actively transport sucrose into microbial cells against a concentration gradient, but have the ability to transport sucrose by facilitated diffusion. These variant sucrose transporter polypeptides also enable faster sucrose utilization in bacteria than the native CscB transporter polypeptide. Sucrose transport by facilitated diffusion mitigates the toxicity associated with excess sucrose uptake because sucrose will not accumulate within the cells to concentrations that are higher than extracellular levels. Therefore, microbial cells having sucrose transport by facilitated diffusion are able to grow over a wider range of sucrose concentrations than cells having active sucrose transport.

In some embodiments, the sucrose transporter polypeptides disclosed herein are variants of the wild-type sucrose transporter polypeptide CscB from E. coli ATCC®13281 (set forth in SEQ ID NO:26, nucleotide coding sequence set forth in SEQ ID NO:25). These sucrose transporter polypeptides have an amino acid change from arginine to alanine at amino acid position 300, i.e., R300A mutation, (SEQ ID NO:100, nucleotide coding sequence set forth in SEQ ID NO:99) or an amino acid change from arginine to leucine at amino acid position 300, i.e., R300L mutation, (SEQ ID NO:102, nucleotide coding sequence set forth in SEQ ID NO:101) and at least one other mutation which results in faster sucrose utilization, as described by Chen et al. (U.S. patent application Ser. No. 13/210,488, filed Aug. 16, 2011), i.e., either an amino acid change or a truncation of the amino acid sequence. Accordingly, in these embodiments, the variant sucrose transporter polypeptides have: an amino acid sequence that has at least 95% identity to an amino acid sequence as set forth in SEQ ID NO:26 based on a Clustal W method of alignment and have an amino acid change from arginine to alanine or arginine to leucine at position 300, and comprise:

(a) at least one amino acid change selected from the group consisting of:
   (i) glutamine to histidine at position 353
   (ii) leucine to proline at position 61;
   (iii) phenylalanine to leucine at position 159;
   (iv) glycine to cysteine at position 162;
   (v) proline to histidine at position 169;
   (vi) leucine to tryptophan at position 61;
   (vii) leucine to histidine at position 61;
   (viii) leucine to phenylalanine at position 61; and
   (ix) leucine to tyrosine at position 61; or
(b) a length of 402 to 407 amino acids from the N-terminus; or
(c) a length of 402 to 407 amino acids from the N-terminus, and at least one of the amino acid changes of (a).

In some embodiments, the sucrose transporter polypeptides are variants of sucrose transporter polypeptides from various sources (see Table 1), having an amino acid change to alanine or leucine at a position equivalent to amino acid position 300 when compared with a reference amino acid sequence of CscB (SEQ ID NO:26). The corresponding amino acid positions in the various sucrose transporter polypeptides, relative to the reference amino acid sequence, can be readily determined by one skilled in the art using sequence alignment algorithms, such as Clustal W, Clustal V, and BLASTP, which are described above. Accordingly, in these embodiments, the variant sucrose transporter polypeptides have an amino acid sequence that has at least 95% identity based on a Clustal W method of alignment to an amino acid sequence selected from the group consisting of SEQ ID NOs:68, 70, 72, 74, 76, 78, 80, 82, 84, 86, 88, 90, 92, 94, 96, and 98, and an amino acid at an equivalent position when compared with a reference amino acid sequence of CscB (SEQ ID NO:26) selected from the group consisting of:

(a) alanine at a position equivalent to position 300; and
(b) leucine at a position equivalent to position 300;

In some embodiments, the sucrose transporter polypeptides are variants of sucrose transporter polypeptides from various sources (see Table 1) having an amino acid change to alanine or leucine at a position equivalent to amino acid position 300 when compared with a reference amino acid sequence of CscB (SEQ ID NO:26), as described above, and further comprise:

(a) at least one of the following amino acids at an equivalent position when compared with the reference amino acid sequence of SEQ ID NO:26:
   (i) histidine at a position equivalent to position 353;
   (ii) proline at a position equivalent to position 61;
   (iii) leucine at a position equivalent to position 159;
   (iv) cysteine at a position equivalent to position 162;
   (v) histidine at a position equivalent to position 169;
   (vi) tryptophan at a position equivalent to position 61;
   (vii) histidine at a position equivalent to position 61;
   (viii) phenylalanine at a position equivalent to position 61;

(ix) tyrosine at a position equivalent to position 61; and/or
(b) truncation at a position equivalent to position 407, 406, 405, 404, 403, or 402 when compared with the reference amino acid sequence of SEQ ID NO:26.

In some embodiments, the variant sucrose transporter polypeptides have an amino acid sequence selected from the group consisting of: SEQ ID NOs:100, 102, 104, 106, 108, 110, and 112.

Also disclosed herein are bacteria comprising in their genome or on at least one recombinant construct a nucleotide sequence encoding a variant sucrose transporter polypeptide and a nucleotide sequence encoding a polypeptide having sucrose hydrolase activity. The nucleotide sequences are each operably linked to the same or a different promoter. These bacteria are able to grow over a wider range of gene expression levels and sucrose concentrations than bacteria having native sucrose transporter polypeptides which actively transport sucrose. Accordingly, in these embodiments, the recombinant bacteria comprise in their genome or on at least one recombinant construct:
 (a) a nucleotide sequence encoding a variant sucrose transporter polypeptide having an amino acid sequence that has at least 95% identity based on a Clustal W method of alignment to an amino acid sequence selected from the group consisting of SEQ ID NOs:26, 68, 70, 72, 74, 76, 78, 80, 82, 84, 86, 88, 90, 92, 94, 96, and 98, and an amino acid at an equivalent position when compared with a reference amino acid sequence of SEQ ID NO:26 selected from the group consisting of:
  (i) alanine at a position equivalent to position 300; and
  (ii) leucine at a position equivalent to position 300; and
 (b) a nucleotide sequence encoding a polypeptide having sucrose hydrolase activity;
wherein (a) and (b) are each operably linked to the same or a different promoter, further wherein the recombinant bacteria are capable of metabolizing sucrose.

In some embodiments, the recombinant bacteria comprise a variant sucrose transporter polypeptide which further comprises:
 (a) at least one of the following amino acids at an equivalent position when compared with the reference amino acid sequence of SEQ ID NO:26:
  (i) histidine at a position equivalent to position 353;
  (ii) proline at a position equivalent to position 61;
  (iii) leucine at a position equivalent to position 159;
  (iv) cysteine at a position equivalent to position 162;
  (v) histidine at a position equivalent to position 169;
  (vi) tryptophan at a position equivalent to position 61;
  (vii) histidine at a position equivalent to position 61;
  (viii) phenylalanine at a position equivalent to position 61;
  (ix) tyrosine at a position equivalent to position 61; and/or
 (b) truncation at a position equivalent to position 407, 406, 405, 404, 403, or 402 when compared with the reference amino acid sequence of SEQ ID NO:26.

Recombinant bacteria comprising a nucleotide sequence encoding a variant sucrose transporter polypeptide, as described above, and a nucleotide sequence encoding a polypeptide having sucrose hydrolase activity may be constructed by introducing the nucleotide sequences into a suitable host bacterium, either into the genome or on at least one recombinant construct, using methods known in the art, as described below. In some embodiments, the recombinant bacteria are capable of metabolizing sucrose to produce glycerol and/or glycerol-derived products.

Suitable host bacteria for use in the construction of the recombinant bacteria disclosed herein include, but are not limited to, organisms of the genera: *Escherichia, Streptococcus, Agrobacterium, Bacillus, Corynebacterium, Lactobacillus, Clostridium, Gluconobacter, Citrobacter, Enterobacter, Klebsiella, Aerobacter, Methylobacter, Salmonella, Streptomyces*, and *Pseudomonas*.

In some embodiments, the host bacterium is selected from the genera: *Escherichia, Klebsiella, Citrobacter,* and *Aerobacter*.

In some embodiments, the host bacterium is *Escherichia coli*.

In some embodiments, the host bacterium is PTS minus. In these embodiments, the host bacterium is PTS minus in its native state, or may be rendered PTS minus through inactivation of a PTS gene as described below.

In production microorganisms, it is sometimes desirable to unlink the transport of sugars and the use of phosphoenolpyruvate (PEP) for phosphorylation of the sugars being transported.

The term "down-regulated" refers to reduction in, or abolishment of, the activity of active protein(s), as compared to the activity of the wild-type protein(s). The PTS may be inactivated (resulting in a "PTS minus" organism) by down-regulating expression of one or more of the endogenous genes encoding the proteins required in this type of transport. Down-regulation typically occurs when one or more of these genes has a "disruption", referring to an insertion, deletion, or targeted mutation within a portion of that gene, that results in either a complete gene knockout such that the gene is deleted from the genome and no protein is translated or a protein has been translated such that it has an insertion, deletion, amino acid substitution or other targeted mutation. The location of the disruption in the protein may be, for example, within the N-terminal portion of the protein or within the C-terminal portion of the protein. The disrupted protein will have impaired activity with respect to the protein that was not disrupted, and can be non-functional. Down-regulation that results in low or lack of expression of the protein, could also result via manipulating the regulatory sequences, transcription and translation factors and/or signal transduction pathways or by use of sense, antisense or RNAi technology, or similar mechanisms known to skilled artisans.

The recombinant bacteria disclosed herein comprise in their genome or on at least one recombinant construct, a nucleotide sequence encoding a polypeptide having sucrose hydrolase activity. Polypeptides having sucrose hydrolase activity have the ability to catalyze the hydrolysis of sucrose to produce fructose and glucose. Polypeptides having sucrose hydrolase activity are known, and include, but are not limited to CscA from *E. coli* wild-type strain EC3132 (set forth in SEQ ID NO:28), encoded by gene cscA (coding sequence set forth in SEQ ID NO:27), CscA from *E. coli* ATCC®13281 (set forth in SEQ ID NO:30), encoded by gene cscA (coding sequence set forth in SEQ ID NO:29); BfrA from *Bifidobacterium* lactis strain DSM 10140$^T$ (set forth in SEQ ID NO:32), encoded by gene bfrA (coding sequence set forth in SEQ ID NO:31); Suc2p from *Saccharomyces cerevisiae* (set forth in SEQ ID NO:34), encoded by gene SUC2 (coding sequence set forth in SEQ ID NO:33); ScrB from *Corynebacterium glutamicum* (set forth in SEQ ID NO:36), encoded by gene scrB (coding sequence set forth in SEQ ID NO:35); ScrB from *Pseudomonas fluorescens* Pf5 (set forth in SEQ ID NO:134), encoded by gene scrB (coding sequence set forth in SEQ ID NO:133), FruP from *Bacillus licheniformis* 14580 (set forth in SEQ ID NO:136), encoded by gene fruA (coding sequence set forth in SEQ ID NO:135), sucrose phosphorylase from *Leuconostoc mesenteroides* DSM 20193 (set forth in SEQ ID NO:38), coding sequence of encoding gene set forth in SEQ ID NO:37; and sucrose phosphorylase from *Bifidobacterium* adolescentis DSM 20083 (set forth in SEQ ID NO:40), encoded by gene sucP (coding sequence set forth in SEQ ID NO:39).

In some embodiments, the polypeptide having sucrose hydrolase activity is classified as EC 3.2.1.26 or EC 2.4.1.7.

In some embodiments, the polypeptide having sucrose hydrolase activity has at least 95% sequence identity, based on the Clustal W method of alignment, to an amino acid sequence as set forth in SEQ ID NO:28, SEQ ID NO:30, SEQ ID NO:32, SEQ ID NO:34, SEQ ID NO:36, SEQ ID NO:38, SEQ ID NO:40, SEQ ID NO:134, or SEQ ID NO:136.

In some embodiments, the polypeptide having sucrose hydrolase activity corresponds substantially to the amino acid sequence set forth in SEQ ID NO:30.

The recombinant bacteria disclosed herein may further comprise in their genome or on at least one recombinant construct, a nucleotide sequence encoding a polypeptide having fructokinase activity to enable the bacteria to utilize the fructose produced by the hydrolysis of sucrose. Polypeptides having fructokinase activity include fructokinases (designated EC 2.7.1.4) and various hexose kinases having fructose phosphorylating activity (EC 2.7.1.3 and EC 2.7.1.1). Fructose phosphorylating activity may be exhibited by hexokinases and ketohexokinases. Representative genes encoding polypeptides from a variety of microorganisms, which may be used to construct the recombinant bacteria disclosed herein, are listed in Table 2. One skilled in the art will know that proteins that are substantially similar to a protein which is able to phosphorylate fructose (such as encoded by the genes listed in Table 2) may also be used.

sucrose hydrolase activity may be used to isolate nucleotide sequences encoding homologous polypeptides from the same or other microbial species. For example, homologs of the genes may be identified using sequence analysis software, such as BLASTN, to search publically available nucleic acid sequence databases. Additionally, the isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202; ligase chain reaction (LCR), Tabor, S. et al., *Proc. Acad. Sci. USA* 82, 1074, 1985); or strand displacement amplification (SDA), Walker, et al., *Proc. Natl. Acad. Sci. U.S.A.,* 89: 392, (1992)). For example, the nucleotide sequence encoding the polypeptides described above may be employed as a hybridization probe for the identification of homologs.

One of ordinary skill in the art will appreciate that genes encoding these polypeptides isolated from other sources may also be used in the recombinant bacteria disclosed herein. Additionally, variations in the nucleotide sequences encoding the polypeptides may be made without affecting the amino acid sequence of the encoded polypeptide due to codon degeneracy, and that amino acid substitutions, deletions or additions that produce a substantially similar protein may be included in the encoded protein.

The nucleotide sequences encoding the polypeptides having sucrose transporter activity and polypeptides having sucrose hydrolase activity may be isolated using PCR (see, e.g., U.S. Pat. No. 4,683,202) with primers designed to bound the desired sequence. Other methods of gene isolation are

TABLE 2

Sequences Encoding Enzymes with Fructokinase Activity

| Source | Gene Name | EC Number | Nucleotide SEQ ID NO: | Protein SEQ ID NO: |
|---|---|---|---|---|
| *Agrobacterium tumefaciens* | scrK (fructokinase) | 2.7.1.4 | 41 | 42 |
| *Streptococcus mutans* | scrK (fructokinase) | 2.7.1.4 | 43 | 44 |
| *Escherichia coli* | scrK (fructokinase | 2.7.1.4 | 45 | 46 |
| *Klebsiella pneumoniae* | scrK (fructokinase | 2.7.1.4 | 47 | 48 |
| *Escherichia coli* | cscK (fructokinase) | 2.7.1.4 | 49 | 50 |
| *Enterococcus faecalis* | cscK (fructokinase) | 2.7.1.4 | 51 | 52 |
| *Saccharomyces cerevisiae* | HXK1 (hexokinase) | 2.7.1.1 | 53 | 54 |
| *Saccharomyces cerevisiae* | HXK2 (hexokinase) | 2.7.1.1 | 55 | 56 |

In some embodiments, the polypeptide having fructokinase activity is classified as EC 2.7.1.4, EC 2.7.1.3, or EC 2.7.1.1.

In some embodiments, the polypeptide having fructokinase activity has at least 95% sequence identity, based on the Clustal W method of alignment, to an amino acid sequence as set forth in SEQ ID NO:42, SEQ ID NO:44, SEQ ID NO:46, SEQ ID NO:48, SEQ ID NO:50, SEQ ID NO:52, SEQ ID NO:54, or SEQ ID NO:56.

In some embodiments, the polypeptide having fructokinase activity has the amino acid sequence set forth in SEQ ID NO:50.

The coding sequence of the genes encoding polypeptides having sucrose transporter activity and polypeptides having well known to one skilled in the art such as by using degenerate primers or heterologous probe hybridization. The nucleotide sequences can also be chemically synthesized or purchased from vendors such as DNA2.0 Inc. (Menlo Park, Calif.), Integrated DNA Technologies (Coralville, Iowa), and GenScript USA Inc. (Piscataway, N.J.). The nucleotide sequences may be codon optimized for expression in the desired host cell.

Expression of the polypeptides may be effected using one of many methods known to one skilled in the art. For example, the nucleotide sequences encoding the polypeptides described above may be introduced into the bacterium on at least one multicopy plasmid, or by integrating one or more copies of the coding sequences into the host genome. The nucleotide sequences encoding the polypeptides may be introduced into the host bacterium separately (e.g., on separate plasmids) or in any combination (e.g., on a single plasmid).

The introduced coding regions that are either on a plasmid(s) or in the genome may be expressed from at least one highly active promoter. An integrated coding region may either be introduced as a part of a chimeric gene having its own promoter, or it may be integrated adjacent to a highly active promoter that is endogenous to the genome or in a highly expressed operon. Suitable promoters include, but are not limited to, CYC1, HIS3, GAL1, GAL10, ADH1, PGK, PHO5, GAPDH, ADC1, TRP1, URA3, LEU2, ENO, and lac, ara, tet, trp, $IP_L$, $IP_R$, T7, tac, and trc (useful for expression in *Escherichia coli*) as well as the amy, apr, npr promoters and various phage promoters useful for expression in *Bacillus*. The promoter may also be the *Streptomyces lividans* glucose isomerase promoter or a variant thereof, described by Payne et al. (U.S. Pat. No. 7,132,527).

In some embodiments, the recombinant bacteria disclosed herein are capable of producing glycerol. Biological processes for the preparation of glycerol using carbohydrates or sugars are known in yeasts and in some bacteria, other fungi, and algae. Both bacteria and yeasts produce glycerol by converting glucose or other carbohydrates through the fructose-1,6-bisphosphate pathway in glycolysis. In the method of producing glycerol disclosed herein, host bacteria may be used that naturally produce glycerol. In addition, bacteria may be engineered for production of glycerol and glycerol derivatives. The capacity for glycerol production from a variety of substrates may be provided through the expression of the enzyme activities glycerol-3-phosphate dehydrogenase (G3PDH) and/or glycerol-3-phosphatase as described in U.S. Pat. No. 7,005,291. Genes encoding these proteins that may be used for expressing the enzyme activities in a host bacterium are described in U.S. Pat. No. 7,005,291. Suitable examples of genes encoding polypeptides having glycerol-3-phosphate dehydrogenase activity include, but are not limited to, GPD1 from *Saccharomyces cerevisiae* (coding sequence set forth in SEQ ID NO:1, encoded protein sequence set forth in SEQ ID NO:2) and GPD2 from *Saccharomyces cerevisiae* (coding sequence set forth in SEQ ID NO:3, encoded protein sequence set forth in SEQ ID NO:4). Suitable examples of genes encoding polypeptides having glycerol-3-phosphatase activity include, but are not limited to, GPP1 from *Saccharomyces cerevisiae* (coding sequence set forth in SEQ ID NO:5, encoded protein sequence set forth in SEQ ID NO:6) and GPP2 from *Saccharomyces cerevisiae* (coding sequence set forth in SEQ ID NO:7, encoded protein sequence set forth in SEQ ID NO:8).

Increased production of glycerol may be attained through reducing expression of target endogenous genes. Down-regulation of endogenous genes encoding glycerol kinase and glycerol dehydrogenase activities further enhance glycerol production as described in U.S. Pat. No. 7,005,291. Increased channeling of carbon to glycerol may be accomplished by reducing the expression of the endogenous gene encoding glyceraldehyde 3-phosphate dehydrogenase, as described in U.S. Pat. No. 7,371,558. Down-regulation may be accomplished by using any method known in the art, for example, the methods described above for down-regulation of genes of the PTS system.

Glycerol provides a substrate for microbial production of useful products. Examples of such products, i.e., glycerol derivatives include, but are not limited to, 3-hydroxypropionic acid, methylglyoxal, 1,2-propanediol, and 1,3-propanediol.

In some embodiments, the recombinant bacteria disclosed herein are capable of producing 1,3-propanediol. The glycerol derivative 1,3-propanediol is a monomer having potential utility in the production of polyester fibers and the manufacture of polyurethanes and cyclic compounds. 1,3-Propanediol can be produced by a single microorganism by bioconversion of a carbon substrate other than glycerol or dihydroxyacetone, as described in U.S. Pat. No. 5,686,276. In this bioconversion, glycerol is produced from the carbon substrate, as described above. Glycerol is converted to the intermediate 3-hydroxypropionaldehyde by a dehydratase enzyme, which can be encoded by the host bacterium or can be introduced into the host by recombination. The dehydratase can be glycerol dehydratase (E.C. 4.2.1.30), diol dehydratase (E.C. 4.2.1.28) or any other enzyme able to catalyze this conversion. A suitable example of genes encoding the "α" (alpha), "β" (beta), and "γ" (gamma) subunits of a glycerol dehydratase include, but are not limited to dhaB1 (coding sequence set forth in SEQ ID NO:9), dhaB2 (coding sequence set forth in SEQ ID NO:11), and dhaB3 (coding sequence set forth in SEQ ID NO:13), respectively, from *Klebsiella pneumoniae*. The further conversion of 3-hydroxypropionaldehyde to 1,3-propandeiol can be catalyzed by 1,3-propanediol dehydrogenase (E.C. 1.1.1.202) or other alcohol dehydrogenases. A suitable example of a gene encoding a 1,3-propanediol dehydrogenase is dhaT from *Klebsiella pneumoniae* (coding sequence set forth in SEQ ID NO:57, encoded protein sequence set forth in SEQ ID NO:58).

Bacteria can be recombinantly engineered to provide more efficient production of glycerol and the glycerol derivative 1,3-propanediol. For example, U.S. Pat. No. 7,005,291 discloses transformed microorganisms and a method for production of glycerol and 1,3-propanediol with advantages derived from expressing exogenous activities of one or both of glycerol-3-phosphate dehydrogenase and glycerol-3-phosphate phosphatase while disrupting one or both of endogenous activities glycerol kinase and glycerol dehydrogenase.

U.S. Pat. No. 6,013,494 describes a process for the production of 1,3-propanediol using a single microorganism comprising exogenous glycerol-3-phosphate dehydrogenase, glycerol-3-phosphate phosphatase, dehydratase, and 1,3-propanediol oxidoreductase (e.g., dhaT). U.S. Pat. No. 6,136,576 discloses a method for the production of 1,3-propanediol comprising a recombinant microorganism further comprising a dehydratase and protein X (later identified as being a dehydratase reactivation factor peptide).

U.S. Pat. No. 6,514,733 describes an improvement to the process where a significant increase in titer (grams product per liter) is obtained by virtue of a non-specific catalytic activity (distinguished from 1,3-propanediol oxidoreductase encoded by dhaT) to convert 3-hydroxypropionaldehyde to 1,3-propanediol. Additionally, U.S. Pat. No. 7,132,527 discloses vectors and plasmids useful for the production of 1,3-propanediol.

Increased production of 1,3-propanediol may be achieved by further modifications to a host bacterium, including down-regulating expression of some target genes and up-regulating, expression of other target genes, as described in U.S. Pat. No. 7,371,558. For utilization of glucose as a carbon source in a PTS minus host, expression of glucokinase activity may be increased.

Additional genes whose increased or up-regulated expression increases 1,3-propanediol production include genes encoding:
  phosphoenolpyruvate carboxylase typically characterized as EC 4.1.1.31 cob(I)alamin adenosyltransferase, typically characterized as EC 2.5.1.17 non-specific catalytic activity that is sufficient to catalyze the interconversion of 3-HPA and 1,3-propanediol, and specifically excludes 1,3-propanediol oxidoreductase(s), typically these enzymes are alcohol dehydrogenases Genes whose reduced or down-regulated expression increases 1,3-propanediol production include genes encoding:

aerobic respiration control protein
methylglyoxal synthase
acetate kinase
phosphotransacetylase
aldehyde dehydrogenase A
aldehyde dehydrogenase B
triosephosphate isomerase
phosphogluconate dehydratase In some embodiments, the recombinant bacteria disclosed herein are capable of producing 3-hydroxypropionic acid. 3-Hydroxypropionic acid has utility for specialty synthesis and can be converted to commercially important intermediates by known art in the chemical industry, e.g., acrylic acid by dehydration, malonic acid by oxidation, esters by esterification reactions with alcohols, and 1,3-propanediol by reduction. 3-Hydroxypropionic acid may be produced biologically from a fermentable carbon source by a single microorganism, as described in copending and commonly owned U.S. Patent No. 2011/0144377 A1. In one representative biosynthetic pathway, a carbon substrate is converted to 3-hydroxypropionaldehyde, as described above for the production of 1,3-propanediol. The 3-hydroxypropionaldehyde is converted to 3-hydroxypropionic acid by an aldehyde dehydrogenase. Suitable examples of aldehyde dehydrogenases include, but are not limited to, AldB (SEQ ID NO:16), encoded by the E. coli gene aldB (coding sequence set forth in SEQ ID NO:15); AldA (SEQ ID NO:18), encoded by the E. coli gene aldA (coding sequence set forth in SEQ ID NO:17); and AldH (SEQ ID NO:20), encoded by the E. coli gene aldH (coding sequence as set forth in SEQ ID NO:19).

Many of the modifications described above to improve 1,3-propanediol production by a recombinant bacterium can also be made to improve 3-hydroxypropionic acid production. For example, the elimination of glycerol kinase prevents glycerol, formed from G3P by the action of G3P phosphatase, from being re-converted to G3P at the expense of ATP. Also, the elimination of glycerol dehydrogenase (for example, gldA) prevents glycerol, formed from DHAP by the action of NAD-dependent glycerol-3-phosphate dehydrogenase, from being converted to dihydroxyacetone. Mutations can be directed toward a structural gene so as to impair or improve the activity of an enzymatic activity or can be directed toward a regulatory gene, including promoter regions and ribosome binding sites, so as to modulate the expression level of an enzymatic activity.

Up-regulation or down-regulation may be achieved by a variety of methods which are known to those skilled in the art. It is well understood that up-regulation or down-regulation of a gene refers to an alteration in the level of activity present in a cell that is derived from the protein encoded by that gene relative to a control level of activity, for example, by the activity of the protein encoded by the corresponding (or non-altered) wild-type gene.

Specific genes involved in an enzyme pathway may be up-regulated to increase the activity of their encoded function(s). For example, additional copies of selected genes may be introduced into the host cell on multicopy plasmids such as pBR322. Such genes may also be integrated into the chromosome with appropriate regulatory sequences that result in increased activity of their encoded functions. The target genes may be modified so as to be under the control of non-native promoters or altered native promoters. Endogenous promoters can be altered in vivo by mutation, deletion, and/or substitution.

Alternatively, it may be useful to reduce or eliminate the expression of certain genes relative to a given activity level. Methods of down-regulating (disrupting) genes are known to those of skill in the art.

Down-regulation can occur by deletion, insertion, or alteration of coding regions and/or regulatory (promoter) regions. Specific down regulations may be obtained by random mutation followed by screening or selection, or, where the gene sequence is known, by direct intervention by molecular biology methods known to those skilled in the art. A particularly useful, but not exclusive, method to effect down-regulation is to alter promoter strength.

Furthermore, down-regulation of gene expression may be used to either prevent expression of the protein of interest or result in the expression of a protein that is non-functional. This may be accomplished for example, by 1) deleting coding regions and/or regulatory (promoter) regions, 2) inserting exogenous nucleic acid sequences into coding regions and/regulatory (promoter) regions, and 3) altering coding regions and/or regulatory (promoter) regions (for example, by making DNA base pair changes). Specific disruptions may be obtained by random mutation is followed by screening or selection, or, in cases where the gene sequences in known, specific disruptions may be obtained by direct intervention using molecular biology methods know to those skilled in the art. A particularly useful method is the deletion of significant amounts of coding regions and/or regulatory (promoter) regions.

Methods of altering recombinant protein expression are known to those skilled in the art, and are discussed in part in Baneyx, Curr. Opin. Biotechnol. (1999) 10:411; Ross, et al., J. Bacteriol. (1998) 180:5375; deHaseth, et al., J. Bacteriol. (1998) 180:3019; Smolke and Keasling, Biotechnol. Bioeng. (2002) 80:762; Swartz, Curr. Opin. Biotech. (2001) 12:195; and Ma, et al., J. Bacteriol. (2002) 184:5733.

Recombinant bacteria containing the necessary changes in gene expression for metabolizing sucrose in the production of microbial products including glycerol and glycerol derivatives, as described above, may be constructed using techniques well known in the art.

The construction of the recombinant bacteria disclosed herein may be accomplished using a variety of vectors and transformation and expression cassettes suitable for the cloning, transformation and expression of coding regions that confer the ability to utilize sucrose in the production of glycerol and its derivatives in a suitable host microorganism. Suitable vectors are those which are compatible with the bacterium employed. Suitable vectors can be derived, for example, from a bacterium, a virus (such as bacteriophage T7 or a M-13 derived phage), a cosmid, a yeast or a plant. Protocols for obtaining and using such vectors are known to those skilled in the art (Sambrook et al., supra).

Initiation control regions, or promoters, which are useful to drive expression of coding regions for the instant invention in the desired host bacterium are numerous and familiar to those skilled in the art. Virtually any promoter capable of driving expression is suitable for use herein. For example, any of the promoters listed above may be used.

Termination control regions may also be derived from various genes native to the preferred hosts. Optionally, a termination site may be unnecessary; however, it is most preferred if included.

For effective expression of the instant polypeptides, nucleotide sequences encoding the polypeptides are linked operably through initiation codons to selected expression control regions such that expression results in the formation of the appropriate messenger RNA.

Particularly useful are the vectors pSYCO101, pSYCO103, pSYCO106, and pSYCO109, described in U.S. Pat. No. 7,371,558, and pSYCO400/AGRO, described in U.S. Pat. No. 7,524,660. The essential elements of these vectors are derived from the dha regulon isolated from *Klebsiella pneumoniae* and from *Saccharomyces cerevisiae*. Each vector contains the open reading frames dhaB1, dhaB2, dhaB3, dhaX (coding sequence set forth in SEQ ID NO:59; encoded polypeptide sequence set forth in SEQ ID NO:60), orfX, DAR1, and GPP2 arranged in three separate operons. The nucleotide sequences of pSYCO101, pSYCO103, pSYCO106, pSYCO109, and pSYCO400/AGRO are set forth in SEQ ID NO:62, SEQ ID NO:63, SEQ ID NO:64, SEQ ID NO:65, and SEQ ID NO:66, respectively. The differences between the vectors are illustrated in the chart below [the prefix "p-" indicates a promoter; the open reading frames contained within each "( )" represent the composition of an operon]:

pSYCO101 (SEQ ID NO:62):
    p-trc (Dar1_GPP2) in opposite orientation compared to the other 2 pathway operons,
    p-1.6 long GI (dhaB1_dhaB2_dhaB3_dhaX), and
    p-1.6 long GI (orfY_orfX_orfW).

pSYCO103 (SEQ ID NO:63):
    p-trc (Dar1_GPP2) same orientation compared to the other 2 pathway operons,
    p-1.5 long GI (dhaB1_dhaB2_dhaB3_dhaX), and
    p-1.5 long GI (orfY_orfX_orfW).

pSYCO106 (SEQ ID NO:64):
    p-trc (Dar1_GPP2) same orientation compared to the other 2 pathway operons,
    p-1.6 long GI (dhaB1_dhaB2_dhaB3_dhaX), and
    p-1.6 long GI (orfY_orfX_orfW).

pSYCO109 (SEQ ID NO:65):
    p-trc (Dar1_GPP2) same orientation compared to the other 2 pathway operons,
    p-1.6 long GI (dhaB1_dhaB2_dhaB3_dhaX), and
    p-1.6 long GI (orfY_orfX).

pSYCO400/AGRO (SEQ ID NO:66):
    p-trc (Dar1_GPP2) same orientation compared to the other 2 pathway operons,
    p-1.6 long GI (dhaB1_dhaB2_dhaB3_dhaX), and
    p-1.6 long GI (orff_orfX).
    p-1.20 short/long GI (scrK) opposite orientation compared to the pathway operons.

Once suitable expression cassettes are constructed, they are used to transform appropriate host bacteria. Introduction of the cassette containing the coding regions into the host bacterium may be accomplished by known procedures such as by transformation (e.g., using calcium-permabilized cells, or electroporation) or by transfection using a recombinant phage virus (Sambrook et al., supra). Expression cassettes may be maintained on a stable plasmid in a host cell. In addition, expression cassettes may be integrated into the genome of the host bacterium through homologous or random recombination using vectors and methods well known to those skilled in the art. Site-specific recombination systems may also be used for genomic integration of expression cassettes.

In addition to the cells exemplified, cells having single or multiple mutations specifically designed to enhance the production of microbial products including glycerol and/or its derivatives may also be used. Cells that normally divert a carbon feed stock into non-productive pathways, or that exhibit significant catabolite repression may be mutated to avoid these phenotypic deficiencies.

Methods of creating mutants are common and well known in the art. A summary of some methods is presented in U.S. Pat. No. 7,371,558. Specific methods for creating mutants using radiation or chemical agents are well documented in the art. See, for example, Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.* 36, 227 (1992).

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See, for example, Brock, Supra; DeMancilha et al., *Food Chem.* 14, 313 (1984).

Fermentation media in the present invention comprise sucrose as a carbon substrate. Other carbon substrates such as glucose and fructose may also be present.

In addition to the carbon substrate, a suitable fermentation medium contains, for example, suitable minerals, salts, cofactors, buffers and other components, known to those skilled in the art, suitable for the growth of the cultures and promotion of the enzymatic pathway necessary for production of glycerol and its derivatives, for example 1,3-propanediol. Particular attention is given to Co(II) salts and/or vitamin $B_{12}$ or precursors thereof in production of 1,3-propanediol.

Adenosyl-cobalamin (coenzyme $B_{12}$) is an important cofactor for dehydratase activity. Synthesis of coenzyme $B_{12}$ is found in prokaryotes, some of which are able to synthesize the compound de novo, for example, *Escherichia blattae, Klebsiella* species, *Citrobacter* species, and *Clostridium* species, while others can perform partial reactions. *E. coli*, for example, cannot fabricate the corrin ring structure, but is able to catalyze the conversion of cobinamide to corrinoid and can introduce the 5'-deoxyadenosyl group. Thus, it is known in the art that a coenzyme $B_{12}$ precursor, such as vitamin $B_{12}$, needs be provided in *E. coli* fermentations. Vitamin $B_{12}$ may be added continuously to *E. coli* fermentations at a constant rate or staged as to coincide with the generation of cell mass, or may be added in single or multiple bolus additions.

Although vitamin $B_{12}$ is added to the transformed *E. coli* described herein, it is contemplated that other bacteria, capable of de novo vitamin $B_{12}$ biosynthesis will also be suitable production cells and the addition of vitamin $B_{12}$ to these bacteria will be unnecessary.

Typically bacterial cells are grown at 25 to 40° C. in an appropriate medium containing sucrose. Examples of suitable growth media for use herein are common commercially prepared media such as Luria Bertani (LB) broth, Sabouraud Dextrose (SD) broth or Yeast medium (YM) broth. Other defined or synthetic growth media may also be used, and the appropriate medium for growth of the particular bacterium will be known by someone skilled in the art of microbiology or fermentation science. The use of agents known to modulate catabolite repression directly or indirectly, e.g., cyclic adenosine 2':3'-monophosphate, may also be incorporated into the reaction media. Similarly, the use of agents known to modulate enzymatic activities (e.g., methyl viologen) that lead to enhancement of 1,3-propanediol production may be used in conjunction with or as an alternative to genetic manipulations with 1,3-propanediol production strains.

Suitable pH ranges for the fermentation are between pH 5.0 to pH 9.0, where pH 6.0 to pH 8.0 is typical as the initial condition.

Reactions may be performed under aerobic, anoxic, or anaerobic conditions depending on the requirements of the recombinant bacterium. Fed-batch fermentations may be performed with carbon feed, for example, carbon substrate, limited or excess.

Batch fermentation is a commonly used method. Classical batch fermentation is a closed system where the composition of the medium is set at the beginning of the fermentation and is not subject to artificial alterations during the fermentation. Thus, at the beginning of the fermentation, the medium is inoculated with the desired bacterium and fermentation is permitted to occur adding nothing to the system. Typically, however, "batch" fermentation is batch with respect to the addition of carbon source, and attempts are often made at controlling factors such as pH and oxygen concentration. In batch systems, the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable for use herein and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch to fermentations are common and well known in the art and examples may be found in Brock, supra.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by the turbidity of the medium, is kept constant. Continuous systems strive to maintain steady state growth conditions, and thus the cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using batch, fed-batch or continuous processes and that any known mode of fermentation would be suitable. Additionally, it is contemplated that cells may be immobilized on a substrate as whole cell catalysts and subjected to fermentation conditions for production of glycerol and glycerol derivatives, such as 1,3-propanediol.

In some embodiments, a process for making glycerol, 1,3-propanediol, and/or 3-hydroxypropionic acid from sucrose is provided. The process comprises the steps of culturing a recombinant bacterium, as described above, in the presence of sucrose, and optionally recovering the glycerol, 1,3-propanediol, and/or 3-hydroxypropionic acid produced. The product may be recovered using methods known in the art. For example, solids may be removed from the fermentation medium by centrifugation, filtration, decantation, or the like. Then, the product may be isolated from the fermentation medium, which has been treated to remove solids as described above, using methods such as distillation, liquid-liquid extraction, or membrane-based separation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques described in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

The meaning of abbreviations is as follows: "sec" means second(s), "min" means minute(s), "h" means hour(s), "nm" means nanometers, "µL" means microliter(s), "mL" means milliliter(s), "L" means liter(s), "mM" means millimolar, "M" means molar, "g" means gram(s), "µg" means microgram(s), "bp" means base pair(s), "kbp" means kilobase to pair(s), "rpm" means revolutions per minute, "ATCC" means American Type Culture Collection, Manassas, Va., "$dH_2O$" means distilled water.

Media and Culture Conditions:

Materials and methods suitable for the maintenance and growth of is bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials described for the growth and maintenance of bacterial cells may be obtained from Aldrich Chemicals (Milwaukee, Wis.), BD Diagnostic Systems (Sparks, Md.), Life Technologies (Rockville, Md.), New England Biolabs (Beverly, Mass.), or Sigma Chemical Company (St. Louis, Mo.), unless otherwise specified.

LB (Luria Bertani) medium contains following per liter of medium: Bacto-tryptone (10 g), Bacto-yeast extract (5 g), and NaCl (10 g). Supplements were added as described in the Examples below. All additions were pre-sterilized before they were added to the medium.

Molecular Biology Techniques:

Restriction enzyme digestions, ligations, transformations, and methods for agarose gel electrophoresis were performed as described in Sambrook, J., et al., *Molecular Cloning: A Laboratory Manual*, Second Edition, Cold Spring Harbor Laboratory Press (1989). Polymerase Chain Reactions (PCR) techniques were found in White, B., *PCR Protocols: Current Methods and Applications*, Volume 15 (1993), Humana Press Inc., New York. N.Y.

Examples 1 and 2

Recombinant *E. coli* Strain Comprising a Variant CscB Sucrose Transporter Having a R300A Mutation The purpose of these Examples was to construct a recombinant *E. coli* strain containing a variant CscB sucrose transport gene (coding sequence set forth in SEQ ID NO:99), encoding an R300A variant of CscB (SEQ ID NO:100), and to demonstrate sucrose transport by facilitated diffusion. The protein encoded by the mutant sucrose transport gene was altered in a residue required for $H^+$ translocation, thus eliminating $H^+$/sucrose symport (i.e., active transport of sucrose).

Construction of Expression Vectors:

Two expression vectors were constructed, one using promoter element P1.20 and the second using promoter element P1.5. P1.20 and P1.5 refer to promoter elements derived from the *Streptomyces lividans* glucose isomerase promoter as described in U.S. Pat. No. 7,132,527. These two promoters differ from each other by one base in the −35 region such that P1.20 confers lower expression than does P1.5.

The promoter/multiple cloning site/double terminator regions were synthesized by Integrated DNA Technologies (Coralville, Iowa) and cloned into their pIDTsmart vector, resulting in the construction of plasmids named pDMWP1 and pDMWP3. The sequences of the synthesized regions for vectors pDMWP1 and pDMWP3 are set forth in SEQ ID NO:113 and SEQ ID NO:114, respectively.

A plasmid referred to herein as pDMWP4 was used as the backbone for subsequent constructs. Plasmid pDMWP4 was constructed from plasmid pBR322 by modifying restriction sites as follows. A Scat site and a KpnI site on the 5' end of the TetR gene and an additional KpnI site at the 3' end of the TetR gene were introduced into plasmid pBR322. Additionally, a KpnI site was removed from the middle of the AmpR gene as well. All sites were either added or removed using Stratagene's QuikChange® kits (Stragene, La Jolla, Calif.) following manufacturer's protocols.

Plasmids pDMWP1 and DMWP3 were digested with EcoRI and KpnI. The resulting 438 bp fragment from each construct was individually cloned into pDMWP4, also digested with EcoRI and KpnI, to complete plasmids pDMWP10 and pDMWP12, which are also referred to herein as pBR*P1.5 and pBR*1.20, respectively.

The R300A variant of CscB was given the allele name, cscB3. This mutation was introduced into plasmid pBHRcscBKA (described in U.S. Patent Application Publication No. 2011/0136190, Example 1) by site-directed mutagenesis using Stratagene's QuikChange® Site-Directed Mutagenesis kit following the manufacturer's protocol. Primers ODMWP23 (SEQ ID NO:115) and ODMWP24 (SEQ ID NO:116) were used with plasmid pBHRcscBKA as template in the reaction, creating plasmid pDMWP5. The cscB3 gene was subsequently amplified from pDMWP5 using primers ODMWP31 (SEQ ID NO:117) and ODMWP32 (SEQ ID NO:118) to add HindIII/ClaI sites. The resulting product was cloned into pBADtopo (Invitrogen, Carlsbad, Calif.) creating plasmid pDMWP26.

The HindIII/Cla fragment from pDMWP26 was cloned into HindIII/ClaI digested pDMWP12, creating plasmid pDMWP32, which contained promoter P1.20.

The HindIII/Pac fragment from pDMWP32 was cloned into HindIII/Pac digested pDMWP10, creating pDMWP73, which contained promoter P1.5.

Construction of *E. Coli* Strains with or without Expression of cscB3:

*E. coli* strain PDO3513, an *E. coli* K12 strain [FM5 yihP: cscA+K+B−(Δ61-353, kanR)] that does not have sucrose transporter function, but possesses genes encoding sucrose invertase and fructokinase for downstream metabolism was used as the host strain. *E. coli* strain PDO3513 was constructed from an *E. coli* strain (referred to herein as PDO3085) containing the wild type cscAKB gene cluster from E, coli ATCC®13281, integrated at the yihP gene in *E. coli* strain FM5 (ATCC®No. 53911). The cscAKB gene cluster (SEQ ID NO:61) was integrated at the yihP location in *E. coli* strain FM5 (ATCC® No. 53911) by the Lambda Red method. The cscAKB gene cluster was amplified from plasmid pBHR-cscBKA (SEQ ID NO:119), which was constructed as described in Example 1 of U.S. Patent Application Publication No. 2011/0136190 A1, using yihP cscA primer (SEQ ID NO:120) and yihP cscB primer (SEQ ID NO:121) containing flanking sequences for the yihP gene. Plasmid pBHR-cscBKA, linearized by PstI digest, was used as the PCR template. High fidelity PfuUltra® II Fusion HS DNA polymerase (Stratagene; La Jolla, Calif.) was used in the PCR reaction. PCR was performed using the following cycling conditions: 95° C. for 2 min; 35 cycles of 95° C. for 30 sec, 60° C. for 30 sec, and 72° C. for 4 min; and then 72° C. for 7 min. The resulting PCR product was stored at 4° C. The PCR product was purified using a QIAquick PCR Purification kit (Qiagen, Valencia, Calif.). The purified PCR product was electroporated into *E. coli* strain FM5 containing the pKD46 plasmid (Red recombinase plasmid, GenBank Acc. No. AY048746), encoding lambda recombinases, following the lambda red recombination procedure (Datsenko, K. A. and Wanner, B. L., 2000, *Proc. Natl. Acad. Sci. USA* 97, 6640- 6645). The transformation mixture was plated on MOPS minimal plates containing 10 g/L sucrose. The MOPS minimal plates contained 1×MOPS buffer (Technova, Hollister, Calif.), 1.32 mM $KH_2PO_4$ (Technova), 50 μg/L uracil and 1.5 g/L Bacto agar. Plates were incubated at 37° C. for 2-3 days. Colonies grown on minimal sucrose plates were picked to give *E. coli* strain PDO3085.

The cscB gene in the cluster in PDO3085 was then partially deleted by replacing it with a kanamycin resistance cassette. The kanamycin resistance cassette was amplified from the pKD4 template plasmid (Datsenko and Wanner, *Proc. Natl. Acad. Sci. USA* 97:6640-6645, 2000) using cscB61 up kan primer (SEQ ID NO:91) and cscB353 down kan primer (SEQ ID NO:92). High fidelity PfuUltra® II Fusion HS DNA polymerase (Stratagene; La Jolla, Calif.) was used in the to PCR reaction. PCR was performed using the following cycling conditions: 95° C. for 2 min; 30 cycles of 95° C. for 20 sec, 60° C. for 20 sec, and 72° C. for 1.5 min; and then 72° C. for 3 min. The resulting PCR product was stored at 4° C. The PCR product was purified using the QIAquick PCR Purification kit (Qiagen). The purified PCR product was electroporated into the PDO3085 strain containing the pKD46 plasmid encoding lambda recombinases following the lambda red recombination procedure. The transformation mixture was plated on LB plates containing 25 μg/mL kanamycin. The kanamycin resistance colonies were checked on MOPS+10 g/L sucrose plates to make sure that they were unable to grow on sucrose. Insertion of the kanamycin resistance cassette between residue 61 and 353 of CscB was confirmed by PCR using cscB 5' primer (SEQ ID NO:93) and cscB 3' primer (SEQ ID NO: 94). The resulting FM5 yihP:cscA+K+B– (Δ61-353, kanR) strain was designated as PDO3513.

Plasmids pDMWP10 (the vector alone) and pDMWP73, carrying the mutant cscB3 gene, were introduced independently into E. coli strain PDO3513. The resultant strains were named PDO2768 and PDO2770, respectively.

Growth Characterization of E. Coli Strains with or without Expression of cscB3:

E. coli strains PDO2768 (Example 2, Comparative) and PDO2770 (Example 1) were grown overnight in LB (Luria Bertani) medium containing 100 μg/mL ampicillin at 37° C. The next day, these cultures were diluted 1:50 in MOPS minimal medium (Teknova, Half Moon Bay, Calif.) containing 2 g/L sucrose and 25 μg/mL ampicillin, These cultures were grown at 37° C. with shaking at 250 rpm for 4 hours. The log-phase cultures were diluted 1:100 in the wells of a Bioscreen-C plate (instrument and plates purchased from Growth Curves USA, Piscataway N.J.) with 150 μL of MOPS minimal medium (Teknova, Half Moon Bay, Calif.) containing 2 g/L glucose or 16 g/L sucrose. The cultures were grown at 37° C. in triplicate with continuous shaking and the optical density was monitored. The optical densities of the two cultures at 40 hours after inoculation are given in Table 3.

TABLE 3

Optical Density of Cultures Growing on Glucose or Sucrose at 40 Hours

| Carbon Source | Example 1 PDO2770 | Example 2, Comparative PDO2768 |
| --- | --- | --- |
| 2 g/L glucose | 0.583 ± 0.045 | 0.572 ± 0.022 |
| 16 g/L sucrose | 0.892 ± 0.023 | 0.012 ± 0.003 |

As can be seen from the data in Table 3, both strains grew well with glucose as a sole carbon source. In contrast, the control strain (i.e., vector only strain) PDO2768 (Example 2, Comparative) was unable to grow with sucrose as sole carbon source, while PDO2770 (Example 1), the strain expressing the mutant cscB3 gene encoding a sucrose transporter unable to translocate H$^+$ ion was able to grow with sucrose as sole carbon source, Thus, net translocation of sucrose across the membrane must have occurred without translocation of a H$^+$ ion.

Example 3

Recombinant E. Coli Strain Comprising a Variant CscB Sucrose Transporter Having R300A and Q353H Mutations The purpose of this Example was to construct a recombinant E. coli strain containing a variant CscB sucrose transport gene (coding sequence set forth in SEQ ID NO:103), encoding CscB having R300A and Q353H mutations (SEQ ID NO:104), and to demonstrate improved sucrose transport by facilitated diffusion with the additonal mutation conferring a Q353H alteration in cscB3.

Construction of Expression Vectors:

For ease of cloning into a smaller vector, the KanR gene from pBHRcscBKAmutB (described in U.S. Patent Application Publication No. 2011/0136190, Example 1) was removed by digesting the plasmid with PstI and religating, creating plasmid pDMWP6. The new vector was 1240 bp smaller than the parent. The mutant cscB gene in this vector confers the Q353H variation with improved sucrose transport (Jahreis et al., J. Bacteriol. 184:5307-5316, 2002) as compared to the wild type sucrose symporter. It was not known if this mutation would improve sucrose transport by facilitated diffusion.

A mutation conferring the R300A variation was introduced into plasmid pDMWP6 by site-directed mutagenesis using Stratagene's QuikChange® Site-Directed Mutagenesis kit following the manufacturer's protocol. Primers ODMWP23 (SEQ ID NO:115) and ODMWP24 (SEQ ID NO:116) were used with plasmid pDMWP6 as template in the reaction, creating plasmid pDMWP15. The cscB5 gene (containing R300A and Q353H mutations) was subsequently amplified from pDMWP6 using primers ODMWP31 (SEQ ID NO:117) and ODMWP32 (SEQ ID NO:118) to add HindIII/ClaI sites. The resulting product was cloned into pBADtopo (Invitrogen, Carlsbad, Calif.), creating plasmid pDMWP27.

The HindIII/Cla fragment from pDMWP27 was cloned into HindIII/ClaI digested pDMWP12, creating pDMWP33, which contained the P1.20 promoter.

The HindIII/Pac fragment from pDMWP33 was cloned into HindIII/Pac digested pDMWP10, creating pDMWP66, which contained the P1.5 promoter.

Construction of E. Coli Strain with Expression of cscB5:

Plasmid pDMWP66 (pBR*p1.5csc5) was transformed into strain PDO3513, to give strain PDO2771.

Growth Characterization of E. Coli Strains with Expression of cscB3 or cscB5:

E. coli strains PDO2770 (with pBR*p1.5csc3, described in Examples 1 and 2) and PDO2771 (with pBR*p1.5csc5) were grown overnight in LB (Luria Bertani) medium containing 100 μg/mL ampicillin at 37° C. The next day, these cultures were diluted 1:50 in MOPS minimal medium (Teknova, Half Moon Bay, Calif.) containing 2 g/L sucrose and 25 μg/mL ampicillin, These cultures were grown at 37° C. with shaking at 250 rpm for 4 hours. The log-phase cultures were diluted 1:100 in the wells of a Bioscreen-C plate (instrument and plates purchased from Growth Curves USA, Piscataway N.J.) with 150 μL MOPS minimal medium (Teknova, Half Moon Bay, Calif.) containing 2 g/L glucose or 16 g/L sucrose. The cultures were grown at 37° C. in triplicate with continuous shaking and the optical density was monitored. The growth on sucrose was much faster in cultures of strain PDO2771 than cultures of strain PDO2770. At 14 hours after inoculation, the optical density of the PDO2770 culture growing on 16 g/L sucrose was 0.060±0.024 while that of the PDO2771 culture growing on 16 g/L sucrose was 0.647±0.009. As a measure of the health of the inoculum cultures, the growth on glucose was measured. Both strains grew well with glucose as a sole carbon source. At 14 hours after inoculation, the optical density of the PDO2770 culture growing on glucose was 0.639±0.037 and the optical density of the PDO2771 culture growing on glucose was 0.693±0.070. These results demonstrate that the strain expressing CscB5, the sucrose transporter with both Q353H and R300A mutations, was able to grow much better with sucrose as sole carbon source than did the strain expressing CscB3 (R300A) alone. Because the CscB5 protein still carries a mutation in a residue essential for H$^+$ translocation, it must be transporting sucrose without translocation of a H$^+$ ion. Thus, the transporter encoded by the gene with the double mutation is an improved facilitated diffusion sucrose transporter.

Examples 4-6

Growth on Sucrose of Recombinant *E. coli* Strains Comprising Mutant or Wild Type Sucrose Transporters The purpose of these Examples was to show that a recombinant *E. coli* strain comprising a variant of CscB having R300A and Q353H mutations was able to grow at a wider range of sucrose concentrations than *E. coli* strains comprising the wild type sucrose transporter.

Construction of Expression Vectors:

The wild type *E. coli* cscB gene was originally amplified from pBHRcscBKA (SEQ ID NO:119), described in U.S. Patent Application Publication No. 2011/0136190, Example 1) with primers ODMWP31 (SEQ ID NO:117) and ODMWP32 (SEQ ID NO:118), allowing the addition of both HindIII and ClaI sites at the 5' and 3' ends of the gene, respectively. The PCR fragment was cloned into pBADtopo (Invitrogen, Carlsbad, Calif.), creating plasmid pDMWP25.

The HindIII/Cla fragment from pDMWP25 was cloned into HindIII/Cla digested pDMWP12, creating pDMWP31, which contained promoter P1.20.

The HindIII/Pac digested fragment from pDMWP31 was cloned into the HindIII/Pac digested pDMWP10, creating pDMWP71, which contained promoter P1.5.

Construction of *E. Coli* Strains Comprising the Wild Type Sucrose Transporter CscB:

Plasmids pDMWP31 (pBR*p1.20cscB) and pDMWP71 (pBR*p1.5cscB) were transformed independently into strain PDO3513, to give strains PDO2625 and PDO2769, respectively.

Growth Characterization of Strains with Expression of cscB5 or Wild Type cscB:

The two *E. coli* strains with plasmids encoding the wild type sucrose symporter, PDO2625 (Example 5, Comparative) and PDO2769 (Example 6, Comparative), and a strain with a plasmid carrying the improved sucrose uniporter, PDO2771 (Example 4, with pBR*p1.5csc5, described in Example 3), were grown overnight in LB (Luria Bertani) medium containing 100 µg/mL ampicillin at 37° C. The next day, these cultures were diluted 1:50 in MOPS minimal medium (Teknova, Half Moon Bay, Calif.) containing 2 g/L sucrose and 25 µg/mL ampicillin, These cultures were grown at 37 is ° C. with shaking at 250 rpm for 4 hours. The log-phase cultures were diluted 1:100 in the wells of a Bioscreen-C plate (instrument and plates purchased from Growth Curves USA, Piscataway N.J.) with 150 µL of MOPS minimal medium (Teknova, Half Moon Bay, Calif.) containing 2 g/L glucose or 2, 4, 8, 16, or 32 g/L sucrose. The cultures were grown at 37° C. in triplicate with continuous shaking and the optical density was monitored. The growth on various concentrations of sucrose was followed. Table 4 shows the optical density at 14 hours after inoculation for the cultures of PDO2771, PDO2625, and PDO2769.

TABLE 4

Optical Density of Cultures Growing on Glucose or Various Concentrations of Sucrose at 14 Hours

| Carbon Source | Example 4 PDO2771 (pBR1.5cscB5) | Example 5, Comparative PDO2625 (pBR*p1.20cscB) | Example 6, Comparative PDO2769 (pBR*p1.5cscB) |
|---|---|---|---|
| 2 g/L glucose | 0.693 ± 0.070 | 0.593 ± 0.005 | 0.668 ± 0.013 |
| 2 g/L sucrose | 0.071 ± 0.036 | 0.452 ± 0.028 | 0.654 ± 0.007 |
| 4 g/L sucrose | 0.343 ± 0.184 | 0.719 ± 0.007 | 0.716 ± 0.011 |
| 8 g/L sucrose | 0.745 ± 0.004 | 0.655 ± 0.010 | 0.094 ± 0.012 |
| 16 g/L sucrose | 0.647 ± 0.009 | 0.107 ± 0.007 | 0.060 ± 0.005 |
| 32 g/L sucrose | 0.576 ± 0.006 | 0.049 ± 0.002 | 0.058 ± 0.006 |

As shown by the results in Table 4, all three strains grew well on 2 g/L glucose, indicating that the inoculum cultures were viable. The growth of the PDO2625 strain (Example 5, Comparative) and PDO2769 strain (Example 6, Comparative) was better than that of PDO2771 strain (Example 4) at low sucrose concentrations of 2 or 4 g/L. However at the higher sucrose concentrations of 16 or 32 g/L, PDO2771 maintained good growth while the growth of PDO2525 and PDO2769 was severely inhibited. These results demonstrate that the strain expressing CscB5, the sucrose facilitated diffusion transporter, was able to grow at a wider range of sucrose concentrations than the strains expressing the wild type sucrose symporter. Thus, facilitated diffusion, or uniport, has an advantage of allowing growth under conditions at which the symporter does not allow growth.

Examples 7-10

PDO Production from Sucrose with a Strain Comprising a Variant of CscB Sucrose Transporter Having R300A and Q353H Mutations and a Strain Comprising the Wild Type Sucrose Transporter CscB The purpose of these Examples was to show that a recombinant *E. coli* strain comprising a variant of CscB having R300A and Q353H mutations gave better PDO production when grown on sucrose than a recombinant *E. coli* strain comprising the wild type sucrose transporter CscB.

A strain for testing the function of sucrose transporters for PDO production was constructed using PDO producing strain TTab pSYCO400/AGRO. *E. coli* strain TTab pSYCO400/AGRO, a PTS minus strain, was constructed as follows. Strain TTab was generated by deletion of the aldB gene from strain TT aldA, described in U.S. Pat. No. 7,371,558 (Example 17). Briefly, an aldB deletion was made by first replacing 1.5 kbp of the coding region of aldB in *E. coli* strain MG1655 with the FRT-CmR-FRT cassette of the pKD3 plasmid (Datsenko and Wanner, *Proc. Natl. Acad. Sci. USA* 97:6640-6645, 2000). A replacement cassette was amplified with the primer pair SEQ ID NO:99 and SEQ ID NO:100 using pKD3 as the template. The primer SEQ ID NO:99 contains 80 bp of homology to the 5'-end of aldB and 20 bp of homology to pKD3. Primer SEQ ID NO:100 contains 80 bp of homology to the 3' end of aldB and 20 bp homology to pKD3. The PCR products were gel-purified and electroporated into MG1655/pKD46 competent cells (U.S. Pat. No. 7,371,558). Recombinant strains were selected on LB (Luria Bertani) plates with 12.5 mg/L of chloramphenicol. The deletion of the aldB gene was confirmed by PCR, using the primer pair SEQ ID NO:101 and SEQ ID NO:102. The wild-type strain gave a 1.5 kbp PCR product while the recombinant strain gave a characteristic 1.1 kbp PCR product. A P1 lysate was prepared and used to move the mutation to the TT aldA strain to form the TT aldAΔaldB::Cm strain. A chloramphenicol-resistant clone was checked by genomic PCR with the primer pair SEQ ID NO:101 and SEQ ID NO:102 to ensure that the mutation was present. The chloramphenicol resistance marker was removed using the FLP recombinase (Datsenko and Wanner, supra) to create TTab. Strain TTab was then transformed with pSYCO400/AGRO (set forth in SEQ ID NO:84), described in U.S. Pat. No. 7,524,660 (Example 4), to generate strain TTab pSYCO400/AGRO.

As described in the cited references, strain TTab is a derivative of *E. coli* strain FM5 (ATCC® No. 53911) containing the following to modifications:
  deletion of glpK, gidA, ptsHI, crr, add, arcA, mgsA, qor, ackA, pta, aldA and aldB genes;
  upregulation of galP, glk, btuR, ppc, and yqhD genes; and downregulation of gapA gene.

Plasmid pSYCO400/AGRO contains genes encoding a glycerol production pathway (DAR1 and GPP2) and genes encoding a glycerol dehydratase and associated reactivating factor (dhaB123, dhaX, orfX, orfY), as well as a gene encoding a fructokinase (scrK).

Strain TTab pSYCO400/AGRO was used as a recipient for P1 transduction. The donor strain was PDO3513, constructed as described in Examples 1 and 2, and selection for growth was on LB plates with 25 μg/mL kanamycin. A colony resistant to kanamycin and spectinomycin was purified and named PDO2737 [TTab/pSYCO400AGRO yihP::cscKBΔ(61-353) KanR&A].

Strain PDO2737 was transformed with plasmids encoding the wild type sucrose transporter, pDMWP31 (pBR*p1.20cscB) and pDMWP71 (pBR*p1.5cscB) described in Examples 4-6, to yield strains PDO2815 and PDO2818, respectively. In addition, strain PDO2737 was transformed with plasmids encoding a facilitated diffusion sucrose transporter, pDMWP33 (pBR*p1.20csc5) and pDMWP66 (pBR*p1.5csc5), described in Example 3, to yield strains PDO2965 and PDO2966, respectively.

To test for production of PDO and glycerol, these four *E. coli* strains were grown overnight in L-Broth, Miller's Modification (Teknova, Half Moon Bay, Calif.) supplemented with 100 mg/L spectinomycin and 100 mg/L ampicillin at 33° C. These cultures were used to inoculate shake flasks at an optical density of 0.01 units measured at 550 nm in MOPS minimal medium (Teknova, Half Moon Bay, Calif.) supplemented with 10 g/L sucrose. Vitamin B12 was added to the medium to a concentration of 0.1 mg/L. The cultures were incubated at 34° C. with shaking (225 rpm) for 44 hours. Samples of the cultures were then to filtered and used for the determination of the concentrations of sucrose, glycerol and 1,3-propanediol (PDO) in the broth by high performance liquid chromatography.

Chromatographic separation was achieved using an Aminex HPX-87P column (Bio-Rad, Hercules, Calif.) with an isocratic mobile phase of distilled-deionized water at a flow rate of 0.5 mL/min and a column temperature of 85° C. Fluted compounds were quantified by refractive index detection with reference to a standard curve prepared from commercially purchased pure compounds dissolved to known concentrations in MOPS minimal medium. Retention times were sucrose at 12.2 min, 1,3-propanediol at 17.9 min, and glycerol at 23.6 min. Table 5 shows the residual sucrose and molar yield of PDO and glycerol (mol PDO+mol glycerol/mol glucose equivalent), in the cultures of these four strains.

TABLE 5

Sucrose Utilization and PDO and Glycerol Production

| Example | Strain | 44 hour sucrose g/L | Molar Yield (mol PDO + glycerol/mol glucose equivalent) |
|---|---|---|---|
| Example 7, Comparative | PDO2815 (P1.20cscB) | 6.65 | 0.780 |
| Example 8, Comparative | PDO2818 (P1.5cscB) | 9.23 | 0.660 |
| Example 9 | PDO2965 (P1.20cscB5) | 4.80 | 1.014 |
| Example 10 | PDO2966 (P1.5cscB5) | 1.78 | 1.066 |

As can be seen from the results in Table 5, there was more sucrose remaining in the cultures expressing the wild type sucrose transporter CscB (Comparative Examples 7 and 8) than was left in the cultures expressing the facilitated diffusion transporter, CscB5 (Examples 9 and 10), indicating faster sucrose utilization with the facilitated diffusion transporter under these conditions. The molar yield of PDO and glycerol from sucrose was substantially higher for the strains expressing the facilitated diffusion transporter. Thus sucrose transport by facilitated diffusion was shown to be better than with the wild type transporter for PDO and glycerol production.

Examples 11-14

Recombinant *E. Coli* Strain Comprising a Variant CscB Sucrose Transporter Having R300A, Q353H and L61P Mutations The purpose of these Examples was to demonstrate that recombinant *E. coli* strains comprising variants of CscB having an L61P mutation in addition to an R300A and/or Q353H mutations (SEQ ID NO:106, encoded by SEQ ID NO:105) have improved sucrose transport by facilitated diffusion. The L61P variation confers improved sucrose transport to the CscB sucrose symporter, as described in copending and commonly owned U.S. patent application Ser. No. 13/210,488, but it was not known if this mutation would improve transport by facilitated diffusion, or if the combination of L61P and Q535H would have still further improved transport.

Construction of Expression Vectors:

The cscB16 allele contains two mutations, L61P and R300A. Plasmid pDMWP32 (described in Examples 1 and 2), which contains the R300A mutation was further mutated to introduce an L61P mutation. The mutation was introduced into pDMWP32 by site directed mutagenesis using Stratagene's QuikChange® Site-Directed Mutagenesis kit, and oligonucleotides ODMWP33 (SEQ ID NO:122) and ODMWP34 (SEQ ID NO:123) following the manufacturer's protocol, creating plasmid pDMWP54.

The cscB17 allele contains three mutations, L61P, R300A and Q353H. Plasmid pDMWP33 (described in Example 3), which contains the R300A and Q353H mutations was further mutated to introduce an L61P mutation. The mutation was introduced into pDMWP33 by site directed mutagenesis using Stratagene's QuikChange® Site-Directed Mutagenesis kit, and oligonucleotides ODMWP33 (SEQ ID NO:122) and ODMWP34 (SEQ ID NO:123) following the manufacturer's protocol, creating plasmid pDMWP55. The HindIII/Pac fragment from pDMWP55 was cloned into HindIII/Pac digested pDMWP10, to create the P1.5-containing version of the construct, plasmid pDMWP79.

Construction of E. coli Strains

Two of the plasmids described above, pDMWP54 (pBR*p1.20cscb16) and pDMWP55 (pBR*p1.20cscB17), were transformed independently into strain PDO3513, to give strains PDO2636 and PDO2637, respectively. In addition, plasmids pDMWP32 (pBR*1.20cscB3, described in Examples 1 and 2) and pDMWP33 (pBR*1.20cscB5, described in Example 3) were transformed into strain PDO3513, to give strains PDO2626 and PDO2627, respectively.

Growth Characterization of Strains with Expression of cscB3, cscB5, cscB16, or cscB17:

The four E. coli strains described above were grown overnight in LB (Luria Bertani) medium containing 100 µg/mL of ampicillin at 37° C. The next day, these cultures were diluted 1:100 in LB medium containing 100 µg/mL of ampicillin, These cultures were grown at 37° C. with shaking at 250 rpm for 4 hours. The log-phase cultures were diluted 1:100 in the wells of a Bioscreen-C plate (instrument and plates purchased from Growth Curves USA, Piscataway N.J.) with 150 µL of MOPS minimal medium (Teknova, Half Moon Bay, Calif.) containing 2 g/L glucose or 2 g/L sucrose. The cultures were grown at 37° C. in triplicate with continuous shaking and the optical density was monitored. Table 6 shows the mean and standard deviation of the optical density readings at 10 hours after inoculation.

TABLE 6

Growth in Glucose or Sucrose of Strains Expressing Various Sucrose Uniporters Measured by Optical Density at 10 hours.

| Example | Strain | cscB allele and variant amino acids | 2 g/L glucose | 2 g/L sucrose |
|---|---|---|---|---|
| Example 11 | PDO2626 | cscB3 (R300A) | 0.710 ± 0.007 | 0.064 ± 0.006 |
| Example 12 | PDO2627 | cscB5 (R300A Q353H) | 0.702 ± 0.005 | 0.211 ± 0.006 |
| Example 13 | PDO2636 | cscB16 (L61P R300A) | 0.710 ± 0.005 | 0.609 ± 0.017 |
| Example 14 | PDO2637 | cscB17 (L61P R300A Q353H) | 0.703 ± 0.001 | 0.732 ± 0.009 |

As can be seen from the data in Table 6, all four strains grew well on glucose indicating that the inoculum cultures were healthy. Under these growth conditions, there was very little growth of strain PDO2626 expressing the facilitated diffusion transporter CscB3 with the R300A mutation. Comparatively, the growth was dramatically improved in strain PDO2636 expressing CscB16 (L61P and R300A). Likewise, L61P added to R300A Q353H improved growth as seen by comparing the growth of PDO2637 with PDO2627. These results demonstrate that the strain expressing variant sucrose facilitated diffusion transporter with the L61P mutation improved growth with sucrose as sole carbon source. Each of the variant CscB proteins carries the R300A mutation in a residue essential for $H^+$ translocation, thus each must be transporting sucrose without translocation of $H^+$ ion. Accordingly, the transporters encoded by the genes conferring the L61P variation are improved facilitated diffusion sucrose transporters.

Examples 15-17

Growth on Sucrose of Recombinant E. Coli Strains Comprising Mutant or Wild Type Sucrose Transporters The purpose of these Examples was to show that a recombinant E. coli strain comprising a variant of CscB having R300A, Q353H, and L61P mutations was able to grow at a wider range of sucrose concentrations than E. coli strains comprising the wild type sucrose transporter.

Construction of E. Coli Strain Comprising the Variant of CscB Having R300A, Q353H, and L61P Mutations:

Plasmid pDMWP79 (pBR*p1.5cscB17, described in Examples 11-14) was transformed into strain PDO3513, to give strain PDO2773.

Growth Characterization of E. coli Strains:

Strain PDO2773 (Example 15) and two E. coli strains with plasmids encoding the wild type sucrose symporter, PDO2625 (Example 16, Comparative) and PDO2769 (Example 17, Comparative), both described in Examples 4-6, were grown overnight in LB (Luria Bertani) medium containing 100 µg/mL ampicillin at 37° C. The next day, these cultures were diluted 1:50 in MOPS minimal medium (Teknova, Half Moon Bay, Calif.) containing 2 g/L sucrose and 25 µg/mL ampicillin, These cultures were grown at 37° C. with shaking at 250 rpm for 4 hours. The log-phase cultures were diluted 1:100 in the wells of a Bioscreen-C plate (instrument and plates purchased from Growth Curves USA, Piscataway N.J.) with 150 µL MOPS minimal medium (Teknova, Half Moon Bay, Calif.) containing 2 g/L glucose or 2, 4, 8, 16, or 32 g/L sucrose. The cultures were grown at 37° C. in triplicate with continuous shaking and the optical density was monitored. The growth on various concentrations of sucrose was followed. Table 7 shows the optical density at 14 hours after inoculation for the cultures of PDO2773, PDO2625, and PDO2769.

TABLE 7

Optical Density of Strains Growing on Glucose or Various Concentrations of Sucrose at 14 Hours

|  | Example 15 PDO2773 (pBR1.5cscB17) | Example 16, Comparative PDO2625 pBR*p1.20cscB | Example 17, Comparative PDO2769 pBR*p1.5cscB |
|---|---|---|---|
| 2 g/L glucose | 0.669 ± 0.042 | 0.593 ± 0.005 | 0.668 ± 0.013 |
| 2 g/L sucrose | 0.474 ± 0.115 | 0.452 ± 0.028 | 0.654 ± 0.007 |
| 4 g/L sucrose | 0.744 ± 0.043 | 0.719 ± 0.007 | 0.716 ± 0.011 |
| 8 g/L sucrose | 0.657 ± 0.052 | 0.655 ± 0.010 | 0.094 ± 0.012 |
| 16 g/L sucrose | 0.666 ± 0.008 | 0.107 ± 0.007 | 0.060 ± 0.005 |
| 32 g/L sucrose | 0.538 ± 0.015 | 0.049 ± 0.002 | 0.058 ± 0.006 |

As can be seen from the data in Table 7, all three strains grew well on 2 g/L glucose, indicating that the inoculum cultures were viable. The growth of the PDO2625 strain (Example 16, Comparative) and PDO2769 strain (Example 17, Comparative) was similar to the growth of PDO2771 (Example 15) at low sucrose concentrations of 2 or 4 g/L. However at the higher sucrose concentrations of 16 or 32 g/L, PDO2771 maintained good growth while the growth of PDO2525 and PDO2769 was severely inhibited. These results demonstrate that the strain expressing CscB17, the improved sucrose facilitated diffusion transporter with three altered residues, L61P, R300A, Q353H, was able to grow at a much wider range of sucrose concentrations than the strains expressing the wild type sucrose symporter. Thus, this improved facilitated diffusion transporter has an advantage over sucrose transport by a symport mechanism.

Examples 18-21

PDO Production from Sucrose with a Strain Comprising a Variant CscB Sucrose Transporter Having R300A, Q353H, and L61P Mutations and a Strain Comprising the Wild Type Sucrose Transporter CscB The purpose of these Examples was to show that a recombinant *E. coli* strain comprising a variant of CscB having R300A, Q353H, and L61P mutations gave better PDO production when grown on sucrose than a recombinant *E. coli* strain comprising the wild type sucrose transporter CscB.

*E. coli* strain PDO2737 [TTab/pSYCO400AGRO yihP::cscKBΔ(61-353)KanR&A, described in Examples 7-10, was transformed independently with plasmids pDMWP55 (pBR*P1.20cscB17, described in Examples 11-14) and pDMWP79 (pBR*P1.5csscB17, described in Examples 11-14) to make strains PDO2816 and PDO2819, respectively. These two strains and two strains expressing the wild type cscB symporter, PDO2815 and PDO2818 (described in Examples 7-10) were grown overnight in L-Broth, Miller's Modification (Teknova, Half Moon Bay, Calif.) supplemented with 100 mg/L spectinomycin and 100 mg/L ampicillin at 33° C. These cultures were used to inoculate shake flasks at an optical density of 0.01 units measured at 550 nm in MOPS minimal medium (Teknova, Half Moon Bay, Calif.) supplemented with 10 g/L sucrose. Vitamin B12 was added to the medium to a concentration of 0.1 mg/L. The cultures were incubated at 34° C. with shaking (225 rpm) for 48 hours. Samples of the cultures were then filtered and used in determination of the concentrations of sucrose, glycerol and 1,3-propanediol (PDO) in the broth by high performance liquid chromatography.

Chromatographic separation was achieved using an Aminex HPX-87P column (Bio-Rad, Hercules, Calif.) with an isocratic mobile phase of distilled-deionized water at a flow rate of 0.5 mL/min and a column temperature of 85° C. Eluted compounds were quantified by refractive index detection with reference to a standard curve prepared from commercially purchased pure compounds dissolved to known concentrations in MOPS minimal medium. Retention times were sucrose at 12.2 min, 1,3-propanediol at 17.9 min, and glycerol at 23.6 min. Table 8 shows the residual sucrose and molar yield of PDO and glycerol (mol PDO+mol glycerol/mol glucose equivalent), in the cultures of these four strains.

TABLE 8

Sucrose utilization and PDO and Glycerol Production

| Example | Strain | 44 hour sucrose g/L | Molar Yield (mol PDO + glycerol/mol glucose equivalent) |
|---|---|---|---|
| Example 18, Comparative | PDO2815 (P1.20cscB) | 0.85 | 1.09 |
| Example 19, Comparative | PDO2818 (P1.5cscB) | 8.19 | 1.12 |
| Example 20 | PDO2816 (P1.20cscB17) | 0.00 | 1.14 |
| Example 21 | PDO2819 (P1.5cscB17) | 0.00 | 1.21 |

As can be seen by the results in Table 8, sucrose was completely utilized in 48 hours only in the two cultures expressing the improved facilitated diffusion transporter CscB17 (Examples 20 and 21). Furthermore, the molar yield of PDO and glycerol was greater in the cultures expressing CscB17 than in those with the wild-type sucrose symporter CscB (Comparative Examples 18 and 19). Thus, sucrose transport by facilitated diffusion was shown to be advantageous for PDO and glycerol production.

Examples 22-24

Recombinant *E. Coli* Strains Comprising Variants of Sucrose Transporter Gene scrT1 from *Citrobacter* sp. 30_2

The purpose of these Examples was to construct recombinant *E. coli* strains containing mutant transporter genes from *Citrobacter* sp. 30_2 and to demonstrate sucrose transport by facilitated diffusion. The protein encoded by the mutant sucrose transport gene was altered in a residue required for $H^+$ translocation, thus eliminating W/sucrose symport.

Construction of Expression Vectors:

Plasmid pDMWP12-scrT1, carrying a gene encoding a transporter protein from *Citrobacter* sp. 30_2, was constructed as follows. Vector pDMWP3 was obtained from Integrated DNA Technologies, Inc. (Coralville, 10). The pDMWP3 vector was constructed by cloning a promoter/MCS/double terminator region (set forth in SEQ ID NO:124), synthesized by Integrated DNA Technologies, Inc., into the pIDT-SMART vector (Integrated DNA Technologies, Inc.). Vector pDMWP4 was constructed from plasmid pBR322. A sca1 site and a kpn1 site on the 5' end of the TetR gene and an additional kpn1 site at the 3' end of the TetR gene were introduced into plasmid pBR322. Additionally, a kpn1 site was removed from the middle of the AmpR gene, All restriction sites were either added or removed using Stratagene's QuikChange® Site-Directed Mutagenesis kit (Stratagene, La Jolla, Calif.) following the manufacturer's protocols. Vector pDMWP3 was digested with EcoR1 and Kpn1 and the resulting 438 bp fragment was cloned into vector pDMWP4, which was also digested with EcoR1 and Kpn1, to give vector pDMWP12, which is also referred to herein as pBR*P1.20. The scrT1 transporter gene from *Citrobacter* sp. 30_2 was codon optimized for expression in *E. coli*. The codon optimized sequence, set forth in SEQ ID NO:125, was synthesized by GenScript USA Inc. (Piscataway, N.J.). The synthetic gene was subcloned into vector pDMWP12 at restriction sites of HindIII and XmaI to yield pDMWP12-scrT1. This subcloning was done at GenScript. The presence of the transporter gene in pDMWP12-scrT1 was confirmed by sequence analysis.

The residue equivalent to R300 of *E. coli* CscB was found by multiple sequence alignment to be an arginine residue at position 305. R305 was mutated independently with two sets of primers to introduce an R305A mutation (SEQ ID NO:108, encoded by SEQ ID NO:107) and an R305L mutation (SEQ ID NO:110, encoded by SEQ ID NO:109). Site directed mutagenesis, using Stratagene's QuikChange® Site-Directed Mutagenesis kit was employed. Oligonucleotides ODMWP97 (SEQ ID NO:126) and ODMWP98 (SEQ ID NO:127) were used to introduce the R305A mutation, creating plasmid pDMWP112. Oligonucleotides ODMWP99 (SEQ ID NO:128) and ODMWP100 (SEQ ID NO:129) were used to introduce the R305L mutation, creating pDMWP113.

Construction of E. Coli Strains Comprising the Variant Citrobacter Sp. Sucrose Transporter:

Plasmids pDMWP112 and pDMWP113 were introduced into E. coli strain PDO3513 (described in Examples 1 and 2). The resultant strains were named PDO2896 and PDO2897, respectively. Additionally, the vector pDMWP12 (described in Examples 1 and 2) was introduced into strain PDO3513 to yield strain PDO2576.

Growth Characterization of E. Coli Strains:

E. coli strains PDO2576 (Example 22, Comparative), PDO2896 (Example 23), and PDO2897 (Example 24) were grown overnight in LB (Luria Bertani) medium containing 100 µg/mL ampicillin at 37° C. The next day, these cultures were diluted 1:50 in LB (Luria Bertani) medium containing 100 µg/mL ampicillin. These cultures were grown at 37° C. with shaking at 250 rpm for 4 hours. The log-phase cultures were diluted 1:100 in the wells of a Bioscreen-C plate (instrument and plates purchased from Growth Curves USA, Piscataway N.J.) with 150 µL MOPS minimal medium (Teknova, Half Moon Bay, Calif.) containing 2 g/L glucose or 8 g/L sucrose. The cultures were grown at 37° C. in triplicate with continuous shaking and the optical density was monitored. The optical density of the cultures measured at 6 hours after inoculation is shown in Table 9.

TABLE 9

Optical Density of Cultures Growing on Glucose or Sucrose at 6 Hours

| Carbon Source | Example 22, Comparative PDO2576 | Example 23 PDO2896 | Example 24 PDO2897 |
| --- | --- | --- | --- |
| 2 g/L glucose | 0.506 ± 0.001 | 0.561 ± 0.021 | 0.569 ± 0.014 |
| 8 g/L sucrose | 0.030 ± 0.002 | 0.439 ± 0.017 | 0.451 ± 0.003 |

As can be seen from the data in Table 9, all of the strains grew well with glucose as a sole carbon source indicating that the inoculum cultures were viable. In contrast, the control strain PDO2576 (Example 22, Comparative) was unable to grow with sucrose as sole carbon source, while the strains expressing the mutant scrT1 genes encoding a sucrose transporter unable to translocate ion (Examples 23 and 24) were able to grow with sucrose as sole carbon source. Thus, net translocation of sucrose across the membrane must have occurred without translocation of a $H^+$ ion.

Examples 25 and 26

Recombinant E. coli Strains Comprising Variants of Sucrose Transporter Gene scrT7 from Bifidobacterium longum The purpose of these Examples was to construct a recombinant E. coli strain containing a mutant transporter gene from Bifidobacterium longum NCC2705 and to demonstrate sucrose transport by facilitated diffusion. The protein encoded by the mutant sucrose transport gene was altered in a residue required for $H^+$ translocation, thus eliminating $H^+$/sucrose symport.

Construction of Expression Vectors:

Plasmid pDMWP12-scrT7, carrying a gene encoding a transporter protein from Bifidobacterium longum NCC2705, was constructed using plasmid pDMWP12 (described in Examples 1 and 2 and Examples 22-24). The scrT7 sucrose transporter gene from Bifidobacterium longum was codon optimized for expression in E. coli. The codon optimized sequence, set forth in SEQ ID NO:130, was synthesized by GenScript USA Inc. (Piscataway, N.J.). The synthetic gene was subcloned into vector pDMWP12 at restriction sites of HindIII and XmaI. This subcloning was done at Genscript. The presence of the transporter gene in the vectors was confirmed by sequence analysis.

The residue equivalent to R300 of E. coli CscB was found by multiple sequence alignment to be an arginine residue at position 312. Plasmid pDMWP12-scrT7 was mutated to introduce an R312A mutation (SEQ ID NO:112, encoded by SEQ ID NO:111). Site directed mutagenesis, using Stratagene's QuikChange® Site-Directed Mutagenesis kit, was employed. Oligonucleotides ODMWP101 (SEQ ID NO:131) and ODMWP102 (SEQ ID NO:132) were used to introduce the R312A mutation, creating plasmid pDMWP114.

Construction of E. coli Strains Comprising the Variant Bifidobacterium longum Sucrose Transporter:

Plasmid pDMWP114 was introduced into E. coli strain PDO3513 (described in Examples 1 and 2). The resultant strain was named PDO2898. Additionally, the vector pDMWP12 (described in Examples 1 and 2) was introduced into PDO3513 to yield strain PDO2576.

Growth Characterization of E. coli Strains:

E. coli strains PDO2576 (Example 25, Comparative) and PDO2898 (Example 26) were grown overnight in LB (Luria Bertani) medium containing 100 µg/mL ampicillin at 37° C. The next day, these cultures were diluted 1:50 in LB (Luria Bertani) medium containing 100 µg/mL ampicillin. These cultures were grown at 37° C., with shaking at 250 rpm for 4 hours. The log-phase cultures were diluted 1:100 in the wells of a Bioscreen-C plate (instrument and plates purchased from Growth Curves USA, Piscataway N.J.) with 150 µL MOPS minimal medium (Teknova, Half Moon Bay, Calif.) containing 2 g/L glucose or 8 g/L sucrose. The cultures were grown at 37° C. in triplicate with continuous shaking and the optical density was monitored. The optical density of the cultures measured at 6 hours after inoculation is shown in Table 10.

TABLE 10

Optical Density of Cultures Growing on Glucose or Sucrose at 6 Hours

| Carbon Source | Example 25, Comparative PDO2576 | Example 26 PDO2898 |
| --- | --- | --- |
| 2 g/L glucose | 0.506 ± 0.001 | 0.531 ± 0.011 |
| 8 g/L sucrose | 0.030 ± 0.002 | 0.268 ± 0.005 |

As can be seen from the data in Table 10, both of the strains grew well with glucose as a sole carbon source indicating that the inoculum cultures were viable. In contrast, the control strain PDO2576 (Example 25, Comparative) was unable to grow with sucrose as sole carbon source, while the strain expressing the mutant scrT7 gene encoding a sucrose transporter unable to translocate $H^+$ ion (Example 26) was able to grow with sucrose as sole carbon source. Thus, net translocation of sucrose across the membrane must have occurred without translocation of a $H^+$ ion.

What is claimed is:

1. A variant sucrose transporter polypeptide having an amino acid sequence that has at least 95% identity to an amino acid sequence as set forth in SEQ ID NO:26 based on a Clustal W method of alignment and comprising an amino acid change from arginine to leucine at position 300, an amino acid change from glutamine to histidine at position 353, and an amino acid change from leucine to proline at position 61.

2. A variant sucrose transporter polypeptide having an amino acid sequence that has at least 95% identity based on a Clustal W method of alignment to an amino acid sequence selected from the group consisting of SEQ ID NOs: 68, 70, 72, 74, 76, 78, 80, 82, 84, 86, 88, 90, 92, 94, 96, and 98, and comprising a leucine at a position equivalent to position 300 when compared with a reference amino acid sequence of SEQ ID NO:26.

3. The variant sucrose transporter polypeptide of claim 2, wherein the variant sucrose transporter polypeptide further comprises a histidine at a position equivalent to position 353 and a proline at a position equivalent to position 61 when compared with the reference amino acid sequence of SEQ ID NO:26.

* * * * *